US010982258B2

(12) United States Patent
Vigneault et al.

(10) Patent No.: US 10,982,258 B2
(45) Date of Patent: Apr. 20, 2021

(54) METHODS OF SEQUENCING, DETERMINING, PAIRING, AND VALIDATING THERAPEUTIC AGENTS AND DISEASE SPECIFIC ANTIGENS

(71) Applicant: AbVitro LLC, Seattle, WA (US)

(72) Inventors: Francois Vigneault, Yarrow Point, WA (US); Adrian Wrangham Briggs, Seattle, WA (US); Christopher Ryan Clouser, Seattle, WA (US); Stephen Jacob Goldfless, Seattle, WA (US); Sonia Timberlake, Brookline, MA (US)

(73) Assignee: AbVitro LLC, Boston, MA (US)

( * ) Notice: Subject to any disclaimer, the term of this patent is extended or adjusted under 35 U.S.C. 154(b) by 110 days.

(21) Appl. No.: 15/570,075

(22) PCT Filed: Apr. 27, 2016

(86) PCT No.: PCT/US2016/029556
§ 371 (c)(1),
(2) Date: Oct. 1, 2018

(87) PCT Pub. No.: WO2016/176322
PCT Pub. Date: Nov. 3, 2016

(65) Prior Publication Data
US 2019/0024145 A1 Jan. 24, 2019

Related U.S. Application Data

(60) Provisional application No. 62/153,041, filed on Apr. 27, 2015.

(51) Int. Cl.
*C12Q 1/68* (2018.01)
*C12Q 1/6809* (2018.01)
(Continued)

(52) U.S. Cl.
CPC ...... *C12Q 1/6809* (2013.01); *C07K 14/70503* (2013.01); *C07K 16/00* (2013.01);
(Continued)

(58) Field of Classification Search
None
See application file for complete search history.

(56) References Cited

U.S. PATENT DOCUMENTS 5,296,351 A 3/1994 Morley et al.
9,181,591 B2 11/2015 Robins et al.
(Continued)

FOREIGN PATENT DOCUMENTS

JP 2014528714 A 10/2014
WO WO 2005/059176 A1 6/2005
(Continued)

OTHER PUBLICATIONS

Shugay et al., Towards Error-Free Profiling of Immune Repertoires, Nat. Methods, Jun. 2014;11(6):653-5. doi: 10.1038/nmeth.2960. Epub May 4, 2014.*
(Continued)

*Primary Examiner* — Aaron A Priest
(74) *Attorney, Agent, or Firm* — Finnegan, Henderson, Farabow, Garrett & Dunner LLP

(57) ABSTRACT

Provided herein are methods and composition for immune repertoire sequencing and single cell barcoding. The methods and compositions can be used to pair any two sequences originating from a single cell, such as heavy and light chain antibody sequences, for antibody discovery, disease and immune diagnostics, and low error sequencing.

37 Claims, 27 Drawing Sheets

(51) Int. Cl.

| | |
|---|---|
| *C12Q 1/6869* | (2018.01) |
| *C07K 14/705* | (2006.01) |
| *C07K 16/00* | (2006.01) |
| *C12N 15/85* | (2006.01) |
| *C12Q 1/6811* | (2018.01) |
| *C12Q 1/6848* | (2018.01) |
| *C12Q 1/6853* | (2018.01) |
| *C12Q 1/6876* | (2018.01) |

(52) U.S. Cl.
CPC ............ *C07K 16/005* (2013.01); *C12N 15/85* (2013.01); *C12Q 1/6811* (2013.01); *C12Q 1/6848* (2013.01); *C12Q 1/6853* (2013.01); *C12Q 1/6869* (2013.01); *C12Q 1/6876* (2013.01); *C12Q 2563/185* (2013.01)

(56) References Cited

U.S. PATENT DOCUMENTS

| | | | | |
|---|---|---|---|---|
| 9,816,088 | B2* | 11/2017 | Vigneault | C12N 15/1065 |
| 10,590,483 | B2 | 3/2020 | Vigneault et al. | |
| 2009/0098555 | A1* | 4/2009 | Roth | C12Q 1/6816 435/6.12 |
| 2012/0245039 | A1* | 9/2012 | Roth | C12Q 1/6874 506/2 |
| 2013/0005584 | A1 | 1/2013 | Faham et al. | |
| 2015/0133317 | A1* | 5/2015 | Robinson | C07K 16/1271 506/4 |
| 2016/0333108 | A1* | 11/2016 | Forman | C07K 14/7051 |
| 2017/0009274 | A1* | 1/2017 | Abate | B01F 5/0655 |

FOREIGN PATENT DOCUMENTS

| | | |
|---|---|---|
| WO | WO 2012/148497 A2 | 11/2012 |
| WO | WO 2013/039889 A1 | 3/2013 |
| WO | WO 2013/188872 A1 | 12/2013 |
| WO | WO 2014/130685 A1 | 8/2014 |
| WO | WO 2014/144495 | 9/2014 |
| WO | WO 2015/031691 A1 | 3/2015 |

OTHER PUBLICATIONS

Islam et al., Highly Multiplexed and Strand-Specific Single-Cell RNA 5' End Sequencing, Nat Protoc., Apr. 5, 2012;7(5):813-28. doi: 10.1038/nprot.2012.022.*

Kinde et al., Detection and quantification of rare mutations with massively parallel sequencing, PNAS Jun. 7, 2011 108 (23) 9530-9535; https://doi.org/10.1073/pnas.1105422108.*

Fabrizio et al., "Abstract 643: Identification novel pancreatic cancer-specific antibodies and their target antigens through a next generation immune sequencing platform." AACR 106$^{th}$ Annual Meeting, 75(15): entire document.

Georgiou et al., "The promise and challenge of high-throughput sequencing of the antibody repertoire," Nat. Biotechnol. 32(2): 158-168 (2014).

PCT International Search Report and Written Opinion dated Aug. 5, 2016, issued in corresponding International Application No. PCT/US2016/029556 (9 pages).

D.F. Lake et al., "Construction and binding analysis of recombinant single-chain TCR derived from tumor-infiltrating lymphocytes and a cytotoxic T lymphocyte clone directed against MAGE-1," The Japanese Society for Immunology, International Immunology, vol. 11, No. 5, 1999, 7 pages.

E. Tran et al., Supplementary Materials for "Cancer immunotherapy based on mutation-specific CD4+ T cells in a patient with epithelial cancer," Science 344, 641, May 9, 2014, 29 pages.

H. S. Robins et al., "Digital genomic quantification of tumor-infiltrating lymphocytes," NIH Public Access, Author Manuscript, Jun. 4, 2014, 19 pages.

Pavoni, et al., "Tumor-infiltrating B lymphocytes as an efficient source of highly specific immunoglobulins recognizing tumor cells," BMC Biotechnology., 2007, vol. 70; 7, pp. 1-17.

* cited by examiner

Pairing of B cells (naive, memory & plasma cells)

| | |
|---|---:|
| B-cells into emulsion | 500,000 |
| Illumina 2x300bp raw sequence reads | 13,670,330 |
| Properly barcoded VH/VL reads | 11,594,330 |
| Distinct droplet barcodes observed | 358,780 |
| Total pairs (90% accuracy[1]) | 197,865 |
| High stringency pairs (p=0.0006) | 72,030 |
| Total pairing efficiency | 40% |

1- Measured by cell line spike-in

FIG. 13

METHODS OF SEQUENCING, DETERMINING, PAIRING, AND VALIDATING THERAPEUTIC AGENTS AND DISEASE SPECIFIC ANTIGENS

CROSS-REFERENCE

This application is a U.S. National Phase Application under U.S.C. § 371 of International Application No. PCT/US2016/029556, filed Apr. 27, 2016, which claims priority to U.S. Provisional Application No. 62/153,041, filed Apr. 27, 2015, which is incorporated herein by reference in its entirety.

BACKGROUND

The immune system employs several strategies to generate a repertoire of T-cell and B-cell antigen receptors. The diversity of these receptors is sufficient to recognize the universe of potential pathogens. B lymphocytes mature to express antibodies (immunoglobulins, Igs) that occur as heterodimers of a heavy (H) a light (L) chain polypeptide, while T lymphocytes express heterodimeric T-cell receptors (TCR). The immune system also acts as an extrinsic tumor suppressor that neoplastic cells must evade to survive. However, tumor cells can employ mechanisms to escape immune recognition and can lead to tumor outgrowth. These include immunoediting, whereby neoplastic cells that express highly immunogenic tumor antigens are eliminated, and down-regulation of immunogenic tumor antigens. The immune system's lack of tumor specificity, antigenic modulation by tumor cells, and abnormal expression of MHC molecules and other factors, prevent detection of the tumor.

SUMMARY OF THE DISCLOSURE

Methods are disclosed comprising determining a sequence of an antigen-binding molecule such as an immunoglobulin (Ig) or TCR, or binding portion thereof, expressed by, e.g., exogenously or endogenously, an immune cell, such as a tumor infiltrating lymphocyte (TIL). In some aspects, the antigen-binding molecule has a high affinity for an antigen of a tissue, e.g., a disease specific-antigen. The disclosed methods in some aspects can be used to determine, detect, and/or select a TIL from a diseased biological sample (e.g., a diseased tissue sample) having high affinity for an antigen expressed on or in a tissue and/or of a tissue, e.g., a disease specific-antigen. The disclosed methods in some aspects can be used to discover and/or identify antibodies, including antigen-binding portions of full-length antibodies, TCRs, therapeutic targets, and biomarkers. Among the disclosed methods are those employ high-throughput, accurate, and minimally biased sequencing methods to sequence polynucleotides, such as lymphocyte polynucleotides, e.g., Ig and TCR polynucleotides. The methods in some aspects utilize accurate sequencing methods, such as those described in WO2014144495, WO2012048340, and WO2012048341; and U.S. Provisional App. Nos. 62/050,549, 62/051,832, 61/938,227, and 62/031,405, the contents of each of which are herein incorporated by reference herein in their entirety. The methods disclosed can be used, e.g., for pairing of natural heavy and light chain and/or alpha and beta TCR chain or gamma and delta TCR chain sequences, for example, to identify such sequences that are present within pairs of such chains that exist naturally, e.g., in a single cell and/or expressed in a complex together on the cell surface. The methods disclosed in some embodiments comprise sequencing polynucleotides from a biological sample obtained from a diseased organism. The biological sample can be a diseased sample, e.g., a solid tumor sample. In some instances, the biological sample comprises a plurality of TILs containing the polynucleotides to be sequenced.

The methods, in some embodiments, further include selecting one or more polynucleotides of the lymphocytes containing the sequenced polynucleotides, such as Ig or TCR polynucleotides, e.g., paired heavy and light chain antibody polynucleotides or paired alpha and beta chain TCR polynucleotides. The selecting is based on sequencing data obtained from the sequencing step described above. The methods, in some aspects, further include producing a polypeptide encoded by the selected polynucleotide, e.g., an Ig or TCR polypeptide encoded by the selected polynucleotide. The methods, in some embodiments, further include identifying an antigen of the polypeptide encoded by the polynucleotide of the selected lymphocyte, e.g., through use of a recombinantly expressed or synthesized Ig or TCR polypeptide.

In some aspects, the disclosed methods comprise providing a biological sample comprising at least one tumor-infiltrating lymphocyte (TIL) and at least one non-TIL cell. In some aspects, the disclosed methods comprise sequencing a polynucleotide encoding an Ig or a TCR polypeptide from the at least one TIL and from the at least one non-TIL cell, thereby obtaining sequence information. In some aspects, the disclosed methods further comprise steps of selecting an Ig or TCR polynucleotide sequence from a TIL of the at least one TIL and at least one non-TIL cell based on the sequence information and/or producing an Ig or TCR polypeptide encoded by the polynucleotide sequence selected. In some aspects, the methods further comprise identifying a target antigen of the produced Ig or TCR polypeptide.

In some aspects, the disclosed methods comprise sequencing a polynucleotide encoding an Ig or a TCR polypeptide from at least one TIL from a biological sample from a subject and a polynucleotide encoding an Ig or a TCR polypeptide from at least one non-TIL cell from the biological sample from the subject, thereby obtaining sequence information; comparing the sequence information obtained to sequence information obtained from a corresponding normal adjacent tissue sample; and selecting an Ig or TCR polynucleotide sequence from a TIL of the at least one TIL and at least one non-TIL cell based on the comparing. In some embodiments, the disclosed methods further comprise steps of producing an Ig or TCR polypeptide encoded by the polynucleotide sequence selected; and/or identifying a target antigen of the produced Ig or TCR polypeptide.

In some embodiments, the disclosed methods comprise identifying a target antigen of an Ig or TCR polypeptide produced from a TIL. In some embodiments, the disclosed methods comprise sequencing a polynucleotide encoding an Ig or a TCR polypeptide from at least one TIL from a biological sample from a subject and a polynucleotide encoding an Ig or a TCR polypeptide from at least one non-TIL cell from the biological sample from the subject, thereby obtaining sequence information; comparing the sequence information obtained to sequence information obtained from a corresponding normal adjacent tissue sample; and selecting an Ig or TCR polynucleotide sequence from a TIL of the at least one TIL and at least one non-TIL cell based on the comparing; producing an Ig or TCR polypeptide encoded by the polynucleotide sequence selected; and identifying a target antigen of the produced Ig or TCR polypeptide.

In some aspects, the disclosed methods comprise providing a biological sample from a first subject, the biological sample comprising at least one tumor-infiltrating lymphocyte (TIL) and at least one non-TIL cell; sequencing a polynucleotide encoding an Ig or a TCR polypeptide from the at least one TIL and from the at least one non-TIL cell, thereby obtaining sequence information; comparing the sequence information to sequence information obtained from a biological sample from a second subject, wherein the first and second subject have the same disease; selecting an Ig or TCR polynucleotide sequence from a TIL of the at least one TIL and at least one non-TIL cell based on the comparing; producing an Ig or TCR polypeptide encoded by the polynucleotide sequence selected; and identifying a target antigen of the produced Ig or TCR polypeptide.

In some aspects, a morphology of the at least one TIL is unknown. In some aspects, a morphology of the at least one TIL is unknown. In some aspects, a phenotype of the at least one TIL is unknown. In some aspects, a phenotype of the at least one non-TIL cell is unknown.

In some aspects, the at least one TIL and the at least one non-TIL cells are present in the biological sample at a ratio of 1:10,000 or less. In some aspects, the TIL and the non-TIL cells are present in the biological sample at a ratio of 1:100,000 or less. In some aspects, the TIL and the non-TIL cells are present in the biological sample at a ratio of 1:1,000,000 or less.

In some embodiments, the polynucleotide encoding an Ig or a TCR polypeptide from at least one TIL from a biological sample from a subject and a polynucleotide encoding an Ig or a TCR polypeptide from at least one non-TIL cell from the biological sample from the subject are present in the biological sample at a ratio of 1:10,000 or less, 1:100,000 or less, or 1:1,000,000 or less. In some embodiments of the presently disclosed methods, the the polynucleotide encoding an Ig or a TCR polypeptide from at least one TIL from a biological sample from a subject and a polynucleotide encoding an Ig or a TCR polypeptide from at least one non-TIL cell from the biological sample from the subject are present during the sequencing step at a ratio of 1:10,000 or less, 1:100,000 or less, or 1:1,000,000 or less.

In some aspects, the selecting comprises performing a bioinformatics analysis of the sequence information. In some aspects, the selecting comprises determining an expression level of a polynucleotide of the sequence information. In some aspects, the selecting comprises aligning polynucleotide sequences of the sequence information. In some aspects, the selecting is based on an expression level of the polynucleotide encoding an Ig or a TCR polypeptide. In some aspects, the selecting is based on a pattern of mutation from a germline sequence of a polynucleotide encoding an Ig or a TCR polypeptide. In some aspects, the selecting is based on a level of a mutation from a germline sequence of a polynucleotide encoding an Ig or a TCR polypeptide in the sequence information. In some aspects, the selecting is based on a presence of a polynucleotide encoding an Ig or a TCR polypeptide in the sequence information and the absence of the selected polynucleotide sequence in a set of sequence information from normal cells. In some aspects, the selecting is based on an enrichment of a polynucleotide encoding an Ig or a TCR polypeptide in the sequence information and the absence of the selected polynucleotide sequence in a second set of sequence information from normal cells. In some aspects, the selecting is based on an isotype profile of a polynucleotide encoding an Ig or a TCR polypeptide in the sequence information. In some aspects, the selecting is based on a phylogenetic cluster of a polynucleotide encoding an Ig or a TCR polypeptide in the sequence information. In some aspects, the selecting is based on a size of a phylogenetic cluster of a polynucleotide encoding an Ig or a TCR polypeptide in the sequence information. In some aspects, the selecting is based on a similarity between a sequence of a polynucleotide encoding an Ig or a TCR polypeptide in the sequence information, and a sequence of another set of sequence information from a diseased biological sample.

In some aspects, the diseased biological sample comprises a plurality of lymphocytes from a diseased biological sample from a first subject with the disease, and a plurality of lymphocytes from a diseased biological sample from a second subject with the disease.

In some aspects, the selecting is based on a lack of similarity between a sequence of a polynucleotide encoding an Ig or a TCR polypeptide in the sequence information, and a sequence of another set of sequence information from a normal biological sample.

In some aspects, the normal biological sample is a normal adjacent tissue sample. In some aspects, the normal biological sample comprises a plurality of lymphocytes from a normal biological sample from a first subject without the disease, and a plurality of lymphocytes from a normal biological sample from a second subject without the disease.

In some aspects, the method comprises determining the specificity of the produced Ig or TCR polypeptide to a diseased tissue or a diseased biological sample or a diseased cell. In some aspects, the determining the specificity comprises determining an affinity of the produced Ig or TCR polypeptides for the diseased tissue or the diseased biological sample or the diseased cell and an affinity of the produced Ig or TCR polypeptides for a corresponding normal adjacent tissue or a corresponding normal cell of the same tissue type.

In some aspects, the method comprises identifying the produced Ig or TCR polypeptide that kills a diseased cell. In some aspects, the identified produced Ig or TCR polypeptide kills the diseased cell by binding directly to the diseased cell.

In some aspects, the producing comprises synthesizing or recombinantly expressing the Ig or TCR polypeptide. In some aspects, the at least one non-TIL cell comprises epithelial cells, lymphocytes, cancer cells, or a combination thereof. In some aspects, the at least one TIL comprises at least one T-cell, at least one B-cell, or a combination thereof.

In some aspects, the biological sample is a cancer biopsy. In some aspects, the biological sample is a normal tissue biopsy. In some aspects, the biological sample comprises extravascular tissue. In some aspects, the Ig or TCR polypeptide encoded by the selected polynucleotide sequence is a recombinant polypeptide. In some aspects, the target analyte is specific to a diseased biological sample. In some aspects, the target analyte is specific to a diseased cell of the biological sample. In some aspects, the target analyte is specific to a cancer cell.

In some aspects, the sequencing is high-throughput sequencing. In some aspects, the sequencing is sequencing by synthesis, hybridization, or ligation. In some aspects, the sequencing does not comprise sequencing the entire immune repertoire. In some aspects, the sequencing is massive parallel sequencing.

In some aspects, the method does not comprise use of a multiplex of primers or a multiplex of primers attached to a solid support. In some aspects, the method does not employ a multiplicity of primers comprising a sequence that is complementary to an Ig or TCR variable domain region. In some aspects, the method does not employ a step of isolating a polynucleotide from the at least one TIL or the at least one non-TIL cell prior to the sequencing.

In some aspects, the biological sample is not blood. In some aspects, the biological sample is solid tissue sample. In some aspects, the biological sample is from an organ. In some aspects, the biological sample comprises a three dimensional structure. In some aspects, the biological sample comprises cancerous cells or precancerous cells. In some aspects, the biological sample comprises healthy tissue aberrantly targeted by the immune system of the subject.

In some aspects, the at least one non-TIL cell comprises 1,000, 5,000, 10,000, 20,000, 30,000, 40,000, 50,000, 1000, 000, 500,000, or $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, or $9\times10^{12}$ or more non-TIL cells.

In some aspects, the at least one TIL comprises 1,000, 5,000, 10,000, 20,000, 30,000, 40,000, 50,000, 1000,000, 500,000, or $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, or $9\times10^{12}$ or more TILs.

In some aspects, the selected polynucleotide sequence comprises from 1-500 unique Ig or TCR polynucleotide sequences. In some aspects, the selected polynucleotide sequence comprises at most 1, 2, 3, 4, 5, 6, 7, 8, 9, 10, 15, 20, 30, 40, 50, 60, 70, 80, 90, 100, 125, 150, 175, 200, 225, 250, 275, 300, 325, 350, 375, 400, 425, 450, 475, or 500 unique Ig or TCR polynucleotide sequences.

In some aspects, the selected polynucleotide sequence comprises a TCR polynucleotide sequence from a T-cell. In some aspects, the selected polynucleotide sequence comprises an Ig polynucleotide sequence from a B-cell. In some aspects, the at least one TIL and at least one non-TIL cell of the biological sample are not sorted based on an extracellular cell marker prior to the sequencing. In some aspects, the at least one TIL and at least one non-TIL cell of the biological sample are not sorted based on a cell marker prior to the sequencing. In some aspects, the at least one TIL and at least one non-TIL cell of the biological sample are not sorted prior to the sequencing.

In some aspects, the sequenced polynucleotide comprises an Ig polynucleotide encoding an Ig heavy chain (IgH). In some aspects, the method further comprises pairing the IgH with an Ig light chain (IgL) from a same B-cell. In some aspects, the sequenced polynucleotide comprises an Ig polynucleotide encoding an IgL. In some aspects, the method further comprises pairing the IgL with an IgH from a same B-cell. In some aspects, the sequenced polynucleotide comprises an Ig polynucleotide encoding an IgH and an Ig polynucleotide encoding an IgL. In some aspects, the IgL is paired with the IgH from a same B-cell. In some aspects, the method further comprises pairing an IgL with an IgH from a same B-cell. In some aspects, the sequenced polynucleotide comprises a TCR polynucleotide encoding a TCRα chain. In some aspects, the method further comprises pairing the TCRα chain with a TCRβ chain from a same T-cell. In some aspects, the sequenced polynucleotide comprises a TCR polynucleotide encoding a TCRβ chain. In some aspects, the method further comprises pairing the TCRβ chain with a TCRα chain from a same T-cell. In some aspects, the sequenced polynucleotide comprises a TCR polynucleotide encoding a TCRα chain and a TCR polynucleotide encoding a TCRβ chain.

In some aspects, the TCRα chain is paired with the TCRβ chain from a same T-cell. In some aspects, the method further comprises pairing TCRα chain with a TCRβ chain from a same T-cell. In some aspects, the method further comprises generating a database of paired IgLs and IgHs. In some aspects, the method further comprises generating a database of paired TCRα and TCRβ chains.

In some aspects, the polynucleotide encoding an Ig or a TCR polypeptide comprises a variable region. In some aspects, the polynucleotide encoding an Ig comprises a heavy chain variable region ($V_H$). In some aspects, the polynucleotide encoding an Ig comprises a light chain variable region ($V_L$). In some aspects, the polynucleotide encoding a TCR comprises a TCRα chain variable region. In some aspects, the polynucleotide encoding a TCR comprises a TCRβ chain variable region. In some aspects, the polynucleotide encoding a TCR comprises a TCRγ chain variable region. In some aspects, the polynucleotide encoding a TCR comprises a TCRδ chain variable region. In some aspects, the variable region comprises a CDR1, CDR2, CDR3, a hypermutation region, or any combination thereof. In some aspects, the variable region comprises a V segment, a D segment, a J segment, or any combination thereof. In some aspects, the polynucleotide encoding an Ig or a TCR polypeptide comprises a TCR constant domain region. In some aspects, the TCR constant domain region comprises a TCRα constant domain, a TCRβ constant domain, or a combination thereof. In some aspects, the region of a polynucleotide encoding an Ig or a TCR polypeptide comprises an Ig constant domain region. In some aspects, the Ig constant domain region comprises an IgH constant domain selected from the group consisting of $CH_1$, $CH_2$, $CH_3$, and $CH_4$.

In some aspects, the Ig constant domain region comprises two, three, or four IgH constant domains selected from the group consisting of $CH_1$, $CH_2$, $CH_3$, and $CH_4$. In some aspects, the Ig constant domain region comprises a IgH constant domain from an Ig isotype selected from the group consisting from IgM, IgD, IgA, IgE, IgG, and combinations thereof. In some aspects, the Ig isotype of the selected polynucleotide sequence is an IgG isotype sequence. In some aspects, the Ig constant domain region comprises an IgL constant domain ($C_L$). In some aspects, the Ig constant domain region comprises a $C_L$ from an IgL isotype selected from the group consisting from Igκ, Igλ, and combinations thereof. In some aspects, the Ig isotype of the selected polynucleotide sequence is Igκ.

In some aspects, the polynucleotide encoding the Ig or TCR polypeptide comprises a framework region sequence comprising a germline framework sequence.

In some aspects, the polynucleotide encoding the Ig or TCR polypeptide comprises a $V_H$ sequence comprising a germline $V_H$ sequence, a $V_L$ sequence comprising a germline $V_L$ sequence, a TCRα variable region sequence comprising a germline TCRα variable region sequence, a TCRβ variable region sequence comprising a germline TCRβ variable region sequence, a TCRγ variable region sequence comprising a germline TCRγ variable region sequence, a TCRδ variable region sequence comprising a germline TCRδ variable region sequence, or a combination thereof.

In some aspects, the polynucleotide encoding the Ig or TCR polypeptide comprises a framework region sequence comprising one or more mutated framework residues. In some aspects, a mutated framework residue of the one or more mutated framework residues of the Ig or TCR polypeptide encoded by the selected polynucleotide sequence is a residue that is found in one or more of the top 5 percent most expressed IgH, IgL, TCRα, TCRβ, TCRγ or TCRδ polynucleotides from two or more subjects with a disease. In some aspects, the Ig or TCR polypeptide encoded by the selected polynucleotide sequence comprises a specific Ig isotype. In some aspects, the specific Ig isotype is IgA, IgG, IgM, IgD, or IgE. In some aspects, the specific isotype is IgG.

In some aspects, the sequence information comprises at least about 1,000, 5,000, 10,000, 20,000, 30,000, 40,000, 50,000, 1000,000, 500,000, or $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, or $9\times10^{12}$ unique Ig or TCR sequences.

In some aspects, the sequence information comprises at least about 1,000, 5,000, 10,000, 20,000, 30,000, 40,000, 50,000, 1000,000, 500,000, or $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, or $9\times10^{12}$ sequence reads.

In some aspects, the sequence information comprises at least one Ig or TCR sequence from the at least one TIL that encodes for an Ig or TCR polypeptide with a $K_d$ of about $1\times10^{-7}M$, $1\times10^{-8}M$, $1\times10^{-9}M$, $1\times10^{-10}$ M, $1\times10^{-11}M$, $1\times10^{-12}M$, or less for a disease-associated protein or a disease-specific protein. In some aspects, the sequence information does not comprise an Ig or TCR sequence from the at least one non-TIL cell that encodes for a an Ig or TCR polypeptide with a $K_d$ of $1\times10^{-7}M$, $1\times10^{-8}M$, $1\times10^{-9}M$, $1\times10^{-10}$ M, $1\times10^{-11}M$, $1\times10^{-12}M$, or less for a disease-associated protein or a disease-specific protein. In some aspects, the produced Ig or TCR polypeptide encoded by the selected polynucleotide sequence has a $K_d$ of about $1\times10^{-7}M$, $1\times10^{-8}M$, $1\times10^{-9}M$, $1\times10^{-10}$ M, $1\times10^{-11}M$, $1\times10^{-12}M$, or less for a disease-associated protein or a disease-specific protein. In some aspects, the selected polynucleotide sequence that encodes for the produced Ig or TCR polypeptide encodes an Ig or TCR polypeptide with a $K_d$ of about $1\times10^{-7}M$, $1\times10^{-8}M$, $1\times10^{-9}M$, $1\times10^{-10}$ M, $1\times10^{-11}M$, $1\times10^{-12}M$, or less for a disease-associated protein or a disease-specific protein.

In some aspects, a TIL comprising the selected polynucleotide sequence is present in an amount of about 1-500 per a total number of the at least one TIL and the at least one non-TIL cell of the biological sample. In some aspects, a TIL comprising the selected polynucleotide sequence is present in an amount of about one, two, three, four, or five per a total number of the at least one TIL and the at least one non-TIL cell of the biological sample. In some aspects, a TIL of the at least one TIL comprising the selected polynucleotide sequence is present in an amount of about one per at least 1,000, 5,000, 10,000, 20,000, 30,000, 40,000, 50,000, 1000, 000, 500,000, or $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$ $1\times10$, $2\times10^{12}$, $3\times10^{12}$, $4\times10^{12}$, $5\times10^{12}$, $6\times10^{12}$, $7\times10^{12}$, $8\times10^{12}$, or $9\times10^{12}$ total immune cells in the biological sample. In some aspects, a TIL of the at least one TIL comprising the selected polynucleotide sequence is present in an amount of about one per at least 1,000, 5,000, 10,000, 20,000, 30,000, 40,000, 50,000, 1000,000, 500,000, or $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11\ 11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, or $9\times10^{12}$ total lymphocytes in the biological sample. In some aspects, a TIL of the at least one TIL comprising the selected polynucleotide sequence is present in an amount of about one per at least 1,000, 5,000, 10,000, 20,000, 30,000, 40,000, 50,000, 1000,000, 500,000, or $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$ $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, or $9\times10^{12}$ of the at least one non-TIL cells in the biological sample. In some aspects, the at least one TIL is present in an amount of about one per at least 1,000, 5,000, 10,000, 20,000, 30,000, 40,000, 50,000, 1000,000, 500,000, or $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, or $9\times10^{12}$ of the at least one non-TIL cells in the biological sample. In some aspects, a ratio of disease-associated or disease-specific lymphocytes to total lymphocytes in the biological sample is about one per at least 1,000, 5,000, 10,000, 20,000, 30,000, 40,000, 50,000, 1000,000, 500,000, or $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, or $9\times10^{12}$ lymphocytes in a biological sample that are not disease-associated or disease specific lymphocytes.

In some aspects, the error rate of the sequencing is less than or equal to 0.00001%, 0.0001%, 0.001%, or 0.01%.

In some aspects, the sequencing comprises determining sequences with at least about 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, 99.99%, or 100% accuracy or confidence.

In some aspects, amplification errors are minimized, eliminated, or less than 0.01%, 0.001%, 0.0001%, 0.00001%, 0.000001%, or 0.0000001%.

In some aspects, the sequencing comprises sequencing the polynucleotide encoding an Ig or a TCR polypeptide of at least 1,000, 5,000, 10,000, 20,000, 30,000, 40,000, 50,000, 1000,000, 500,000, or $1 \times 10^6$, $2 \times 10^6$, $3 \times 10^6$, $4 \times 10^6$, $5 \times 10^6$, $6 \times 10^6$, $7 \times 10^6$, $8 \times 10^6$, $9 \times 10^6$, $1 \times 10^7$, $2 \times 10^7$, $3 \times 10^7$, $4 \times 10^7$, $5 \times 10^7$, $6 \times 10^7$, $7 \times 10^7$, $8 \times 10^7$, $9 \times 10^7$, $1 \times 10^8$, $2 \times 10^8$, $3 \times 10^8$, $4 \times 10^8$, $5 \times 10^8$, $6 \times 10^8$, $7 \times 10^8$, $8 \times 10^8$, $9 \times 10^8$, $1 \times 10^9$, $2 \times 10^9$, $3 \times 10^9$, $4 \times 10^9$, $5 \times 10^9$, $6 \times 10^9$, $7 \times 10^9$, $8 \times 10^9$, $9 \times 10^9$, $1 \times 10^{10}$, $2 \times 10^{10}$, $3 \times 10^{10}$, $4 \times 10^{10}$, $5 \times 10^{10}$, $6 \times 10^{10}$, $7 \times 10^{10}$, $8 \times 10^{10}$, $9 \times 10^{10}$, $1 \times 10^{11}$, $2 \times 10^{11}$, $3 \times 10^{11}$, $4 \times 10^{11}$, $5 \times 10^{11}$, $6 \times 10^{11}$, $7 \times 10^{11}$, $8 \times 10^{11}$, $9 \times 10^{11}$, $1 \times 10^{12}$, $2 \times 10^{12}$, $3 \times 10^{12}$, $4 \times 10^{12}$, $5 \times 10^{12}$, $6 \times 10^{12}$, $7 \times 10^{12}$, $8 \times 10^{12}$ or $9 \times 10^{12}$ of the at least one TIL and the at least one non-TIL cell.

In some aspects, at least 1,000, 5,000, 10,000, 20,000, 30,000, 40,000, 50,000, 1000,000, 500,000, or $1 \times 10^6$, $2 \times 10^6$, $3 \times 10^6$, $4 \times 10^6$, $5 \times 10^6$, $6 \times 10^6$, $7 \times 10^6$, $8 \times 10^6$, $9 \times 10^6$, $1 \times 10^7$, $2 \times 10^7$, $3 \times 10^7$, $4 \times 10^7$, $5 \times 10^7$, $6 \times 10^7$, $7 \times 10^7$, $8 \times 10^7$, $9 \times 10^7$, $1 \times 10^8$, $2 \times 10^8$, $3 \times 10^8$, $4 \times 10^8$, $5 \times 10^8$, $6 \times 10^8$, $7 \times 10^8$, $8 \times 10^8$, $9 \times 10^8$, $1 \times 10^9$, $2 \times 10^9$, $3 \times 10^9$, $4 \times 10^9$, $5 \times 10^9$, $6 \times 10^9$, $7 \times 10^9$, $8 \times 10^9$, $9 \times 10^9$, $1 \times 10^{10}$, $2 \times 10^{10}$, $3 \times 10^{10}$, $4 \times 10^{10}$, $5 \times 10^{10}$, $6 \times 10^{10}$, $7 \times 10^{10}$, $8 \times 10^{10}$, $9 \times 10^{10}$, $1 \times 10^{11}$, $2 \times 10^{11}$, $3 \times 10^{11}$, $4 \times 10^{11}$, $5 \times 10^{11}$, $6 \times 10^{11}$, $7 \times 10^{11}$, $8 \times 10^{11}$, $9 \times 10^{11}$, $1 \times 10^{12}$, $2 \times 10^{12}$, $3 \times 10^{12}$, $4 \times 10^{12}$, $5 \times 10^{12}$, $6 \times 10^{12}$, $7 \times 10^{12}$, $8 \times 10^{12}$, or $9 \times 10^{12}$ of the polynucleotides encoding an Ig or a TCR polypeptide are sequenced.

In some aspects, the method is performed in a positive amount of time that is less than or equal to 4 weeks, 3 weeks, 2 weeks, 1 week, 6 days, 5 days, 5 days, 4 days, 3 days, 2 days, 1 day, 18 hours, 12 hours, 9 hours, 6 hours, 3 hours, 2 hours, or 1 hour.

In some aspects, the polynucleotides encoding an Ig or a TCR from the biological sample comprises at least 1,000, 5,000, 10,000, 20,000, 30,000, 40,000, 50,000, 1000,000, 500,000, or $1 \times 10^6$, $2 \times 10^6$, $3 \times 10^6$, $4 \times 10^6$, $5 \times 10^6$, $6 \times 10^6$, $7 \times 10^6$, $8 \times 10^6$, $9 \times 10^6$, $1 \times 10^7$, $2 \times 10^7$, $3 \times 10^7$, $4 \times 10^7$, $5 \times 10^7$, $6 \times 10^7$, $7 \times 10^7$, $8 \times 10^7$, $9 \times 10^7$, $1 \times 10^8$, $2 \times 10^8$, $3 \times 10^8$, $4 \times 10^8$, $5 \times 10^8$, $6 \times 10^8$, $7 \times 10^8$, $8 \times 10^8$, $9 \times 10^8$, $1 \times 10^9$, $2 \times 10^9$, $3 \times 10^9$, $4 \times 10^9$, $5 \times 10^9$, $6 \times 10^9$, $7 \times 10^9$, $8 \times 10^9$, $9 \times 10^9$, $1 \times 10^{10}$, $2 \times 10^{10}$, $3 \times 10^{10}$, $4 \times 10^{10}$, $5 \times 10^{10}$, $6 \times 10^{10}$, $7 \times 10^{10}$, $8 \times 10^{10}$, $9 \times 10^{10}$, $1 \times 10^{11}$, $2 \times 10^{11}$, $3 \times 10^{11}$, $4 \times 10^{11}$, $5 \times 10^{11}$, $6 \times 10^{11}$, $7 \times 10^{11}$, $8 \times 10^{11}$, $9 \times 10^{11}$, $1 \times 10^{12}$, $2 \times 10^{12}$, $3 \times 10^{12}$, $4 \times 10^{12}$, $5 \times 10^{12}$, $6 \times 10^{12}$, $7 \times 10^{12}$, $8 \times 10^{12}$, or $9 \times 10^{12}$ polynucleotides encoding an Ig or a TCR.

In some aspects, prior to the sequencing the method comprises: forming a plurality of first vessels each comprising: a single cell of the at least one TIL or the at least one non-TIL cell from the biological sample, and a single solid support; copying onto the single solid support: a first copy of a first polynucleotide encoding an Ig or a TCR from the single cell, and a second copy of a second polynucleotide encoding an Ig or a TCR from the single cell; forming a plurality of second vessels each comprising a single solid support from the plurality of first vessels, and a barcoded polynucleotide; and amplifying the first copy, the second copy, and the barcode with a first set of primers, and a second set of primers, wherein a primer of the first set is complimentary to a primer of the second set; thereby forming a library of first and second single TIL or non-TIL barcoded sequences.

In some aspects, the plurality of first vessels are contained in a single reaction environment. In some embodiments, a single reaction environment indicates that the vessels are not separated from each other by physical barriers, e.g. into individual wells of a plate.

In some aspects, the first and second single TIL or non-TIL barcoded sequences comprise the same barcode. In some aspects, the method further comprises fusing the first and second single TIL or non-TIL barcoded sequences. In some aspects, the first and second single TIL or non-TIL barcoded sequences are fused.

In some aspects, prior to the sequencing the method further comprises: forming a plurality of first vessels each comprising: a single cell from the at least one TIL or the at least one non-TIL cell from the biological sample, and a solid support; copying onto the solid support: a first copy of a first polynucleotide encoding an Ig or a TCR from the single cell, wherein the first copy is attached to a first barcoded polynucleotide, and a second copy of a second polynucleotide encoding an Ig or a TCR from the single cell, wherein the second copy is attached to a second barcoded polynucleotide; amplifying: the first copy and the first barcode, and the second copy and the second barcode, with: a forward primer, and a reverse primer. Thereby forming a library of uniquely paired barcoded sequences from the single cell; forming a plurality of second vessels each comprising a single solid support from the plurality of first vessels; amplifying in the second vessel: the first barcode with a first forward barcode primer and a first reverse barcode primer, and the second barcode with a second forward barcode primer and a second reverse barcode primer; wherein a first barcode primer is complimentary to a second barcode primer or a first barcode primer sequence is a palindrome of a second barcode primer sequence; thereby forming a library of amplified first and second barcodes.

In some aspects, the method further comprises fusing the amplified first and second barcodes from (e).

In some aspects, the fused amplified first and second barcodes are fused in the second vessel.

In some aspects, the first and second barcodes comprise different barcodes.

In some aspects, the different barcodes are unique.

In some aspects, the different barcodes are unique barcode pairs.

In some aspects, the first and second barcodes comprise the same barcode.

In some aspects, the same barcode of the first and second barcodes is unique.

In some aspects, prior to the sequencing the method further comprises: forming a plurality of vessels each comprising a single cell from the at least one TIL or the at least one non-TIL cell from the biological sample; a plurality of molecular barcoded polynucleotides; and a vessel barcoded polynucleotide; producing: a first complementary polynucleotide that is complementary to a first polynucleotide encoding an Ig or a TCR from the single cell, and a second complementary polynucleotide that is complementary to a second polynucleotide encoding an Ig or a TCR from the single cell; attaching: a first molecular barcoded polynucleotide of the plurality to the first complementary polynucleotide, and a second molecular barcoded polynucleotide to the second complementary polynucleotide, thereby forming a first and a second single TIL or non-TIL single-barcoded polynucleotide; and attaching the vessel barcoded polynucleotide, or an amplified product thereof to the first single TIL or non-TIL single-barcoded polynucleotide, and the second single TIL or non-TIL single-barcoded polynucleotide, thereby forming a library of first and a second single cell dual-barcoded sequences.

In some aspects, prior to the sequencing the method further comprises: producing a first complementary polynucleotide from a polynucleotide encoding a $V_H$ or TCRα or TCRγ from the at least one TIL or the at least one non-TIL cell from the biological sample; and a second complementary polynucleotide from a polynucleotide encoding a $V_L$ or TCRβ or TCR from the at least one TIL or the at least one non-TIL cell from the biological sample with: a first primer comprising a region complementary to a same region of polynucleotides encoding an Ig or a TCR from the at least one TIL or the at least one non-TIL cell from the biological sample; a second primer comprising a region complementary to a same region of polynucleotides encoding an Ig or a TCR; a reverse transcriptase comprising a non-template terminal transferase activity, wherein 3 or more identical non-template nucleotides are added to the 3' end of the first and second complementary polynucleotides; a plurality of molecular barcoded polynucleotides, each comprising: a molecular barcode, a 5' end region complementary to a region of a vessel barcoded polynucleotide, and a 3' end region complementary to the 3 or more non-template nucleotides; and a vessel barcoded polynucleotide, thereby forming a first and a second single TIL or non-TIL single-barcoded polynucleotide; amplifying the vessel barcoded polynucleotide, thereby forming a first and a second single TIL or non-TIL dual-barcoded polynucleotide; and amplifying the first and second single TIL or non-TIL dual-barcoded polynucleotide, thereby forming a library of sequences comprising a variable region of the $V_H$, $V_L$, TCRα, TCRβ, TCRγ, or TCR polynucleotides; and sequencing one or more of the sequences of the library wherein the library represents an immune state of the sample, wherein the producing is performed in a vessel of a plurality of vessels, wherein the vessel comprises a single cell from the at least one TIL or the at least one non-TIL cell from the biological sample. In some aspects, the molecular barcode of the first and second molecular barcoded polynucleotides are different. In some aspects, the first and second single TIL or non-TIL single-barcoded polynucleotides comprise a different molecular barcode. In some aspects, the first and second single TIL or non-TIL dual-barcoded sequences comprise a different molecular barcode. In some aspects, the first and second single TIL or non-TIL dual-barcoded sequences comprise the same vessel barcode. In some aspects, the plurality of molecular barcoded polynucleotides are not amplified products.

In some aspects, the at least one TIL and the at least one non-TIL cell are from a biological sample from a subject with a disease. In some aspects, the subject is an animal. In some aspects, the animal is a mammal. In some aspects, the mammal is a human. In some aspects, the polynucleotide encoding an Ig or a TCR polypeptide is isolated from the biological sample. In some aspects, the polynucleotide encoding an Ig or a TCR polypeptide is not isolated from the biological sample.

In some aspects, the biological sample from a subject with the disease comprises a plurality of biological samples from 2 or more subjects with the disease. In some aspects, the plurality of biological samples comprises at least 3, 4 5, 10, 20, 30, 40, 50, 60, 70, 80, 90 or 100, 200, 300, 400, 500, 600, 700, 800, 900, 1000, 2000, 3000, 4000, 5000, 6000, 7000, 8000, 9000, 10,0000, 100,000, or 1,000,000 or more samples In some aspects, the disease is an autoimmune disease. In some aspects, the disease is a cancer. In some aspects, the disease is a precancerous disease.

In some aspects, the method further comprises correcting amplification errors. In some aspects, the method further comprises correcting sequencing errors. In some aspects, the method further comprises binning or grouping sequences comprising a same barcode sequence. In some aspects, the method further comprises binning or grouping sequences comprising a same barcode sequence using a computer or algorithm. In some aspects, the method further comprises clustering sequences with at least about 90%, 95%, or 99% sequence homology. In some aspects, the method further comprises aligning sequences with at least about 90%, 95%, or 99% sequence homology. In some aspects, the clustering or aligning is performed with the aid of a computer or algorithm. In some aspects, the method further comprises comparing sequence reads to a germline sequence and determining a somatic hypermutation accumulation of the sequence reads. In some aspects, the method further comprises determining an isotype distribution of the sequences.

In some aspects, the Ig or TCR polypeptide encoded by the selected polynucleotide sequence does not substantially interact with a cell of normal adjacent tissue. In some aspects, the Ig or TCR polypeptide encoded by the selected polynucleotide sequence does not substantially bind to a cell from a same tissue in a subject without the disease.

In some aspects, the producing comprises expressing a recombinant Ig or TCR polypeptide encoded by the selected polynucleotide sequence. In some aspects, the producing comprises expressing 1, 2, 3, 4, 5, 6, 7, 8, 9, 10, 15, 20, 25, 50, 100, 200, 300, 400, or 500 or more recombinant Ig or TCR polypeptides each encoded by a selected polynucleotide sequence. In some aspects, the producing comprises cloning a sequence of the selected polynucleotide sequence into a vector. In some aspects, the vector is a cloning vector. In some aspects, the vector is an expression vector. In some aspects, the producing comprises contacting a cell with a polynucleotide comprising a sequence of the selected polynucleotide sequence that encodes for an Ig or TCR polypeptide. In some aspects, the contacting comprises transfecting. In some aspects, the producing comprises expressing the recombinant Ig or TCR polypeptide encoded by the selected polynucleotide sequence in a cell. In some aspects, the cell is a mammalian cell. In some aspects, the mammalian cell is a Chinese Hamster Ovary (CHO) cell or a HEK293 cell. In some aspects, the method further comprises purifying the produced recombinant Ig or TCR polypeptide encoded by the selected polynucleotide sequence. In some aspects, the method further comprises isolating the produced recombinant Ig or TCR polypeptide encoded by the selected polynucleotide sequence. In some aspects, the recombinant Ig or TCR polypeptide encoded by the selected polynucleotide sequence comprises a heterologous tag. In some aspects, the heterologous tag is a purification tag. In some aspects, the cell is a bacterial cell or an insect cell.

In some aspects, the identifying comprises comparing Ig or TCR sequences to a database comprising Ig or TCR sequence data. In some aspects, the identifying comprises performing a whole genome siRNA screen. In some aspects, the identifying comprises performing a protein display screen with the Ig or TCR polypeptide encoded by the selected polynucleotide sequence. In some aspects, the protein display screen is a phage display screen. In some aspects, the protein display screen is a ribosome display screen. In some aspects, the identifying comprises performing a yeast-two-hybrid screen. In some aspects, the identifying comprises performing 2D gel electrophoresis. In some aspects, the identifying comprises screening the Ig or TCR polypeptide encoded by the selected polynucleotide sequence with a protein array. In some aspects, the protein array comprises at least about 10, 20, 30, 40, 50, 60, 70, 80, 90, 95, 96, 97, 98, or 99 percent or more proteins of a human proteome. In some aspects, the identifying comprises performing a proteome screen against the Ig or TCR polypeptide encoded by the selected polynucleotide sequence. In some aspects, the identifying comprises performing immunoprecipitation with the Ig or TCR polypeptide encoded by the selected polynucleotide sequence. In some aspects, the identifying comprises performing mass spectrometry. In some aspects, the identifying comprises performing antibody-dependent cell-mediated cytotoxicity (ADCC) assay with the Ig or TCR polypeptide encoded by the selected polynucleotide sequence. In some aspects, the identifying comprises determining the specificity of the Ig or TCR polypeptide encoded by the selected polynucleotide sequence. In some aspects, the identifying comprises performing a binding assay. In some aspects, the identifying comprises contacting the Ig or TCR polypeptide encoded by the selected polynucleotide sequence with at least one target analyte candidate.

In some aspects, the target analyte candidate is on a solid support. In some aspects, the target analyte candidate is in solution (e.g., a ribosome display). In some aspects, the Ig or TCR polypeptide encoded by the selected polynucleotide sequence is on a solid support. In some aspects, the Ig or TCR polypeptide encoded by the selected polynucleotide sequence is in solution. In some aspects, the solid support is an array. In some aspects, the solid support is a bead.

In some aspects, the target analyte to which the Ig or TCR polypeptide encoded by the selected polynucleotide sequence binds is unknown.

In some aspects, the target analyte to which the Ig or TCR polypeptide encoded by the selected polynucleotide sequence binds is unknown at the time the selected polynucleotide sequence is selected. In some aspects, a target analyte is described comprising a target analyte identified by a method disclosed herein. In some aspects, the identified target analyte is a disease-associated or a disease-specific target analyte. In some aspects, the identified target analyte is a polypeptide with an extracellular region. In some aspects, an isolated, purified, Ig or TCR polypeptide is described wherein the isolated, purified, Ig or TCR polypeptide is encoded by the selected polynucleotide sequence of a method described herein. In some aspects, an isolated, purified, IgL polypeptide is described wherein the isolated, purified, IgL polypeptide is encoded by an Ig polynucleotide of the selected polynucleotide sequence of a method described herein. In some aspects, an isolated, purified, IgH polypeptide is described wherein the isolated, purified, IgH polypeptide is encoded by an Ig polynucleotide of the selected polynucleotide sequence of a method described herein. In some aspects, an isolated, purified, antibody encoded by an IgH and an IgL polynucleotide is described comprising an isolated, purified, antibody encoded by a selected polynucleotide sequence of a method described herein. In some aspects, an isolated, purified, Fab fragment of an Ig polypeptide is described comprising an isolated, purified, Fab fragment of an Ig polypeptide encoded by the selected polynucleotide sequence of a method described herein. In some aspects, an isolated, purified, F(ab)$_2$ fragment of an Ig polypeptide is described comprising an isolated, purified, F(ab)$_2$ fragment of an Ig polypeptide encoded by the selected polynucleotide sequence of a method described herein. In some aspects, an isolated, purified, Fv fragment of an Ig polypeptide is described comprising an isolated, purified, Fv fragment of an Ig polypeptide encoded by the selected polynucleotide sequence of a method described herein. In some aspects, an isolated, purified, ScFv fragment of an Ig polypeptide is described comprising an isolated, purified, ScFv fragment of an Ig polypeptide encoded by the selected polynucleotide sequence of a method described herein. In some aspects, an isolated, purified, fragment of a TCRα polypeptide is described comprising an isolated, purified, fragment of a TCRα polypeptide encoded by the selected polynucleotide sequence of a method described herein. In some aspects, an isolated, purified, fragment of a TCRβ polypeptide is described comprising an isolated, purified, fragment of a TCRβ polypeptide encoded by the selected polynucleotide sequence of a method described herein. In some aspects, an isolated, purified, fragment of a TCRα and a TCRβ polypeptide is described comprising an isolated, purified, fragment of a TCRα and a TCRβ polypeptide encoded by a selected polynucleotide sequence of a method described herein. In some aspects, the identified target analyte of the Ig or TCR polypeptide encoded by the selected polynucleotide sequence is a biomarker of the disease.

In some aspects, a method of treating a subject in need thereof is described, the method comprising administering the Ig or TCR polypeptide encoded by a selected polynucleotide sequence of a method described herein, or a fragment thereof, to a subject with the disease. In some aspects, the Ig or TCR polypeptide encoded by the selected polynucleotide sequence is a human therapeutic polypeptide. In some aspects, the Ig or TCR polypeptide encoded by the selected polynucleotide sequence is a neutralizing polypeptide. In some aspects, a method of treating a subject in need thereof is described, the method comprising administering an inhibitor of the identified target analyte of the Ig or TCR polypeptide encoded by a selected polynucleotide sequence of a method described herein, or a fragment thereof, to a subject with the disease. In some aspects, the inhibitor is selected from the group consisting of a small molecule, a nucleic acid, a polypeptide, and combinations thereof. In some aspects, the inhibitor is a polypeptide inhibitor, wherein the polypeptide inhibitor is the Ig or TCR polypeptide encoded by the selected polynucleotide sequence. In some aspects, the inhibitor is a nucleic acid inhibitor, wherein the nucleic acid inhibitor is a siRNA nucleic acid. In some aspects, the inhibitor is a nucleic acid inhibitor, wherein the nucleic acid inhibitor is used for gene therapy.

INCORPORATION BY REFERENCE

All publications, patents, and patent applications mentioned in this specification are herein incorporated by reference in their entirety for all purposes, to the same extent as if each individual publication, patent, or patent application is specifically and individually indicated to be incorporated by reference.

For example, all publications and patents mentioned herein are incorporated herein by reference in their entirety for the purpose of describing and disclosing the kits, compositions, and methodologies that are described in the publications, which might be used in connection with the methods, kits, and compositions described herein. The documents discussed herein are provided solely for their disclosure prior to the filing date of the present application. Nothing herein is to be construed as an admission that the inventors described herein are not entitled to antedate such disclosure by virtue of prior invention or for any other reason.

BRIEF DESCRIPTION OF THE DRAWINGS

The novel features described herein are set forth with particularity in the appended claims. A better understanding of the features and advantages of the features described herein will be obtained by reference to the following detailed description that sets forth illustrative examples, in which the principles of the features described herein are utilized, and the accompanying drawings of which:

FIG. 13 exemplifies accuracy and stringency data resulting from performing the methods described herein for the pairing of naive, memory, and plasma B-cells FIG. 14 exemplifies a schematic a graph showing the expected increase in the ratio of high stringency pairs to total pairs and total number of high stringency pairs and antibody pairs expected to be paired over a the depicted time period.

DETAILED DESCRIPTION

Figure 1A:
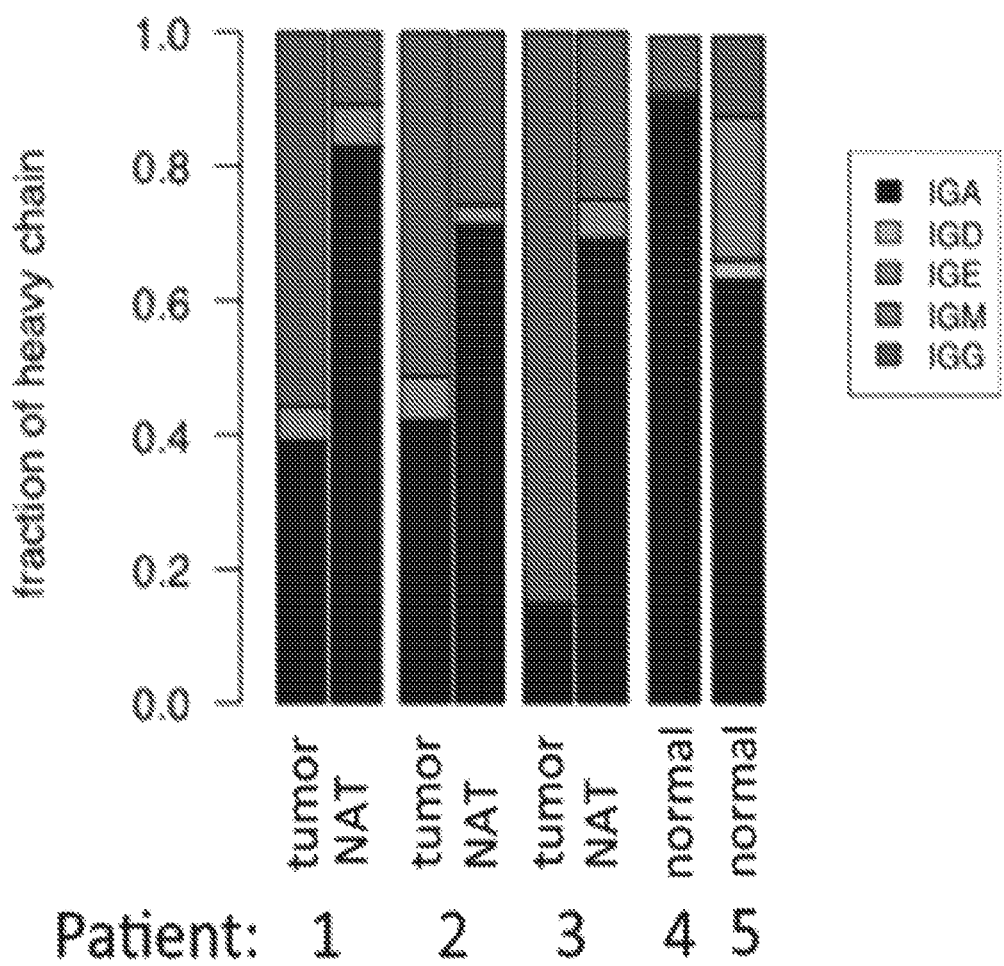
FIG. 1A exemplifies a graph showing that the antibody repertoire reveals that pancreatic tumor samples show similarities in their antibody profile that can be differentiated from normal samples.
Figure 1B:
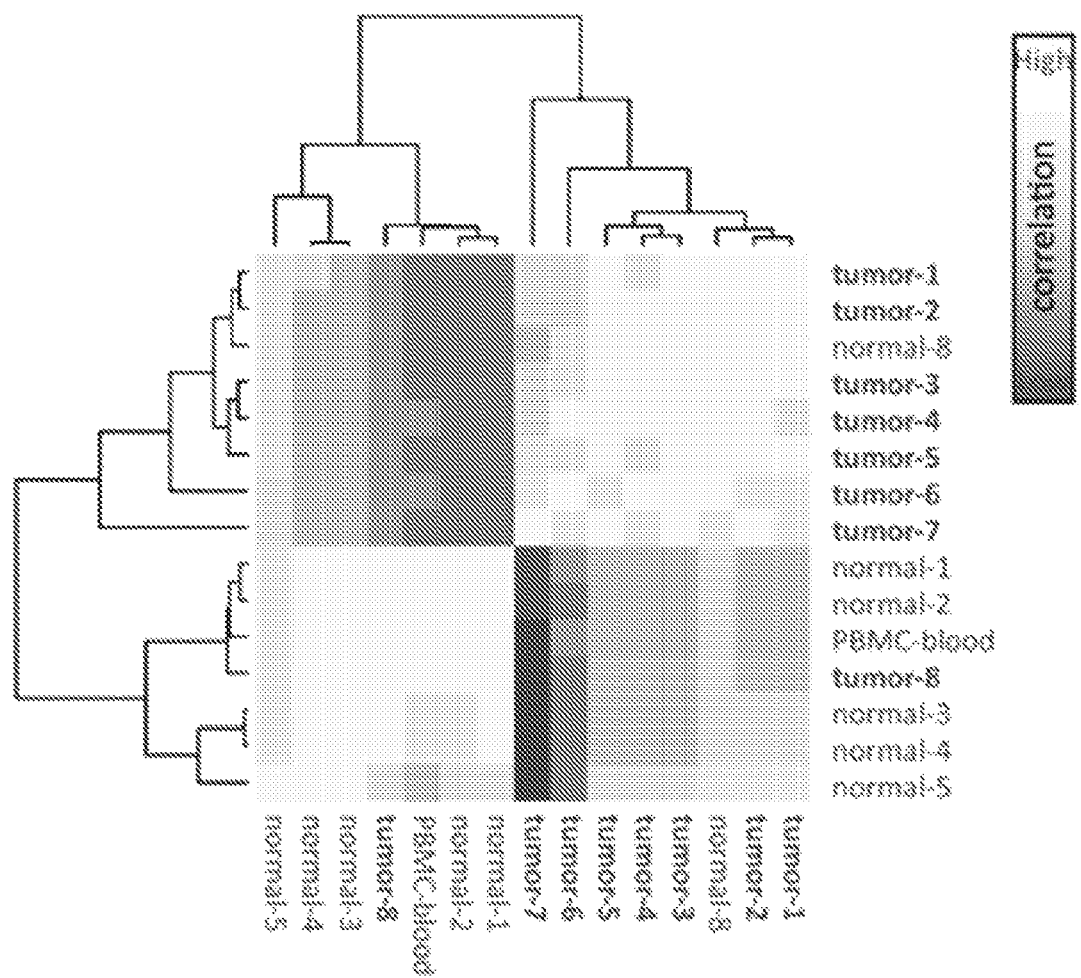
FIG. 1B exemplifies a heat map of the correlation of the antibody profiles of multiple PDAC tumor samples.
Figure 2A:
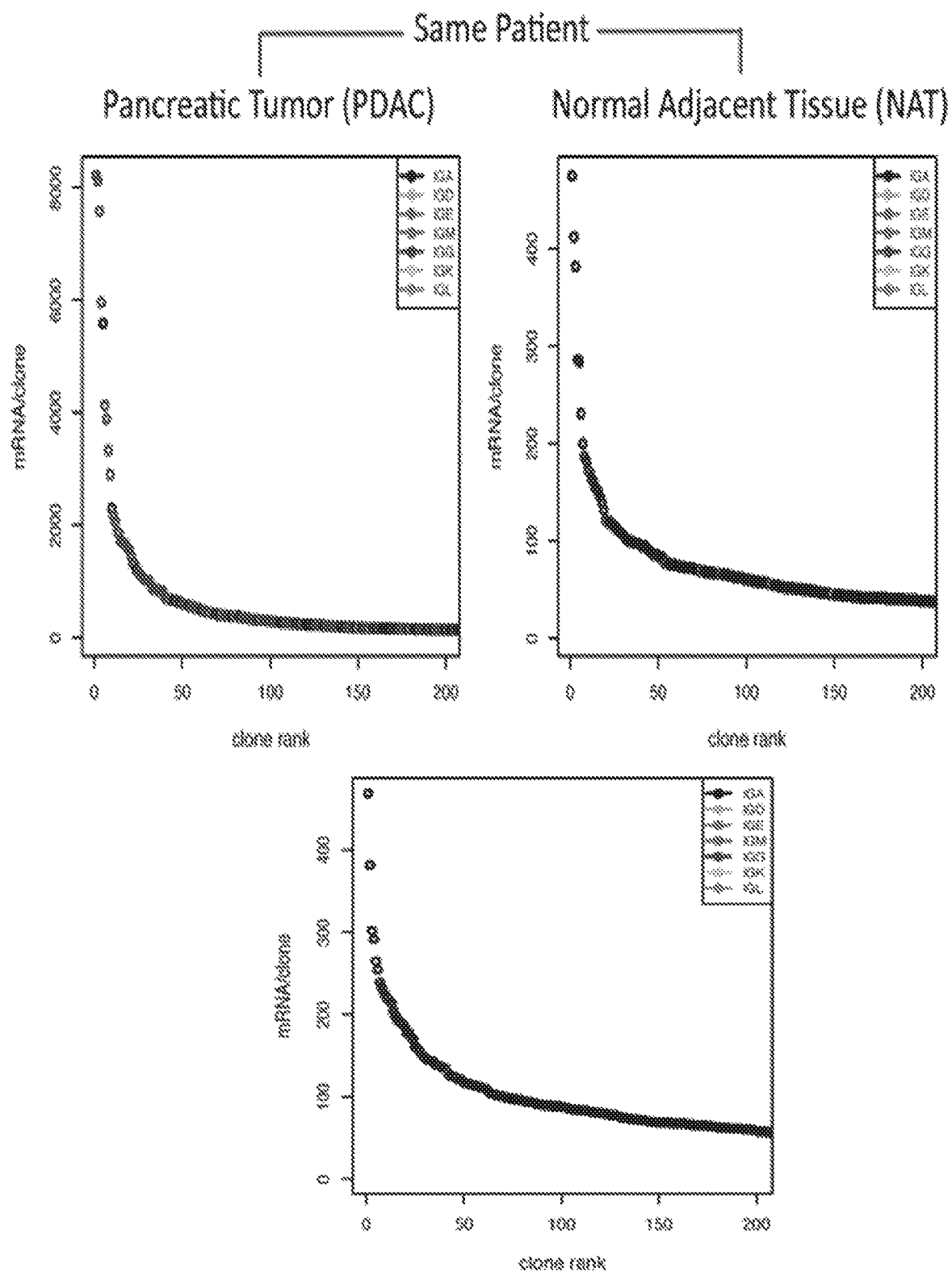
FIG. 2A exemplifies graphs demonstrating that in the majority of prostate ductal adenocarncimoa (PDAC) samples analyzed, tumor resection tissues are heavily dominated by the presence of B-cells expressing IgG antibodies, suggesting a target specific immune response. Matched normal tissue samples are similar to normal pancreatic tissue samples with a predominant IgA response. The scale of expression of these IgG antibodies denotes a significant oligoclonal response, usually indicative of a strong and specific immune response.
Figure 2B:
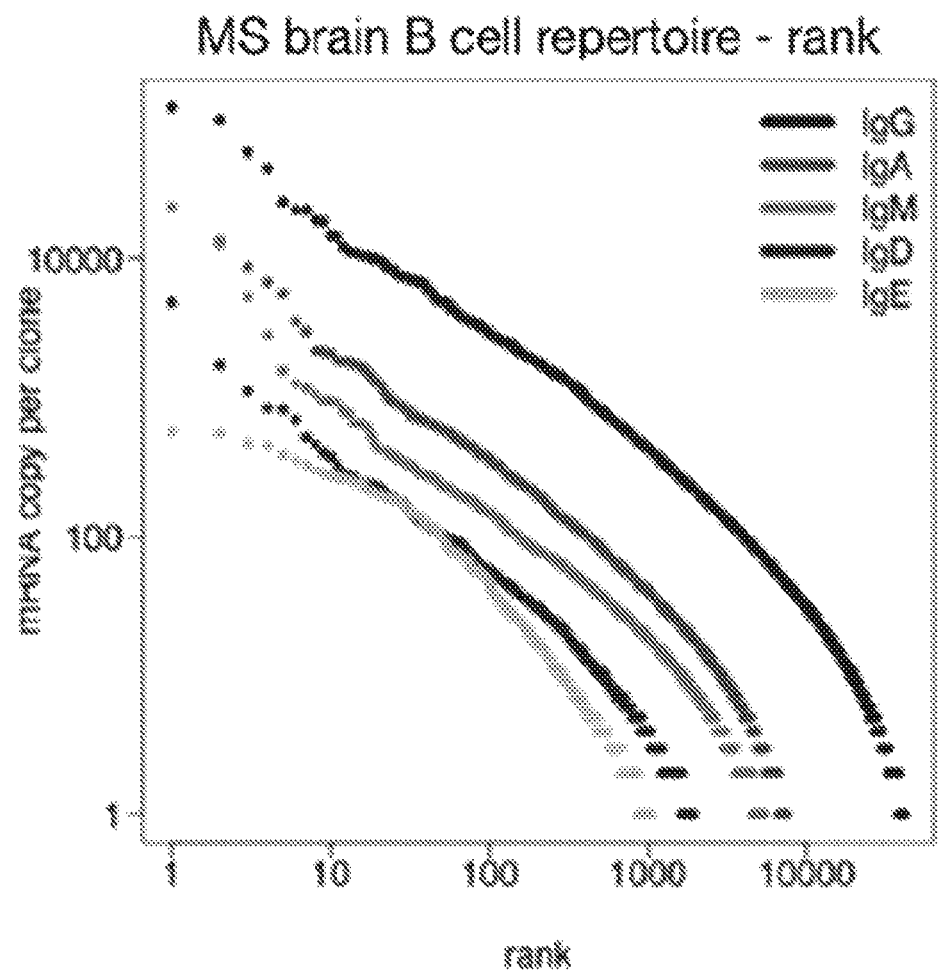
FIG. 2B exemplifies a graph showing an abnormal response and the presence of B-cells expressing high-frequency oligoclonal antibody in a brain biopsy of a Multiple Sclerosis sample.
Figure 3A:
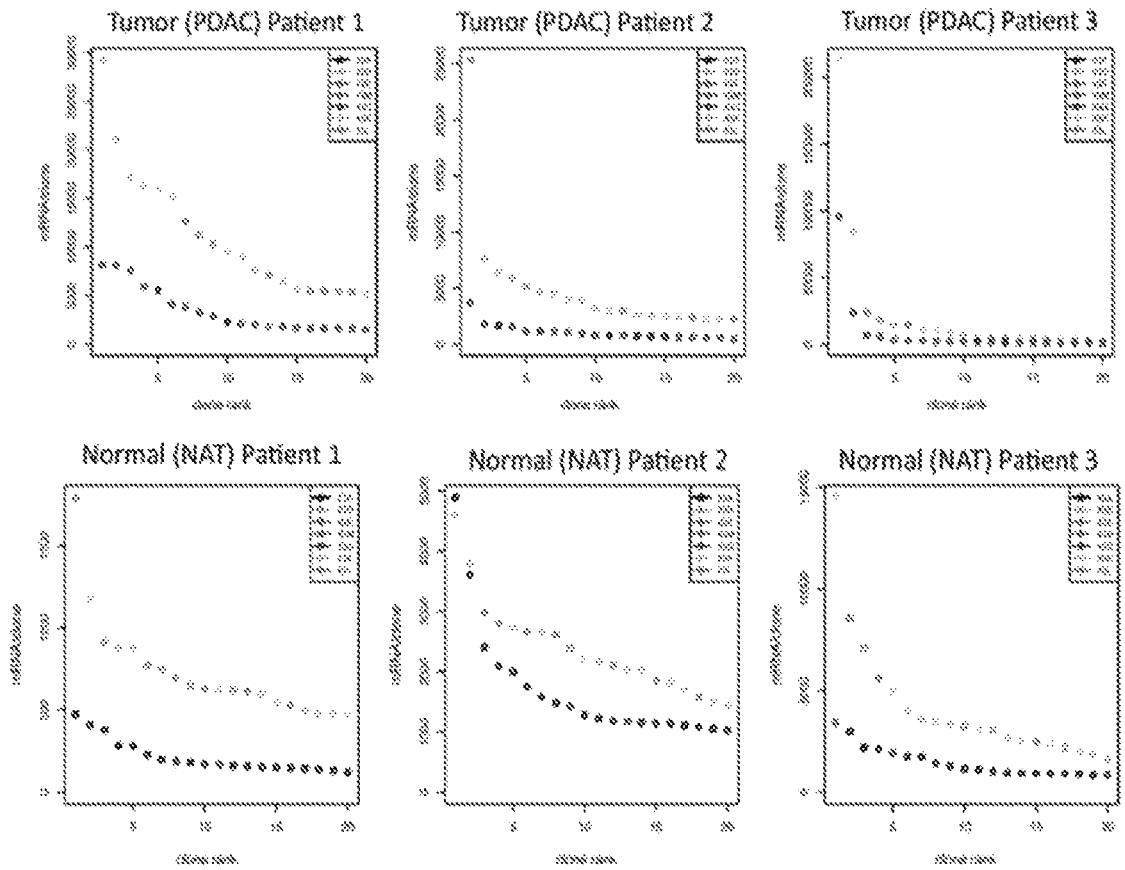
FIG. 3A exemplifies a graph of the total number of mRNAs/clone vs. clone rank of immune sequencing of two PDAC tumor samples and corresponding normal adjacent tissue samples. The results demonstrate that the overall immune response to PDAC is dominated by the IgG isotype, while in normal adjacent tissue (NAT) the immune cells are dominated by the IgA isotype.
Figure 3B:
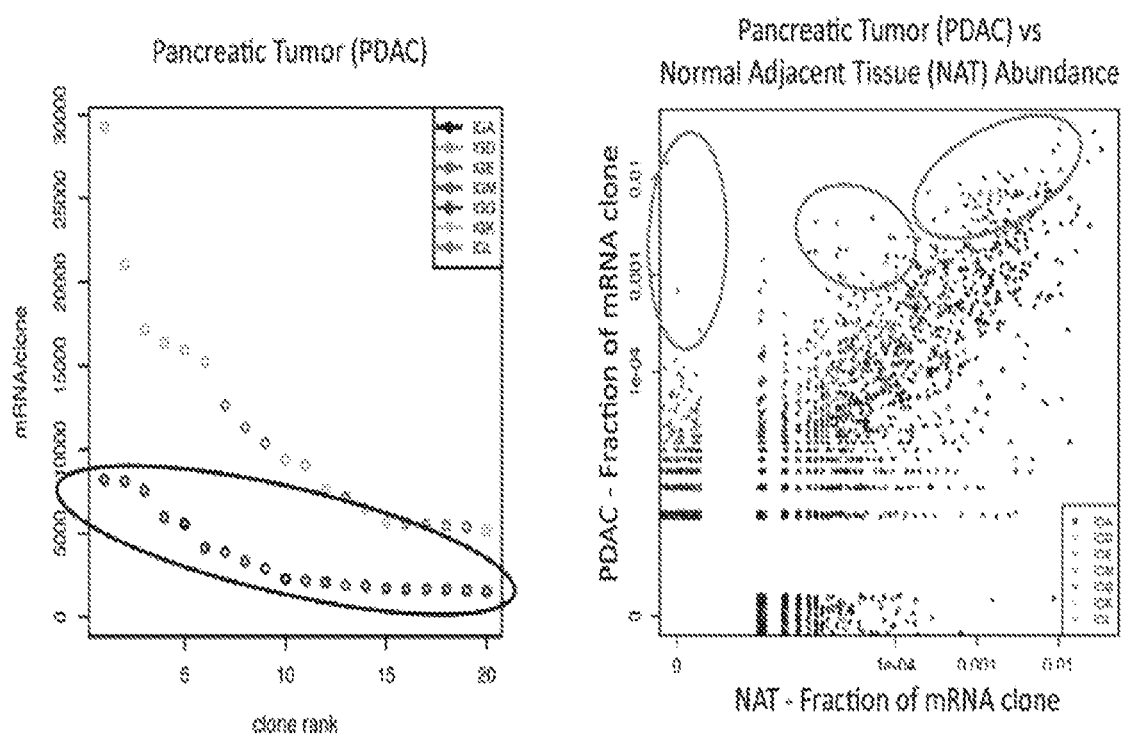
FIG. 3B exemplifies graphs of the total number of mRNAs/clone vs. clone rank and the PDAC fraction of mRNA clones vs. NAT fraction of mRNA clones. The results demonstrate that the tumor samples are also almost exclusively dominated by the presence of the B-cells expressing IgG, for the most abundantly expressed antibodies.
Figure 4:
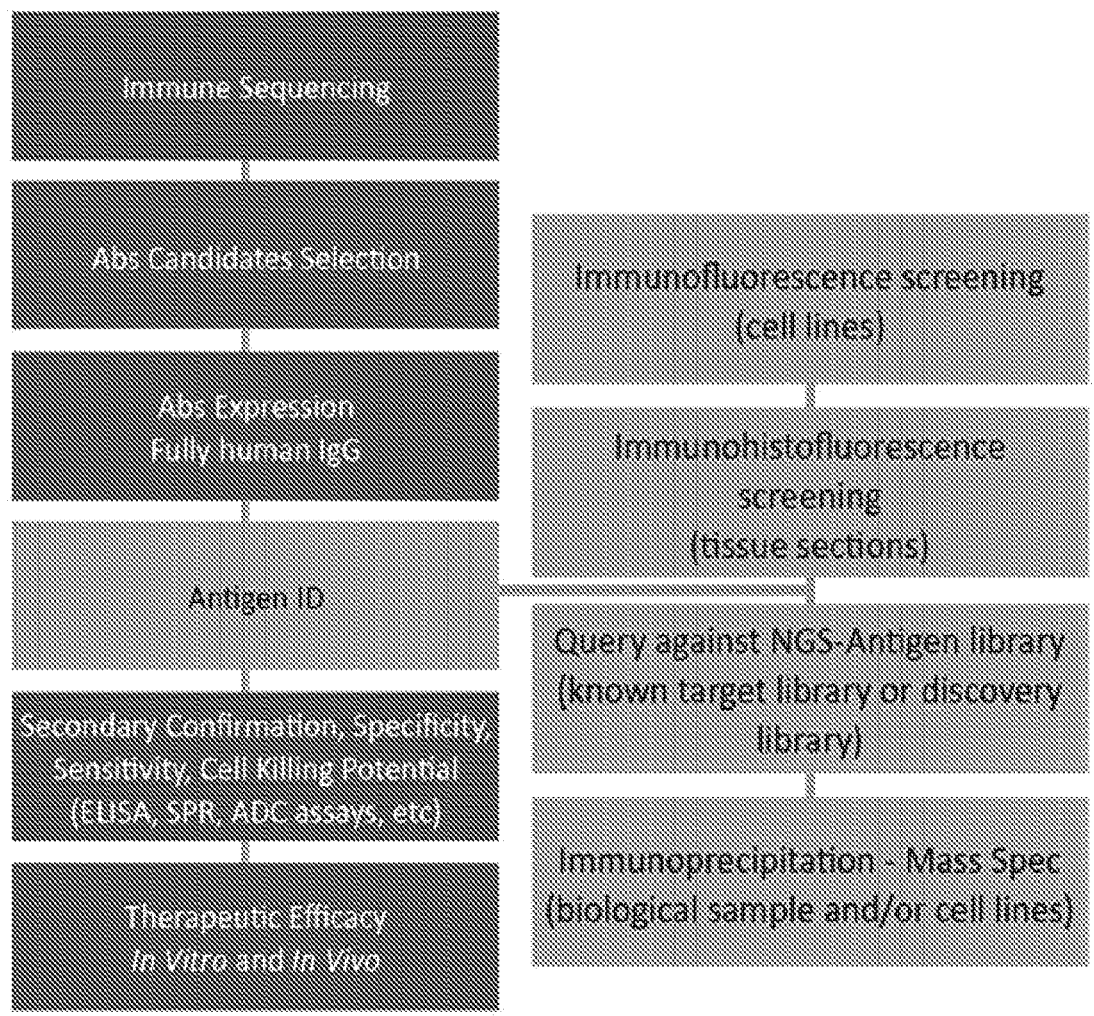
FIG. 4 exemplifies a flow chart of an exemplary method disclosed herein including immune sequencing, antibody selection, antibody production, validating of an antibody, identifying the antigen of the antibody, and determining the therapeutic efficacy of the antibody.
Figure 5:
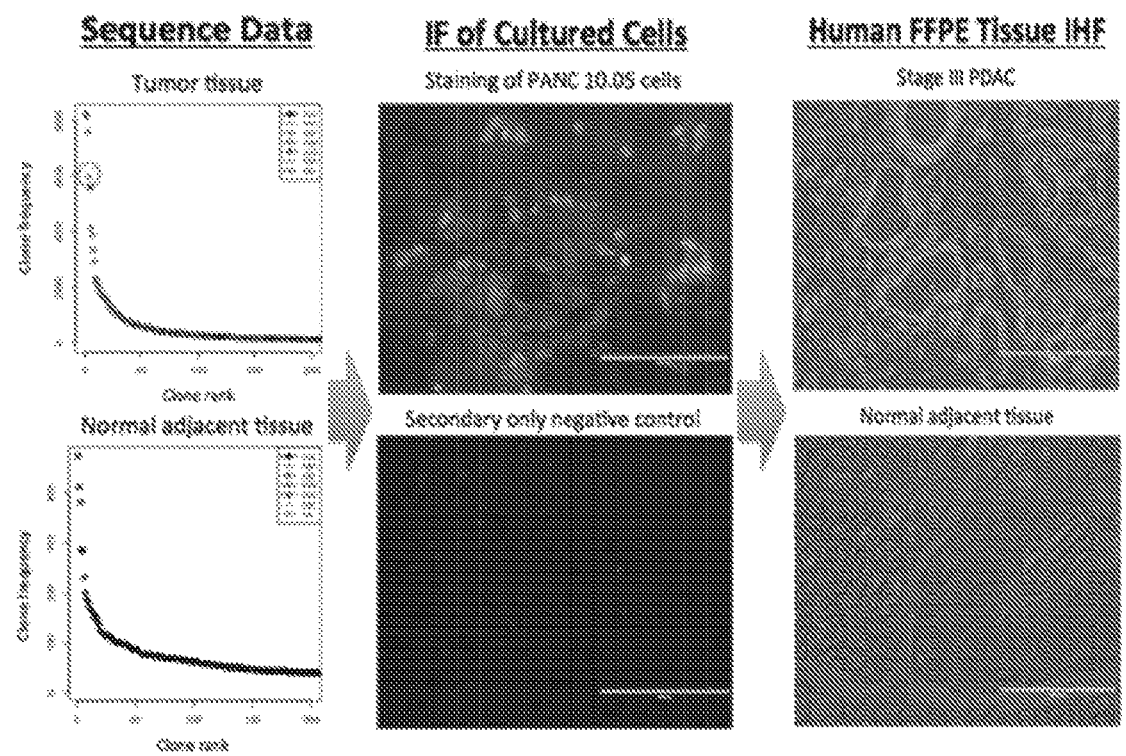
FIG. 5 exemplifies a flow chart of the steps of an exemplary method disclosed herein. Sequence data from normal and tumor tissue samples were used to select one or more antibodies that would demonstrate high affinity and specificity to a tumor specific antigen. The antibodies are produced recombinantly and used for immunofluorescence assays to validate the selected antibodies by staining diseased tissue and comparing to staining of normal adjacent tissue. Selected antibodies that are validated by immunofluorescence assays are then assayed in an immunohistochemical fluorescent assay of FFPE human tissue. Antibodies that pass this validation stage can be utilized in the methods disclosed herein to identify a biomarker or a disease specific antigen.
Figure 6A:
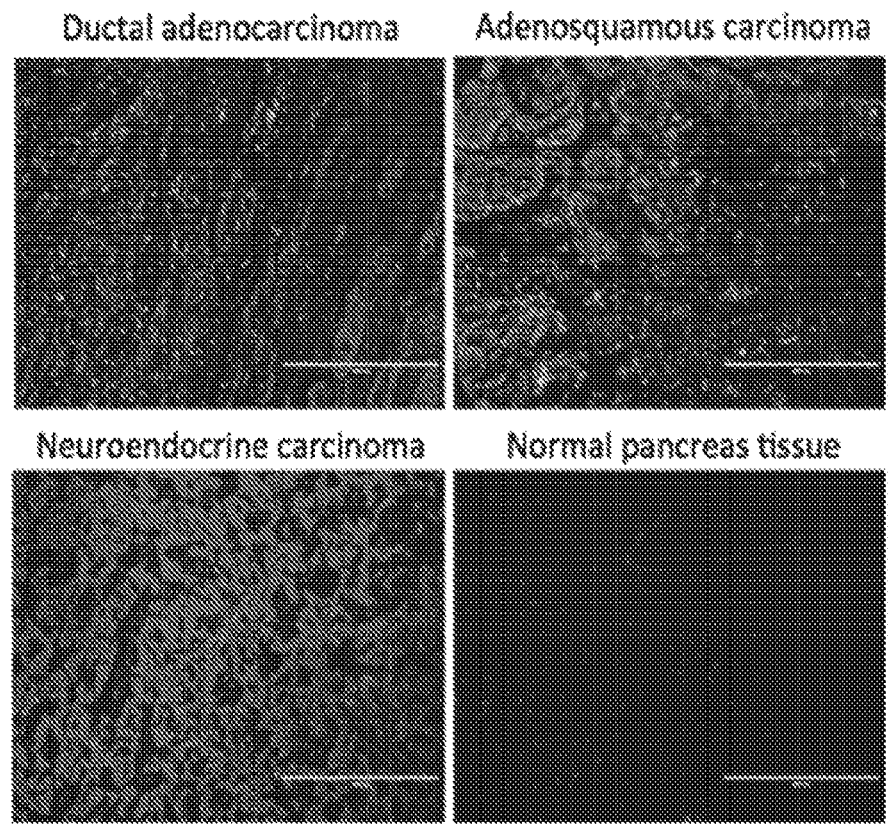
FIG. 6A exemplifies immunostaining with an antibody that demonstrates strong binding to ductal adenocarcinoma, adenosquamous carcinoma, and neuroendocrine carcinoma, but minimal staining to normal pancreatic tissue.
Figure 6B:
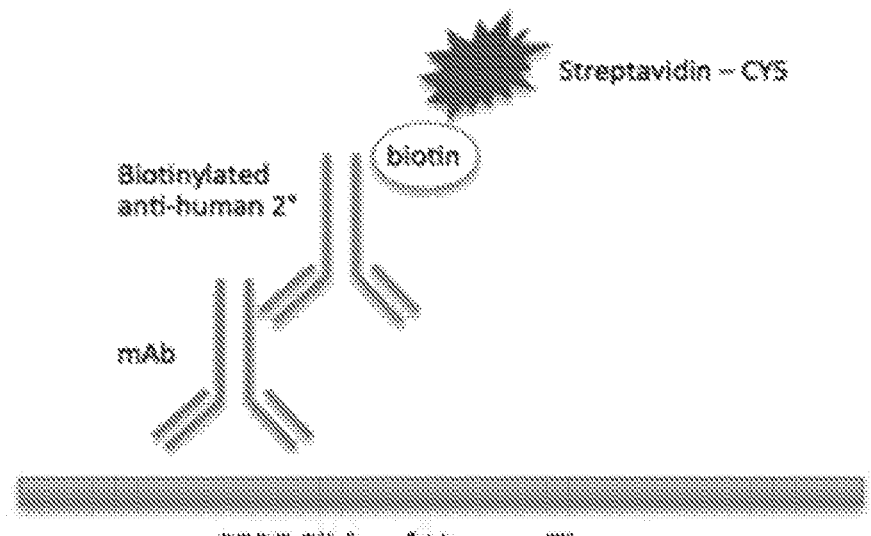
FIG. 6B exemplifies a schematic of an exemplary immunoconjugate formed to detect binding of an antibody to an FFPE slide of human tissue.
Figure 7A:
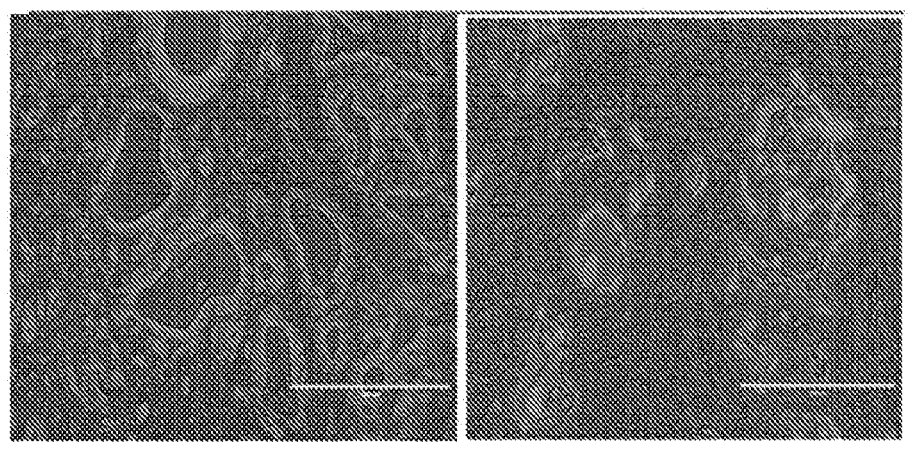
FIG. 7A exemplifies immunostaining with antibody A1-22 from an epithelial cell PDAC sample and a stromal cell PDAC sample. Cantuzumab shows no staining of stromal cells and only stains epithelial cells. This indicates that targeting a stromal antigen can have clinical benefit for PDAC.
Figure 7B:
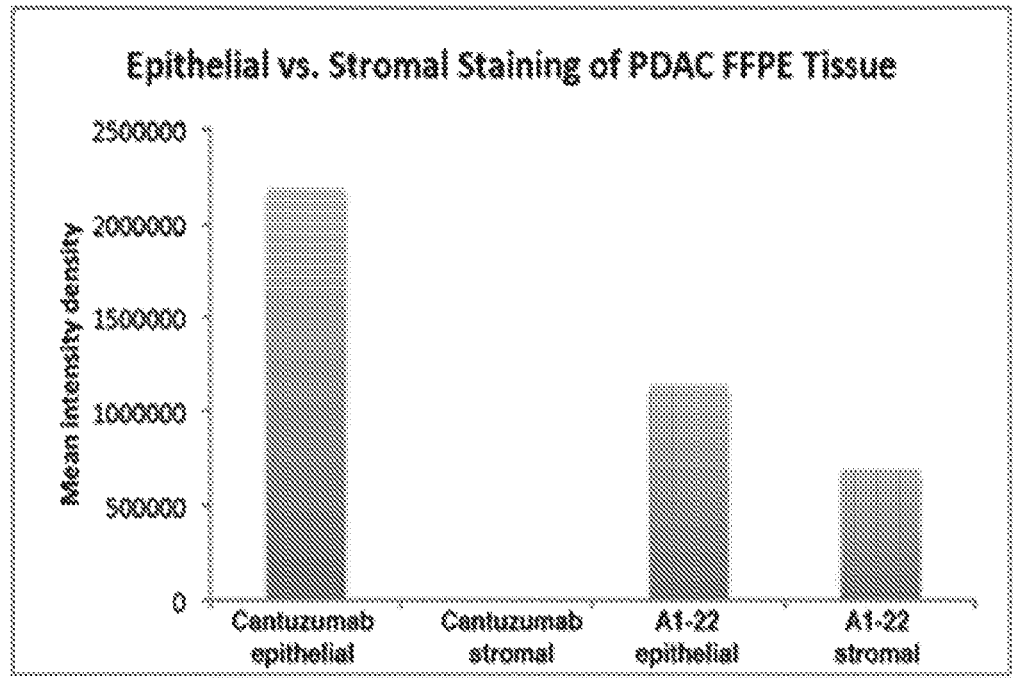
FIG. 7B exemplifies immunostaining with antibody A1-22 from a squamous cell lung carcinoma sample, which has a similar phenotypic cellular evolution as PDAC, demonstrating strong, specific staining over normal lung tissue. Cantuzumab shows no staining of either tissue.
Figure 8A:
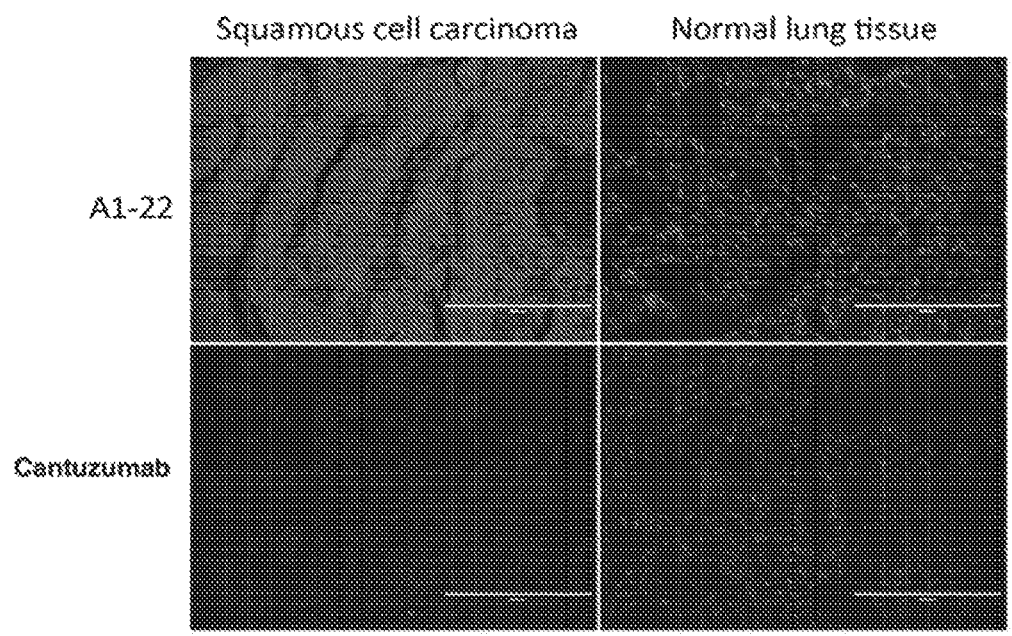
FIG. 8A exemplifies immunostaining with antibody A1-22 from a squamous cell lung carcinoma sample, which has a similar phenotypic cellular evolution as PDAC, demonstrating strong, specific staining over normal lung tissue. Cantuzumab shows no staining of either tissue.
Figure 8B:
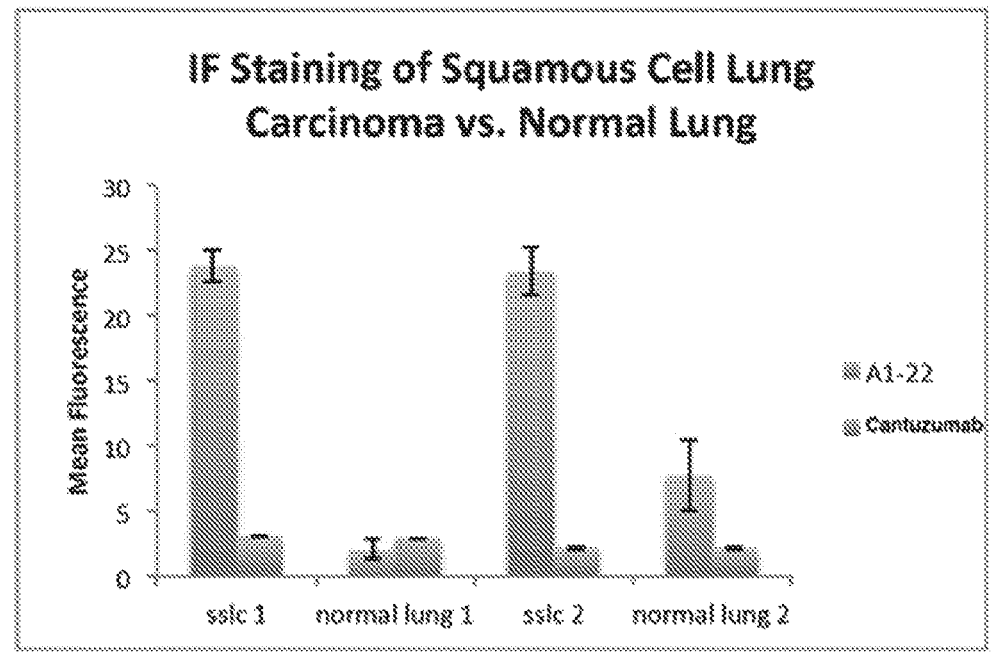
FIG. 8B exemplifies a graph of the mean fluorescence obtained by immunofluorescent staining the samples depicted in FIG. 8A.
Figure 9A:
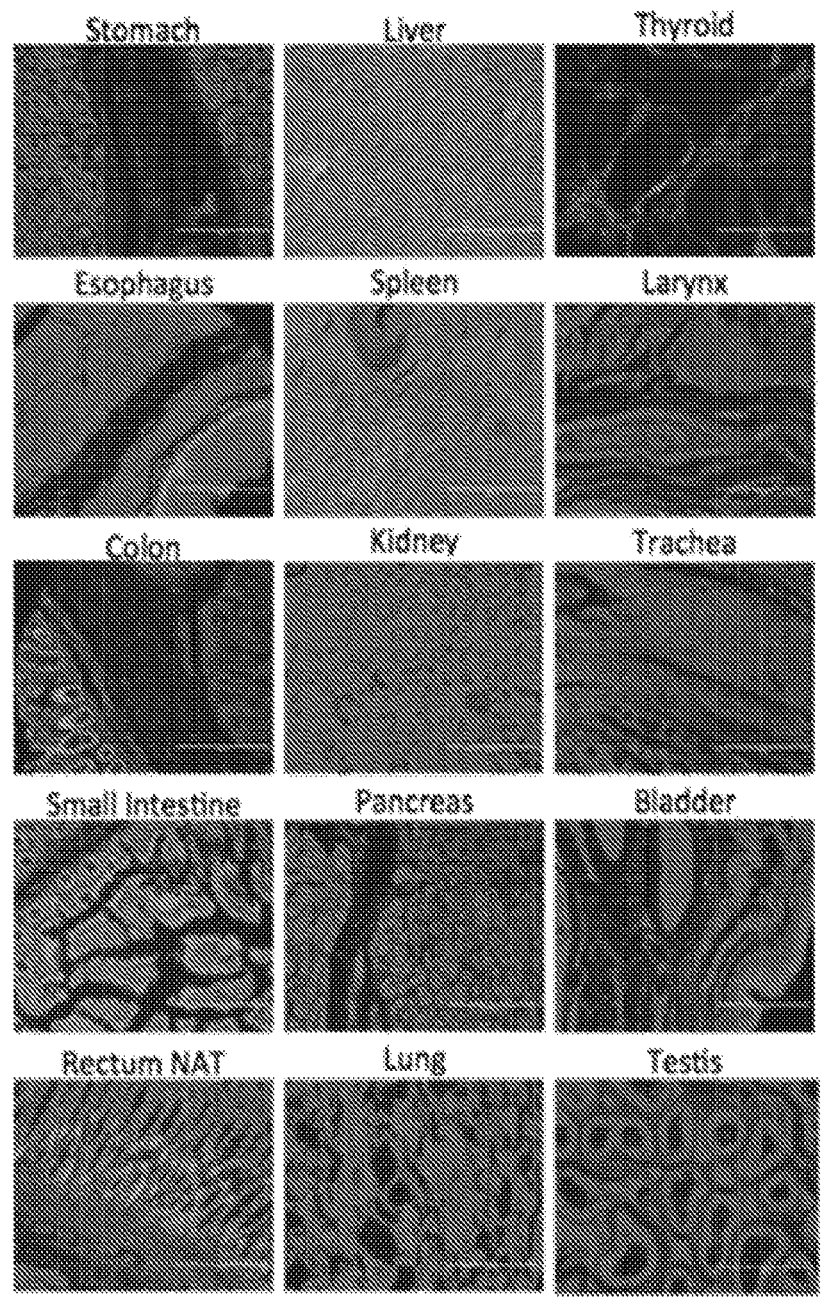
FIG. 9A exemplifies immunostaining with antibody A1-99 from a chronic pancreatitis sample. Strong staining is seen in all of the normal tissues indicated, suggesting the disease can be autoimmune.
Figure 9B:
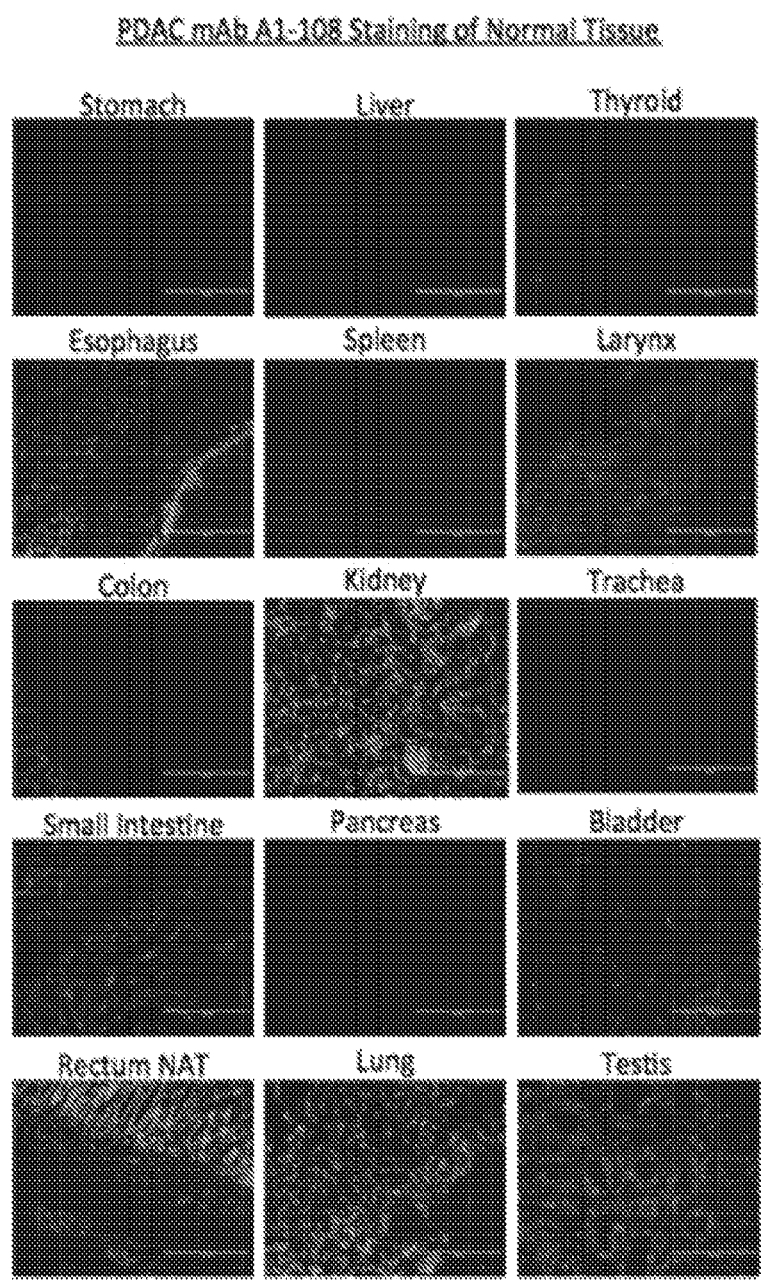
FIG. 9B exemplifies immunostaining with antibody A1-108 from a PDAC sample. Minimal staining is seen in all of the normal tissues indicated.
Figure 10:
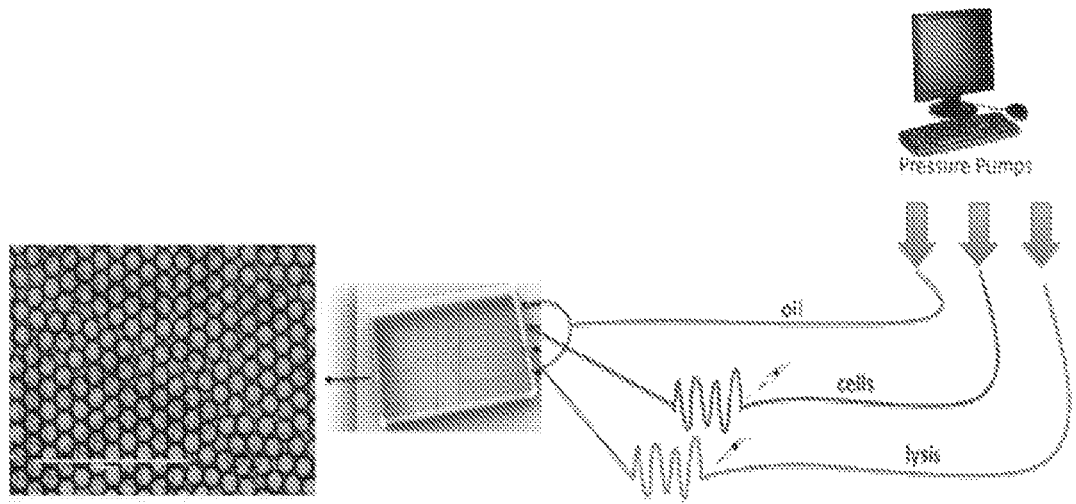
FIG. 10 exemplifies a schematic of a system for generating an emulsion containing a plurality of droplets, each containing a single cell. The cells can be lysed in these individual compartments.
Figure 11:
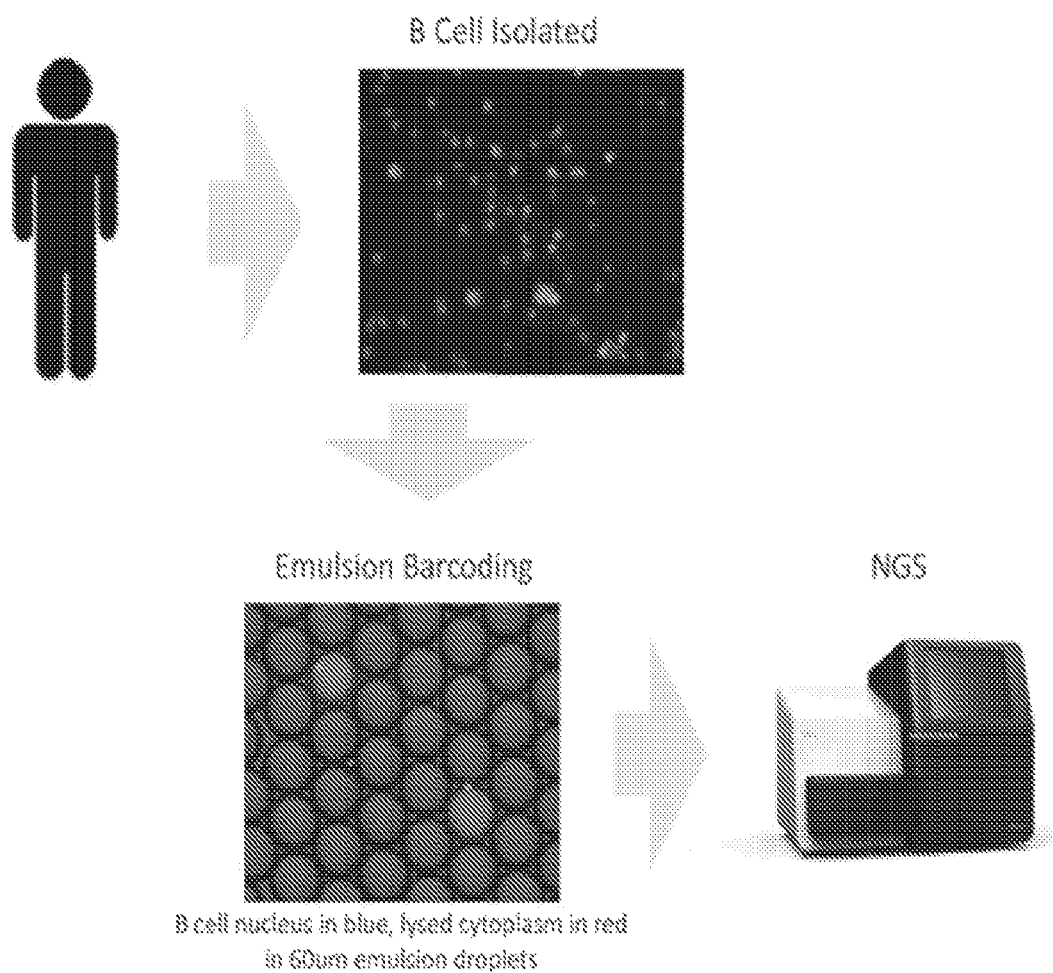
FIG. 11 exemplifies a schematic of an exemplary method of sequencing polynucleotides in a high throughput format where a B-cell is isolated from a biological sample into an individual emulsion where it is lysed and sequenced.
Figure 12:
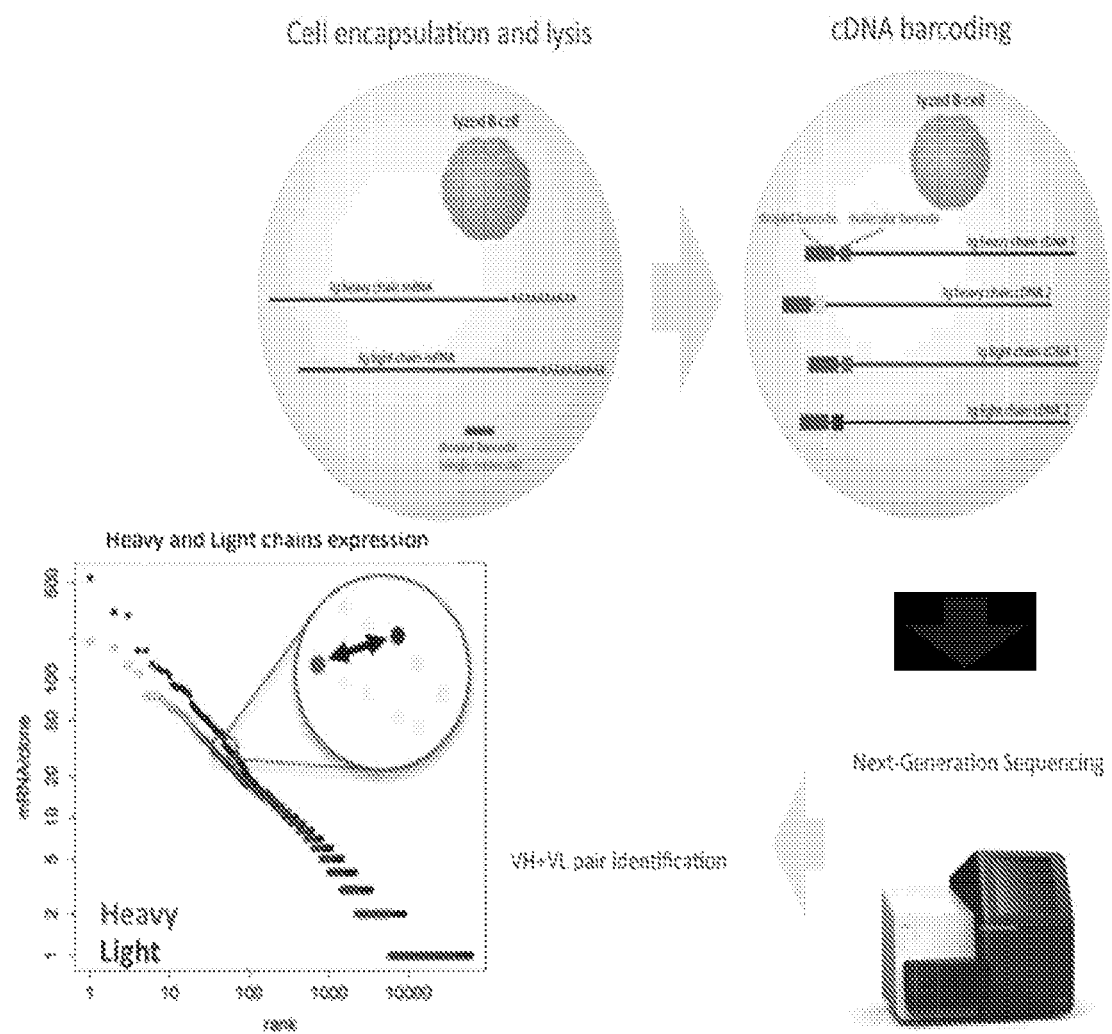
FIG. 12 exemplifies a schematic of an exemplary method of sequencing polynucleotides in a high throughput format where a B-cell is isolated from a biological sample into an individual emulsion where it is lysed and sequenced such that the heavy and light chains of the individual cell are paired after sequencing the individual chains through the use of a droplet barcode and a molecular barcode.
Figure 14:
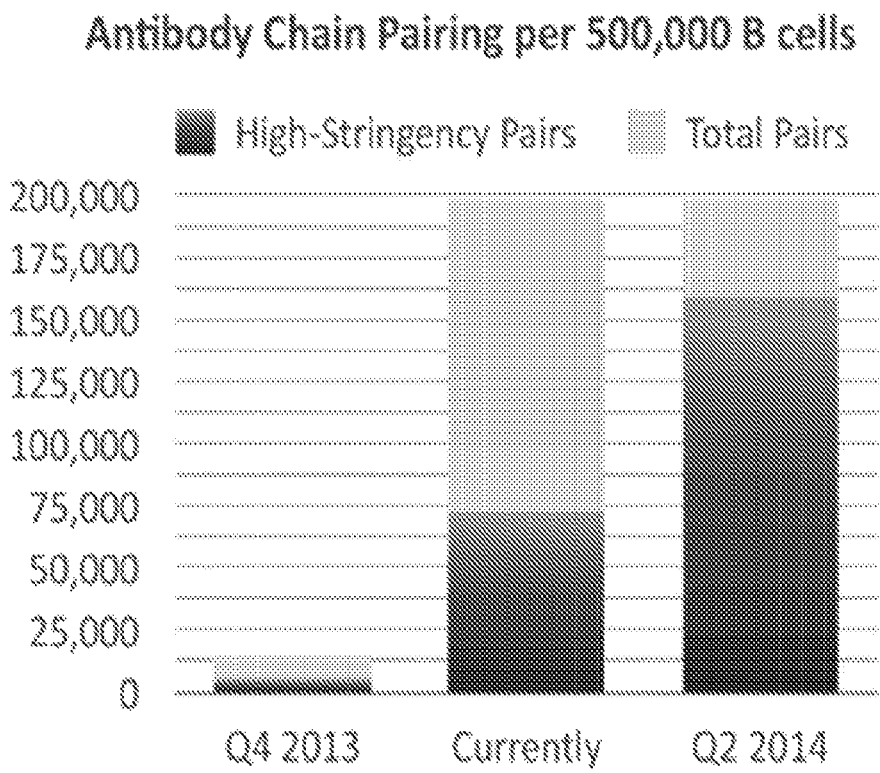
Figure 15:
FIG. 15 exemplifies a schematic comparing some exemplary advantages and technical solutions over known methods of immune repertoire sequencing and antibody pairing that the methods disclosed herein offer.
Figure 16:
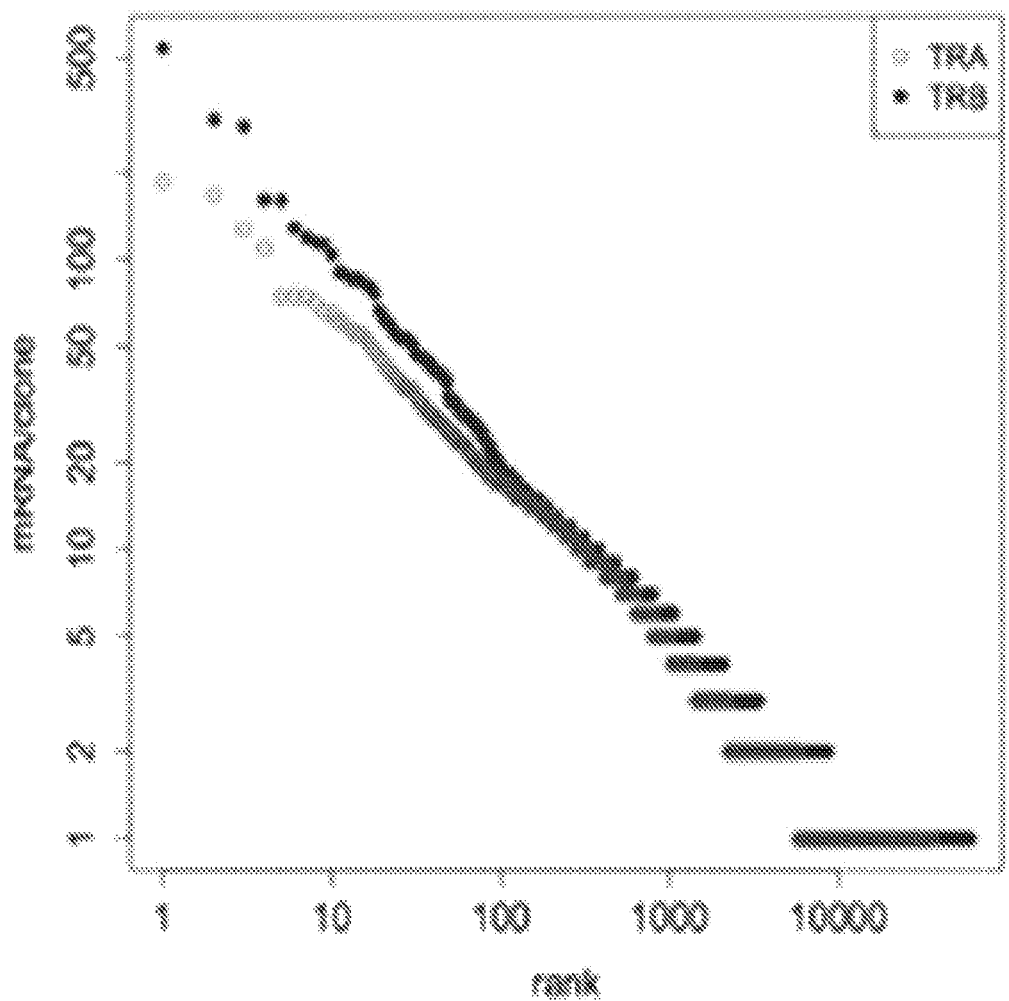
FIG. 16 exemplifies a graph of the rank abundance expression of TCRs obtained from immune sequencing of a diseased sample. The number of mRNAs for TCRα and TCRβ of each clone plotted against the rank of the depicted T-cell clones.
Figure 17:
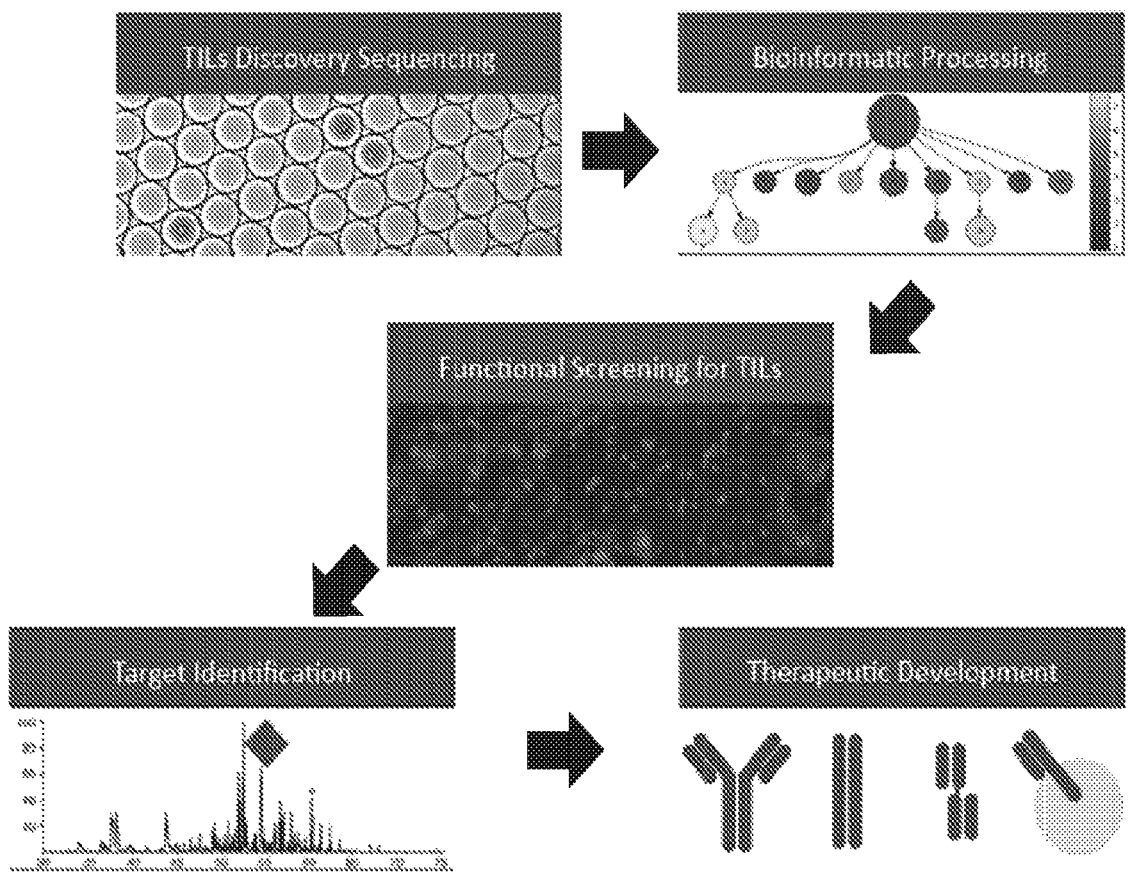
FIG. 17 exemplifies a flow chart of the steps of an exemplary method disclosed herein. Sequence data from normal and tumor tissue samples were collected followed by bioinformatics processing of the sequence data. One or more antibodies or TCRs of a TIL are selected based on a number of criteria including, for example, mRNA abundance, clonal expansion, and somatic hypermutation. Selected antibodies are then produced recombinantly. The recombinant antibodies or TCRs are then tested for high affinity and specificity to a tumor specific antigen using immunofluorescence assays by staining diseased tissue and comparing to staining of normal adjacent tissue. Selected antibodies validated by immunofluorescence assays are then assayed in an immunohistochemical fluorescent assay of FFPE human tissue. Antibodies that pass this validation stage are then utilized in immunoprecipitation assays and mass spectrometry is used to determine the antigens to which the antibodies are targeted.

Several aspects are described below with reference to example applications for illustration. It should be understood that numerous specific details, relationships, and methods are set forth to provide a full understanding of the features described herein. One having ordinary skill in the relevant art, however, will readily recognize that the features described herein can be practiced without one or more of the specific details or with other methods. The features described herein are not limited by the illustrated ordering of acts or events, as some acts can occur in different orders and/or concurrently with other acts or events. Furthermore, not all illustrated acts or events are required to implement a methodology in accordance with the features described herein.

The terminology used herein is for the purpose of describing particular cases only and is not intended to be limiting. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising".

The term "about" or "approximately" can mean within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, within 5-fold, and more preferably within 2-fold, of a value. Where particular values are described in the application and claims, unless otherwise stated the term "about" meaning within an acceptable error range for the particular value should be assumed.

Definitions

The term "candidate" when referring to a polynucleotide or polypeptide molecule refers to a polynucleotide or polypeptide from a lymphocyte selected based on sequencing information as described herein the disclosed methods herein.

The terms "infiltrating" or "tumor infiltrating" immune cells refer to a heterogeneous population of immune cells from a biological sample, such as a diseased or tumor tissue sample. Infiltrating immune cells include cells of the myeloid lineage (granulocytes, macrophages, and myeloid-derived suppressor cells) and the lymphocyte lineage (T-cells, B-cells, and natural killer (NK) cells).

The term "antibody" refers to an immunoglobulin (Ig) whether natural or partly or wholly synthetically produced. The term "T-cell receptor" ("TCR") refers to a molecule, whether natural or partly or wholly synthetically produced, found on the surface of T lymphocytes (T-cells) that recognizes antigens bound to major histocompatibility complex (MEW) molecules. Polypeptides or proteins having a binding domain which is an antigen-binding domain or is homologous to an antigen-binding domain are included. The term further includes "antigen-binding fragments" and other interchangeable terms for similar binding fragments such as described below. Complementarity determining region (CDR) grafted antibodies and TCRs and other humanized antibodies and TCRs (including CDR modifications and framework region modifications) are also contemplated by these terms.

Native antibodies and native immunoglobulins are usually heterotetrameric glycoproteins of about 150,000 Daltons, composed of two identical light (L) chains and two identical heavy (H) chains. Each light chain is typically linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains ($C_H$). Each light chain has a variable domain at one end ($V_L$) and a constant domain ($C_L$) at its other end; the constant domain of the light chain is aligned with the first constant domain of the heavy chain, and the light-chain variable domain is aligned with the variable domain of the heavy chain. Particular amino acid residues are believed to form an interface between the light- and heavy-chain variable domains.

The ability of T-cells to recognize antigens associated with various cancers or infectious organisms is conferred by its TCR, which is made up of both an alpha ($\alpha$) chain and a beta ($\beta$) chain or a gamma ($\gamma$) and a delta ($\delta$) chain. The proteins which make up these chains are encoded by DNA, which employs a unique mechanism for generating the tremendous diversity of the TCR. This multi-subunit immune recognition receptor associates with the CD3 complex and binds peptides presented by the MHC class I and II proteins on the surface of antigen-presenting cells (APCs). Binding of a TCR to the antigenic peptide on the APC is a central event in T-cell activation, which occurs at an immunological synapse at the point of contact between the T-cell and the APC.

Each TCR contains variable complementarity determining regions (CDRs), as well as framework regions (FRs) and a constant region. The amino acid sequence of the third complementarity-determining region (CDR3) loops of the $\alpha$ and $\beta$ chain variable domains is largely determines the sequence diversity of $\alpha\beta$ T-cells arising from recombination between variable (V$\beta$), diversity (D$\beta$), and joining (J$\beta$) gene segments in the $\beta$ chain locus, and between analogous V$\alpha$ and J$\alpha$ gene segments in the $\alpha$ chain locus, respectively. The existence of multiple such gene segments in the TCR $\alpha$ and $\beta$ chain loci allows for a large number of distinct CDR3 sequences to be encoded. Independent addition and deletion of nucleotides at the V$\beta$-D$\beta$, D$\beta$-J$\beta$, and V$\alpha$-J$\alpha$ junctions during the process of TCR gene rearrangement further increases CDR3 sequence diversity. In this respect, immunocompetence is reflected in the diversity of TCRs.

The $\gamma\delta$ TCR is distinctive from the $\alpha\beta$ TCR in that it encodes a receptor that interacts closely with the innate immune system. TCR$\gamma\delta$, is expressed early in development, has specialized anatomical distribution, has unique pathogen and small-molecule specificities, and has a broad spectrum of innate and adaptive cellular interactions. Early in ontogeny, as the restricted subsets of TCR$\gamma\delta$ cells populate various tissues prenatally, a biased pattern of TCR$\gamma$ V and J segment expression is established. Thus, extensive peripheral expansion following stimulation by environmental exposure to pathogens and toxic molecules causes much of the diverse TCR$\gamma$ repertoire in adult tissues.

Igs expressed by B-cells are proteins consisting of four polypeptide chains, two heavy chains (IgHs) and two light chains (IgLs), forming an $H_2L_2$ structure. Each pair of IgH and IgL chains contains a hypervariable domain, consisting of a $V_L$ and a $V_H$ region, and a constant domain. The IgH chains of Igs are of several types: $\mu$, $\delta$, $\gamma$, $\alpha$, and $\beta$. The diversity of Igs within an individual is mainly determined by the hypervariable domain. Similar to the TCR, the V domain of IgH chains is created by the combinatorial joining of the $V_H$, $D_H$, and $J_H$ gene segments. Independent addition and deletion of nucleotides at the $V_H$-$D_H$, $D_H$-$J_H$, and $V_H$-$J_H$ junctions during the process of Ig gene rearrangement further increases hypervariable domain sequence diversity. Here, immunocompetence is reflected in the diversity of Igs.

The term "variable" with reference to antibody chains, e.g., heavy and light chains, or TCR chains, e.g., alpha ($\alpha$) and beta chains or gamma ($\gamma$) and delta ($\delta$) chains, refers to portions of the antibody or TCR chains which differ in sequence among antibodies or TCRs and participate in the binding and specificity of each particular antibody or TCR for its particular antigen. Such variability is concentrated in three segments called hypervariable regions both in the light chain and the heavy chain variable domains or the alpha and beta variable domains. The more highly conserved portions of variable domains are called the framework region (FR). The variable domains of native heavy and light chains each comprise four FRs (FR1, FR2, FR3 and FR4, respectively), connected by three hypervariable regions. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991), pages 647-669). The constant domains are not involved directly in binding an antibody or TCR to an antigen, but exhibit various effector functions, e.g., participation of the antibody in antibody-dependent cellular toxicity.

The term "hypervariable region" refers to the amino acid residues of an antibody or TCR which are responsible for antigen-binding. The hypervariable region comprises amino acid residues from a "complementarity determining region" or "CDR." "Framework" or "FR" residues are those variable domain residues other than the hypervariable region residues as herein defined.

Antibodies can be assigned to different classes Depending on the amino acid sequence of the constant domain of their heavy chains, including IgA, IgD, IgE, IgG, and IgM, and several of these can be further divided into subclasses (isotypes), e.g., IgG1, IgG2, IgG3, IgG4, IgA, and IgA2.

The heavy chain constant domains that correspond to the different classes of immunoglobulins are called $\alpha$, $\delta$, $\epsilon$, $\gamma$, and $\mu$, respectively.

The light chains of antibodies from any vertebrate species can be assigned to one of two clearly distinct types, called kappa ($\kappa$) and lambda ($\lambda$), based on the amino acid sequences of their constant domains.

The term "monoclonal antibody" refers to an antibody molecule synthesized by a single clone of immune cells. The modifier "monoclonal" indicates the character of the antibody as being obtained from a substantially homogeneous population of antibodies, and is not to be construed as requiring production of the antibody by any particular method. For example, monoclonal antibodies can be made by the hybridoma method first described by Kohler and Milstein, Nature 256:495 (1975); Eur. J. Immunol. 6:511 (1976), by recombinant DNA techniques, or can also be isolated from phage antibody libraries.

The term "polyclonal antibody" refers to a population of antibody molecules synthesized by a population of immune cells.

"Antibody fragments" and "TCR fragments" comprise a portion of a full length antibody or TCR, generally the antigen binding or variable domain thereof. Examples of antibody and TCR fragments include, but are not limited to, Fab, Fab', F(ab')$_2$, Fv, and scFv fragments, linear antibodies or TCRs, single-chain antibody or TCR molecules, diabodies, and multispecific antibodies or TCRs formed from antibody or TCR fragments.

The terms "Single-chain Fv" or "scFv" refer to antibody or TCR fragments that comprise the variable heavy chain ($V_H$) and variable light chain ($V_L$) domains of an antibody or the variable alpha chain (Vα) and variable beta chain (Vβ) domains of a TCR or the variable alpha chain (Vγ) and variable beta chain (Vδ) domains of a TCR, wherein these domains are present in a single polypeptide chain. Generally, the Fv polypeptide further comprises a polypeptide linker between the $V_H$ and $V_L$ domains or Vα and VP domains or Vγ and Vδ domains which enables the scFv to form the desired structure for antigen binding.

The term "diabody" refers to small antibody and/or TCR fragments with two antigen-binding sites, which fragments comprise a $V_H$ connected to a $V_L$ in the same polypeptide chain ($V_H$—$V_L$) or a Vα connected to a VP in the same polypeptide chain (Vα-Vβ) or a Vγ connected to a Vδ in the same polypeptide chain (Vγ-Vδ). By using a linker that is too short to allow pairing between the two domains on the same chain, the domains are forced to pair with the complementary domains of another chain and create two antigen-binding sites. Exemplary diabodies are described more fully in, for example, EP404097 and WO93111161.

The terms "bispecific antibody" or "bispecific TCR" refer to an antibody or TCR that shows specificities to two different types of antigens. The terms as used herein specifically include, without limitation, antibodies and TCRs which show binding specificity for a target antigen and to another target that facilitates delivery to a particular tissue. Similarly, multi-specific antibodies and TCRs have two or more binding specificities.

The terms "linear antibody" and linear "TCR" refer to a pair of tandem Fd segments ($V_H$—$C_{H1}$-$V_H$-$C_{H1}$ or Vα-Cα$_1$-Vα-Cα$_1$) which form a pair of antigen binding regions. Linear antibodies and TCRs can be bispecific or monospecific, for example, as described by Zapata et al., Protein Eng. 8(10):1057-1062 (1995).

The terms "antibody library" or "TCR library" refer to a collection of antibodies or TCRs or antibody or TCR fragments. An antibody or TCR repertoire can, for example, be used to select a particular antibody or TCR, or screen for a particular property, such as binding ability, binding specificity, ability of gastrointestinal transport, stability, affinity, and the like. The term specifically includes antibody and TCR libraries, including all forms of combinatorial libraries, such as, for example, antibody phage display libraries, including, without limitation, single-chain Fv (scFv) and Fab antibody and TCR phage display libraries from any source, including naïve, synthetic and semi-synthetic libraries.

The terms "target nucleic acid molecule," "target molecule," "target polynucleotide," "target polynucleotide molecule," refer to any nucleic acid of interest.

The term "tumor-infiltrating lymphocytes" (TILs) refers to lymphocytes infiltrating into the stroma of cancer nodules.

The terms "synthetic polynucleotide" or "synthetic polypeptide," refer to the corresponding polynucleotide or polypeptide sequence or portion thereof, or amino acid sequence or portion thereof, is derived from a sequence that has been designed, or synthesized de novo, or modified, compared to an equivalent naturally-occurring sequence. Synthetic polynucleotides or polypeptides can be prepared by methods known in the art, including but not limited to, the chemical synthesis of nucleic acid or amino acid sequences.

The term "antigen-binding domain" refers to one or more fragments of an antibody or TCR that retain the ability to specifically bind to an antigen. Non-limiting examples of antibody fragments included within such terms include, but are not limited to, (i) a Fab fragment, a monovalent fragment consisting of the $V_L$, $V_H$, $C_L$ and $C_{H1}$ domains; (ii) a F(ab')$_2$ fragment, a bivalent fragment containing two Fab fragments linked by a disulfide bridge at the hinge region; (iii) a Fd fragment consisting of the $V_H$ and $C_{H1}$ domains; (iv) a Fv fragment containing the $V_L$ and $V_H$ domains of a single arm of an antibody, (v) a dAb fragment (Ward et al., (1989) Nature 341:544 546), which containing a $V_H$ domain; and (vi) an isolated CDR. Additionally included in this definition are antibodies comprising a single heavy chain and a single light chain or TCRs comprising a single alpha chain or a single beta chain.

"F(ab')$_2$" and "Fab'" moieties can be produced by treating an Ig with a protease such as pepsin and papain, and include antibody fragments generated by digesting immunoglobulin near the disulfide bonds existing between the hinge regions in each of the two heavy chains. For example, papain cleaves IgG upstream of the disulfide bonds existing between the hinge regions in each of the two heavy chains to generate two homologous antibody fragments in which a light chain composed of $V_L$ and $C_L$, and a heavy chain fragment composed of $V_H$ and $C_{Hγ1}$ (γ1 region in the constant region of the heavy chain) are connected at their C terminal regions through a disulfide bond. Each of these two homologous antibody fragments is called Fab'. Pepsin also cleaves IgG downstream of the disulfide bonds existing between the hinge regions in each of the two heavy chains to generate an antibody fragment slightly larger than the fragment in which the two above-mentioned Fab' are connected at the hinge region. This antibody fragment is called F(ab')$_2$.

The Fab fragment also contains the constant domain of the light chain and the first constant domain ($C_H1$) of the heavy chain. Fab' fragments differ from Fab fragments by the addition of a few residues at the carboxyl terminus of the heavy chain $C_H1$ domain including one or more cysteine(s) from the antibody hinge region. Fab'-SH is the designation herein for Fab' in which the cysteine residue(s) of the constant domains bear a free thiol group. F(ab')$_2$ antibody fragments originally are produced as pairs of Fab' fragments which have hinge cysteines between them.

"Fv" refers to an antibody or TCR fragment which contains a complete antigen-recognition and antigen-binding site. This region consists of a dimer of one heavy chain and one light chain variable domain or one TCRα chain and one TCRβ chain in tight, non-covalent association. It is in this configuration that the three CDRs of each variable domain interact to define an antigen-binding site on the surface of the $V_H$-$V_L$ dimer or Vα-Vβ dimer or Vγ-Vδ dimer. Collectively, a combination of one or more of the CDRs from each of the $V_H$ and $V_L$ chains or Vα-Vβ chains or Vγ-Vδ chains confer antigen-binding specificity to the antibody or TCR. For example, it would be understood that, for example, the CDRH3 and CDRL3 could be sufficient to confer antigen-binding specificity to an antibody or TCR when transferred to $V_H$ and $V_L$ chains or Vα and Vβ chains or Vγ and Vδ chains of a recipient selected antibody, TCR, or antigen-binding fragment thereof and this combination of CDRs can be tested for binding, affinity, etc. Even a single variable domain (or half of an Fv comprising only three CDRs specific for an antigen) has the ability to recognize and bind antigen, although likely at a lower affinity than when combined with a second variable domain. Furthermore, although the two domains of a Fv fragment ($V_L$ and $V_H$ or Vα and Vβ or Vγ and Vs), are coded for by separate genes, they can be joined using recombinant methods by a synthetic linker that enables them to be made as a single protein chain in which the $V_L$ and $V_H$ or Vα and Vβ or Vδ and Vγ regions pair to form monovalent molecules (known as single chain Fv (scFv); Bird et al. (1988) Science 242: 423-426; Huston et al. (1988) Proc. Natl. Acad. Sci. USA 85:5879-5883; and Osbourn et al. (1998) Nat. Biotechnol. 16:778). Such scFvs are also intended to be encompassed within the term "antigen-binding portion" of an antibody. Any $V_H$ and $V_L$ sequences of specific scFv can be linked to an Fc region cDNA or genomic sequences, in order to generate expression vectors encoding complete Ig (e.g., IgG) molecules or other isotypes. $V_H$ and $V_L$ can also be used in the generation of Fab, Fv or other fragments of Igs using either protein chemistry or recombinant DNA technology.

Antigen-binding polypeptides also include heavy chain dimers such as, for example, antibodies from camelids and sharks. Camelid and shark antibodies comprise a homodimeric pair of two chains of V-like and C-like domains (neither has a light chain). Since the $V_H$ region of a heavy chain dimer IgG in a camelid does not have to make hydrophobic interactions with a light chain, the region in the heavy chain that normally contacts a light chain is changed to hydrophilic amino acid residues in a camelid. $V_H$ domains of heavy-chain dimer IgGs are called $V_{HH}$ domains. Shark Ig-NARs comprise a homodimer of one variable domain (termed a V-NAR domain) and five C-like constant domains (C-NAR domains). In camelids, the diversity of antibody repertoire is determined by the CDRs 1, 2, and 3 in the $V_H$ or $V_{HH}$ regions. The CDR3 in the camel $V_{HH}$ region is characterized by its relatively long length, averaging 16 amino acids (Muyldermans et al., 1994, Protein Engineering 7(9): 1129).

"Humanized" forms of non-human (e.g., murine) antibodies or TCRs include chimeric antibodies or TCRs which contain minimal sequence derived from a non-human Ig or TCR. For the most part, humanized antibodies or TCRs are human Igs or TCRs (recipient antibody or TCR) in which one or more of the CDRs of the recipient are replaced by CDRs from a non-human species antibody or TCR (donor antibody or TCR) such as mouse, rat, rabbit or non-human primate having the desired specificity, affinity and binding function. In some instances, one or more FR amino acid residues of the human Ig or TCR are replaced by corresponding non-human amino acid residues. Furthermore, humanized antibodies or TCRs can contain residues which are not found in the recipient antibody or TCR, or in the donor antibody or TCR. These modifications can be made to refine antibody or TCR performance, if needed. A humanized antibody or TCR can comprise substantially all of at least one and, in some instances two, variable domains, in which all or substantially all of the hypervariable regions correspond to those of a non-human immunoglobulin or TCR and all, or substantially all, of the FRs are those of a human immunoglobulin or TCR sequence. The humanized antibody or TCR optionally can also include at least a portion of an immunoglobulin or TCR constant region (Fc), typically that of a human immunoglobulin or TCR. See, e.g., Jones et al., Nature 321: 522-525 (1986); Reichmann et al., Nature 332: 323-329 (1988); and Presta, Curr. Op. Struct. Biol. 2: 593-596 (1992).

The term "germline sequences" refers to the genetic sequences from the germline (the haploid gametes and those diploid cells from which they are formed). The germline DNA contains multiple gene segments that encode a single Ig heavy or light chain, or a single TCRα or TCRβ chain. These gene segments are carried in the germ cells but cannot be transcribed and translated until they are arranged into functional genes. During B-cell and T-cell differentiation in the bone marrow, these gene segments are randomly shuffled by a dynamic genetic system capable of generating more than $10^8$ specificities. Most of these gene segments are published and collected by the germline database.

The term "affinity" refers to the equilibrium constant for the reversible binding of two agents and is expressed as Kd. Affinity of a binding protein to a ligand such as affinity of an antibody for an epitope can be, for example, from about 100 nanomolar (nM) to about 0.1 nM, from about 100 nM to about 1 picomolar (pM), or from about 100 nM to about 1 femtomolar (fM). The term "avidity" refers to the resistance of a complex of two or more agents to dissociation after dilution.

The term "epitope" refers to that portion of an antigen or other macromolecule capable of forming a binding interaction with the variable region binding pocket of an antibody or TCR. Such binding interactions can be manifested as an intermolecular contact with one or more amino acid residues of one or more CDRs. Antigen binding can involve, for example, a CDR3, a CDR3 pair, or in some instances, interactions of up to all six CDRs of the $V_H$ and $V_L$ chains. An epitope can be a linear peptide sequence (i.e., "continuous") or can be composed of noncontiguous amino acid sequences (i.e., "conformational" or "discontinuous"). An antibody or TCR can recognize one or more amino acid sequences; therefore an epitope can define more than one distinct amino acid sequence. Epitopes recognized by antibodies and TCRs can be determined by peptide mapping and sequence analysis techniques well known to one of skill in the art. Binding interactions are manifested as intermolecular contacts with one or more amino acid residues of a CDR.

The term "specific" refers to a situation in which an antibody or TCR will not show any significant binding to molecules other than the antigen containing the epitope recognized by the antibody or TCR. The term is also applicable where for example, an antigen binding domain is specific for a particular epitope which is carried by a number of antigens, in which case the selected antibody, TCR, or antigen-binding fragment thereof carrying the antigen binding domain will be able to bind to the various antigens carrying the epitope. The terms "preferentially binds" or "specifically binds" mean that the antibodies, TCRs, or fragments thereof bind to an epitope with greater affinity than it binds unrelated amino acid sequences, and, if cross-reactive to other polypeptides containing the epitope, are not toxic at the levels at which they are formulated for administration to human use. In one aspect, such affinity is at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1000-fold greater than the affinity of the antibody, TCR, or fragment thereof for unrelated amino acid sequences. The term "binding" refers to a direct association between two molecules, due to, for example, covalent, electrostatic, hydrophobic, and ionic and/or hydrogen-bond interactions under physiological conditions, and includes interactions such as salt bridges and water bridges, as well as any other conventional means of binding.

The term "pharmaceutically acceptable" refers to molecular entities and compositions that are physiologically tolerable and do not typically produce an allergic or similar untoward reaction, such as gastric upset, dizziness and the like, when administered to a human.

The term "unit dose" when used in reference to a therapeutic composition refers to physically discrete units suitable as unitary dosage for humans, each unit containing a predetermined quantity of active material calculated to produce the desired therapeutic effect in association with the required diluent; i.e., carrier, or vehicle.

The term "packaging material" refers to a physical structure housing the components of the kit. The packaging material can maintain the components sterilely and can be made of material commonly used for such purposes (e.g., paper, corrugated fiber, glass, plastic, foil, ampules, etc.). The label or packaging insert can include appropriate written instructions. Kits, therefore, can additionally include labels or instructions for using the kit components in any method of the invention. A kit can include a compound in a pack, or dispenser together with instructions for administering the compound in a method described herein.

The term "prevention" refers to prophylaxis, prevention of onset of symptoms, prevention of progression of a disease or disorder associated with excess levels of protein or correlated with protein activity.

The terms "inhibition," "treatment" and "treating" are used interchangeably and refer to, for example, stasis of symptoms, prolongation of survival, partial or full amelioration of symptoms, and partial or full eradication of a condition, disease or disorder associated with excess levels of protein or correlated with protein activity. For example, treatment of cancer includes, but is not limited to, stasis, partial or total elimination of a cancerous growth or tumor. Treatment or partial elimination includes, for example, a fold reduction in growth or tumor size and/or volume such as about 2-fold, about 3-fold, about 4-fold, about 5-fold, about 10-fold, about 20-fold, about 50-fold, or any fold reduction in between. Similarly, treatment or partial elimination can include a percent reduction in growth or tumor size and/or volume of about 1%, 2%, 3%, 4%, 5%, 10%, 20%, 30%, 40%, 50%, 60%, 70%, 80%, 90%, 95% or any percentage reduction in between.

Methods of Identifying Targets of Lymphocytes

In healthy preimmune subjects, T-cells that recognize disease associated antigens are mostly if not exclusively in the naive T-cell compartment. The frequency of antigen-specific T-cells in naive persons is about $1\times10^{-5}$, and about $1\times10^9$ T-cells are needed for adoptive immunotherapy utilizing TILs (ATCI) of leukemia. Thus, antigen-specific ATCI requires massive expansion of antigen-specific T-cells, which has to be performed ex vivo in humans. Unfortunately, most methods for ex vivo expansion lead to an exhaustion of antigen-primed T-cells, which have shortened telomeres and lose functional attributes.

Greater than 50% of advanced melanoma patients responded to ATCI (Dudley et al., 2005). However, translating this approach to other cancers has been difficult for the reasons described above and because the numbers of TILs that can be isolated are low. Total numbers of TILs that can be isolated from a tissue before ex vivo expansion can be less than about $50\times10^8$, $25\times10^8$, $10\times10^8$, $5\times10^8$, $1\times10^8$, $50\times10^7$, $25\times10^7$, $10\times10^7$, $5\times10^7$, $1\times10^7$, $50\times10^6$, $25\times10^6$, $10\times10^6$, $5\times10^6$, $1\times10^6$, $50\times10^5$, $25\times10^5$, $10\times10^5$, $5\times10^5$, $1\times10^5$ or less. Of the total number of cells isolated from a tissue, the percent of TILs can be less than about 70%, 65%, 60%, 55%, 50%, 45%, 40%, 35%, 30%, 25%, 20%, 15%, 10%, 5% or less. Current methods to even determine the numbers and ratios of different lymphocyte subtypes that have infiltrated a tissue that is diseased, such as a solid tumor, are also inefficient and difficult. In solid tumors, inaccurate ratios lead to disease mis-prognoses.

Because of thymic selection during T-cell development, and because many tumor antigens are self-antigens, circulating T-cells have already been greatly exposed to tumor antigens in cancer-bearing patients. Natural TCRs expressed on circulating T-cells generally have low affinity for self-antigens ($K_D$ range 1-100 μM). Such circulating T-cells are less responsive to autologous cancer cells because cancer cells generally express small amounts of epitope/HLA complexes on their surface. Further, the number of TILs with high affinity for cancer specific-antigens is incredibly low compared to the large number of immune cells lacking such specificity. The percent of TILs with high affinity for cancer specific-antigens compared to immune cells lacking such specificity can be less than about 50%, 40%, 30%, 20%, 15%, 10%, 9%, 8%, 7%, 6%, 5%, 4%, 3%, 2%, 1% or less. Thus, a great need exists for methods of identifying infiltrating T-cells that have high affinity for disease-specific antigens in a sample containing an exponentially greater amount of T-cells and other immune cells that are not disease-specific.

Quantitative characterization of the number of B-cells and T-cells can be achieved based on detection of functionally rearranged immunoglobulin and TCR encoding genes using biological samples from which such lymphocytes can be readily isolated in substantial numbers, such as blood, lymph or other biological fluids. In these samples, B-cells and T-cells exist as particles in fluid suspension. However, current approaches to quantify lymphocytes in tissues or organs from which B-cells and T-cells cannot be readily isolated are far more limited. For example, in order to detect lymphocytes in solid tissue and solid tumor samples, histological detection in small, non-representative samples is required. These labor intensive and semi-quantitative techniques typically use immunohistochemistry or in situ hybridization on fixed or frozen biopsy specimen sections. Such time-consuming and labor-intensive steps can prevent recovery of lymphocytes from the sample due to loss or destruction of a portion of the sample in the course of handling. These and related limitations of the current approaches compromise the quality of quantitative data that can be obtained.

Efforts to obtain meaningful quantitative data from such approaches are severely limited with regard to the number of lymphocytes that can have infiltrated a tissue. For example, a high statistical significance cannot be achieved when data collection depends on the number of events that can be detected by observation of a finite number of small fields on microscope slides. Furthermore, a tissue sample must be mechanically and/or enzymatically dissociated to produce a single-cell suspension that is amenable to flow immunocytofluorimetric analysis.

Although tumor infiltrating T-cell lymphocytes have been studied in depth in some cancer types (e.g., prostate ductal adenocarcinoma (PDAC)), detection and characterization of cancer-specific B-cells in the tumor environment has thus far remained substantially unknown. Furthermore, the limits of the immunohistochemical techniques applied to the T-cells were largely from retrospective clinical studies and prevent a detailed analysis of different TIL populations and evaluation of their functional properties in the tumor microenvironment. Although quantitative analysis of the number of infiltrating T-cells finds uses in prognoses, there still exists a need for a method to identify the TCR sequences of disease specific T-cells.

Although quantitative analysis of the number of infiltrating B-cells also finds uses in prognoses, there still exists a need for a method to identify the Ig sequences of disease-specific B-cells. There have been minimal attempts to discover the Ig sequences of tumor infiltrating B-lymphocytes. Even fewer attempts have been made to discover targets of these lymphocytes (as opposed to T-cells) and none with success. Unsuccessful attempts by others can be explained by the low statistical chance of finding a relevant antibody, due to the naturally large amount of B-cells without specificity to disease antigens that are present in both diseased and normal samples. Current approaches to study infiltrating lymphocytes are of low throughput and are ineffective to yield therapeutic antibodies due to the sheer size of the immune repertoire in organisms. To identify a novel disease associated antigen, lengthy gene and protein functional studies are typically conducted. Thus, a great need exists for methods of identifying infiltrating B-cells that have high affinity for disease-specific antigens in a sample containing an exponentially greater amount of non-disease specific B-cells and other immune cells.

Clearly a need exists for methods for identifying and selecting disease-specific lymphocytes in a complex biological sample containing many lymphocytes that are not disease specific and other cells that are not lymphocytes. Further, there is a need for methods of identifying targets of disease-specific lymphocytes. The presently described instances utilize high-throughput and highly accurate, non-biased immune repertoire sequencing combined with bioinformatics and proteomic approaches to address these needs and offer other related advantages.

Immune Sequencing

Methods are provided in which nucleic acids from a sample are manipulated in order to generate libraries of polynucleotides for sequencing. In a general sense, amplification of immune cell and/or T-cell genetic material, e.g. reverse transcription polymerase chain reaction (reverse transcription-PCR) is employed to generate cDNA and amplify genetic material of immune cells, including lymphocytes. In some instances, immunoglobulin sequences are obtained from nucleic acids of B-cells. In some instances, T-cell receptor sequences are obtained from nucleic acids of T-cells. In some instances, nucleic acids are RNA. In some instances, nucleic acids comprise IgH or TCRβ chain or (V, D, J segments) nucleic acids, IgL or TCRα chain (V, J segments) nucleic acids, or both. In some instances, nucleic acids comprise TCRγ chain nucleic acids, TCR chain nucleic acids, or both.

Samples

Samples include, but are not limited to, a biological, environmental, medical, subject, or patient sample or a sample containing a polynucleotide, such as a polynucleotide. Any biological sample containing lymphocytes can be used in the disclosed methods. Any biological sample containing polynucleotides can be used in the disclosed methods. For example, a sample can be a biological sample from a subject containing lymphocytes comprising RNA or DNA encoding an Ig or TCR polypeptide. The polynucleotides can be extracted from the biological sample, or the sample can be directly subjected to the methods without extraction or purification of the polynucleotides. The sample can be extracted or isolated DNA or RNA. A sample can also be total RNA or DNA extracted from a biological specimen, a cDNA library, viral, or genomic DNA. In one instance, polynucleotides are isolated from a biological sample containing a variety of other components, such as proteins, lipids and non-template nucleic acids. Nucleic acid template molecules can be obtained from any cellular material, obtained from an animal, plant, bacterium, fungus, or any other cellular organism. In certain instances, the polynucleotides are obtained from a single cell. Polynucleotides can be obtained directly from an organism or from a biological sample obtained from an organism. A tissue or body fluid specimen can be used as a source for nucleic acids for sequencing using the disclosed methods. Polynucleotides can also be isolated from cultured cells, such as a primary cell culture or a cell line. The cells or tissues from which nucleic acids are obtained can be diseased or infected with a virus or other intracellular pathogen.

In certain instances, immune cells, such as TILs, can be isolated from a subject or host, such as a human or other animal, that has been immunized or that is suffering from an infection, cancer, an autoimmune condition, or any other diseases to identify a pathogen-, tumor-, and/or disease specific antibody of potential clinical significance. For example, the human can be diagnosed with a disease or be exhibiting symptoms of a disease. For example, the human can be one that is exposed to and/or who can make useful Igs or TCRs against an infectious agent (e.g., viruses, bacteria, parasites, prions, etc), antigen, or disease. For example, the animal can be one that is exposed to and/or who can make useful antibodies or TCRs against an infectious agent (e.g., viruses, bacteria, parasites, prions, etc), antigen, or disease. Certain immune cells from immunized hosts make Igs or TCRs to one or more antigens in question, e.g., one or more unknown antigens. In some instances, the lymphocyte pool can be enriched for the desired immune cells by any suitable method, such as screening and sorting the cells using fluorescence-activated cell sorting (FACS), magnetic activated cell sorting (MACS), panning or other screening method to generate a plurality of immune cells from a sample, such as an immune cell library, before Igs or TCRs chains are sequenced, Igs or TCRs are made, or an expression library is made. In some instances, the immune cell library of the present invention contains at least 2 subsets of or individual immune cells expressing different antibodies or TCRs. For example, an immune cell library can contain at least 5, 10, 100, 250, 500, 750, 1,000; 2,500; 5,000; 10,000; 25,000; 50,000; 75,000; 10,000; 250,000; 500,000; 750,000; 1,000, 000; 2,500,000; 5,000,000; 7,500,000; or 10,000,000 or more subsets of or individual immune cells expressing different Igs or TCRs. The methods of the present invention maximize immune cell sequencing, and afford very high diversity.

In some instances, immune cells from non-immunized human or non-human donors are utilized. The naive repertoire of an animal (the repertoire before antigen challenge) provides the animal with antibodies that can bind with moderate affinity ($K_a$ of about $1\times10^{-6}$ to $1\times10^{-7}$ M) to essentially any non-self molecule. The sequence diversity of antibody binding sites is not encoded directly in the germ-line but is assembled in a combinatorial manner from V gene segments. Immunizations trigger any immune cell making a $V_H$-$V_L$ combination or $V\alpha$-$V\beta$ combination or $V\gamma$-$V\delta$ combination that binds the immunogen to proliferate (clonal expansion) and to secrete the corresponding antibody or TCR as noted above. However, the use of spleen cells and/or immune cells or other lymphocytes from an unimmunized or non-diseased subject, or from normal adjacent tissue of a diseased subject, can provide a representation of a control antibody or TCR library. This also permits a comparison of a diseased library to a non-diseased library for selecting a lymphocyte as described in some instances herein. This also can permit the construction of a subsequent B-cell antibody library or T-cell TCR library using any animal species.

In some instances, the starting material is peripheral blood. The peripheral blood cells can be enriched for a particular cell type (e.g., mononuclear cells; red blood cells; $CD4^+$ cells; $CD8^+$ cells; immune cells; T-cells, NK cells, or the like). The peripheral blood cells can also be selectively depleted of a particular cell type (e.g., mononuclear cells; red blood cells; $CD4^+$ cells; $CD8^+$ cells; immune cells; T-cells, NK cells, or the like).

In some instances, the starting material can be a tissue sample comprising an extravascular tissue or solid tissue, with non-limiting examples including brain, liver, lung, kidney, prostate, ovary, spleen, lymph node (including tonsil), thyroid, pancreas, heart, skeletal muscle, intestine, larynx, esophagus, and stomach. In other instances, the starting material can be cells containing nucleic acids, and in particular immune cells. In some instances, the starting material can be a sample containing nucleic acids, from any organism, from which genetic material can be obtained.

In some instances, a sample is a fluid, e.g., blood, saliva, lymph, or urine. In some instances, in order to obtain sufficient nucleic acid for testing, a blood volume of at least 0.001, 0.005, 0.01, 0.05, 0.1, 0.5, 1, 2, 3, 4, 5, 10, 20, 25, 30, 35, 40, 45, or 50 mL is drawn. In some instances, a sample is not a blood sample. In some instances, a sample is not a fluid sample. In some instances, a sample is a solid sample.

A sample can be taken from a subject with a condition. In some instances, the subject from whom a sample is taken can be a patient, for example, a cancer patient or a patient suspected of having cancer. The subject can be a mammal, e.g., a human, and can be male or female. In some instances, the female is pregnant. The sample can be a tumor biopsy. The biopsy can be performed by, for example, a health care provider, including a physician, physician assistant, nurse, veterinarian, dentist, chiropractor, paramedic, dermatologist, oncologist, gastroenterologist, or surgeon.

In some instances, non-nucleic acid materials can be removed from the starting material using enzymatic treatments (such as protease digestion).

Nucleic acid molecules include, but are not limited to, deoxyribonucleic acid (DNA) and/or ribonucleic acid (RNA). Nucleic acid molecules can be synthetic or derived from naturally occurring sources. In one instance, nucleic acid molecules are isolated from a biological sample containing a variety of other components, such as proteins, lipids and non-template nucleic acids. Nucleic acid template molecules can be obtained from any cellular material, obtained from an animal, plant, bacterium, fungus, or any other cellular organism. In certain instances, the nucleic acid molecules are obtained from a single cell. Nucleic acid molecules can be obtained directly from an organism or from a biological sample obtained from an organism, e.g., extravascular tissue or a solid tumor biopsy. Any tissue or body fluid specimen can be used as a source for nucleic acid for use in the invention.

A sample can comprise total RNA extracted from a biological specimen, a cDNA library, viral, or genomic DNA. In certain instances, the nucleic acid molecules are bound as to other molecules such as proteins, enzymes, substrates, antibodies, binding agents, beads, small molecules, peptides, or any other molecule Generally, nucleic acid can be extracted from a biological sample by a variety of techniques such as those described by Sambrook and Russell, Molecular Cloning: A Laboratory Manual, Third Edition, Cold Spring Harbor, N.Y. (2001). Nucleic acid molecules can be single-stranded, double-stranded, or double-stranded with single-stranded regions (for example, stem- and loop-structures).

One or more samples can be from one or more sources. One or more of samples can be from two or more sources. One or more of samples can be from one or more subjects. One or more of samples can be from two or more subjects. One or more of samples can be from the same subject. One or more subjects can be from the same species. One or more subjects can be from different species. The one or more subjects can be healthy. The one or more subjects can be affected by a disease, disorder or condition.

A sample can be taken from a subject with a condition. In some instances, the subject from whom a sample is taken can be a patient, for example, a cancer patient or a patient suspected of having cancer. The subject can be a mammal, e.g., a human, and can be male or female. In some instances, the female is pregnant. The sample can be a tumor biopsy. The biopsy can be performed by, for example, a health care provider, including a physician, physician assistant, nurse, veterinarian, dentist, chiropractor, paramedic, dermatologist, oncologist, gastroenterologist, or surgeon.

In some instances, the polynucleotides are bound to other molecules such as proteins, enzymes, substrates, antibodies, binding agents, beads, small molecules, peptides, or any other molecule. In some instances, the polynucleotides are not bound to a solid support. Nucleic acids can be extracted from a biological sample by a variety of techniques (Sambrook et al., Molecular Cloning: A Laboratory Manual, Third Edition, Cold Spring Harbor, N.Y. (2001)).

A plurality of samples can comprise at least 2, 3, 4, 5, 10, 20, 30, 40, 50, 60, 70, 80, 90 or 100 or more samples. The plurality of samples can comprise at least about 100, 200, 300, 400, 500, 600, 700, 800, 900 or 1,000 or more samples. The plurality of samples can comprise at least about 1,000; 2,000; 3,000; 4,000; 5000; 6,000; 7,000; 8,000; 9,000; 10,000; 100,000; 1,000,000; or more samples. For example, the plurality of samples can comprise at least about 10,000 samples.

A first sample can comprise one or more cells and the second sample can comprise one or more cells. The one or more cells of the first sample can be of the same cell type as the one or more cells of the second sample. The one or more cells of the first sample can be of a different cell type as one or more different cells of the plurality of samples.

The plurality of samples can be obtained concurrently. A plurality of samples can be obtained at the same time. The plurality of samples can be obtained sequentially. A plurality of samples can be obtained over a course of years, 100 years, 10 years, 5 years, 4 years, 3 years, 2 years or 1 year of obtaining one or more different samples. One or more samples can be obtained within about one year of obtaining one or more different samples. One or more samples can be obtained within 12 months, 11 months, 10 months, 9 months, 8 months, 7 months, 6 months, 4 months, 3 months, 2 months or 1 month of obtaining one or more different samples. One or more samples can be obtained within 30 days, 28 days, 26 days, 24 days, 21 days, 20 days, 18 days, 17 days, 16 days, 15 days, 14 days, 13 days, 12 days, 11 days, 10 days, 9 days, 8 days, 7 days, 6 days, 5 days, 4 days, 3 days, 2 days or 1 day of obtaining one or more different samples. One or more samples can be obtained within about 24 hours, 22 hours, 20 hours, 18 hours, 16 hours, 14 hours, 12 hours, 10 hours, 8 hours, 6 hours, 4 hours, 2 hours or 1 hour of obtaining one or more different samples. One or more samples can be obtained within about 60 seconds, 45 seconds, 30 seconds, 20 seconds, 10 seconds, 5 seconds, 2 seconds or 1 second of obtaining one or more different samples. One or more samples can be obtained within less than one second of obtaining one or more different samples.

Polynucleotides for Sequencing

The methods disclosed comprise amplification and sequencing of a polynucleotide molecule, such as a polynucleotide molecule from a cell. In some instances, methods provided herein are directed to amplification and sequencing of two or more regions of a polynucleotide molecule. In some instances, the methods disclosed comprise amplification and sequencing of two or more polynucleotide molecules. In one aspect, polynucleotides are RNA. In one aspect, polynucleotides are genomic nucleic acids. DNA derived from the genetic material in the chromosomes of a particular organism can be genomic DNA. In preferred instances, polynucleotides include sequences comprising variable regions of an antibody produced by an immune cell. In some instances, polynucleotides include sequences comprising a variable region of a heavy chain of an antibody or TCRα chain produced by an immune cell. In some instances, polynucleotides include sequences comprising a variable region of a light chain of an antibody or TCRβ chain produced by an immune cell.

Polynucleotides can be obtained from virtually any source and can be prepared using methods known in the art. For example, polynucleotides can be directly isolated without amplification using methods known in the art, including without limitation extracting a fragment of genomic DNA or mRNA from an organism or a cell (e.g., an immune cell) to obtain polynucleotides. A polynucleotide can also encompass cDNA generated from RNA (such as mRNA) through reverse transcription-PCR. In some instances, a polynucleotide is an RNA molecule. In some instances, a polynucleotide is an mRNA molecule, or a cDNA produced from the mRNA molecule. In some instances, a polynucleotide is an mRNA molecule, or cDNA molecule produced from the mRNA molecule, from a single immune cell. In some instances, polynucleotides are mRNA molecules, or cDNA molecules produced from the mRNA molecules, from individual immune cells. In some instances, polynucleotides are mRNA molecules encoding an antibody or TCR sequence from a single immune cell. In some instances, polynucleotides are mRNA molecules encoding heavy chain antibody or TCRα chain sequences from individual immune cells. In some instances, polynucleotides are mRNA molecules encoding a heavy chain antibody or TCRα chain sequence from a single immune cell. In some instances, polynucleotides are mRNA molecules encoding light chain antibody or TCRβ chain sequences from individual immune cells. In some instances, polynucleotides are mRNA molecules encoding a light chain antibody or TCRβ chain sequence from a single immune cell. In some instances, polynucleotides are mRNA molecules encoding antibody or TCR variable sequences from individual immune cells. In some instances, polynucleotides are mRNA molecules encoding a variable antibody or TCR sequence from a single immune cell. In some instances, polynucleotides are mRNA molecules encoding variable light chain antibody or TCRβ chain sequences from individual immune cells. In some instances, polynucleotides are mRNA molecules encoding a variable light chain antibody or TCRβ chain sequence from a single immune cell. In some instances, polynucleotides are mRNA molecules encoding variable heavy chain antibody or TCRα chain sequences from individual immune cells. In some instances, polynucleotides are mRNA molecules encoding a variable heavy chain antibody or TCRα chain sequence from a single immune cell. In some instances, a polynucleotide can be a cell-free nucleic acid, e.g., DNA or RNA.

In some instances, a plurality of Ig and/or TCR polynucleotides are sequenced. For example, a plurality of $V_H$ and/or $V_L$ and/or $V\alpha$ and/or $V\beta$ and/or $V\gamma$-$V\delta$ polynucleotides are sequenced. In some instances, 1, 2, 3, 4, 5, 6, 7, 8, 9, or 10 immunoglobulin or TCR polynucleotides are sequenced. In some instances at least about 10, 20, 30, 40, 50, 60, 70, 80, 90, 100, 150, 200, 250, 300, 350, 400, 450, 500, 550, 600, 650, 700, 750, 800, 850, 900, 1000, 1500, 2000, 3000, 4000, 5000, 6000, 7000, 8000, 9000, 10,000, 11,000, 12,000, 13,000, 14,000, 15,000, 16,000, 17,000, 18,000, 19,000, 20,000, 25,000, 30,000, 35,000, 40,000, 45,000, 50,000, 60,000, 70,000, 80,000, 90,000, 100,000, 200,000, 300,000, 400,000, 500,000, 600,000, 700,000, 800,000, 900,000, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, or $9\times10^{12}$ immunoglobulin or TCR polynucleotides are sequenced. In some instances, at most about 10, 20, 30, 40, 50, 60, 70, 80, 90, 100, 150, 200, 250, 300, 350, 400, 450, 500, 550, 600, 650, 700, 750, 800, 850, 900, 1000, 1500, 2000, 3000, 4000, 5000, 6000, 7000, 8000, 9000, 10,000, 11,000, 12,000, 13,000, 14,000, 15,000, 16,000, 17,000, 18,000, 19,000, 20,000, 25,000, 30,000, 35,000, 40,000, 45,000, 50,000, 60,000, 70,000, 80,000, 90,000, 100,000, 200,000, 300,000, 400,000, 500,000, 600,000, 700,000, 800,000, 900,000, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, or $9\times10^{12}$ immunoglobulin or TCR polynucleotides are sequenced. In some instances, 10-20, 10-30, 10-40, 10-30, 10-40, 10-50, 10-60, 10-70, 10-80, 10-90, 10-100, 50-60, 50-70, 50-80, 50-90, 50-100, 100-200, 100-300, 100-400, 100-300, 100-400, 100-500, 100-600, 100-700, 100-800, 100-900, 100-1000, 500-600, 500-700, 500-800, 500-900, 500-1000, 1000-2000, 1000-3000, 1000-4000, 1000-3000, 1000-4000, 1000-5000, 1000-6000, 1000-7000, 1000-8000, 1000-9000, 1000-10000, 5000-6000, 5000-7000, 5000-8000, 5000-9000, 5000-10000, $1$-$1\times10^5$, $1$-$2\times10^5$, $1$-$3\times10^5$, $1$-$4\times10^5$, $1$-$5\times10^5$, $1$-$6\times10^5$, $1$-$7\times10^5$, $1$-$8\times10^5$, $9\times10^5$, $1$-$1\times10^6$, $1$-$2\times10^6$, $1$-$3\times10^6$, $1$-$4\times10^6$, $1$-$5\times10^6$, $1$-$6\times10^6$, $1$-$7\times10^6$, $1$-$8\times10^6$, $9\times10^6$, $1\times10^7$, $1$-$2\times10^7$, $1$-$3\times10^7$, $1$-$4\times10^7$, $1$-$5\times10^7$, $1$-$6\times$ $10^7$, $1$-$7\times10^7$, $1$-$8\times10^7$, $1$-$9\times10^7$, $1$-$1\times10^8$, $1$-$2\times10^8$, $1$-$3\times10^8$, $1$-$4\times10^8$, $1$-$5\times10^8$, $1$-$6\times10^8$, $1$-$7\times10^8$, $1$-$8\times10^8$, $1$-$9\times10^8$, $1$-$1\times10^9$, $1$-$2\times10^9$, $1$-$3\times10^9$, $1$-$4\times10^9$, $1$-$5\times10^9$, $1$-$6\times10^9$, $1$-$7\times10^9$, $1$-$8\times10^9$, $1$-$9\times10^9$, $1$-$1\times10^{10}$, $1$-$2\times10^{10}$, $1$-$3\times10^{10}$, $1$-$4\times10^{10}$, $1$-$5\times10^{10}$, $1$-$6\times10^{10}$, $1$-$7\times10^{10}$, $1$-$8\times10^{10}$, $1$-$9\times10^{10}$, $1$-$1\times10^{11}$, $1$-$2\times10^{11}$, $1$-$3\times10^{11}$, $1$-$4\times10^{11}$, $1$-$5\times10^{11}$, $1$-$6\times10^{11}$, $1$-$7\times10^{11}$, $1$-$8\times10^{11}$, $1$-$9\times10^{11}$, $1$-$1\times10^{12}$, $1$-$2\times10^{12}$, $1$-$3\times10^{12}$, $1$-$4\times10^{12}$, $1$-$5\times10^{12}$, $1$-$6\times10^{12}$, $1$-$7\times10^{12}$, $1$-$8\times10^{12}$, or $1$-$9\times10^{12}$ immunoglobulin or TCR polynucleotides are sequenced.

In some instances, a sequenced immunoglobulin or TCR polynucleotide is about 10, 20, 30, 40, 50, 60, 70, 80, 90, 100, 150, 200, 250, 300, 350, 400, 450, 500, 550, 600, 650, 700, 750, 800, 850, 900, 1000, 1500, 2000, 3000, 4000, 5000, 6000, 7000, 8000, 9000, 10,000, 11,000, 12,000, 13,000, 14,000, 15,000, 16,000, 17,000, 18,000, 19,000, or 20,000 bases or base-pairs in length. In some instances, a sequenced immunoglobulin or TCR polynucleotide is at least about 10, 20, 30, 40, 50, 60, 70, 80, 90, 100, 150, 200, 250, 300, 350, 400, 450, 500, 550, 600, 650, 700, 750, 800, 850, 900, 1000, 1500, 2000, 3000, 4000, 5000, 6000, 7000, 8000, 9000, 10,000, 11,000, 12,000, 13,000, 14,000, 15,000, 16,000, 17,000, 18,000, 19,000, or 20,000 bases or base-pairs in length. In some instances, a sequenced immunoglobulin or TCR polynucleotide is at most about 10, 20, 30, 40, 50, 60, 70, 80, 90, 100, 150, 200, 250, 300, 350, 400, 450, 500, 550, 600, 650, 700, 750, 800, 850, 900, 1000, 1500, 2000, 3000, 4000, 5000, 6000, 7000, 8000, 9000, 10,000, 11,000, 12,000, 13,000, 14,000, 15,000, 16,000, 17,000, 18,000, 19,000, or 20,000 bases or base-pairs in length. In some instances, a sequenced immunoglobulin or TCR polynucleotide is from about 10-20, 10-30, 10-40, 10-30, 10-40, 10-50, 10-60, 10-70, 10-80, 10-90, 10-100, 50-60, 50-70, 50-80, 50-90, 50-100, 100-200, 100-300, 100-400, 100-300, 100-400, 100-500, 100-600, 100-700, 100-800, 100-900, 100-1000, 500-600, 500-700, 500-800, 500-900, 500-1,000, 1,000-2,000, 1,000-3,000, 1,000-4,000, 1,000-5,000, 1,000-6,000, 1,000-7,000, 1,000-8,000, 1,000-9,000, 1,000-10,000, 5,000-6,000, 5,000-7,000, 5,000-8,000, 5,000-9,000, or 5,000-10,000 bases or base-pairs in length. In some instances, the average length of the a sequenced immunoglobulin or TCR polynucleotide, or fragments thereof, can be less than about 100, 200, 300, 400, 500, or 800 base pairs, or less than about 5, 10, 20, 30, 40, 50, 60, 70, 80, 90, 100, 110, 120, 130, 140, 150, 160, 170, 180, 190, or 200 nucleotides, or less than about 1, 2, 3, 4, 5, 10, 20, 30, 40, 50, 60, 70, 80, 90, 100 kilobases. In some instances, a sequenced immunoglobulin or TCR polynucleotide from a relative short template is about 40, 45, 50, 55, 60, 65, 70, 75, 80, 85, 90, 95, or 100 bases. In certain instances, sequencing data are aligned against known or expected sequences using a database containing sequences or immunoglobulin sequences associated with a disease or condition.

In one aspect, a method is disclosed comprising determining the sequence of each of a plurality of polynucleotides from immune cells, e.g., a library of sequences. In some instances, the polynucleotides are from immune cells of a normal (i.e. non-diseased) sample (normal library). In one aspect, a method is disclosed comprising determining the sequence of each of a plurality of polynucleotides from infiltrating immune cells. The polynucleotides can be from immune cells from a diseased sample (diseased library).

Single Cell Barcoding

In some instances, a method can comprise determining the sequence of each of a plurality of polynucleotides of a diseased sample and determining the sequence of each of a plurality of polynucleotides of a normal sample. The method can comprise comparing sequence information from the diseased sample to sequence information of the normal sample. For example, using high-throughput sequencing techniques coupled with methods of barcoding the polynucleotides in the libraries, bioinformatics can be used to compare millions to trillions of sequence reads of diseased samples to normal samples.

Single cell barcoding with a vessel barcode and/or a molecular barcode. Vessels, such as water in oil emulsions, can be created in such way that resulting vessels contain 1 cell or less per vessel. The vessels can be created in such way that resulting vessels contain 1 vessel barcode per vessel. The vessels can be created in such way that resulting vessels contain 1 molecular barcoded polynucleotide per vessel. The vessels can be created in such way that resulting vessels contain 2 or more, or a plurality of, molecular barcoded polynucleotides per vessel. The cells/vessels can be subject to an RNA or DNA single barcoding protocol as described herein, and the vessel barcode and one or more molecular barcode of each vessel can be fused with a target of interest, such as a cell polynucleotide. In some instances, matching vessel barcoded polynucleotides can be fused to cell components present in the same vessel as the one or more molecular barcoded polynucleotides. Following sequencing, vessel barcode and molecular barcode deconvolution can be used to identify which RNA (or DNA) originated from which cell. In some instances, vessels, such as water in oil emulsions, can be created in such way that resulting emulsions contained 1 cell or more per emulsion. In some instances, water in oil emulsions can be created in such way that resulting emulsions contain 1 vessel barcoded polynucleotide and 2 or more molecular barcoded polynucleotides per vessel. In some instances, vessels can be created in such way that resulting vessels contain more than 1 vessel barcoded polynucleotide and 2 or more molecular barcoded polynucleotides per vessel. In some instances, a vessel barcode and molecular barcode can be introduced into vessels when in solution. In some instances, a vessel barcode and molecular barcode can be introduced into vessels when not attached to a solid support, such as a bead.

In some aspects, single cells can be isolated inside an emulsion, which can act as a compartment. The cells can be lysed and transcripts from the cell can be barcoded. Each of the transcripts can be fused with a molecular barcode or vessel barcode, in such way that when 2 or more RNA transcripts are detected with the same vessel barcode, they can be determined to have originated from the same starting cell. This can be applied to many different types of sequences. One particular application can be linking $V_H$ and $V_L$ chains of antibody sequences. One particular application can be linking $V\alpha$ and $V\beta$ chains of TCR sequences. One particular application can be linking $V\gamma$ and $V\delta$ chains of TCR sequences.

One or more single cells can be isolated in one or more emulsions, in the presence of a vessel barcode and molecular barcodes, so that one droplet of the one or more emulsions can contain a maximum of 1 cell or less. Cells can be lysed chemically by a buffer contained in an emulsion or by freeze thaw, thereby releasing the contents of a cell in an emulsion.

RNAs of a single cell can be reverse transcribed into cDNA. A reverse transcription reaction can be done with a reverse transcriptase that possesses non-template terminal transferase activity which adds ~3 cytosine residues as described above. All reverse transcription buffers, enzymes, and nucleotides can be present when forming an emulsion. In some instances, a primer can be generalized (such as polynucleotide comprising a poly dT sequence) to target all mRNA. In some instances, DNA can be used. In some instances, more than 2 RNAs can be targeted.

In some instances, a vessel barcode can be linked to a RNA during reverse transcription. In some instances, a molecular barcode can be linked to a RNA during reverse transcription. In some instances, a vessel barcode and molecular barcode can be linked to a RNA during reverse transcription.

A reverse transcription reaction can be conducted in a presence of a 3' tagging polynucleotide. A 3' tagging polynucleotide can comprise a P7 segment which can be used for annealing a sequencing primer. A 3' tagging polynucleotide can comprise a vessel barcode or a molecular barcode. A 3' tagging polynucleotide can comprise 3 ribo-guanine residues on a 3' end (rGrGrG) (RNA bases) that can be complementary to and annealed to a strand produced by a reverse transcription enzyme. Thus, a vessel barcode and molecular barcode can be added to a terminal end of a cDNA in this same emulsion by reverse transcription enzymes. In some instances, guanine residues can be used instead of ribo-guanine (DNA nucleotide instead of RNA nucleotide). Upon annealing of a 3' tagging polynucleotide to a CCC of a cDNA strand, a reverse transcriptase continues extending a cDNA into a 3' tagging polynucleotide, thereby creating a molecular barcoded tag to all cDNAs in a reaction. Upon annealing of a 3' tagging polynucleotide to a region of a molecular barcoded cDNA, a reverse transcriptase or polymerase continues extending a molecular barcoded cDNA into another 3' tagging polynucleotide, thereby creating a vessel barcoded tag to all cDNAs in a reaction. In some instances, template switching can be done in a separate reaction instead of being done at the same time a reverse transcription reaction can be conducted. In some instances, a 3' tagging polynucleotide can be added after a reverse transcription reaction, and enzymes such as a reverse transcriptase or polymerase can be used to extend into a tagging polynucleotide in a similar fashion. Because a 3' tagging polynucleotide can harbor a unique degenerate molecular barcode on each single molecule, each cDNA can be uniquely tagged with a molecular barcode. Because a 3' tagging polynucleotide can harbor a same degenerate vessel barcode on each single molecule from a single vessel, each cDNA can be tagged with a vessel barcode unique to the vessel.

Barcodes

A barcode can be a molecular barcode or a vessel barcode. In some instances, a barcode, such as a molecular barcode or a vessel barcode, can each have a length within a range of from 2 to 36 nucleotides, 4 to 36 nucleotides, or from 6 to 30 nucleotides, or from 8 to 20 nucleotides, 2 to 20 nucleotides, 4 to 20 nucleotides, or from 6 to 20 nucleotides. In certain aspects, the melting temperatures of barcodes within a set are within 10° C. of one another, within 5° C. of one another, or within 2° C. of one another. In certain aspects, the melting temperatures of barcodes within a set are not within 10° C. of one another, within 5° C. of one another, or within 2° C. of one another. In other aspects, barcodes are members of a minimally cross-hybridizing set. For example, the nucleotide sequence of each member of such a set can be sufficiently different from that of every other member of the set that no member can form a stable duplex with the complement of any other member under stringent hybridization conditions. In some instances, the nucleotide sequence of each member of a minimally cross-hybridizing set differs from those of every other member by at least two nucleotides. Barcode technologies are described in Winzeler et al. (1999) Science 285:901; Brenner (2000) Genome Biol. 1:1 Kumar et al. (2001) Nature Rev. 2:302; Giaever et al. (2004) Proc. Natl. Acad. Sci. USA 101:793; Eason et al. (2004) Proc. Natl. Acad. Sci. USA 101:11046; and Brenner (2004) Genome Biol. 5:240.

As used herein, a molecular barcode comprises information that is unique to a single molecule from a single cell or from a single vessel or two or more molecules of a plurality or library of molecules from 2 or more single cells or from two or more single vessels. As used herein, a vessel barcode comprises information that is unique to polynucleotides from a single cell or from a single vessel, compared to polynucleotides from a different single cell or from a different single vessel. In some instances the unique information comprises a unique sequence of nucleotides. For example, the sequence of the molecular barcode or a vessel barcode can be determined by determining the identity and order of the unique or random sequence of nucleotides comprising the molecular barcode or a vessel barcode. In some instances the unique information cannot be used to identify the sequence of a polynucleotide. For example, a molecular barcode can be attached to one polynucleotide, but the molecular barcode cannot be used to determine the polynucleotide to which it is attached. In some instances the unique information is not a known sequence linked to the identity of the sequence of a polynucleotide. For example, a vessel barcode can be attached to one or more polynucleotides, but the vessel barcode cannot be used to determine which of the one or more polynucleotides to which it is attached. In some instances, the unique information comprises a random sequence of nucleotides. In some instances the unique information comprises one or more unique sequences of nucleotides on a polynucleotide. In some instances the unique information comprises a degenerate nucleotide sequence or degenerate barcode. A degenerate barcode can comprise a variable nucleotide base composition or sequence. For example, a degenerate bar code can be a random sequence. In some instances, a complement sequence of a molecular barcode or a vessel barcode is also a molecular barcode or a vessel barcode sequence.

A molecular barcode or vessel barcode can comprise any length of nucleotides. For example a molecular barcode or a vessel barcode can comprise at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 500, or 1000 nucleotides. For example a molecular barcode or a vessel barcode can comprise at most about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 500, or 1000 nucleotides. In some instances, a molecular barcode or a vessel barcode has a particular length of nucleotides. For example, a molecular barcode or a vessel barcode can be about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 500, or 1000 nucleotides in length.

In some instances, each molecular barcode or a vessel barcode in a plurality of molecular barcodes or vessel barcodes has at least about 2 nucleotides. For example, each molecular barcode or a vessel barcode in a plurality of molecular barcodes or vessel barcodes can be at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 500, or 1000 nucleotides in length. In some instances, each molecular barcode or a vessel barcode in a plurality of molecular barcodes or vessel barcodes can be at most about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 500, or 1000 nucleotides in length. In some instances, each molecular barcode or a vessel barcode in a plurality of molecular barcodes or vessel barcodes has the same length of nucleotides. For example, each molecular barcode or a vessel barcode in a plurality of molecular barcodes or vessel barcodes can be 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 500, or 1000 nucleotides in length. In some instances, one or more molecular barcodes or vessel barcodes in a plurality of molecular barcodes or vessel barcodes have a different length of nucleotides. For example one or more first molecular barcodes or vessel barcodes in a plurality of molecular barcodes or vessel barcodes can have about, or at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 500, or 1000 nucleotides and one or more second molecular barcodes or vessel barcodes in a plurality of molecular barcodes or vessel barcodes can have about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 500, or 1000 nucleotides, wherein the number of nucleotides of the one or more first molecular barcodes or vessel barcodes is different than the one or more second molecular barcodes or vessel barcodes.

The number of molecular barcodes can be in excess of the total number of molecules to be labeled in a plurality of vessels. The number of vessel barcodes can be in excess of the total number of molecules to be labeled in a plurality of vessels. For example, the number of molecular barcodes or vessel barcodes can be at least about 2, 3, 4, 5, 6, 7, 8, 9, 10, 15, 20, 30, 40, 50, 60, 70, 80, 90, or 100 times greater than the total number of molecules to be labeled in a plurality of vessels. The number of different molecular barcodes can be in excess of the total number of molecules to be labeled in a plurality of vessels. In some instances, the number of different molecular barcodes is at least about 1, 1.5, 2, 2.5, 3, 3.5, 4, 4.5, 5, 6, 7, 8, 9, 10, 15, 20, 30, 40, 50, 60, 70, 80, 90, or 100 times greater than the total number of molecules to be labeled in a plurality of vessels. The number of different molecular barcodes in a single vessel can be in excess of the number of different molecules to be labeled in the single vessel. In some instances, the number of different molecular barcodes in a single vessel is at least about 1, 1.5, 2, 2.5, 3, 3.5, 4, 4.5, 5, 6, 7, 8, 9, 10, 15, 20, 30, 40, 50, 60, 70, 80, 90, or 100 times greater than the number of different molecules to be labeled in the single vessel.

The number of different vessel barcodes can be less than the total number of molecules to be labeled in a plurality of vessels. In some instances, the number of different vessel barcodes is at least about 1, 1.5, 2, 2.5, 3, 3.5, 4, 4.5, 5, 6, 7, 8, 9, 10, 15, 20, 30, 40, 50, 60, 70, 80, 90, or 100 times less than the total number of molecules to be labeled in a plurality of vessels. The number of amplified product molecules from a vessel barcoded polynucleotide molecule in a single vessel can be in excess of the number of different molecules to be labeled in the single vessel. In some instances, the number of amplified product molecules from a vessel barcoded polynucleotide molecule in a single vessel is at least about 1, 1.5, 2, 2.5, 3, 3.5, 4, 4.5, 5, 6, 7, 8, 9, 10, 15, 20, 30, 40, 50, 60, 70, 80, 90, or 100 times greater than the number of different molecules to be labeled in the single vessel. The number of vessel barcoded polynucleotide molecules in a single vessel can be less than the number of different molecules to be labeled in the single vessel. In some instances, the number of vessel barcoded polynucleotide molecules in a single vessel is at least about 1, 1.5, 2, 2.5, 3, 3.5, 4, 4.5, 5, 6, 7, 8, 9, 10, 15, 20, 30, 40, 50, 60, 70, 80, 90, or 100 times less than the number of different molecules to be labeled in the single vessel. The number of vessel barcoded polynucleotide molecules in a single vessel can be one molecule. The number of unamplified vessel barcoded polynucleotide molecules in a single vessel can be one molecule.

In some instances, at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, or 100% of the different molecular barcodes have the same concentration. In some instances, at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, or 100% of the different vessel barcodes have the same concentration. In some instances, at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, or 100% of the different molecular barcodes have a different concentration. In some instances, at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, or 100% of the different vessel barcodes have a different concentration.

The molecular barcodes or vessel barcodes in a population of molecular barcodes or vessel barcodes can have at least 10, 15, 20, 25, 30, 35, 40, 45, 50, 60, 70, 80, 90, 100, 200, 300, 400, 500, 600, 700, 800, 900, 1000 or more different sequences. For example, the molecular barcodes or vessel barcodes in a population can have at least 2,000, 3,000, 4,000, 5,000, 6,000, 7,000, 8,000, 9,000, 10,000, 15,000, 20,000, 25,000, 30,000, 35,000, 40,000, 45,000, 50,000, 60,000, 70,000, 80,000, 90,000, 100,000, 200,000, 300,000, 400,000, 500,000, 600,000, 700,000, 800,000, 900, 000, 1,000,000 or more different sequences. Thus, a plurality of molecular barcodes or vessel barcodes can be used to generate at least 10, 15, 20, 25, 30, 35, 40, 45, 50, 60, 70, 80, 90, 100, 200, 300, 400, 500, 600, 700, 800, 900, 1000 or more different sequences from one or more polynucleotides, such as polynucleotides. For example, a plurality of molecular barcodes or vessel barcodes can be used to generate at least 2,000, 3,000, 4,000, 5,000, 6,000, 7,000, 8,000, 9,000, 10,000, 15,000, 20,000, 25,000, 30,000, 35,000, 40,000, 45,000, 50,000, 60,000, 70,000, 80,000, 90,000, 100,000, 200,000, 300,000, 400,000, 500,000, 600,000, 700,000, 800, 000, 900,000, $1 \times 10^6$, $2 \times 10^6$, $3 \times 10^6$, $4 \times 10^6$, $5 \times 10^6$, $6 \times 10^6$, $7 \times 10^6$, $8 \times 10^6$, $9 \times 10^6$, $1 \times 10^7$, $2 \times 10^7$, $3 \times 10^7$, $4 \times 10^7$, $5 \times 10^7$, $6 \times 10^7$, $7 \times 10^7$, $8 \times 10^7$, $9 \times 10^7$, $1 \times 10^8$, $2 \times 10^8$, $3 \times 10^8$, $4 \times 10^8$, $5 \times 10^8$, $6 \times 10^8$, $7 \times 10^8$, $8 \times 10^8$, $9 \times 10^8$, $1 \times 10^9$, $2 \times 10^9$, $3 \times 10^9$, $4 \times 10^9$, $5 \times 10^9$, $6 \times 10^9$, $7 \times 10^9$, $8 \times 10^9$, $9 \times 10^9$, $1 \times 10^{10}$, $2 \times 10^{10}$, $3 \times 10^{10}$, $4 \times 10^{10}$, $5 \times 10^{10}$, $6 \times 10^{10}$, $7 \times 10^{10}$, $8 \times 10^{10}$, $9 \times 10^{10}$, $1 \times 10^{11}$, $2 \times 10^{11}$, $3 \times 10^{11}$, $4 \times 10^{11}$, $5 \times 10^{11}$, $6 \times 10^{11}$, $7 \times 10^{11}$, $8 \times 10^{11}$, $9 \times 10^{11}$, $1 \times 10^{12}$, $2 \times 10^{12}$, $3 \times 10^{12}$, $4 \times 10^{12}$, $5 \times 10^{12}$, $6 \times 10^{12}$, $7 \times 10^{12}$, $8 \times 10^{12}$, $9 \times 10^{12}$ or more different sequences from one or more polynucleotides. For example, a plurality of molecular barcodes or vessel barcodes can be used to generate at least about 10, 15, 20, 25, 30, 35, 40, 45, 50, 60, 70, 80, 90, 100, 200, 300, 400, 500, 600, 700, 800, 900, 1000, 2000, 3000, 4000, 5000, 6000, 7000, 8000, 9000, 10,000, 15,000, 20,000, 25,000, 30,000, 35,000, 40,000, 45,000, 50,000, 60,000, 70,000, 80,000, 90,000, 100,000, 200,000, 300,000, 400,000, 500,000, 600,000, 700,000, 800,000, 900,000, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, $9\times10^{12}$ or more different sequences from at least about 10, 15, 20, 25, 30, 35, 40, 45, 50, 60, 70, 80, 90, 100, 200, 300, 400, 500, 600, 700, 800, 900, 1000, 2000, 3000, 4000, 5000, 6000, 7000, 8000, 9000, 10,000, 15,000, 20,000, 25,000, 30,000, 35,000, 40,000, 45,000, 50,000, 60,000, 70,000, 80,000, 90,000, 100,000, 200,000, 300,000, 400,000, 500,000, 600,000, 700,000, 800,000, 900,000, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, $9\times10^{12}$ or more polynucleotides.

In some instances, one or more molecular barcodes are used to group or bin sequences. In some instances, one or more molecular barcodes are used to group or bin sequences, wherein the sequences in each bin contain the same molecular barcode. In some instances, one or more molecular barcodes or vessel barcodes are used to group or bin sequences, wherein the sequences in each bin comprise an amplicon set. In some instances, one or more molecular barcodes are used to group or bin sequences, wherein the sequences in each bin comprise a plurality of sequences wherein the polynucleotides from which the plurality of sequences are generated are derived from the same polynucleotide molecule in an amplification reaction.

In some instances, one or more vessel barcodes are used to group or bin sequences. In some instances, one or more vessel barcodes are used to group or bin sequences, wherein the sequences in each bin contain the same vessel barcode. In some instances, one or more vessel barcodes are used to group or bin sequences, wherein the sequences in each bin comprise one or more amplicon sets. In some instances, one or more vessel barcodes are used to group or bin sequences, wherein the sequences in each bin comprise a plurality of sequences wherein the polynucleotides from which the plurality of sequences are generated are derived from the polynucleotides from a single vessel or single cell.

In some instances, one or more molecular barcodes and vessel barcodes are used to group or bin sequences. In some instances, one or more molecular barcodes and vessel barcodes are used to group or bin sequences, wherein the sequences in each bin contain the same molecular barcode and same vessel barcode. In some instances, one or more molecular barcodes and vessel barcodes are used to group or bin sequences, wherein the sequences in each bin comprise one or more amplicon sets. In some instances, one or more molecular barcodes and vessel barcodes are used to group or bin sequences, wherein the sequences in each bin comprise a plurality of sequences wherein the polynucleotides from which the plurality of sequences are generated are derived from the same polynucleotide in an amplification reaction and from the same single cell or vessel. In some instances, one or more molecular barcodes and vessel barcodes are not used to align sequences.

In some instances, one or more molecular barcodes are not used to align sequences. In some instances, one or more molecular barcodes are used to align sequences. In some instances, one or more molecular barcodes are used to group or bin sequences, and a target specific region is used to align sequences. In some instances, one or more vessel barcodes are not used to align sequences. In some instances, one or more vessel barcodes are used to align sequences. In some instances, one or more vessel barcodes are used to group or bin sequences, and a target specific region is used to align sequences. In some instances, one or more molecular barcodes and vessel barcodes are used to align sequences. In some instances, one or more molecular barcodes and vessel barcodes are used to group or bin sequences, and a target specific region is used to align sequences.

In some instances, the aligned sequences contain the same molecular barcode. In some instances, the aligned sequences contain the same vessel barcode. In some instances, the aligned sequences contain the same molecular barcode and vessel barcode. In some instances, one or more molecular barcodes or vessel barcodes are used align sequences, wherein the aligned sequences comprise two or more sequences from an amplicon set. In some instances, one or more molecular barcodes or vessel barcodes are used to align sequences, wherein the aligned sequences comprise a plurality of sequences wherein the polynucleotides from which the plurality of sequences are generated are derived from the same polynucleotide molecule in an amplification reaction. In some instances, one or more molecular barcodes or vessel barcodes are used to align sequences, wherein the aligned sequences comprise a plurality of sequences wherein the polynucleotides from which the plurality of sequences are generated are derived from a single cell or single vessel.

Droplet Generation

Splitting a sample of a plurality of cells into small reaction volumes, coupled with molecular and vessel barcoding of polynucleotides from, or derived from, an individual cell from the plurality of cells can enable high throughput sequencing of a repertoire of sequences, such as biomarker sequences.

Splitting a sample of a plurality of cells into small reaction volumes, coupled with molecular and vessel barcoding of polynucleotides from, or derived from, an individual cell from the plurality of cells can enable high throughput sequencing of a repertoire of sequences, such as sequences representing a percentage of the transcriptome of an organism. For example, a repertoire of sequences can comprise a plurality of sequences representing at least about 0.00001%, 0.00005%, 0.00010%, 0.00050%, 0.001%, 0.005%, 0.01%, 0.05%, 0.1%, 0.5%, 1%, 2%, 2.5%, 3%, 3.5%, 4%, 4.5%, 5%, 6%, 7%, 8%, 9%, 10%, 15%, 20%, 30%, 35%, 40%, 45, 50%, 55%, 60%, 65%, 70%, 75%, 80%, 85%, 90%, 95%, 98%, 99%, or 100% of the transcriptome of an organism.

Splitting a sample of immune cells into small reaction volumes, coupled with molecular and vessel barcoding of polynucleotides from, or derived from, an individual immune cell from the plurality of immune cells can enable high throughput sequencing of a library or repertoire of heavy and light chain sequences or TCRα an TCRβ chain sequences. These methods can also allow for pairing of the heavy and light chains or TCRα and TCRβ chains after sequencing based on the barcoded sequences. Splitting a sample into small reaction volumes as described herein can also enable the use of reduced amounts of reagents, thereby lowering the material cost of the analysis.

In some instances, the reverse transcription reaction and/or the amplification reaction (e.g., PCR) are carried out in droplets, such as in droplet digital PCR. In certain aspects, the invention provides fluidic compartments to contain all or a portion of a target material. In some instances, a compartment is droplet. While reference is made to "droplets" throughout the specification, that term is used interchangeably with fluid compartment or vessel and fluid partition unless otherwise indicated. Except where indicated otherwise, "droplet" is used for convenience and any fluid partition or compartment can be used. The droplets used herein can include emulsion compositions (or mixtures of two or more immiscible fluids), such as described in U.S. Pat. No. 7,622,280. The droplets can be generated by devices described in WO/2010/036352. The term emulsion, as used herein, can refer to a mixture of immiscible liquids (such as oil and water). Oil-phase and/or water-in-oil emulsions allow for the compartmentalization of reaction mixtures within aqueous droplets. The emulsions can comprise aqueous droplets within a continuous oil phase. The emulsions provided herein can be oil-in-water emulsions, wherein the droplets are oil droplets within a continuous aqueous phase. The droplets provided herein are designed to prevent mixing between compartments, with each compartment protecting its contents from evaporation and coalescing with the contents of other compartments.

The mixtures or emulsions described herein can be stable or unstable. The emulsions can be relatively stable and have minimal coalescence. Coalescence occurs when small droplets combine to form progressively larger ones. In some instances, less than 0.00001%, 0.00005%, 0.00010%, 0.00050%, 0.001%, 0.005%, 0.01%, 0.05%, 0.1%, 0.5%, 1%, 2%, 2.5%, 3%, 3.5%, 4%, 4.5%, 5%, 6%, 7%, 8%, 9%, or 10% of droplets generated from a droplet generator coalesce with other droplets. The emulsions can also have limited flocculation, a process by which the dispersed phase comes out of suspension in flakes.

Droplets can be generated having an average diameter of about, less than about, or more than about, or at least about 0.001, 0.01, 0.05, 0.1, 1, 5, 10, 20, 30, 40, 50, 60, 70, 80, 100, 120, 130, 140, 150, 160, 180, 200, 300, 400, or 500 microns. Droplets can have an average diameter of about 0.001 to about 500, about 0.01 to about 500, about 0.1 to about 500, about 0.1 to about 100, about 0.01 to about 100, or about 1 to about 100 microns. Microfluidic methods of producing emulsion droplets using microchannel cross-flow focusing or physical agitation are known to produce either monodisperse or polydisperse emulsions. The droplets can be monodisperse droplets. The droplets can be generated such that the size of the droplets does not vary by more than plus or minus 5% of the average size of the droplets. In some instances, the droplets are generated such that the size of the droplets does not vary by more than plus or minus 2% of the average size of the droplets. A droplet generator can generate a population of droplets from a single sample, wherein none of the droplets vary in size by more than plus or minus about 0.1%, 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10% of the average size of the total population of droplets.

Higher mechanical stability can be useful for microfluidic manipulations and higher-shear fluidic processing (e.g., in microfluidic capillaries or through 90 degree turns, such as valves, in fluidic path). Pre- and post-thermally treated droplets or capsules can be mechanically stable to standard pipet manipulations and centrifugation.

A droplet can be formed by flowing an oil phase through an aqueous sample. The aqueous phase can comprise a buffered solution and reagents for performing an amplification reaction, including cells, nucleotides, nucleotide analogues, molecular barcoded polynucleotides, vessel barcoded polynucleotides primers, template nucleic acids, and enzymes, such as a DNA polymerase, RNA polymerase, and/or reverse transcriptase.

The aqueous phase can comprise a buffered solution and reagents for performing an amplification reaction with or without a solid surface, such as a bead. The buffered solution can comprise about, more than about, or less than about 1, 5, 10, 15, 20, 30, 50, 100, or 200 mM Tris. In some instances, the concentration of potassium chloride can be about, more than about, or less than about 10, 20, 30, 40, 50, 60, 80, 100, 200 mM. The buffered solution can comprise about 15 mM Tris and 50 mM KCl. The nucleotides can comprise deoxyribonucleotide triphosphate molecules, including dATP, dCTP, dGTP, and dTTP, in concentrations of about, more than about, or less than about 50, 100, 200, 300, 400, 500, 600, or 700 µm each. In some instances dUTP is added within the aqueous phase to a concentration of about, more than about, or less than about 50, 100, 200, 300, 400, 500, 600, or 700, 800, 900, or 1000 µm. In some instances, magnesium chloride or magnesium acetate ($MgCl_2$) is added to the aqueous phase at a concentration of about, more than about, or less than about 1.0, 2.0, 3.0, 4.0, or 5.0 mM. In some instances, magnesium acetate or magnesium is used. In some instances, magnesium sulfate is used.

A non-specific blocking agent such as BSA or gelatin from bovine skin can be used, wherein the gelatin or BSA is present in a concentration range of approximately 0.1-1% w/v. Other possible blocking agents can include betalactoglobulin, casein, dry milk, or other common blocking agents. In some instances, preferred concentrations of BSA and gelatin are about 0.1% w/v.

Primers for amplification within the aqueous phase can have a concentration of about, more than about, or less than about 0.05, 0.1, 0.2, 0.3, 0.4, 0.5, 0.6, 0.7, 0.8, 0.9, 1.0, 1.2, 1.5, 1.7, or 2.0 µm. Primer concentration within the aqueous phase can be about 0.05 to about 2, about 0.1 to about 1.0, about 0.2 to about 1.0, about 0.3 to about 1.0, about 0.4 to about 1.0, or about 0.5 to about 1.0 µm. The concentration of primers can be about 0.5 µm. Amenable ranges for nucleic acid concentrations in PCR include, but are not limited to from about 1 pg and about 500 ng.

In some instances, the aqueous phase can also comprise additives including, but not limited to, non-specific background/blocking nucleic acids (e.g., salmon sperm DNA), biopreservatives (e.g. sodium azide), PCR enhancers (e.g. Betaine, Trehalose, etc.), and inhibitors (e.g. RNAse inhibitors). Other additives can include, e.g., dimethyl sulfoxide (DMSO), glycerol, betaine (mono)hydrate (N,N,N-trimethylglycine=[caroxy-methyl] trimethylammonium), trehalose, 7-Deaza-2'-deoxyguanosine triphosphate (dC7GTP or 7-deaza-2'-dGTP), BSA (bovine serum albumin), formamide (methanamide), tetramethylammonium chloride (TMAC), other tetraalkylammonium derivatives (e.g., tetraethyammonium chloride (TEA-Cl) and tetrapropylammonium chloride (TPrA-Cl), non-ionic detergent (e.g., Triton X-100, Tween 20, Nonidet P-40 (NP-40)), or PREXCEL-Q. In some instances, the aqueous phase can comprise 0, 1, 2, 3, 4, 5, 6, 7, 8, 9, or 10 different additives. In other instances, the aqueous phase can comprise at least 0, 1, 2, 3, 4, 5, 6, 7, 8, 9, or 10 different additives.

In some instances, a non-ionic Ethylene Oxide/Propylene Oxide block copolymer can be added to the aqueous phase in a concentration of about 0.1%, 0.2%, 0.3%, 0.4%, 0.5%, 0.6%, 0.7%, 0.8%, 0.9%, or 1.0%. Common biosurfactants include non-ionic surfactants such as Pluronic F-68, Tetronics, Zonyl FSN. Pluronic F-68 can be present at a concentration of about 0.5% w/v.

In some instances magnesium sulfate can be substituted for magnesium chloride, at similar concentrations. A wide range of common, commercial PCR buffers from varied vendors can be substituted for the buffered solution.

The emulsion can be formulated to produce highly monodisperse droplets having a liquid-like interfacial film that can be converted by heating into microcapsules having a solid-like interfacial film; such microcapsules can behave as bioreactors able to retain their contents through a reaction process such as PCR amplification. The conversion to microcapsule form can occur upon heating. For example, such conversion can occur at a temperature of greater than about 50° C., 60° C., 70° C., 80° C., 90° C., or 95° C. In some instances this heating occurs using a thermocycler. During the heating process, a fluid or mineral oil overlay can be used to prevent evaporation. Excess continuous phase oil can or cannot be removed prior to heating. The biocompatible capsules can be resistant to coalescence and/or flocculation across a wide range of thermal and mechanical processing. Following conversion, the capsules can be stored at about, more than about, or less than about 3° C., 4° C., 5° C., 6° C., 7° C., 8° C., 9° C. 10° C., 15° C., 20° C., 25° C., 30° C., 35° C., or 40° C.

The microcapsules can contain one or more polynucleotides and can resist coalescence, particularly at high temperatures. Accordingly, PCR amplification reactions can occur at a very high density (e.g., number of reactions per unit volume). In some instances, greater than 100,000, 500,000, 1,000,000, 1,500,000, 2,000,000, 2,500,000, 5,000,000, or 10,000,000 separate reactions can occur per ml. In some instances, the reactions occur in a single well, e.g., a well of a microtiter plate, without inter-mixing between reaction volumes. The microcapsules can also contain other components necessary to enable a reverse transcription, primer extension, and/or PCR reaction to occur, e.g., primers, probes, dNTPs, DNA or RNA polymerases, etc. These capsules exhibit resistance to coalescence and flocculation across a wide range of thermal and mechanical processing.

In some instances, the amplifying step is carried out by performing digital PCR, such as microfluidic-based digital PCR or droplet digital PCR.

Droplets can be generated using microfluidic systems or devices. As used herein, the "micro-" prefix (for example, as "microchannel" or "microfluidic"), generally refers to elements or articles having widths or diameters of less than about 1 mm, and less than about 100 microns (micrometers) in some instances. In some instances, the element or article includes a channel through which a fluid can flow. Additionally, "microfluidic", as used herein, refers to a device, apparatus or system that includes at least one microscale channel.

Microfluidic systems and devices have been described in a variety of contexts, typically in the context of miniaturized laboratory (e.g., clinical) analysis. Other uses have been described as well. For example, International Patent Application Publication Nos. WO2001/89788; WO2006/040551; WO2006/040554; WO2004/002627; WO 2008/063227; WO2004/091763; WO2005/021151; WO2006/096571; WO2007/089541; WO2007/081385 and WO2008/063227.

A droplet generally includes an amount of a first sample fluid in a second carrier fluid. Any technique known in the art for forming droplets can be used with methods of the invention. An exemplary method comprises flowing a stream of the sample fluid containing the target material (e.g., immune cell) such that it intersects two opposing streams of flowing carrier fluid. The carrier fluid is immiscible with the sample fluid. Intersection of the sample fluid with the two opposing streams of flowing carrier fluid results in partitioning of the sample fluid into individual sample droplets containing the target material.

The carrier fluid can be any fluid that is immiscible with the sample fluid. An exemplary carrier fluid is oil. In certain instances, the carrier fluid includes a surfactant.

The same method can be applied to create individual droplets that contain other reagents such as reagents for an amplification reaction such as a polymerase chain reaction (PCR), or a non-PCR based amplification reaction such as multi-strand displacement amplification, or other methods known to one of ordinary skill in the art. Suitable reagents for conducting PCR-based amplification reactions are known to those of ordinary skill in the art and include, but are not limited to, DNA polymerases, forward and reverse primers, deoxyribonucleotide triphosphates (dNTPs), and one or more buffers.

In certain instances, fluidic compartments are formed by providing one or more of a first fluid partition (e.g., a droplet) comprising a target material (e.g., an immune cell and/or a solid support such as a bead) and a second fluid (e.g., as a fluid stream or within droplets). The first and second fluids are merged to form a droplet. Merging can be accomplished by application of an electric field to the two fluids. In certain instances, the second fluid contains reagents for conducting an amplification reaction, such as a polymerase chain reaction or an amplification reaction.

Reverse Transcription

In some instances, polynucleotides for sequencing are prepared from RNA by reverse transcription. In some instances, polynucleotides for sequencing are prepared from DNA by primer extension, such as using a polymerase.

The methods described herein can be used in coupled reverse transcription-PCR (reverse transcription-PCR). For example, reverse transcription and PCR can be carried out in two distinct steps. For example, a cDNA copy of the sample mRNA can be synthesized using either a polynucleotide dT primer, a sequence specific primer, a universal primer, or any primer described herein.

Reverse transcription and PCR can be carried out in a single closed vessel reaction. For example, three primers can be employed, one for reverse transcription and two for PCR. The primer for reverse transcription can bind to the mRNA 3' to the position of the PCR amplicon. Although not essential, the reverse transcription primer can include RNA residues or modified analogs such as 2'-O-methyl RNA bases, which will not form a substrate for RNase H when hybridized to the mRNA.

The temperature to carry out the reverse transcription reaction depends on the reverse transcriptase being used. In some instances, a thermostable reverse transcriptase is used and the reverse transcription reaction is carried out at about 37° C. to about 75° C., at about 37° C. to about 50° C., at about 37° C. to about 55° C., at about 37° C. to about 60° C., at about 55° C. to about 75° C., at about 55° C. to about 60° C., at about 37° C., or at about 60° C. In some instances, a reverse transcriptase that transfers 3 or more non-template terminal nucleotides to an end of the transcribed product is used.

A reverse transcription reaction and the PCR reaction described herein can be carried out in various formats known in the art, such as in tubes, microtiter plates, microfluidic devices, or, preferably, droplets.

A reverse transcription reaction can be carried out in volumes ranging from 5 µL to 100 or in 10 µL to 20 µL reaction volumes. In droplets, reaction volumes can range from 1 pL to 100 nL or 10 pL to 1 nL. In some instances, the reverse transcription reaction is carried out in a droplet having a volume that is about or less than 1 nL. In some instances, a PCR reaction is in a droplet having a reaction volume ranges from 1 pL to 100 nL preferably 10 pL to 1 nL. In some instances, the PCR reaction is carried out in a droplet having a volume that is about or less than 1 nL. In some instances, a reverse transcription reaction and a PCR reaction are carried out in the same droplet having a reaction volume ranges from 1 pL to 100 nL or 10 pL to 1 nL. In some instances, the reverse transcription reaction and the PCR reaction are carried out in a droplet having a volume that is about or less than 1 nL or a volume that is about or less than 1 pL. In some instances, a reverse transcription reaction and a PCR reaction are carried out in a different droplet. In some instances, a reverse transcription reaction and a PCR reaction are carried out in a plurality of droplets each having a reaction volume ranges from 1 pL to 100 nL or 10 pL to 1 nL. In some instances, the reverse transcription reaction and the PCR reaction are carried out in a plurality of droplets each having a volume that is about or less than 1 nL.

In some instances, a first PCR reaction is in a first droplet having a reaction volume ranges from 1 pL to 100 nL preferably 10 pL to 1 nL and a second PCR reaction is in a second droplet having a reaction volume ranges from 1 pL to 100 nL preferably 10 pL to 1 nL. In some instances, a first PCR reaction is in a first droplet having a volume that is about or less than 1 nL, and a second PCR reaction is in a second droplet having a volume that is about or less than 1 nL.

In some instances, a first PCR reaction and a second PCR reaction are carried out in a plurality of droplets each having a reaction volume ranges from 1 pL to 100 nL or 10 pL to 1 nL. In some instances, a first PCR reaction and a second PCR reaction are carried out in a plurality of droplets each having a volume that is about or less than 1 nL.

RNA can be reverse transcribed into cDNA using one or more reverse transcription primers. The one or more reverse transcription primers can comprise a region complementary to a region of the RNA, such as a constant region (e.g., a heavy or light chain constant region or a poly-A tail of mRNA). In some instances, the reverse transcription primers can comprise a first reverse transcription primer with a region complementary to a constant region of a first RNA, and a second reverse transcription primer with a region complementary to a constant region of a second RNA. In some instances, the reverse transcription primers can comprise a first reverse transcription primer with a region complementary to a constant region of a first RNA, and one or more reverse transcription primers with a region complementary to a constant region of one or more RNAs, respectively.

In some instances, reverse transcription primers do not comprise a barcode. In some instances, reverse transcription primers do comprise a barcode.

Reverse transcription primers can further comprise a region that is not complementary to a region of the RNA. In some instances, the region that is not complementary to a region of the RNA is 5' to a region of the primers that is complementary to the RNA. In some instances, the region that is not complementary to a region of the RNA is 3' to a region of the primers that is complementary to the RNA. In some instances, the region that is not complementary to a region of the RNA is a 5' overhang region. In some instances, the region that is not complementary to a region of the RNA comprises a priming site for amplification and/or a sequencing reaction. In some instances cDNA molecules can be barcoded with a molecular barcode and a vessel barcode and amplified by one or more PCR reactions, such as a first and/or a second PCR reaction. The first and/or second PCR reaction can utilize a pair of primers or a plurality of primer pairs. The first and/or second PCR reaction can utilize a plurality of forward/reverse primers and a reverse primer. The first and/or second PCR reaction can utilize a plurality of forward/reverse primers and a forward primer. A first and/or second primer of a plurality of forward/reverse primers can be a forward/reverse primer containing a region complementary to the cDNA molecules or barcoded cDNA molecules. A first and/or second primer of a plurality of forward/reverse primers can be a forward/reverse primer containing a region complementary to the barcoded cDNA molecules.

In some instances, a plurality of forward/reverse primers comprises one or more forward/reverse primers wherein each of the forward/reverse primers in the plurality of forward/reverse primers comprises a region complementary to one or more upstream or downstream regions to a V segment of the cDNAs or barcoded cDNAs. For example, a plurality of forward/reverse primers comprises a forward/reverse primer comprising a region complementary to a upstream or downstream region to a V segment of the cDNAs or barcoded cDNAs and one or more other forward/reverse primers comprising a region complementary to one or more other upstream or downstream regions to a V segment of the cDNAs or barcoded cDNAs. For example, a plurality of forward/reverse primers comprises a first and/or second forward/reverse primer comprising a region complementary to a first and/or second upstream or downstream region to a V segment of the cDNAs or barcoded cDNAs and a second forward/reverse primer comprising a region complementary to a second upstream or downstream region to a V segment of the cDNAs or barcoded cDNAs. For example, a plurality of forward/reverse primers comprises a first and/or second forward/reverse primer comprising a region complementary to a first and/or second upstream or downstream region to a V segment of the cDNAs or barcoded cDNAs, a second forward/reverse primer comprising a region complementary to a second upstream or downstream region to a V segment of the cDNAs or barcoded cDNAs, and a third forward/reverse primer comprising a region complementary to a third upstream or downstream region to a V segment of the cDNAs or barcoded cDNAs, etc. The primers in the plurality of forward/reverse primers can be used to anneal to all possible upstream or downstream regions of all V segments expressed by the cells, such as immune cells, e.g., B-cells and T-cells, in the sample.

In some instances, a plurality of forward/reverse primers comprises one or more forward/reverse primers wherein each of the forward/reverse primers in the plurality of forward/reverse primers comprises a region complementary to one or more upstream or downstream regions to a C segment of the cDNAs or barcoded cDNAs. For example, a plurality of forward/reverse primers comprises a forward/reverse primer comprising a region complementary to a upstream or downstream region to a C segment of the cDNAs or barcoded cDNAs and one or more other forward/reverse primers comprising a region complementary to one or more other upstream or downstream regions to a C segment of the cDNAs or barcoded cDNAs. For example, a plurality of forward/reverse primers comprises a first and/or second forward/reverse primer comprising a region complementary to a first and/or second upstream or downstream region to a C segment of the cDNAs or barcoded cDNAs and a second forward/reverse primer comprising a region complementary to a second upstream or downstream region to a C segment of the cDNAs or barcoded cDNAs. For example, a plurality of forward/reverse primers comprises a first and/or second forward/reverse primer comprising a region complementary to a first and/or second upstream or downstream region to a C segment of the cDNAs or barcoded cDNAs, a second forward/reverse primer comprising a region complementary to a second upstream or downstream region to a C segment of the cDNAs or barcoded cDNAs, and a third forward/reverse primer comprising a region complementary to a third upstream or downstream region to a C segment of the cDNAs or barcoded cDNAs, etc. The primers in the plurality of forward/reverse primers can be used to anneal to all possible upstream or downstream regions of all C segments expressed by the cells, such as immune cells, e.g., B-cells and, in the sample.

In some instances, a plurality of forward/reverse primers comprises one or more forward/reverse primers wherein each of the forward/reverse primers in the plurality of forward/reverse primers comprises a region complementary to one or more upstream or downstream regions to a molecular barcode of the barcoded cDNAs. For example, a plurality of forward/reverse primers comprises a forward/reverse primer comprising a region complementary to a upstream or downstream region to a molecular barcode of the barcoded cDNAs and one or more other forward/reverse primers comprising a region complementary to one or more other upstream or downstream regions to a molecular barcode of the barcoded cDNAs. For example, a plurality of forward/reverse primers comprises a first and/or second forward/reverse primer comprising a region complementary to a first and/or second upstream or downstream region to a molecular barcode of the barcoded cDNAs and a second forward/reverse primer comprising a region complementary to a second upstream or downstream region to a molecular barcode of the barcoded cDNAs. For example, a plurality of forward/reverse primers comprises a first and/or second forward/reverse primer comprising a region complementary to a first and/or second upstream or downstream region to a molecular barcode of the barcoded cDNAs, a second forward/reverse primer comprising a region complementary to a second upstream or downstream region to a molecular barcode of the barcoded cDNAs, and a third forward/reverse primer comprising a region complementary to a third upstream or downstream region to a molecular barcode of the barcoded cDNAs, etc. The primers in the plurality of forward/reverse primers can be used to anneal to all possible upstream or downstream regions of all molecular barcodes expressed by the cells, such as immune cells, e.g., B-cells and T-cells, in the sample.

In some instances, a plurality of forward/reverse primers comprises one or more forward/reverse primers wherein each of the forward/reverse primers in the plurality of forward/reverse primers comprises a region complementary to one or more upstream or downstream regions to a vessel barcode of the barcoded cDNAs. For example, a plurality of forward/reverse primers comprises a forward/reverse primer comprising a region complementary to a upstream or downstream region to a vessel barcode of the barcoded cDNAs and one or more other forward/reverse primers comprising a region complementary to one or more other upstream or downstream regions to a vessel barcode of the barcoded cDNAs. For example, a plurality of forward/reverse primers comprises a first and/or second forward/reverse primer comprising a region complementary to a first and/or second upstream or downstream region to a vessel barcode of the barcoded cDNAs and a second forward/reverse primer comprising a region complementary to a second upstream or downstream region to a vessel barcode of the barcoded cDNAs. For example, a plurality of forward/reverse primers comprises a first and/or second forward/reverse primer comprising a region complementary to a first and/or second upstream or downstream region to a vessel barcode of the barcoded cDNAs, a second forward/reverse primer comprising a region complementary to a second upstream or downstream region to a vessel barcode of the barcoded cDNAs, and a third forward/reverse primer comprising a region complementary to a third upstream or downstream region to a vessel barcode of the barcoded cDNAs, etc. The primers in the plurality of forward/reverse primers can be used to anneal to all possible upstream or downstream regions of all vessel barcodes expressed by the cells, such as immune cells, e.g., B-cells and T-cells, in the sample.

The forward/reverse primers in the plurality of forward/reverse primers further comprise a region that is not complementary to a region of the RNA. In some instances, the region that is not complementary to a region of the RNA is 5' to a region of the forward/reverse primers that is complementary to the RNA (i.e. an upstream or downstream region of a V segment). In some instances, the region that is not complementary to a region of the RNA is 3' to a region of the forward/reverse primers that is complementary to the RNA. In some instances, the region that is not complementary to a region of the RNA is a 5' overhang region. In some instances, the region that is not complementary to a region of the RNA comprises a priming site for amplification and/or a second sequencing reaction. In some instances, the region that is not complementary to a region of the RNA comprises a priming site for amplification and/or a third sequencing reaction. In some instances, the region that is not complementary to a region of the RNA comprises a priming site for a second and a third sequencing reaction. In some instances, the sequence of the priming site for the second and the third sequencing reaction are the same. Using the one or more forward/reverse primers and a reverse primer as described herein, the cDNA molecules are amplified using suitable reagents known in the art. In some instances, a region is complementary to a region of the RNA, such as the constant region or a poly-A tail of mRNA.

Amplification

Thermocycling reactions can be performed on samples contained in reaction volumes (e.g., droplets). Any DNA polymerase that catalyzes primer extension can be used, including but not limited to E. coli DNA polymerase, Klenow fragment of E. coli DNA polymerase 1, T7 DNA polymerase, T4 DNA polymerase, Taq polymerase, Pfu DNA polymerase, Vent DNA polymerase, bacteriophage 29, REDTaq™, Genomic DNA polymerase, or sequenase. In some instances, a thermostable DNA polymerase is used. A hot start PCR can also be performed wherein the reaction is heated to 95° C. for two minutes prior to addition of the polymerase or the polymerase can be kept inactive until the first heating step in cycle 1. Hot start PCR can be used to minimize nonspecific amplification. Any number of PCR cycles can be used to amplify the DNA, e.g., about, more than about, or less than about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45 cycles. The number of amplification cycles can be about 1-45, 10-45, 20-45, 30-45, 35-45, 10-40, 10-30, 10-25, 10-20, 10-15, 20-35, 25-35, 30-35, or 35-40.

Amplification of nucleic acids can be performed by any means known in the art. Nucleic acids can be amplified by polymerase chain reaction (PCR) or isothermal DNA amplification. Examples of PCR techniques that can be used include, but are not limited to, quantitative PCR, quantitative fluorescent PCR (QF-PCR), multiplex fluorescent PCR (MF-PCR), real time PCR (reverse transcription-PCR), single cell PCR, restriction fragment length polymorphism PCR (PCR-RFLP), PCR-RFLP/reverse transcription-PCR-RFLP, hot start PCR, nested PCR, in situ polony PCR, in situ rolling circle amplification (RCA), digital PCR (dPCR), droplet digital PCR (ddPCR), bridge PCR, PicoTiter PCR and emulsion PCR. Other suitable amplification methods include the ligase chain reaction (LCR), transcription amplification, molecular inversion probe (MIP) PCR, self-sustained sequence replication, selective amplification of polynucleotide sequences, consensus sequence primed polymerase chain reaction (CP-PCR), arbitrarily primed polymerase chain reaction (AP-PCR), degenerate polynucleotide-primed PCR (DOP-PCR) and nucleic acid based sequence amplification (NABSA). Other amplification methods that can be used herein include those described in U.S. Pat. Nos. 5,242,794; 5,494,810; 4,988,617; and 6,582,938, as well as include Q beta replicase mediated RNA amplification. Amplification can be isothermal amplification, e.g., isothermal linear amplification.

In some instances, amplification does not occur on a solid support. In some instances, amplification does not occur on a solid support in a droplet. In some instances, amplification does occur on a solid support when the amplification is not in a droplet.

An amplification reaction can comprise one or more additives. In some instances, the one or more additives are dimethyl sulfoxide (DMSO), glycerol, betaine (mono)hydrate (N,N,N-trimethylglycine=[caroxy-methyl] trimethylammonium), trehalose, 7-Deaza-2'-deoxyguanosine triphosphate (dC7GTP or 7-deaza-2'-dGTP), BSA (bovine serum albumin), formamide (methanamide), tetramethylammonium chloride (TMAC), other tetraalkylammonium derivatives (e.g., tetraethyammonium chloride (TEA-Cl) and tetrapropylammonium chloride (TPrA-Cl), non-ionic detergent (e.g., Triton X-100, Tween 20, Nonidet P-40 (NP-40)), or PREXCEL-Q. In some instances, an amplification reaction can comprise 0, 1, 2, 3, 4, 5, 6, 7, 8, 9, or 10 different additives. In other instances, an amplification reaction can comprise at least 0, 1, 2, 3, 4, 5, 6, 7, 8, 9, or 10 different additives.

Primers

One or more pairs of primers can be used in a amplification reaction; one primer of a primer pair can be a forward primer and one primer of a primer pair can be a reverse primer.

In some instances, a first pair of primers can be used in the amplification reaction; one primer of the first pair can be a forward primer complementary to a sequence of a first polynucleotide molecule and one primer of the first pair can be reverse primer can be complementary to a second sequence of the first polynucleotide molecule, and a first locus can reside between the first sequence and the second sequence. In some instances, the first locus comprises a $V_H$ sequence. In some instances, the second locus comprises a Vα sequence. In some instances, the second locus comprises a Vγ sequence.

In some instances, a second pair of primers can be used in the amplification reaction; one primer of the second pair can be a forward primer complementary to a first sequence of a second polynucleotide molecule and one primer of the second pair can be a reverse primer complementary to a second sequence of the second polynucleotide molecule, and a second locus can reside between the first sequence and the second sequence. In some instances, the second locus comprises a $V_L$ sequence. In some instances, the second locus comprises a Vβ sequence. In some instances, the second locus comprises a Vδ sequence.

In some instances, a third pair of primers can be used in the amplification reaction; one primer of the third pair can be a forward primer complementary to a first sequence of a third polynucleotide molecule and one primer of the third pair can be a reverse primer complementary to a second sequence of the third polynucleotide molecule, and a third locus can reside between the first sequence and the second sequence. In some instances, the third locus comprises a barcode, such as a molecular barcode or vessel barcode.

The length of the forward primer and the reverse primer can depend on the sequence of the polynucleotide and the locus. For example, the length and/or $T_M$ of the forward primer and reverse primer can be optimized. In some case, a primer can be about, more than about, or less than about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 nucleotides in length. In some instances, a primer is about 15 to about 20, about 15 to about 25, about 15 to about 30, about 15 to about 40, about 15 to about 45, about 15 to about 50, about 15 to about 55, about 15 to about 60, about 20 to about 25, about 20 to about 30, about 20 to about 35, about 20 to about 40, about 20 to about 45, about 20 to about 50, about 20 to about 55, or about 20 to about 60 nucleotides in length.

A primer can be a single-stranded DNA prior to binding a polynucleotide. In some instances, the primer initially comprises double-stranded sequence. Short primer molecules can generally require cooler temperatures to form sufficiently stable hybrid complexes with a polynucleotide. In some instances, a primer need not reflect the exact sequence of the polynucleotide, but can be sufficiently complementary to hybridize with the polynucleotide. In some instances, a primer can be partially double-stranded before binding to a polynucleotide. A primer with double-stranded sequence can have a hairpin loop of about, more than about, or less than about 3, 4, 5, 6, 7, 8, 9, 10, 11, 12, 13, 14, 15, 16, 17, 18, 19, or 20 bases. A double stranded portion of a primer can be about, more than about, less than about, or at least about 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 base-pairs. The design of suitable primers for the amplification of a given polynucleotide is well known in the art.

Primers can incorporate additional features that allow for the detection or immobilization of the primer but do not alter a basic property of the primer (e.g., acting as a point of initiation of DNA synthesis). For example, primers can contain an additional nucleic acid sequence at the 5' end which does not hybridize to a nucleic acid, but which facilitates cloning or further amplification, or sequencing of an amplified product. For example, the additional sequence can comprise a primer binding site, such as a universal primer binding site. A region of the primer which is sufficiently complementary to a polynucleotide to hybridize can be referred to herein as a hybridizing region.

In another case, a primer utilized in methods and compositions described herein can comprise one or more universal nucleosides. Non-limiting examples of universal nucleosides are 5-nitroindole and inosine, as described in U.S. Pub. Nos. 20090325169 and 20100167353.

Primers can be designed according to known parameters for avoiding secondary structures and self-hybridization. Different primer pairs can anneal and melt at about the same temperatures, for example, within 1° C., 2° C., 3° C., 4° C., 5° C., 6° C., 7° C., 8° C., 9° C. or 10° C. of another primer pair. In some instances, greater than 1, 2, 3, 4, 5, 6, 7, 8, 9, 10, 15, 20, 25, 30, 35, 40, 45, 50, 100, 200, 500, 1000, 5000, 10,000 or more primers are used.

Primers can be prepared by a variety of methods including but not limited to cloning of appropriate sequences and direct chemical synthesis using methods well known in the art (Narang et al., Methods Enzymol. 68:90 (1979); Brown et al., Methods Enzymol. 68:109 (1979)). Primers can also be obtained from commercial sources. The primers can have an identical melting temperature. The primers can have non-identical melting temperatures. The lengths of the primers can be extended or shortened at the 5' end or the 3' end to produce primers with desired melting temperatures. One of the primers of a primer pair can be longer than the other primer. The 3' annealing lengths of the primers, within a primer pair, can differ. Also, the annealing position of each primer pair can be designed such that the sequence and length of the primer pairs yield the desired melting temperature. An equation for determining the melting temperature of primers smaller than 25 base pairs is the Wallace Rule ($T_d=2(A+T)+4(G+C)$). Computer programs can also be used to design primers. The Tm (melting or annealing temperature) of each primer can be calculated using software programs. The annealing temperature of the primers can be recalculated and increased after any cycle of amplification, including but not limited to cycle 1, 2, 3, 4, 5, cycles 6-10, cycles 10-15, cycles 15-20, cycles 20-25, cycles 25-30, cycles 30-35, or cycles 35-40. After the initial cycles of amplification, the 5' half of the primers can be incorporated into the products from each loci of interest; thus the $T_m$ can be recalculated based on both the sequences of the 5' half and the 3' half of each primer.

Conducting the one or more reactions of the methods disclosed herein can comprise the use of one or more primers. As used herein, a primer comprises a double-stranded, single-stranded, or partially single-stranded polynucleotide that is sufficiently complementary to hybridize to a polynucleotide. A primer can be a single-stranded DNA prior to binding a polynucleotide. In some instances, the primer initially comprises double-stranded sequence. A primer site includes the area of the polynucleotide to which a primer hybridizes. In some instances, primers are capable of acting as a point of initiation for template-directed nucleic acid synthesis. For example, primers can initiate template-directed nucleic acid synthesis when four different nucleotides and a polymerization agent or enzyme, such as DNA or RNA polymerase or reverse transcriptase. A primer pair includes 2 primers: a first primer with a 5' upstream region that hybridizes with a 5' end of a sequence, and a second primer with a 3' downstream region that hybridizes with the complement of the 3' end of the polynucleotide sequence. A primer set includes 2 or more primers: a first primer or first plurality of primers with a 5' upstream region that hybridizes with a 5' end of a polynucleotide sequence or plurality of polynucleotide sequences, and a second primer or second plurality of primers with a 3' downstream region that hybridizes with the complement of the 3' end of the polynucleotide sequence or plurality of polynucleotide sequences. In some instances, a primer comprises a target specific sequence. In some instances, a primer comprises a sample barcode sequence. In some instances, a primer comprises a universal priming sequence. In some instances, a primer comprises a PCR priming sequence. In some instances, a primer comprises a PCR priming sequence used to initiate amplification of a polynucleotide. (Dieffenbach, PCR Primer: A Laboratory Manual, 2nd Edition (Cold Spring Harbor Press, New York (2003)). The universal primer binding site or sequence allows the attachment of a universal primer to a polynucleotide and/or amplicon. Universal primers are well known in the art and include, but are not limited to, −47F (M13F), alfaMF, AOX3', AOX5', BGHr, CMV-30, CMV-50, CVMf, LACrmt, lamgda gt10F, lambda gt 10R, lambda gt11F, lambda gt11R, M13 rev, M13Forward (−20), M13Reverse, male, p10SEQPpQE, pA-120, pet4, pGAP Forward, pGLRVpr3, pGLpr2R, pKLAC14, pQEFS, pQERS, pucU1, pucU2, reversA, seqIREStam, seqIRESzpet, seqori, seqPCR, seqpIRES−, seqpIRES+, seqpSecTag, seqpSecTag+, seqretro+PSI, SP6, T3-prom, T7-prom, and T7-termInv. As used herein, attach can refer to both or either covalent interactions and noncovalent interactions. Attachment of the universal primer to the universal primer binding site can be used for amplification, detection, and/or sequencing of the polynucleotide and/or amplicon. The universal primer binding site can comprise at least about 1, 2, 3, 4, 5, 6, 7, 8, 9, 10, 11, 12, 13, 14, 15, 16, 17, 18, 19, 20, 30, 40, 50, 60, 70, 80, 90, 100, 200, 300, 400, 500, 600, 700, 800, 900, or 1000 nucleotides or base pairs. In another example, the universal primer binding site comprises at least about 1500, 2000, 2500, 3000, 3500, 4000, 4500, 5000, 5500, 6000, 6500, 7000, 7500, 8000, 8500, 9000, 9500, or 10000 nucleotides or base pairs. In some instances, the universal primer binding site comprises 1-10, 10-20, 10-30 or 10-100 nucleotides or base pairs. In some instances, the universal primer binding site comprises from about 1-90, 1-80, 1-70, 1-60, 1-50, 1-40, 1-30, 1-20, 1-10, 2-90, 2-80, 2-70, 2-60, 2-50, 2-40, 2-30, 2-20, 2-10, 1-900, 1-800, 1-700, 1-600, 1-500, 1-400, 1-300, 1-200, 1-100, 2-900, 2-800, 2-700, 2-600, 2-500, 2-400, 2-300, 2-200, 2-100, 5-90, 5-80, 5-70, 5-60, 5-50, 5-40, 5-30, 5-20, 5-10, 10-90, 10-80, 10-70, 10-60, 10-50, 10-40, 10-30, 10-20, 10-10, 5-900, 5-800, 5-700, 5-600, 5-500, 5-400, 5-300, 5-200, 5-100, 10-900, 10-800, 10-700, 10-600, 10-500, 10-400, 10-300, 10-200, 10-100, 25-900, 25-800, 25-700, 25-600, 25-500, 25-400, 25-300, 25-200, 25-100, 100-1000, 100-900, 100-800, 100-700, 100-600, 100-500, 100-400, 100-300, 100-200, 200-1000, 200-900, 200-800, 200-700, 200-600, 200-500, 200-400, 200-300, 300-1000, 300-900, 300-800, 300-700, 300-600, 300-500, 300-400, 400-1000, 400-900, 400-800, 400-700, 400-600, 400-500, 500-1000, 500-900, 500-800, 500-700, 500-600, 600-1000, 600-900, 600-800, 600-700, 700-1000, 700-900, 700-800, 800-1000, 800-900, or 900-1000 nucleotides or base pairs.

The one or more primers can anneal to at least a portion of a plurality of polynucleotides. The one or more primers can anneal to the 3' end and/or 5' end of the plurality of polynucleotides. The one or more primers can anneal to an internal region of the plurality of polynucleotides. The internal region can be at least about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 150, 200, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 650, 700, 750, 800, 850, 900 or 1000 nucleotides from the 3' ends or 5' ends the plurality of polynucleotides. The one or more primers can comprise a fixed panel of primers. The one or more primers can comprise at least one or more custom primers. The one or more primers can comprise at least one or more control primers. The one or more primers can comprise at least one or more housekeeping gene primers. The one or more primers can comprise a universal primer. The universal primer can anneal to a universal primer binding site. In some instances, the one or more custom primers anneal to a specific region, complements thereof, or any combination thereof. The one or more primers can comprise a universal primer. The one or more primers primer can be designed to amplify or perform primer extension, reverse transcription, linear extension, non-exponential amplification, exponential amplification, PCR, or any other amplification method of one or more polynucleotides A specific region of a polynucleotide that a primer binds to can comprise at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 150, 200, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 650, 700, 750, 800, 850, 900 or 1000 nucleotides or base pairs. In another example, the target specific region comprises at least about 1500, 2000, 2500, 3000, 3500, 4000, 4500, 5000, 5500, 6000, 6500, 7000, 7500, 8000, 8500, 9000, 9500, or 10000 nucleotides or base pairs. In some instances, the target specific region of a polynucleotide that a primer binds to comprises from about 5-10, 10-15, 10-20, 10-30, 15-30, 10-75, 15-60, 15-40, 18-30, 20-40, 21-50, 22-45, 25-40, 7-9, 12-15, 15-20, 15-25, 15-30, 15-45, 15-50, 15-55, 15-60, 20-25, 20-30, 20-35, 20-45, 20-50, 20-55, 20-60, 2-900, 2-800, 2-700, 2-600, 2-500, 2-400, 2-300, 2-200, 2-100, 25-900, 25-800, 25-700, 25-600, 25-500, 25-400, 25-300, 25-200, 25-100, 100-1000, 100-900, 100-800, 100-700, 100-600, 100-500, 100-400, 100-300, 100-200, 200-1000, 200-900, 200-800, 200-700, 200-600, 200-500, 200-400, 200-300, 300-1000, 300-900, 300-800, 300-700, 300-600, 300-500, 300-400, 400-1000, 400-900, 400-800, 400-700, 400-600, 400-500, 500-1000, 500-900, 500-800, 500-700, 500-600, 600-1000, 600-900, 600-800, 600-700, 700-1000, 700-900, 700-800, 800-1000, 800-900, or 900-1000 nucleotides or base pairs.

Primers can be designed according to known parameters for avoiding secondary structures and self-hybridization. In some instances, different primer pairs can anneal and melt at about the same temperatures, for example, within 1° C., 2° C., 3° C., 4° C., 5° C., 6° C., 7° C., 8° C., 9° C. or 10° C. of another primer pair. In some instances, one or more primers in a plurality of primers can anneal and melt at about the same temperatures, for example, within 1, 2, 3, 4, 5, 6, 7, 8, 9 or 10° C. of another primer in the plurality of primers. In some instances, one or more primers in a plurality can anneal and melt at different temperatures than another primer in the plurality of primers.

A plurality of primers for one or more steps of the methods described herein can comprise a plurality of primers comprising about, at most about, or at least about 1, 2, 3, 4, 5, 6, 7, 8, 9, 10, 11, 12, 13, 14, 15, 16, 17, 18, 19, 20, 30, 40, 50, 60, 70, 80, 90, 100, 200, 300, 400, 500, 600, 700, 800, 900, 1000, 1500, 2000, 3000, 4000, 5000, 6000, 7000, 8000, 9000, 10,000, 11,000, 12,000, 13,000, 14,000, 15,000, 16,000, 17,000, 18,000, 19,000, 20,000, 30,000, 40,000, 50,000, 60,000, 70,000, 80,000, 90,000, 100,000, 200,000, 300,000, 400,000, 500,000, 600,000, 700,000, 800,000, 900, 000, 1,000,000, 50,000,000, 100,000,000 same or different primers. For example, each primer in a plurality of primers can comprise a same or different sequence that binds to a specific region of a polynucleotide.

Enzymes

The methods and kits disclosed herein can comprise one or more enzymes. Examples of enzymes include, but are not limited to ligases, reverse transcriptases, polymerases, and restriction nucleases.

In some instances, attachment of an adaptor to polynucleotides comprises the use of one or more ligases. Examples of ligases include, but are not limited to, DNA ligases such as DNA ligase I, DNA ligase III, DNA ligase IV, and T4 DNA ligase, and RNA ligases such as T4 RNA ligase I and T4 RNA ligase II.

The methods and kits disclosed herein can further comprise the use of one or more reverse transcriptases. In some instances, the reverse transcriptase is a HIV-1 reverse transcriptase, M-MLV reverse transcriptase, AMV reverse transcriptase, and telomerase reverse transcriptase. In some instances, the reverse transcriptase is M-MLV reverse transcriptase.

In some instances, the methods and kits disclosed herein comprise the use of one or more proteases In some instances, the methods and kits disclosed herein comprise the use of one or more polymerases. Examples of polymerases include, but are not limited to, DNA polymerases and RNA polymerases. In some instances, the DNA polymerase is a DNA polymerase I, DNA polymerase II, DNA polymerase III holoenzyme, and DNA polymerase IV. Commercially available DNA polymerases include, but are not limited to, Bst 2.0 DNA Polymerase, Bst 2.0 WarmStart™ DNA Polymerase, Bst DNA Polymerase, Sulfolobus DNA Polymerase IV, Taq DNA Polymerase, 9° N™ m DNA Polymerase, Deep VentR™ (exo-) DNA Polymerase, Deep VentR™ DNA Polymerase, Hemo KlenTaq™, LongAmp® Taq DNA Polymerase, OneTaq® DNA Polymerase, Phusion® DNA Polymerase, Q5™ High-Fidelity DNA Polymerase, Therminator™ γ DNA Polymerase, Therminator™ DNA Polymerase, Therminator™ II DNA Polymerase, Therminator™ III DNA Polymerase, VentR® DNA Polymerase, VentR® (exo−) DNA Polymerase, Bsu DNA Polymerase, phi29 DNA Polymerase, T4 DNA Polymerase, T7 DNA Polymerase, Terminal Transferase, Titanium® Taq Polymerase, KAPA Taq DNA Polymerase and KAPA Taq Hot Start DNA Polymerase.

In some instances, the polymerase is an RNA polymerases such as RNA polymerase I, RNA polymerase II, RNA polymerase III, *E. coli* Poly(A) polymerase, phi6 RNA polymerase (RdRP), Poly(U) polymerase, SP6 RNA polymerase, and T7 RNA polymerase.

Additional Reagents

The methods and kits disclosed herein can comprise the use of one or more reagents. Examples of reagents include, but are not limited to, PCR reagents, ligation reagents, reverse transcription reagents, enzyme reagents, hybridization reagents, sample preparation reagents, affinity capture reagents, solid supports such as beads, and reagents for nucleic acid purification and/or isolation.

A solid support can comprise virtually any insoluble or solid material, and often a solid support composition is selected that is insoluble in water. For example, a solid support can comprise or consist essentially of silica gel, glass (e.g. controlled-pore glass (CPG)), nylon, Sephadex®, Sepharose®, cellulose, a metal surface (e.g. steel, gold, silver, aluminum, silicon and copper), a magnetic material, a plastic material (e.g., polyethylene, polypropylene, polyamide, polyester, polyvinylidene difluoride (PVDF)) and the like. Examples of beads for use according to the instances can include an affinity moiety that allows the bead to interact with a nucleic acid molecule. A solid phase (e.g. a bead) can comprise a member of a binding pair (e.g. avidin, streptavidin or derivative thereof). For instance, the bead can be a streptavidin-coated bead and a nucleic acid molecule for immobilization on the bead can include a biotin moiety. In some instances, each polynucleotide molecule can include two affinity moieties, such as biotin, to further stabilize the polynucleotide. Beads can include additional features for use in immobilizing nucleic acids or that can be used in a downstream screening or selection processes. For example, the bead can include a binding moiety, a fluorescent label or a fluorescent quencher. In some instances, the bead can be magnetic. In some instances, the solid support is a bead. Examples of beads include, but are not limited to, streptavidin beads, agarose beads, magnetic beads, Dynabeads®, MACS® microbeads, antibody conjugated beads (e.g., anti-immunoglobulin microbead), protein A conjugated beads, protein G conjugated beads, protein A/G conjugated beads, protein L conjugated beads, polynucleotide-dT conjugated beads, silica beads, silica-like beads, anti-biotin microbead, anti-fluoro chrome microbead, and BcMag™ Carboxy-Terminated Magnetic Beads. Beads or particles can be swellable (e.g., polymeric beads such as Wang resin) or non-swellable (e.g., CPG). In some instances a solid phase is substantially hydrophilic. In some instances a solid phase (e.g. a bead) is substantially hydrophobic. In some instances a solid phase comprises a member of a binding pair (e.g. avidin, streptavidin or derivative thereof) and is substantially hydrophobic or substantially hydrophilic. In some instances, a solid phase comprises a member of a binding pair (e.g. avidin, streptavidin or derivative thereof) and has a binding capacity greater than about 1350 pmoles of free capture agent (e.g. free biotin) per mg solid support. In some instances the binding capacity of solid phase comprising a member of a binding pair is greater than 800, 900, 1000, 1100, 1200, 1250, 1300, 1350, 1400, 1450, 1500, 1600, 1800, 2000 pmoles of free capture agent per mg solid support. Other examples of beads that are suitable for the invention are gold colloids or beads such as polystyrene beads or silica beads. Substantially any bead radii can be used. Examples of beads can include beads having a radius ranging from 150 nm to 10 μm. Other sizes can also be used.

The methods and kits disclosed herein can comprise the use of one or more buffers. Examples of buffers include, but are not limited to, wash buffers, ligation buffers, hybridization buffers, amplification buffers, and reverse transcription buffers. In some instances, the hybridization buffer is a commercially available buffer, such as TMAC Hyb solution, SSPE hybridization solution, and ECONO™ hybridization buffer. The buffers disclosed herein can comprise one or more detergents.

The methods and kits disclosed herein can comprise the use of one or more carriers. Carriers can enhance or improve the efficiency of one or more reactions disclosed herein (e.g., ligation reaction, reverse transcription, amplification, hybridization). Carriers can decrease or prevent non-specific loss of the molecules or any products thereof (e.g., a polynucleotide and/or amplicon). For example, the carrier can decrease non-specific loss of a polynucleotide through absorption to surfaces. The carrier can decrease the affinity of a polynucleotide to a surface or substrate (e.g., container, Eppendorf tube, pipet tip). Alternatively, the carrier can increase the affinity of a polynucleotide to a surface or substrate (e.g., bead, array, glass, slide, chip). Carriers can protect the polynucleotide from degradation. For example, carriers can protect an RNA molecule from ribonucleases. Alternatively, carriers can protect a DNA molecule from a DNase. Examples of carriers include, but are not limited to, polynucleotides such as DNA and/or RNA, or polypeptides. Examples of DNA carriers include plasmids, vectors, polyadenylated DNA, and DNA polynucleotides. Examples of RNA carriers include polyadenylated RNA, phage RNA, phage MS2 RNA, *E. coli* RNA, yeast RNA, yeast tRNA, mammalian RNA, mammalian tRNA, short polyadenylated synthetic ribonucleotides and RNA polynucleotides. The RNA carrier can be a polyadenylated RNA. Alternatively, the RNA carrier can be a non-polyadenylated RNA. In some instances, the carrier is from a bacteria, yeast, or virus. For example, the carrier can be a polynucleotide or a polypeptide derived from a bacteria, yeast or virus. For example, the carrier is a protein from *Bacillus subtilis*. In another example, the carrier is a polynucleotide from *E. coli*. Alternatively, the carrier is a polynucleotide or peptide from a mammal (e.g., human, mouse, goat, rat, cow, sheep, pig, dog, or rabbit), avian, amphibian, or reptile.

The methods and kits disclosed herein can comprise the use of one or more control agents. Control agents can include control polynucleotides, inactive enzymes, non-specific competitors. Alternatively, the control agents comprise bright hybridization, bright probe controls, nucleic acid templates, spike-in controls, PCR amplification controls. The PCR amplification controls can be positive controls. In other instances, the PCR amplification controls are negative controls. The nucleic acid controls can be of known concentrations. The control agents can comprise one or more labels.

Spike-in controls can be templates that are added to a reaction or sample. For example, a spike-in polynucleotide can be added to an amplification reaction. The spike-in polynucleotide can be added to the amplification reaction any time after the first amplification cycle. In some instances, the spike-in polynucleotide is added to an amplification reaction after cycle number 2, 3, 4, 5, 6, 7, 8, 9, 10, 11, 12, 13, 14, 15, 20, 25, 30, 35, 40, 45, or 50. The spike-in polynucleotide can be added to the amplification reaction any time before the last amplification cycle. The spike-in polynucleotide can comprise one or more nucleotides or nucleic acid base pairs. The spike-in polynucleotide can comprise DNA, RNA, or any combination thereof. The spike-in polynucleotide can comprise one or more labels.

Selection of Lymphocytes from Sequencing Information

The methods disclosed further comprise selecting a lymphocyte or polynucleotide thereof based on an analysis of the sequencing information. The selecting can comprise analyzing the sequencing data obtained from the immune sequencing step, e.g., performing a bioinformatics analysis of the sequencing data. The lymphocyte or polynucleotide thereof can be selected based on one or more parameters or pieces of information contained with the sequencing information. Exemplary parameters or pieces of information contained with the sequencing information that can be used to select a lymphocyte (i.e. an antibody or TCR polynucleotide sequence of a lymphocyte) include, but are not limited to, an amount of expression of an antibody or TCR polynucleotide sequence, a mutation level or pattern of an antibody or TCR polynucleotide sequence, enrichment of a TIL comprising an antibody or TCR polynucleotide sequence in a diseased tissue compared to a normal (non-diseased) tissue, e.g., normal adjacent tissue, an isotype or isotype profile of an antibody or TCR polynucleotide sequence, a phylogenic cluster of an antibody or TCR polynucleotide sequence, the size of a phylogenic cluster of an antibody or TCR polynucleotide sequence, correlation of an antibody or TCR polynucleotide sequence between samples from a plurality of patients with the same disease, similarity (or lack thereof) of an antibody or TCR polynucleotide sequence between samples from a plurality of patients with the same disease, and combinations thereof.

Selecting an antibody or TCR polynucleotide sequence can comprise sequencing a plurality of polynucleotides accurately and efficiently to identify a polynucleotide sequence or lymphocyte comprising the polynucleotide sequence for selecting. In some instances, the method comprises selecting a polynucleotide sequence from a tumor infiltrating lymphocyte. In some instances, the method comprises selecting a polynucleotide sequence encoding for a candidate polypeptide that targets a disease-associated or disease-specific polypeptide. For example, the method can comprise selecting a polynucleotide encoding a $V_H$ or a $V_L$ of an immunoglobulin from a B-cell that targets an oncogene expression product. For example, the method can comprise identifying a polynucleotide encoding a $V\alpha$ or a $V\beta$ of a TCR of a T-cell that targets a disease-associated or disease-specific antigen.

In some instances, the method comprises selecting a polynucleotide sequence from a B-cell. For example, the selected polynucleotide can encode for a candidate polypeptide from a tumor infiltrating B-cell. In some instances, a candidate polypeptide comprises an antibody or fragment thereof. For example, a candidate polypeptide can comprise a variable domain of an antibody. In some instances, a candidate polypeptide comprises an immunoglobulin heavy chain. In some instances, a candidate polypeptide comprises an immunoglobulin light chain. In some instances, a candidate polypeptide comprises an immunoglobulin heavy chain and an immunoglobulin light chain. In some instances, a candidate polypeptide comprises a $V_H$ domain. In some instances, a candidate polypeptide comprises a $V_L$ domain. In some instances, the method comprises selecting a polynucleotide comprising a $V_H$ sequence and a $V_L$ sequence. For example, the method can comprise selecting a polynucleotide comprising a $V_H$ sequence and a $V_L$ sequence from a single B-cell.

In some instances, the method comprises selecting a polynucleotide comprising a $V_H$ sequence from a first sample and a $V_L$ sequence from a second sample. In some instances, the method comprises selecting a polynucleotide comprising a $V_H$ sequence from a first sample and a plurality of $V_L$ sequences from a second sample. In some instances, the method comprises selecting a polynucleotide comprising a $V_H$ sequence from a first sample and a $V_L$ sequence from a plurality of second samples.

In some instances, the method comprises selecting a polynucleotide sequence from a T-cell. For example, the selected polynucleotide can encode for a candidate polypeptide from a tumor infiltrating T-cell. In some instances, the candidate polypeptide is a TCR or fragment thereof. For example, a candidate polypeptide can comprise a variable domain of a TCR. In some instances, a candidate polypeptide comprises a TCRα chain. In some instances, a candidate polypeptide comprises a TCRβ chain. In some instances, a candidate polypeptide comprises a TCRγ chain. In some instances, a candidate polypeptide comprises a TCRδ chain. In some instances, a candidate polypeptide comprises Vα domain of a TCR. In some instances, a candidate polypeptide comprises a Vβ domain of a TCR. In some instances, a candidate polypeptide comprises a Vγ domain of a TCR. In some instances, a candidate polypeptide comprises a Vδ domain of a TCR. In some instances, the method comprises selecting a polynucleotide comprising a Vα sequence and a Vβ sequence. For example, the method can comprise selecting a polynucleotide comprising a Vα sequence and a Vβ sequence from a single T-cell. In some instances, the method comprises selecting a polynucleotide comprising a Vγ sequence and a Vδ sequence. For example, the method can comprise selecting a polynucleotide comprising a Vγ sequence and a Vδ sequence from a single T-cell.

The methods disclosed comprise selecting an immune cell or polynucleotide thereof, such as a tumor infiltrating lymphocyte or polynucleotide thereof, based on sequencing information. An immune cell or polynucleotide thereof, such as an infiltrating immune cell or polynucleotide thereof, can be selected by selecting a polynucleotide sequence of the infiltrating immune cell based on sequencing information. A polynucleotide of an infiltrating immune cell can be selected by determining a sequence of an infiltrating immune cell polynucleotide, e.g., by high-throughput sequencing of a plurality of immune cells from a tissue sample comprising the infiltrating immune cell. The methods of sequencing a polynucleotide for selecting an infiltrating immune cell provided herein typically utilize high-throughput sequencing due to the small absolute number of infiltrating immune cells in the sample and/or the low number of infiltrating immune cells in the sample compared to the number of non-infiltrating immune cells. The sequencing can be performed on a tissue sample comprising one or more infiltrating immune cells without extraction of the one or more infiltrating immune cells prior to the sequencing step.

In some instances, the polynucleotides sequenced from a selected lymphocyte of a sample can be present in the sample at different concentrations or amounts (e.g., different number of molecules). For example, the concentration or amount of one polynucleotide sequenced from a selected lymphocyte can be less than or greater than the concentration or amount of another polynucleotide sequenced from a lymphocyte in the sample. For example, the concentration or amount of one polynucleotide sequenced from a selected lymphocyte can be at least about 1.5, 2, 3, 4, 5, 6, 7, 8, 9, 10, 11, 12, 13, 14, 15, 20, 25, 30, 35, 40, 45, 50, 60, 70, 80, 90, 100, 200, 300, 400, 500, 600, 700, 800, 900, 1000, or more times less than the concentration or amount of at least one polynucleotide sequenced from a lymphocyte in the sample. For example, the concentration or amount of one polynucleotide sequenced from a selected lymphocyte can be at least about 1.5, 2, 3, 4, 5, 6, 7, 8, 9, 10, 11, 12, 13, 14, 15, 20, 25, 30, 35, 40, 45, 50, 60, 70, 80, 90, 100, 200, 300, 400, 500, 600, 700, 800, 900, 1000, or more times greater than the concentration or amount of at least one polynucleotide sequenced from a lymphocyte in the sample. In some instances, the concentration or amount of at least one polynucleotide in the sample is at least about 1.5, 2, 3, 4, 5, 6, 7, 8, 9, 10, 11, 12, 13, 14, 15, 20, 25, 30, 35, 40, 45, 50, 60, 70, 80, 90, 100, 200, 300, 400, 500, 600, 700, 800, 900, 1000, or more times less than the concentration or amount of at least 1.5%, 2%, 3%, 4%, 5%, 6%, 7%, 8%, 9%, 10%, 11%, 12%, 13%, 14%, 15%, 20%, 25%, 30%, 35%, 40%, 45%, 50%, 60%, 70%, 80%, 90%, 100% of the polynucleotides sequenced. In another example, the concentration or amount of one polynucleotide is less than the concentration or amount of another polynucleotide in the sample.

In some diseases, a single lymphocyte progenitor can give rise to many related lymphocyte progeny, each possessing and/or expressing a slightly different TCR, or antibody, due to on-going somatic hypermutation or to disease-related somatic mutation(s), such as base substitutions, aberrant rearrangements, or the like, and therefore a different phylogenic clone. A set of phylogenic clones, such as related phylogenic clones, can be referred to as a phylogenic cluster. In one aspect, selecting an antibody or TCR polynucleotide sequence comprises selecting based on the frequency of a phylogenic done. In one aspect, selecting an antibody or TCR polynucleotide sequence comprises selecting based on the frequency of a phylogenic cluster (i.e., the sum of frequencies of the constituent phylogenic clonotypes of the cluster), rather than a frequency of an individual phylogenic clone.

Phylogenic clones can be identified by one or more measures of relatedness to a parent clone. In one instance, phylogenic clones can be grouped into the same cluster by percent homology, for example. In another instance, phylogenic clones or phylogenic clusters are identified by common usage of V regions, J regions, and/or D regions. For example, a duster can be defined by clones having common J and D regions but different V regions; or it can be defined by clones having the same V and J regions but with different D regions; or it can be defined by a clone that has undergone one or more insertions and/or deletions of from 1-10 bases, or from 1-5 bases, or from 1-3 bases, to generate cluster members. Phylogenic clones of a single sample can be grouped into clusters and clusters from successive samples acquired at different times can be compared with one another. In one aspect of the invention, clusters containing clones correlated with a disease, such as a cancer, are identified among clones determined from samples at the time points. The cluster of correlating clones from the time point can be compared with that of a previous sample to select an Ig or TCR polynucleotide, for example, determining in successive clusters whether a frequency of a particular clone increases or decreases, whether a new correlating clone appears that is known from population studies or databases to be correlating, or the like.

In some instances, selecting a lymphocyte or polynucleotide thereof based on an analysis of the sequencing information can comprise selecting based on an isotype of an antibody or TCR polynucleotide based on an analysis of the sequencing information. For example, selecting a lymphocyte or polynucleotide thereof based on an analysis of the sequencing information can comprise selecting an IgG, IgM, IgA, IgE or IgD antibody. For example, selecting a lymphocyte or polynucleotide thereof based on an analysis of the sequencing information can comprise selecting an IgG antibody.

Cloning and Expression of Polypeptide Encoded by a Polynucleotide of a Selected Lymphocyte
Recombinant and Synthetic Methods and Compositions Antibodies and TCRs encoded by a polynucleotide from a selected lymphocyte can be produced using synthetic and/or recombinant methods and compositions (See, e.g., U.S. Pat. No. 4,816,567). In some instances, an isolated selected polynucleotide encoding a polypeptide is provided. Such nucleic acid can encode an amino acid sequence comprising, for example, the $V_L$ and/or an amino acid sequence comprising the $V_H$ of the antibody. In a further instance, one or more vectors comprising such nucleic acid are provided. A "vector" is a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked.

In a further instance, a host cell comprising such nucleic acid is provided. Host cells are cells into which exogenous nucleic acid has been introduced, including the progeny of such cells. Host cells include "transformants" and "transformed cells," which include the primary transformed cell and progeny derived therefrom without regard to the number of passages. Progeny cannot be completely identical in nucleic acid content to a parent cell, but can contain mutations. Mutant progeny that have the same function or biological activity as screened or selected for in the originally transformed cell are included herein. In one such instance, a host cell comprises (e.g., has been transformed with) a vector comprising a nucleic acid that encodes an amino acid sequence comprising the $V_L$ of the antibody and an amino acid sequence comprising the $V_H$ of the antibody or a first vector comprising a nucleic acid that encodes an amino acid sequence comprising the $V_L$ of the antibody and a second vector comprising a nucleic acid that encodes an amino acid sequence comprising the $V_H$ of the antibody. In some instances, the host cell is eukaryotic, e.g., a Chinese Hamster Ovary (CHO) cell or lymphoid cell (e.g., Y0, NS0, Sp20 cell). In some instances, a method of making a polypeptide encoded by a selected polynucleotide is provided, wherein the method comprises culturing a host cell comprising a selected nucleic acid encoding the polypeptide, under conditions suitable for expression of the polypeptide, and optionally recovering the polypeptide from the host cell or host cell culture medium.

For recombinant production of a polypeptide encoded by a selected polynucleotide, an isolated nucleic acid encoding a polypeptide encoded by a selected polynucleotide, e.g., an antibody, is inserted into one or more vectors for further cloning and/or expression in a host cell. Such nucleic acid can be readily isolated and sequenced using conventional procedures.

Suitable host cells for cloning or expression of polypeptide-encoding vectors include prokaryotic or eukaryotic cells described herein. For example, a polypeptide encoded by a selected polynucleotide can be produced in bacteria, e.g., when glycosylation and Fc effector function are not needed (See, e.g., U.S. Pat. Nos. 5,648,237, 5,789,199, and 5,840,523; Charlton, Methods in Molecular Biology, Vol. 248, pp. 245-254 (2003)). After expression, a polypeptide encoded by a selected polynucleotide can be isolated from the bacterial cell paste in a soluble fraction and can be further purified.

In addition to prokaryotes, eukaryotic microbes such as filamentous fungi or yeast are suitable cloning or expression hosts for polypeptide-encoding vectors (See, e.g., Gerngross, Nat. Biotech. 22:1409-1414 (2004), and Li et al., Nat. Biotech. 24:210-215 (2006)). Suitable host cells for the expression of glycosylated polypeptides, e.g., antibodies, are also derived from multicellular organisms, including invertebrates and vertebrates. Examples of invertebrates include plant and insect cells (See, e.g., U.S. Pat. Nos. 5,959,177, 6,040,498, 6,420,548, 7,125,978, and 6,417,429). Examples of vertebrate cells include mammalian cell lines, monkey kidney CV1 line transformed by SV40 (COS-7); human embryonic kidney line (293 or 293 cells as described, e.g., in Graham et al., J. Gen Virol. 36:59 (1977)); baby hamster kidney cells (BHK); mouse sertoli cells (TM4 cells); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2);

mouse mammary tumor (MMT 060562); TR1 cells; MRC 5 cells; FS4 cells; Chinese hamster ovary (CHO) cells, including DHFR CHO cells; and myeloma cell lines such as Y0, NS0 and Sp2/0. (See, e.g., Yazaki and Wu, Methods in Molecular Biology, Vol. 248, pp. 255-268 (2003)

The terms "Antibody expression library," "TCR expression library," "recombinant antibody library," "recombinant TCR library," "synthetic antibody library," and "synthetic TCR library" refer to a collection of molecules (i.e. two or more molecules) at either the nucleic acid or protein level from two or more selected lymphocytes. Thus, these terms can refer to a collection of expression vectors which encode a plurality of antibody or TCR molecules (i.e. at the nucleic acid level) or can refer to a collection of antibody or TCR molecules after they have been recombinantly produced, e.g., expressed, in an appropriate expression system or synthesized, e.g., using a peptide synthesizer (i.e. at the protein level). Expression vector libraries can be contained in suitable host cells in which they can be expressed. The antibody or TCR molecules which are encoded or expressed in the expression libraries can be in any appropriate format, e.g., can be whole antibody or TCR molecules or can be antibody or TCR fragments, e.g., single chain antibodies (e.g. scFv antibodies), Fv antibodies or TCRs, Fab' antibodies or TCRs, (Fab')$_2$ fragments, diabodies, etc. The terms "encoding" and "coding for" as is nucleic acid sequence "encoding"/"coding for" or a DNA coding sequence of or a nucleotide sequence "encoding"/"coding for" a particular polypeptide, as well as other synonymous terms, refer to a DNA sequence which is transcribed and translated into a polypeptide when placed under the control of appropriate regulatory sequences, e.g., a promoter sequence. A promoter sequence is a DNA regulatory region capable of binding RNA polymerase in a cell and initiating transcription of a downstream (3' direction) coding sequence. The promoter is part of the DNA sequence. This sequence region has a start codon at its 3' terminus. The promoter sequence includes the minimum number of bases with elements necessary to initiate transcription at levels detectable above background. However, after the RNA polymerase binds the sequence and transcription is initiated at the start codon (3' terminus with a promoter), transcription proceeds downstream in the 3' direction. Within the promotor sequence a transcription initiation site (conveniently defined by mapping with nuclease Si) as well as protein binding domains (consensus sequences) responsible for the binding of RNA polymerase are present.

Antibody or TCR molecules identified by, derived from, selected from, or obtainable from the antibody or TCR expression or synthetic libraries form a yet further aspect of the invention. Again these antibody or TCR molecules can be proteins or nucleic acids encoding antibody or TCR molecules, which nucleic acids can in turn be synthesized or incorporated into an appropriate expression vector and/or be contained in a suitable host cell.

The cDNA pool can be subjected to a PCR reaction with polynucleotides that hybridize to a constant region of the heavy chain or TCRα chain of antibody or TCR genes and polynucleotides that hybridize to the 5' end of the $V_H$ chain or Vα chain region of antibody or TCR genes. The cDNA pool can be subjected to a PCR reaction with polynucleotides that hybridize to a constant region of the heavy chain or TCRα chain of antibody or TCR genes and polynucleotides that hybridize to region 5' to the 5' end of the $V_H$ or Vα chain region of a barcoded polynucleotide comprising an antibody or TCR sequence. A PCR reaction is also set up for the amplification of the $V_L$ or Vβ chain pool, e.g., of kappa and lambda classes. The cDNA pool can be subjected to a PCR reaction with polynucleotides that hybridize to a constant region of the light chain or TCRβ chain of antibody or TCR genes and polynucleotides that hybridize to the 5' end of the $V_L$ or TCRβ chain region of antibody or TCR genes. The cDNA pool can be subjected to a PCR reaction with polynucleotides that hybridize to a constant region of the light chain or TCRβ chain of antibody or TCR genes and polynucleotides that hybridize to region 5' to the 5' end of the $V_L$ or Vβ chain region of a barcoded polynucleotide comprising an antibody or TCR sequence. Such oligonucleotides or primers can be designed based on immunoglobulin gene sequence database information.

In some instances, $V_H$ and $V_L$ or Vα and Vβ sequences can be conveniently obtained from a library of $V_H$ and $V_L$ or Vα and Vβ sequences produced by PCR amplification using one or more primers that are not specific for heavy or light chain or TCRα and TCRβ genes and, in particular, for one or both the terminal regions of the $V_H$ and $V_L$ or Vα and Vβ polynucleotides. In some instances, $V_H$ and $V_L$ or Vα and Vβ sequences can be conveniently obtained from a library of $V_H$ and $V_L$ or Vα and Vβ sequences produced by PCR amplification using primers specific to a region of the vessel barcoded polynucleotide. In some instances, $V_H$ and $V_L$ or Vα and Vβ sequences can be conveniently obtained from a library of $V_H$ and $V_L$ or Vα and Vβ sequences produced by PCR amplification using C-gene family-specific primers or C-gene-specific primers. In some instances, $V_H$ and $V_L$ or Vα and Vβ sequences can be conveniently obtained from a library of $V_H$ and $V_L$ or Vα and Vβ sequences produced by PCR amplification using a primer set with a first primer specific to a region of the vessel barcoded polynucleotide and a second primer or plurality of second primers that are C-gene family-specific primers or C-gene-specific primers. In some instances, $V_H$ and $V_L$ or Vα and Vβ sequences can be conveniently obtained from a library of $V_H$ and $V_L$ or Vα and Vβ sequences produced by PCR amplification using a primer set with a first primer specific to a region of the vessel barcoded polynucleotide and a second primer specific to a universal sequence.

In some instances, upon reverse transcription, the resulting cDNA sequences can be amplified by PCR using one or more primers specific for immunoglobulin genes and, in particular, for one or both the terminal regions of the $V_H$ and $V_L$ or Vα and Vβ polynucleotides. In some instances, $V_H$ and $V_L$ or unnatural $V_H$ and $V_L$ or Vα and Vβ sequences can be obtained from a library of $V_H$ and $V_L$ or unnatural $V_H$ and $V_L$ or Vα and Vβ sequences produced by PCR amplification using V-gene family-specific primers or V-gene-specific primers (Nicholls et al., J. Immunol. Meth., 1993, 165:81; WO93/12227) or are designed according to standard art-known methods based on available sequence information. (The natural or unnatural $V_H$ and $V_L$ or Vα and Vβ sequences can be ligated, such as with an intervening spacer sequence (e.g., encoding an in-frame flexible peptide spacer), forming a cassette encoding a single-chain antibody). V region sequences can be conveniently cloned as cDNAs or PCR amplification products for immunoglobulin- or TCR-express sing cells. The natural or unnatural $V_H$ and $V_L$ or Vα and Vβ regions are sequenced, optionally, in the methods described herein and particularly after certain steps as noted (e.g., after single cell PCR; after mammalian or other cell surface display, after FACS screening, and the like). Sequencing can be used, among other reasons, to verify that the level of diversity is at an acceptable level. Sequencing includes, but is not limited to, high-throughput sequencing, deep sequencing, or combinations of the two.

In some instances, it is unnecessary to physically link the natural or unnatural $V_H$ and $V_L$ or Vα and Vβ combinations using the expression or synthesis methods described herein. In some instances, cDNAs encoding a polypeptide from a selected lymphocyte are not physically linked. In some instances, cDNAs, barcoded polynucleotides, or PCR amplified barcoded cDNAs are not physically linked in a same expression vector.

In some instances, natural or unnatural $V_H$ and $V_L$ or Vα and Vβ combinations are physically linked, using, in addition to the cDNA primers, one primer or plurality of primers for the 5' end of the $V_H$ or Vα region gene and another primer or plurality of primers for the 5' end of the $V_L$ or Vβ gene. These primers also contain complementary tails of extra sequence, to allow the self-assembly of the $V_H$ and $V_L$ or Vα and Vβ genes. After PCR amplification and linking, the chance of getting mixed products, in other words, mixed variable regions, is minimal because the amplification and linking reactions are performed within each cell. The risk of mixing can be further decreased by utilizing bulky reagents such as digoxigenin labeled nucleotides to further ensure that V region cDNA pairs do not leave the cellular compartment and intermix, but remain within the cell for PCR amplification and linking. The amplified sequences are linked by hybridization of complementary terminal sequences. After linking, sequences can be recovered from cells for use in further method steps described herein. For example, the recovered DNA can be PCR amplified using terminal primers, if necessary, and cloned into vectors which can be plasmids, phages, cosmids, phagemids, viral vectors or combinations thereof as detailed below. Convenient restriction enzyme sites can be incorporated into the hybridized sequences to facilitate cloning. These vectors can also be saved as a library of linked variable regions for later use.

In some instances in which it is desired to provide additional $V_H$ and $V_L$ or Vα and Vβ or Vγ and Vδ combinations, an expression system is chosen to facilitate this. For example, bacteriophage expression systems allow for the random recombination of heavy- and light-chain sequences. Other suitable expression systems are known to those skilled in the art.

It should be noted that in the case of $V_H$ and $V_L$ or Vα and Vβ or Vγ and Vδ sequences derived from nonhumans, in some instances, it can be preferable to chimerize these sequences with a fully human Fc. As used herein "chimerized" refers to an immunoglobulin or TCR, wherein the heavy and light Ig chain or alpha and beta TCR chain variable regions are not of human origin and wherein the constant regions are of human origin. This is affected by amplifying and cloning the variable domains into a human Fc. The human Fc can be part of the vector, or in a separate molecule, and library of Fc's could also be used. In a preferred instance the chimerized molecules grown in mammalian cells such as CHO cells, screened with FACS twice to enrich the cell population for cells expressing the polypeptide of interest. The chimerized antibodies and TCRs are characterized, by either sequencing followed by functional characterization, or direct functional characterization or kinetics. Growth, screening and characterization are described in detail below.

Once the library of expression vectors has been generated, the encoded antibody or TCR molecules can then be expressed in an appropriate expression system and screened using appropriate techniques which are well known and documented in the art. Thus the above defined method of the invention can comprise the further steps of expressing the library of expression vectors in an appropriate expression system and screening the expressed library for antibodies with desired properties, as explained in further detail below.

As indicated herein, polynucleotides prepared by the methods of the disclosure which comprise a polynucleotide encoding antibody or TCR sequences can include, but are not limited to, those encoding the amino acid sequence of an antibody or TCR fragment, by itself, the noncoding sequence for the entire antibody or TCR or a portion thereof, the coding sequence for an antibody or TCR, fragment or portion, as well as additional sequences, such as the coding sequence of at least one signal leader or fusion peptide, with or without the aforementioned additional coding sequences, such as at least one intron, together with additional, non-coding sequences, including but not limited to, non-coding 5' and 3' sequences, such as the transcribed, nontranslated sequences that play a role in transcription, mRNA processing, including splicing and polyadenylation signals (for example—ribosome binding and stability of mRNA); an additional coding sequence that codes for additional amino acids, such as those that provide additional functionalities. Thus, the sequence encoding an antibody or TCR can be fused to a marker sequence, such as a sequence encoding a peptide that facilitates purification of the fused antibody or TCR comprising an antibody or TCR fragment or portion.

The primary PCR products can then optionally be subjected to a secondary PCR reaction with new polynucleotide sets that hybridize to the 5' and 3' ends of the antibody or TCR variable domains. These polynucleotides advantageously include DNA sequences specific for a defined set of restriction enzymes (i.e. restriction enzyme sites) for subsequent cloning. The selected restriction enzymes must be selected so as not to cut within human antibody or TCR V-gene segments. Such polynucleotides can be designed based on known and publicly available immunoglobulin or TCR gene sequence and restriction enzyme database information. The products of such secondary PCR reactions are repertoires of various variable antibody or TCR fragments/domains. This type of secondary PCR reaction is therefore generally carried out when the expression library format of interest is a scFv or Fv format, wherein only the variable domains of an antibody or TCR are present.

PCR products can also be subjected to a PCR reaction with new primer sets that hybridize to the 5' and 3' ends of the polynucleotides. These polynucleotides can advantageously include DNA sequences specific for a defined set of restriction enzymes (i.e. restriction enzyme sites) for subsequent cloning. The selected restriction enzymes must be selected so as not to cut within human V-gene segments. Such polynucleotides can be designed based on known and publicly available immunoglobulin or TCR gene sequence and restriction enzyme database information.

Libraries of such repertoires of cloned fragments comprising the variable regions, or fragments thereof, derived from the lymphocytes form further aspects of the invention. These libraries comprising cloned variable regions can optionally be inserted into expression vectors to form expression libraries.

In some instances, the PCR reactions can be set up so as to retain all or part of the constant regions of the various chains contained in the isolated immune cell population. This is desirable when the expression library format is a Fab format. Again, libraries of such cloned fragments comprising all or part of the constant regions of chains form further aspects of the invention.

These nucleic acids can conveniently comprise sequences in addition to a polynucleotide of the present invention. For example, a multi-cloning site comprising one or more endonuclease restriction sites can be inserted into the nucleic acid to aid in isolation of the polynucleotide. Also, translatable sequences can be inserted to aid in the isolation of the translated polynucleotide of the present invention. For example, a hexa-histidine marker sequence provides a convenient means to purify the proteins of the present invention. The nucleic acid of the present invention, excluding the coding sequence, is optionally a vector, adapter, or linker for cloning and/or expression of a polynucleotide of the present invention.

Additional sequences can be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known in the art. (See, e.g., Ausubel, supra; or Sambrook, supra).

For example, $V_H$ and $V_L$ chains or $V\alpha$ and $V\beta$ chains or $V\gamma$ and $V\delta$ chains can be cloned into an expression vector for expression in, e.g., 293K cells in, e.g., a full human IgG format. For example, 100-500 Ig or TCR chains can be cloned into an expression vector for expression in cells.

In some embodiments, parallel to sequencing, a library of $V_H$ and $V_L$ chains or $V\alpha$ and $V\beta$ chains or $V\gamma$ and $V\delta$ chains can be recovered, e.g., from vessels, and can be cloned into expression vectors and co-transfected, e.g., for yeast display screening. Cloning this identical library pool is the preferred method compared to splitting a biological sample at the beginning, as some rare immune cells would only be captured in one, or the other assay. For example, a library of human derived $V_H$ and $V_L$ chains or $V\alpha$ and $V\beta$ chains can be expressed regardless of correct or incorrect $V_H$ and $V_L$ pair matching or $V\alpha$ and $V\beta$ pair matching. For example, yeast display screening can then be performed against one or more antigen targets to enrich for potential antibody or TCR candidates. Positive candidate antibodies and TCRs emerging from display technologies, such as a yeast display, can be sequenced and ligands of the candidate antibodies and TCRs can be queried.

In some embodiments, monoclonal antibodies can be made using the hybridoma method first described by Kohler et al., Nature, 256:495 (1975), or can be made by recombinant DNA methods (U.S. Pat. No. 4,816,567). In the hybridoma method, a mouse or other appropriate host animal, such as a hamster, is immunized as hereinabove described to elicit lymphocytes that produce or are capable of producing antibodies that will specifically bind to the protein used for immunization. Alternatively, lymphocytes can be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986)). The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells. Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, J. Immunol., 133:3001 (1984); Brodeur et al., Monoclonal Antibody Production Techniques and Applications, pp. 51-63 (Marcel Dekker, Inc., New York, 1987)). Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA). The binding affinity of the monoclonal antibody can, for example, be determined by the Scatchard analysis of Munson et al., Anal. Biochem., 107:220 (1980). After hybridoma cells are identified that produce antibodies of the desired specificity, affinity, and/or activity, the clones can be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPMI-1640 medium. In addition, the hybridoma cells can be grown in vivo as ascites tumors in an animal. The monoclonal antibodies secreted by the subclones are suitably separated from the culture medium, ascites fluid, or serum by conventional immunoglobulin purification procedures such as, for example, protein A-Sepharose, hydroxyapatite chromatography, gel electrophoresis, dialysis, or affinity chromatography. DNA encoding the monoclonal antibodies is readily isolated and sequenced using conventional procedures (e.g., by using oligonucleotide probes that are capable of binding specifically to genes encoding the heavy and light chains of murine antibodies). Once isolated, the DNA can be placed into expression vectors, which are then transfected into host cells such as *E. coli* cells, simian COS cells, Chinese Hamster Ovary (CHO) cells, or myeloma cells that do not otherwise produce immunoglobulin protein, to obtain the synthesis of monoclonal antibodies in the recombinant host cells. Review articles on recombinant expression in bacteria of DNA encoding the antibody include Skerra et al., Curr. Opinion in Immunol., 5:256-262 (1993) and Pliickthun, Immunol. Revs., 130:151-188 (1992). In a further instance, antibodies or antibody fragments can be isolated from antibody phage libraries generated using the techniques described in McCafferty et al., Nature, 348:552-554 (1990). Clackson et al., Nature, 352: 624-628 (1991) and Marks et al., J. Mol. Biol., 222:581-597 (1991) describe the isolation of murine and human antibodies, respectively, using phage libraries. Subsequent publications describe the production of high affinity (nM range) human antibodies by chain shuffling (Marks et al., Bio/Technology, 10:779-783 (1992)), as well as combinatorial infection and in vivo recombination as a strategy for constructing very large phage libraries (Waterhouse et al., Nuc. Acids. Res., 21:2265-2266 (1993)). Thus, these techniques are viable alternatives to traditional monoclonal antibody hybridoma techniques for isolation of monoclonal antibodies. The DNA also can be modified, for example, by substituting the coding sequence for human heavy- and light-chain constant domains in place of the homologous murine sequences (U.S. Pat. No. 4,816,567; Morrison, et al., Proc. Natl Acad. Sci. USA, 81:6851 (1984)), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

Alternatively, phage display technology (McCafferty et al., Nature, 348:552-553 (1990)) can be used to produce human antibodies or TCRs and antibody fragments or TCRs in vitro, from immunoglobulin or TCR variable (V) domain gene repertoires. According to this technique, antibody or TCR V domain genes are cloned in-frame into either a major or minor coat protein gene of a filamentous bacteriophage, such as M13 or fd, and displayed as functional antibody or TCR fragments on the surface of the phage particle. Because the filamentous particle contains a single-stranded DNA copy of the phage genome, selections based on the functional properties of the antibody or TCR also result in selection of the gene encoding the antibody or TCR exhibiting those properties. Thus, the phage mimics some of the properties of the B-cell or T-cell. Phage display can be performed in a variety of formats; for their review see, e.g., Johnson and Chiswell, Current Opinion in Structural Biology, 3:564-571 (1993). A repertoire of V genes can be constructed and antibodies to a diverse array of antigens (including self-antigens) can be isolated essentially following the techniques described by Marks et al., J. Mol. Biol., 222:581-597 (1991), or Griffith et al., EMBO J., 12:725-734 (1993). See, also, U.S. Pat. Nos. 5,565,332 and 5,573,905. Human antibodies can also be generated by in vitro activated B-cells (see U.S. Pat. Nos. 5,567,610 and 5,229,275).

Various techniques have been developed for the production of antibody or TCR fragments. Traditionally, these fragments were derived via proteolytic digestion of intact antibodies or TCRs (see, e.g., Morimoto et al., J. Biochem. Biophys. Methods, 24:107-117 (1992) and Brennan et al., Science, 229:81 (1985)). However, these fragments can now be produced directly by recombinant host cells. For example, the antibody or TCR fragments can be isolated from the antibody phage libraries discussed above.

In some embodiments, antibody or TCR variable domains are fused to immunoglobulin constant domain sequences. In some embodiments, the fusion comprises an immunoglobulin heavy chain constant domain, comprising at least part of the hinge, CH2, and CH3 regions. In some embodiments, the fusion comprises the first heavy-chain constant region (CH1) containing the site necessary for light chain binding, present in at least one of the fusions. DNAs encoding the immunoglobulin heavy chain fusions and, if desired, the immunoglobulin light chain, can be inserted into separate expression vectors, and are cotransfected into a suitable host organism. This provides for great flexibility in adjusting the mutual proportions of polypeptide fragments in instances when unequal ratios of the polypeptide chains used in the construction provide the optimum yields. It is, however, possible to insert the coding sequences for polypeptide chains in one expression vector when the expression of at least two polypeptide chains in equal ratios results in high yields or when the ratios are of no particular significance.

According to another approach described in U.S. Pat. No. 5,731,168, the interface between a pair of antibody molecules can be engineered to maximize the percentage of heterodimers which are recovered from recombinant cell culture. The preferred interface comprises at least a part of the CH3 domain of an antibody or TCR constant domain. In this method, one or more small amino acid side chains from the interface of the first antibody or TCR molecule are replaced with larger side chains (e.g. tyrosine or tryptophan). Compensatory "cavities" of identical or similar size to the large side chain(s) are created on the interface of the second antibody or TCR molecule by replacing large amino acid side chains with smaller ones (e.g. alanine or threonine). This provides a mechanism for increasing the yield of the heterodimer over other unwanted end-products such as homodimers.

Antibodies and TCRs can be isolated and purified from culture supernatant or other cultures, e.g., by saturated ammonium sulfate precipitation, euglobulin precipitation method, caproic acid method, caprylic acid method, ion exchange chromatography (DEAE or DE52), or affinity chromatography using anti-Ig column or a protein A, G or L column.

In another aspect, nucleotides encoding amino acid sequences of one or more of the CDRs can inserted, for example, by recombinant techniques in restriction endonuclease sites of an existing polynucleotide that encodes an antibody, antigen-binding fragment or binding protein.

For high level production, the most widely used mammalian expression system is one which utilizes the gene amplification procedure offered by dehydrofolate reductase deficient ("dhfr–") Chinese hamster ovary cells. The system is well known to the skilled artisan. The system is based upon the dehydrofolate reductase "dhfr" gene, which encodes the DHFR enzyme, which catalyzes conversion of dehydrofolate to tetrahydrofolate. In order to achieve high production, dhfr– CHO cells are transfected with an expression vector containing a functional DHFR gene, together with a gene that encodes a desired protein.

By increasing the amount of the competitive DHFR inhibitor methotrexate (MTX), the recombinant cells develop resistance by amplifying the dhfr gene. In standard cases, the amplification unit employed is much larger than the size of the dhfr gene.

When large scale production of the protein, such as the antibody or TCR chain, is desired, both the expression level and the stability of the cells being employed are taken into account. In long term culture, recombinant CHO cell populations lose homogeneity with respect to their specific antibody or TCR productivity during amplification, even though they derive from a single, parental clone.

A composition is provided comprising an isolated polynucleotide encoding an antibody, TCR, or antigen-binding fragment thereof from a selected lymphocyte, vectors containing such polynucleotides, and host cells and expression systems for transcribing and translating such polynucleotides into polypeptides.

The present application also provides constructs in the form of plasmids, vectors, transcription or expression cassettes which comprise at least one polynucleotide as above.

The present application also provides a recombinant host cell which comprises one or more constructs as above. A nucleic acid encoding any antibody, TCR or antigen-binding fragments thereof from a selected lymphocyte itself forms an aspect of the present application, as does a method of production of the antibody, TCR, or antigen-binding fragments thereof which method comprises expression from a nucleic acid encoding the antibody, TCR or antigen-binding fragments thereof from the selected lymphocyte. Expression can be achieved by culturing under appropriate conditions recombinant host cells containing the nucleic acid. Following production by expression, an antibody, TCR, or antigen-binding fragment thereof can be isolated and/or purified using any suitable technique, then used as appropriate, e.g., for validation.

Specific antibodies, TCRs, antigen-binding fragments, and encoding nucleic acid molecules and vectors from a selected lymphocyte can be provided as isolated and/or purified, e.g., from their natural environment, in substantially pure or homogeneous form, or, in the case of nucleic acid, free or substantially free of nucleic acid or genes origin other than the sequence encoding a polypeptide with the required function. Nucleic acids can comprise DNA or RNA and can be wholly or partially synthetic.

Systems for cloning and expression of a polypeptide in a variety of different host cells can be used in the disclosed methods. Suitable host cells include, but are not limited to, bacteria, mammalian cells, yeast and baculovirus systems. Mammalian cell lines available in the art for expression of a heterologous polypeptide include Chinese hamster ovary cells, HeLa cells, baby hamster kidney cells, NSO mouse melanoma cells and many others. A common bacterial host is E. coli.

The expression of antibodies, TCRs, and fragments thereof in prokaryotic cells such as E. coli can be used in some instances. For a review, see for example Plückthun, A. Bio/Technology 9: 545-551 (1991). Expression in eukaryotic cells in culture is also available to those skilled in the art as an option for production of the antibodies and antigen-binding fragments described herein, see for recent reviews, for example Raff, M. E. (1993) Curr. Opinion Biotech. 4: 573-576; Trill J. J. et al. (1995) Curr. Opinion Biotech 6: 553-560, each of which is which is incorporated herein by reference in its entirety.

Suitable vectors can be chosen or constructed, containing appropriate regulatory sequences, including promoter sequences, terminator sequences, polyadenylation sequences, enhancer sequences, marker genes and other sequences as appropriate. Vectors can be plasmids, viral e.g. 'phage, or phagemid, as appropriate. For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Short Protocols in Molecular Biology, Second Edition, Ausubel et al. eds., John Wiley & Sons, 1992. The disclosures of Sambrook et al. and Ausubel et al. are incorporated herein by reference in their entirety.

Thus, a further aspect provides a host cell containing a polynucleotide from a selected lymphocyte. A still further aspect provides a method comprising introducing such nucleic acid into a host cell. The introduction can employ any available technique. For eukaryotic cells, suitable techniques can include, for example, calcium phosphate transfection, DEAE Dextran, electroporation, liposome-mediated transfection and transduction using retrovirus or other virus, e.g., vaccinia or, for insect cells, baculovirus. For bacterial cells, suitable techniques can include, for example, calcium chloride transformation, electroporation and transfection using bacteriophage.

The introduction can be followed by causing or allowing expression from the nucleic acid, e.g. by culturing host cells under conditions for expression of the gene.

In one instance, the nucleic acid is integrated into the genome (e.g. chromosome) of the host cell. Integration can be promoted by inclusion of sequences which promote recombination with the genome, in accordance with standard techniques.

The present application also provides a method which comprises using a construct as stated above in an expression system in order to express the antibodies, TCRs, or antigen-binding fragments thereof.

The present application also relates to isolated nucleic acids, such as recombinant DNA molecules or cloned genes, or degenerate variants thereof, mutants, analogs, or fragments thereof, which encode an antibody, TCR, or antigen-binding sequence thereof from a selected lymphocyte that binds a identified using the methods described herein.

Another feature is the expression of the DNA sequences disclosed herein. As is well known in the art, DNA sequences can be expressed by operatively linking them to an expression control sequence in an appropriate expression vector and employing that expression vector to transform an appropriate unicellular host.

Such operative linking of a DNA sequence to an expression control sequence, of course, includes, if not already part of the DNA sequence, the provision of an initiation codon, ATG, in the correct reading frame upstream of the DNA sequence.

Polynucleotides and vectors can be provided in an isolated and/or a purified form (e.g., free or substantially free of polynucleotides of origin other than the polynucleotide encoding a polypeptide with the required function). As used herein, "substantially pure" and "substantially free," refer to a solution or suspension containing less than, for example, 20% or less extraneous material, 10% or less extraneous material, 5% or less extraneous material, 4% or less extraneous material, 3% or less extraneous material, 2% or less extraneous material, or 1% or less extraneous material.

A wide variety of host/expression vector combinations can be employed in expressing the DNA sequences of this invention. Useful expression vectors, for example, can consist of segments of chromosomal, non-chromosomal and synthetic DNA sequences. Suitable vectors include derivatives of SV40 and known bacterial plasmids, e.g., E. coli plasmids col E1, Pcr1, Pbr322, Pmb9 and their derivatives, plasmids such as RP4; phage DNAs, e.g., the numerous derivatives of phage λ, e.g., NM989, and other phage DNA, e.g., M13 and filamentous single stranded phage DNA; yeast plasmids such as the 2 u plasmid or derivatives thereof vectors useful in eukaryotic cells, such as vectors useful in insect or mammalian cells; vectors derived from combinations of plasmids and phage DNAs, such as plasmids that have been modified to employ phage DNA or other expression control sequences; and the like.

Any of a wide variety of expression control sequences—sequences that control the expression of a DNA sequence operatively linked to it—can be used in these vectors to express the DNA sequences. Such useful expression control sequences include, for example, the early or late promoters of SV40, CMV, vaccinia, polyoma or adenovirus, the lac system, the trp system, the TAC system, the TRC system, the LTR system, the major operator and promoter regions of phage λ, the control regions of fd coat protein, the promoter for 3-phosphoglycerate kinase or other glycolytic enzymes, the promoters of acid phosphatase (e.g., Pho5), the promoters of the yeast □-mating factors, and other sequences known to control the expression of genes of prokaryotic or eukaryotic cells or their viruses, and various combinations thereof.

A wide variety of unicellular host cells are also useful in expressing the DNA sequences. These hosts include well-known eukaryotic and prokaryotic hosts, such as strains of *E. coli, Pseudomonas, Bacillus, Streptomyces,* fungi such as yeasts, and animal cells, such as CHO, YB/20, NSO, SP2/0, R1.1, B-W and L-M cells, African Green Monkey kidney cells (e.g., COS 1, COS 7, BSC1, BSC40, and BMT10), insect cells (e.g., Sf9), and human cells and plant cells in tissue culture.

It will be understood that not all vectors, expression control sequences and hosts will function equally well to express the DNA sequences. Neither will all hosts function equally well with the same expression system. However, one skilled in the art will be able to select the proper vectors, expression control sequences, and hosts without undue experimentation to accomplish the desired expression without departing from the scope of this application. For example, in selecting a vector, the host must be considered because the vector must function in it. The vector's copy number, the ability to control that copy number, and the expression of any other proteins encoded by the vector, such as antibiotic markers, will also be considered. One of ordinary skill in the art can select the proper vectors, expression control sequences, and hosts to accomplish the desired expression without departing from the scope of this application. For example, in selecting a vector, the host is considered because the vector functions in it. The vector's copy number, the ability to control that copy number, and the expression of any other proteins encoded by the vector, such as antibiotic markers, can also be considered.

The present application also provides constructs in the form of plasmids, vectors, transcription or expression cassettes as described elsewhere herein which comprise at least one polynucleotide from a selected lymphocyte. Suitable vectors can be chosen or constructed, containing appropriate regulatory sequences, including promoter sequences, terminator sequences, polyadenylation sequences, enhancer sequences, selectable markers and other sequences as appropriate. Vectors can be plasmids, viral e.g., phage, phagemid, etc., as appropriate. For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Short Protocols in Molecular Biology, Second Edition, Ausubel et al. eds., John Wiley & Sons, 1992. The disclosures of Sambrook et al. and Ausubel et al. are incorporated herein by reference.

In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products.

A polynucleotide encoding an antibody, TCR, or antigen-binding fragment thereof from a selected lymphocyte can be prepared recombinantly/synthetically in addition to, or rather than, cloned. The polynucleotide can be designed with the appropriate codons for the antibody, TCR, or antigen-binding fragment thereof. In general, one will select preferred codons for an intended host if the sequence will be used for expression. The complete polynucleotide can be assembled from overlapping oligonucleotides prepared by standard methods and assembled into a complete coding sequence. See, e.g., Edge, Nature, 292:756 (1981); Nambair et al., Science, 223:1299 (1984); Jay et al., J. Biol. Chem., 259:6311 (1984).

A general method for site-specific incorporation of unnatural amino acids into proteins is described in Christopher J. Noren, Spencer J. Anthony-Cahill, Michael C. Griffith, Peter G. Schultz, Science, 244:182-188 (April 1989). This method can be used to create analogs with unnatural amino acids.

As mentioned above, a DNA sequence encoding an antibody, TCR, or antigen-binding fragment thereof can be prepared synthetically rather than cloned.

Variants

In some instances, amino acid sequence variants of a polypeptide encoded by a selected polynucleotide provided herein are contemplated. A variant typically differs from a polypeptide specifically disclosed herein in one or more substitutions, deletions, additions and/or insertions. Such variants can be naturally occurring or can be synthetically generated, for example, by modifying one or more of the above polypeptide sequences of the invention and evaluating one or more biological activities of the polypeptide as described herein and/or using any of a number of techniques well known in the art. For example, it can be desirable to improve the binding affinity and/or other biological properties of a polypeptide encoded by a selected polynucleotide. Amino acid sequence variants of a polypeptide encoded by a selected polynucleotide can be prepared by introducing appropriate modifications into the selected nucleotide sequence encoding the polypeptide, or by peptide synthesis. Such modifications include, for example, deletions from, and/or insertions into and/or substitutions of residues within the amino acid sequences of an antibody. Any combination of deletion, insertion, and substitution can be made to arrive at the final construct, provided that the final construct possesses the desired characteristics, e.g., antigen-binding.

In some instances, a polypeptide encoded by a variant of a selected polynucleotide having one or more amino acid substitutions are provided. Sites of interest for mutagenesis by substitution of antibody polypeptides include the CDRs and FRs. Amino acid substitutions can be introduced into a polypeptide encoded by a selected polynucleotide of interest and the products screened for a desired activity, e.g., retained/improved antigen binding, decreased immunogenicity, or improved ADCC or CDC.

| Original Residue | Exemplary Conserved Substitutions |
| --- | --- |
| Ala (A) | Val; Leu; Ile |
| Arg (R) | Lys; Gln; Asn |
| Asn (N) | Gln; His; Asp, Lys; Arg |
| Asp (D) | Glu; Asn |
| Cys (C) | Ser; Ala |
| Gln (Q) | Asn; Glu |
| Glu (E) | Asp; Gln |
| Gly (G) | Ala |
| His (H) | Asn; Gln; Lys; Arg |
| Ile (I) | Leu; Val; Met; Ala; Phe; Norleucine |
| Leu (L) | Norleucine; Ile; Val; Met; Ala; Phe |
| Lys (K) | Arg; Gln; Asn |
| Met (M) | Leu; Phe; Ile |
| Phe (F) | Trp; Leu; Val; Ile; Ala; Tyr |
| Pro (P) | Ala |
| Ser (S) | Thr |
| Thr (T) | Val; Ser |
| Trp (W) | Tyr; Phe |

| Original Residue | Exemplary Conserved Substitutions |
| --- | --- |
| Tyr (Y) | Trp; Phe; Thr; Ser |
| Val (V) | Ile; Leu; Met; Phe; Ala; Norleucine |

Hydrophobic amino acids include: Norleucine, Met, Ala, Val, Leu, and Ile. Neutral hydrophilic amino acids include: Cys, Ser, Thr, Asn, and Gln. Acidic amino acids include: Asp and Glu. Basic amino acids include: His, Lys, and Arg. Amino acids with residues that influence chain orientation include: Gly and Pro. Aromatic amino acids include: Trp, Tyr, and Phe.

In some instances, substitutions, insertions, or deletions can occur within one or more CDRs, wherein the substitutions, insertions, or deletions do not substantially reduce binding to antigen. For example, conservative substitutions that do not substantially reduce binding affinity can be made in CDRs. Such alterations can be outside of CDR "hotspots" or SDRs. In some instances of the variant $V_H$ and $V_L$ sequences, each CDR either is unaltered, or contains no more than one, two or three amino acid substitutions.

Alterations (e.g., substitutions) can be made in CDRs, e.g., to improve affinity. Such alterations can be made in CDR encoding codons with a high mutation rate during somatic maturation (See, e.g., Chowdhury, Methods Mol. Biol. 207:179-196 (2008)), and the resulting variant can be tested for binding affinity. Affinity maturation (e.g., using error-prone PCR, chain shuffling, randomization of CDRs, or oligonucleotide-directed mutagenesis) can be used to improve affinity (See, e.g., Hoogenboom et al. in Methods in Molecular Biology 178:1-37 (2001)). CDR residues involved in target or antigen binding can be specifically identified, e.g., using alanine scanning mutagenesis or modeling (See, e.g., Cunningham and Wells Science, 244:1081-1085 (1989)). CDR-H3 and CDR-L3 in particular are often targeted. Alternatively, or additionally, a crystal structure of an antigen-antibody or antigen-TCR complex to identify contact points between the antibody or TCR and antigen. Such contact residues and neighboring residues can be targeted or eliminated as candidates for substitution. Variants can be screened to determine whether they contain the desired properties.

Amino acid sequence insertions and deletions include amino- and/or carboxyl-terminal fusions ranging in length from one residue to polypeptides containing a hundred or more residues, as well as intrasequence insertions and deletions of single or multiple amino acid residues. Examples of terminal insertions include an N-terminal methionyl residue. Other insertional variants of the molecule include the fusion to the N- or C-terminus of the antibody or TCR to an enzyme (e.g., for ADEPT) or a polypeptide which increases the serum half-life of the antibody or TCR.

In some instances, a polypeptide encoded by a polynucleotide from a selected lymphocyte is altered to increase or decrease its glycosylation (e.g., by altering the amino acid sequence such that one or more glycosylation sites are created or removed). For example, a carbohydrate attached to an Fc region can be altered. Native antibodies from mammalian cells typically comprise a branched, biantennary oligosaccharide attached by an N-linkage to Asn297 of the CH2 domain of the Fc region (See, e.g., Wright et al. TIBTECH 15:26-32 (1997)). The oligosaccharide can be various carbohydrates, e.g., mannose, N-acetyl glucosamine (GlcNAc), galactose, sialic acid, fucose attached to a GlcNAc in the stem of the biantennary oligosaccharide structure. Modifications of the oligosaccharide in an antibody can be made, for example, to create antibody variants with certain improved properties. Antibody and TCR glycosylation variants can have improved ADCC and/or CDC function.

Accordingly, a polypeptide encoded by a polynucleotide of a selected lymphocyte can be produced by a host cell with one or more of exogenous and/or high endogenous glycosyltransferase activities. Genes with glycosyltransferase activity include β(1,4)-N-acetylglucosaminyltransferase III (GnTIII), α-mannosidase II (ManII), β(1,4)-galactosyltransferase (GalT), β(1,2)-N-acetylglucosaminyltransferase I (GnTI), and β(1,2)-N-acetylglucosaminyltransferase II (GnTII). The glycotranferases can comprise a fusion comprising a Golgi localization domain (See, e.g., Lifely et al., Glycobiology 318:813-22 (1995); Schachter, Biochem. Cell Biol. 64:163-81 (1986); U.S. Prov. Pat. App. Nos. 60/495,142 and 60/441,307; Pat. Pub. Nos. US 2003/0175884 and US 2004/0241817; and WO04/065540). In some instances, a polypeptide encoded by a polynucleotide of a selected lymphocyte can be expressed in a host cell comprising a disrupted or deactivated glycosyltransferase gene. Accordingly, in some instances, the present invention is directed to a host cell comprising (a) an isolated nucleic acid comprising a sequence encoding a polypeptide having a glycosyltransferase activity; and (b) an isolated polynucleotide from a selected lymphocyte encoding an antibody or TCR polypeptide that binds a human target, such as a human disease-specific target. In a particular instance, a modified polypeptide of a polypeptide encoded by a polynucleotide of a selected lymphocyte produced by the host cell has an IgG constant region or a fragment thereof comprising the Fc region. In another particular instance a polypeptide encoded by a polynucleotide of a selected lymphocyte is a humanized antibody or a fragment thereof comprising an Fc region. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

Polypeptides encoded by a polynucleotide from a selected lymphocyte with altered glycosylation produced by the host cells can exhibit increased Fc receptor binding affinity (e.g., increased binding to a Fcγ activating receptor, such as the FcγRIIIa receptor) and/or increased effector function. The increased effector function can be an increase in one or more of the following: increased antibody-dependent cellular cytotoxicity, increased antibody-dependent cellular phagocytosis (ADCP), increased cytokine secretion, increased immune-complex-mediated antigen uptake by antigen-presenting cells, increased Fc-mediated cellular cytotoxicity, increased binding to NK cells, increased binding to macrophages, increased binding to polymorphonuclear cells (PMNs), increased binding to monocytes, increased cross-linking of target-bound antibodies or TCRs, increased direct signaling inducing apoptosis, increased dendritic cell maturation, and increased T-cell priming. Accordingly, in one aspect, the present invention provides glycoforms of a polypeptide encoded by a polynucleotide from a selected lymphocyte having increased effector function as compared to the polypeptide that has not been glycoengineered. (See, e.g., Tang et al., J. Immunol. 179:2815-2823 (2007)).

The present invention is also directed to a method for producing a polypeptide encoded by a polynucleotide from a selected lymphocyte having modified oligosaccharides, comprising (a) culturing a host cell engineered to express at least one nucleic acid encoding a polypeptide having glycosyltransferase activity under conditions which permit the production of a polypeptide encoded by a polynucleotide from a selected lymphocyte, wherein the polypeptide having glycosyltransferase activity is expressed in an amount sufficient to modify the oligosaccharides in the Fc region of the polypeptide encoded by a polynucleotide from a selected lymphocyte produced by said host cell; and (b) isolating the polypeptide encoded by a polynucleotide from a selected lymphocyte. In another instance, there are two polypeptides having glycosyltransferase activity. The polypeptides encoded by a polynucleotide from a selected lymphocyte produced by the methods of the present invention can have increased Fc receptor binding affinity and/or increased effector function.

In some instances, the percentage of bisected N-linked oligosaccharides in the Fc region of a polypeptide encoded by a polynucleotide from a selected lymphocyte is at least about 10% to about 100%, specifically at least about 50%, more specifically, at least about 60%, at least about 70%, at least about 80%, or at least about 90-95% of the total oligosaccharides.

In another instance, a composition is provided comprising a polypeptide encoded by a polynucleotide from a selected lymphocyte engineered to have increased effector function and/or increased Fc receptor binding affinity, produced by the methods described herein. In some instances, the antibody or TCR is an intact antibody or TCR. In some instances, the antibody or TCR is an antibody or TCR fragment containing the Fc region, or a fusion protein that includes a region equivalent to the Fc region of an immunoglobulin or TCR chain.

In one aspect, the present invention provides host cell expression systems for the generation of the antibodies and TCRs of the present invention having modified glycosylation patterns. In particular, the present invention provides host cell systems for the generation of glycoforms of the antibodies and TCRs of the present invention having an improved therapeutic value. Therefore, the invention provides host cell expression systems selected or engineered to express a polypeptide having a glycosyltransferase activity.

Generally, any type of cultured cell line, including the cell lines discussed above, can be used as a background to engineer the host cell lines of the present invention. In some instances, CHO cells, BHK cells, NSO cells, SP2/0 cells, YO myeloma cells, P3x63 mouse myeloma cells, PER cells, PER.C6 cells or hybridoma cells, other mammalian cells, yeast cells, insect cells, or plant cells are used as the background cell line to generate the engineered host cells of the invention.

In some instances, an antibody or TCR provided herein can be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, polypropylene glycol homopolymers, polypropylene oxide/ethylene oxide co-polymers, polyoxyethylated polyols (e.g., glycerol), polyvinyl alcohol, and mixtures thereof. Polyethylene glycol propionaldehyde can have advantages in manufacturing due to its stability in water.

The polymer can be of any molecular weight, and can be branched or unbranched. The number of polymers attached to the antibody or TCR can vary, and if two or more polymers are attached, they can be the same or different molecules.

In another instance, conjugates of an antibody or TCR and nonproteinaceous moiety that can be selectively heated by exposure to radiation are provided. In some instances, the nonproteinaceous moiety is a carbon nanotube (See, e.g., Kam et al., Proc. Natl. Acad. Sci. USA 102: 11600-11605 (2005)). The radiation can be of any wavelength, and includes, but is not limited to, wavelengths that do not harm ordinary cells, but which heat the nonproteinaceous moiety to a temperature at which cells proximal to the antibody- or TCR-nonproteinaceous moiety are killed.

Mutation Frequency

The antibodies or TCRs can comprise a heavy chain, light chain, TCRα, or TCRβ sequence with a mutation frequency of at least about 5%, 6%, 7%, 8%, 9%, 10%, 11%, 12%, 13%, 14%, 15%, 16%, 17%, 18%, 19%, or 20%, or higher from a corresponding germline sequence. For example, antibodies encoded by a polynucleotide from a selected lymphocyte can comprise a CDR3 region that is a light chain sequence with a mutation frequency of at least about 5%, 6%, 7%, 8%, 9%, 10%, 11%, 12%, 13%, 14%, 15%, 16%, 17%, 18%, 19%, or 20%, or higher from a germline sequence. For example, antibodies of the invention can comprise a heavy chain and a light chain sequence with a mutation frequency of at least about 5%, 6%, 7%, 8%, 9%, 10%, 11%, 12%, 13%, 14%, 15%, 16%, 17%, 18%, 19%, or 20%, or higher from a germline sequence.

In some instances, an antibody or TCR encoded by a polynucleotide from a selected lymphocyte is a human antibody or TCR. Human antibodies can be produced using various techniques known in the art (See, e.g., van Dijk and van de Winkel, Curr. Opin. Pharmacol. 5: 368-74 (2001); and Lonberg, Curr. Opin. Immunol. 20:450-459 (2008)). A human antibody or TCR is one which possesses an amino acid sequence which corresponds to that of an antibody or TCR produced by a human or a human cell or derived from a non-human source that utilizes human antibody repertoires or other human antibody-encoding sequences. Human antibodies can be prepared from a polynucleotide from a selected lymphocyte, e.g., a vector comprising a sequence from the polynucleotide from the selected lymphocyte.

Human antibodies can also be made by hybridoma-based methods. For example, human antibodies can be produced from human myeloma and mouse-human heteromyeloma cell lines, using human B-cell hybridoma technology, and other methods (See, e.g., Kozbor J. Immunol., 133: 3001 (1984); Brodeur et al., Monoclonal Antibody Production Techniques and Applications, pp. 51-63 (1987); Boerner et al., J. Immunol., 147: 86 (1991); Li et al., Proc. Natl. Acad., 103:3557-3562 (2006); U.S. Pat. No. 7,189,826; Ni, Xiandai Mianyixue, 26(4):265-268 (2006); Vollmers and Brandlein, Histology and Histopathology, 20(3):927-937 (2005); and Vollmers and Brandlein, Methods and Findings in Experimental and Clinical Pharmacology, 27(3):185-91 (2005)). Human antibodies and TCRs can also be generated by isolating Fv clone variable domain sequences selected from human-derived phage display libraries. Such variable domain sequences can then be combined with a desired human constant domain.

Identification of a Target of a Polypeptides Encoded by a Polynucleotide of a Selected Lymphocyte and Characterization Thereof Methods are disclosed comprising validating or characterizing recombinantly or synthetically produced polypeptides encoded by a polynucleotide from a selected lymphocyte. Polypeptides encoded by a polynucleotide from a selected lymphocyte can be assayed, screed, or characterized for their physical/chemical properties and/or biological activities by various assays known in the art. Disclosed is a method to determine the identity of the target of a polypeptide encoded by a polynucleotide of a selected lymphocyte. The methods disclosed can comprise screening for, or characterizing the physical/chemical properties and/or biological activities of a polypeptide encoded by a polynucleotide of a selected lymphocyte by various assays. The target can be a protein or an antigen such as a tissue-specific protein or antigen. In some instances, the protein or antigen may be a disease-specific protein or antigen, such as a cancer specific protein or antigen.

In one aspect, a polypeptide encoded by a polynucleotide from a selected lymphocyte, e.g., an antibody or TCR, is tested for its antigen binding activity, e.g., by ELISA, Western blot, etc. For example, a polypeptide encoded by a polynucleotide from a selected lymphocyte can be tested for its binding activity to a plurality of antigens or proteins, e.g., using immunoprecipitation and mass spectrometry or a protein array comprising the plurality of proteins or antigens to be tested. A protein array refers to a biochip adapted for the capture of polypeptides. Many protein biochips are described in the art. Methods of producing polypeptide arrays are described, e.g., in De Wildt et al., 2000, Nat. Biotechnol. 18:989-994; Lueking et al., 1999, Anal. Biochem. 270:103-111; Ge, 2000, Nucleic Acids Res. 28, e3, 1-VH; MacBeath and Schreiber, 2000, Science 289: 1760-1763; WO 01/40803 and WO 99/51773A1. Use of arrays allows identification of targets to be performed robotically and/or in a high-throughput manner.

Polypeptides for the array can be spotted at high speed, e.g., using a commercially available robotic apparatus e.g., from Genetic MicroSystems or BioRobotics. The array substrate can be, for example, nitrocellulose, plastic, glass, e.g., surface-modified glass. The array can also include a porous matrix, e.g., acrylamide, agarose, or another polymer. Upon capture on a biochip, analytes can be detected by a variety of detection methods selected from, for example, a gas phase ion spectrometry method, an optical method, an electrochemical method, atomic force microscopy and a radio frequency method. Of particular interest is the use of mass spectrometry, and in particular, SELDI. Optical methods include, for example, detection of fluorescence, luminescence, chemiluminescence, absorbance, reflectance, transmittance, birefringence or refractive index (e.g., surface plasmon resonance, ellipsometry, a resonant mirror method, a grating coupler waveguide method or interferometry). Optical methods include microscopy (both confocal and nonconfocal), imaging methods and non-imaging methods Immunoassays in various formats (e.g., ELISA) are popular methods for detection of analytes captured on a solid phase. Electrochemical methods include voltammetry and amperometry methods. Radio frequency methods include multipolar resonance spectroscopy.

In one aspect, a competition assay can be used to identify a molecule, such as a polypeptide, antibody, or small molecule, which competes with a polypeptide encoded by a selected polynucleotide for binding to a target. In some instances, such a competing molecule binds to the same epitope (e.g., a linear or a conformational epitope) that is bound by polypeptide encoded by a selected polynucleotide. Exemplary epitope mapping methods are known (See, e.g., Morris "Epitope Mapping Protocols," in Methods in Molecular Biology vol. 66 (1996)). In an exemplary competition assay, immobilized target is incubated in a solution comprising a first labeled polypeptide encoded by a selected polynucleotide that binds to the target and a second unlabeled polypeptide that is being tested for its ability to compete with the polypeptide encoded by a selected polynucleotide for binding to the target. The second antibody can be present in a hybridoma supernatant. As a control, immobilized target is incubated in a solution comprising the first labeled polypeptide encoded by a selected polynucleotide but not the second unlabeled molecule. After incubation under conditions permissive for binding of the polypeptide encoded by a selected polynucleotide to the target, excess unbound polypeptide is removed, and the amount of label associated with immobilized target is measured. If the amount of label associated with immobilized target is substantially reduced in the test sample relative to the control sample, then that indicates that the second molecule is competing with the first polypeptide encoded by a selected polynucleotide of a selected lymphocyte for binding to the target (See, e.g., Harlow and Lane Antibodies: A Laboratory Manual Ch. 14 (1996)).

In some instances, an antibody or TCR polypeptide encoded by a polynucleotide of a selected lymphocyte has a dissociation constant ($K_D$) of about 1 μM, 100 nM, 10 nM, 5 nM, 2 nM, 1 nM, 0.5 nM, 0.1 nM, 0.05 nM, 0.01 nM, or 0.001 nM or less (e.g., $10^{-8}$M or less, e.g., from $10^{-8}$M to $10^{-13}$ M, e.g., from $10^{-9}$M to $10^{-13}$ M). Another aspect of the invention provides for a polypeptide encoded by a polynucleotide from a selected lymphocyte with an increased affinity for its target, for example, an affinity matured antibody or TCR. An affinity matured antibody or TCR is an antibody or TCR with one or more alterations in one or more hypervariable regions (HVRs), compared to a parent antibody or TCR which does not possess such alterations, such alterations resulting in an improvement in the affinity of the antibody or TCR for antigen or target. These antibodies and TCRs can bind to a target with a $K_D$ of about $5 \times 10^{-9}$M, $2 \times 10^{-9}$ M, $1 \times 10^{-9}$M, $5 \times 10^{-10}$ M, $2 \times 10^{-9}$ M, $1 \times 10^{-10}$ M, $5 \times 10^{-11}$M, $1 \times 10^{-11}$M, $5 \times 10^{-12}$ M, $1 \times 10^{-12}$M, or less. In some instances, the invention provides an antibody or TCR encoded by a polynucleotide from a selected lymphocyte which has an increased affinity of at least 1.5 fold, 2 fold, 2.5 fold, 3 fold, 4 fold, 5 fold, 10 fold, 20 fold or greater as compared to a germline antibody or TCR. In some instances, a polypeptide encoded by a polynucleotide from a selected lymphocyte exhibits effector function activities, such as, for example, Fc-mediated cellular cytotoxicity, including ADCC activity.

$K_D$ can be measured by any suitable assay. For example, $K_D$ can be measured by a radiolabeled antigen binding assay (RIA) (See, e.g., Chen et al., J. Mol. Biol. 293:865-881 (1999); Presta et al., Cancer Res. 57:4593-4599 (1997)). For example, $K_D$ can be measured using surface plasmon resonance assays (e.g., using a BIACORE®-2000 or a BIACORE®-3000).

In some instances, an antibody or TCR provided herein is a multispecific antibody or TCR, e.g., a bispecific antibody or TCR. Multispecific antibodies or TCRs can be antibodies or TCRs that have binding specificities for at least two different sites (See, e.g., U.S. Pat. Pub. No. US 2008/0069820). In some instances, one of the binding specificities is for a first and the other is for any other target. In some instances, bispecific antibodies or TCRs can bind to two different epitopes of a target. Bispecific antibodies or TCRs can also be used to localize cytotoxic agents to diseased cells or infected cells. Bispecific antibodies or TCRs can be prepared as full length antibodies or TCRs or antibody or TCR fragments.

Exemplary techniques for making multispecific antibodies or TCRs include recombinant co-expression of two immunoglobulin heavy chain-light chain pairs or TCRα chain-TCRβ chain pairs having different specificities, engineering electrostatic steering effects for making Fc-heterodimeric molecules, cross-linking two or more antibodies, TCRs or fragments thereof, using leucine zippers to produce bi-specific antibodies or TCRs, using "diabody" technology for making bispecific antibody or TCR fragments, using single-chain Fv (scFv) dimers, preparing trispecific antibodies or TCRs, and "knob-in-hole" engineering (See, e.g., Milstein and Cuello, Nature 305: 537 (1983); WO09/089004A1; WO93/08829; Traunecker et al., EMBO J. 10: 3655 (1991); U.S. Pat. Nos. 4,676,980 and 5,731,168; Brennan et al., Science, 229: 81 (1985); Kostelny et al., J. Immunol., 148(5):1547-1553 (1992); Hollinger et al., Proc. Natl. Acad. Sci. USA, 90:6444-6448 (1993); Gruber et al., J. Immunol., 152:5368 (1994)); and Tutt et al. J. Immunol. 147: 60 (1991)). Engineered antibodies or TCRs with three or more functional antigen binding sites are also included (See, e.g., US 2006/0025576).

In one aspect, assays are provided for identifying one or more polypeptides encoded by a polynucleotide from a selected lymphocyte having biological activity. In some instances, assays are provided for identifying polypeptides encoded by a polynucleotide from a selected lymphocyte having neutralization activity for the target. Polypeptides encoded by a selected polynucleotide having such biological activity in vivo and/or in vitro are also provided. In some instances, polypeptides encoded by a selected polynucleotide of the invention are tested for such biological activity.

In one aspect, assays are provided for identifying one or more polypeptides encoded by a polynucleotide from a selected lymphocyte having reactivity, high affinity, and/or high specificity to an antigen or target relevant or specific to the pathology of the diseased tissue from which a sample was taken.

In one aspect, assays are provided for identifying one or more polypeptides encoded by a polynucleotide from a selected lymphocyte using a phage, ribosome, or RNA display technique. For example, these techniques can be used to select for the polypeptides encoded by polynucleotides from selected lymphocytes with a relevant reactivity. The comparison of the reactivity before and after the selection can identify those polypeptides that have the reactivity and hence are likely to be pathological. In another instance, the specific display techniques (for example phage, ribosome, or RNA display) can be used in an array format. For example, individual molecules (or amplifications of these individual molecules) carrying individual sequences from the one or more polypeptides encoded by a polynucleotide from a selected lymphocyte can be arrayed either as phages, ribosomes, or RNA. Specific targets or antigens can then be studied to identify the sequence(s) that code for peptides (e.g. Ig or TCR polypeptides) that bind them. Drugs inhibiting antigens relevant to the disease can then be selected based on the identity of the target of the one or more polypeptides encoded by a polynucleotide from a selected lymphocyte.

In some aspects, assays are provided for identifying one or more polypeptides encoded by a polynucleotide from a selected lymphocyte using an immunoassay technique using diseased and or non-diseased samples, such as tissue samples or FFPE samples, or NAT samples. Tissue samples can be cut into a plurality of serial histological sections along substantially parallel planes, for analysis by any of a number of known histological, histochemical, immunohistological, histopathologic, microscopic (including morphometric analysis and/or three-dimensional reconstruction), cytological, biochemical, pharmacological, molecular biological, immunochemical, imaging or other analytical techniques. See, e.g., Bancroft and Gamble, Theory and Practice of Histological Techniques (6th Ed.), 2007 Churchill Livingstone, Oxford, UK; Kieman, Histological and Histochemical Methods: Theory and Practice, 2001 Cold Spring Harbor Laboratory Press, Cold Spring Harbor, N.Y.; M. A. Hayat (Ed.), Cancer Imaging—Vols. 1 and 2, 2007 Academic Press, NY.

Methods of Use

The molecular identification of the disease specific antigens, e.g., cancer antigens, involved in the immune system-mediated destruction of disease specific cells, e.g., cancer cells, are useful for the identification of known drugs and/or the development of specific active drugs, e.g., peptides, nucleic acids, antibodies, and small molecules, that inhibit the identified target using the methods described herein. The molecular identification of the disease specific antigens, e.g., cancer antigens, involved in the immune system-mediated destruction of disease specific cells, e.g., cancer cells, are useful for the development of specific active immunization strategies against diseases (e.g., cancer vaccines) as well as for the in vitro generation of lymphocytes for use in adoptive immunotherapy. Using lymphocytes reactive against human cancer antigens in vitro, it has been possible to screen cDNA or genomic libraries to identify the genes encoding these antigens.

Compositions of Ig or TCR polypeptide encoded by a polynucleotide of a selected lymphocyte, such as antibodies and antigen-binding fragments described herein can be used as non-therapeutic agents (e.g., as affinity purification agents). Generally, in one such instance, a protein of interest is immobilized on a solid phase such a Sephadex resin or filter paper, using conventional methods known in the art. The immobilized protein is contacted with a sample containing the target of interest (or fragment thereof) to be purified, and thereafter the support is washed with a suitable solvent that will remove substantially all the material in the sample except the target protein, which is bound to the immobilized Ig or TCR polypeptide (e.g. antibody). Finally, the support is washed with another suitable solvent, such as glycine buffer, pH 5.0, which will release the target protein. In addition to purification, compositions can be used for detection, diagnosis and therapy of diseases and disorders associated with target protein.

A patient according to one instance of the present application, is a mammal (e.g., a human) who exhibits one or more clinical manifestations and/or symptoms of a disease or disorder, e.g., the same disease or disorder as the diseased sample. In certain situations, the patient can be asymptomatic and yet still have clinical manifestations of the disease or disorder.

A selected antibody, TCR, or antigen-binding fragment thereof can be conjugated to a therapeutic moiety or be a fusion protein containing a therapeutic moiety. A selected antibody, TCR, or antigen-binding fragment thereof can be conjugated to a detectable moiety or be a fusion protein containing a detectable moiety. In one instance, the selected antibody, TCR, or antigen-binding fragment thereof can be conjugated to both a therapeutic moiety and a detectable moiety. A selected antibody, TCR, or antigen-binding fragment thereof can be conjugated to, or recombinantly engineered with, an affinity tag (e.g., a purification tag).

Antibodies, TCRs, or antigen-binding fragments thereof provided herein are such that they can be conjugated or linked to a therapeutic moiety and/or an imaging or a detectable moiety and/or an affinity tag. Methods for conjugating or linking polypeptides are well known in the art. Associations (binding) between compounds and labels include any means known in the art including, but not limited to, covalent and non-covalent interactions, chemical conjugation as well as recombinant techniques.

Diagnostics

Anti-protein antibodies, TCRs, and fragments thereof can be used for in vivo and in vitro detection, diagnostic and/or monitoring purposes. Target protein (and in some instances, excess or mutant protein) can be involved in multiple diseases and disorders. Treatment of target protein related diseases and conditions depends, in part, upon their diagnosis, and the antibodies, TCRs, and antigen-binding fragments thereof described herein are useful for the diagnosis of excess or mutant target protein or for diagnosis for diseases and conditions associated with target protein activity.

Provided herein is method of detecting levels of target protein in a sample or a subject comprising (i) contacting an antibody, TCR, or antigen binding fragment thereof with a sample from a subject, and (ii) detecting a complex of the selected antibody, TCR, or antigen-binding fragment thereof and protein.

In one instance, the selected antibody, TCR, or antigen-binding fragment further comprises a detectable moiety. Detection can occur in vitro, in vivo or ex vivo. In vitro assays for the detection and/or determination (quantification, qualification, etc.) of target protein with the selected antibodies, TCRs, or antigen-binding fragments thereof include but are not limited to, for example, ELISAs, RIAs and western blots. In vitro detection, diagnosis or monitoring of target protein can occur by obtaining a sample (e.g., a biopsy sample) from a patient and testing the sample in, for example, a standard ELISA assay. For example, a 96-well microtiter plate can be coated with a selected antibody, TCR, or antigen-binding fragment thereof described herein, washed and coating with PBS-Tween/BSA to inhibit non-specific binding. The sample can be serially diluted and placed in duplicate wells compared to a serially-diluted standard curve of target protein. After incubating and washing the wells, an anti-target protein antibody or TCR labeled with biotin can be added, followed by addition of streptavidin-alkaline phosphatase. The wells can be washed and a substrate (horseradish peroxidase) added to develop the plate. The plate can be read using a conventional plate reader and software.

When detection occurs in vivo, contacting occurs via administration of the antibody, TCR, or antigen binding fragment thereof using any conventional means such as those described elsewhere herein. In such methods, detection of target protein (and in some instances excess levels of target protein) in a sample or a subject can be used to diagnose a disease or disorder associated with, or correlated with the activity of target protein such as those diseases and disorders described herein.

In the in vivo detection, diagnosis or monitoring of target protein, a patient is administered a selected antibody, TCR, or antigen-binding fragment thereof that binds to a target protein, which selected antibody, TCR, or antigen-binding fragment thereof is bound to a detectable moiety. The detectable moiety can be visualized using art-recognized methods such as, but not limited to, magnetic resonance imaging (MRI), fluorescence, radioimaging, light sources supplied by endoscopes, laparoscopes, or intravascular catheter (i.e., via detection of photoactive agents), photoscanning, positron emission tomography (PET) scanning, whole body nuclear magnetic resonance (NMR), radioscintography, single photon emission computed tomography (SPECT), targeted near infrared region (NIR) scanning, X-ray, ultrasound, etc. such as described, for example, in U.S. Pat. Nos. 6,096,289, 7,115,716, 7,112,412, U.S. Patent Application No. 20030003048 and U.S. Patent Application No. 20060147379, each of which is incorporated herein in its entirety by reference. Labels for detecting compounds using such methods are also known in the art and described in such patents and applications and are incorporated herein by reference. Visualization of the detectable moiety can allow for detection, diagnosis, and/or monitoring of a condition or disease associated with target protein.

Additional diagnostic assays that utilize antibodies or TCRs specific to the desired target protein, i.e., target protein, are known in the art and are also contemplated herein.

In the detection, diagnosis or monitoring of conditions and diseases, a subject patient can be administered a composition of a selected antibody, TCR, or antigen-binding fragment thereof, which selected Ig or TCR polypeptide is conjugated to a detectable moiety. The moiety can be visualized using art-recognized methods such as those described above. Visualization of the detectable moiety can allow for detection, diagnosis, and/or monitoring of conditions and diseases.

Thus, compositions are provided comprising Ig or TCR polypeptides (e.g. antibodies, TCRs, and antigen-binding fragments thereof) against target protein which are useful for detecting or diagnosing excess levels of target protein or target protein associated with a disease or disorder, potentially indicating need for therapeutic treatment. In certain instances, the antibodies or TCRs comprise a selected and optionally humanized anti-target protein antibody or TCR described herein. In other instances the antibody or TCR polypeptide encoded by a polynucleotide of a selected lymphocyte further comprises a second agent. Such an agent can be a molecule or moiety such as, for example, a reporter molecule or a detectable label. Detectable labels/moieties for such detection methods are known in the art and are described in more detail below. Reporter molecules are any moiety which can be detected using an assay. Non-limiting examples of reporter molecules which have been conjugated to polypeptides include enzymes, radiolabels, haptens, fluorescent labels, phosphorescent molecules, chemiluminescent molecules, chromophores, luminescent molecules, photoaffinity molecules, colored particles or ligands, such as biotin. Detectable labels include compounds and/or elements that can be detected due to their specific functional properties, and/or chemical characteristics, the use of which allows the polypeptide to which they are attached to be detected, and/or further quantified if desired. Many appropriate detectable (imaging) agents are known in the art, as are methods for their attachment to polypeptides (see, for e.g., U.S. Pat. Nos. 5,021,236; 4,938,948; and 4,472,509, each of which is hereby incorporated by reference).

Methods of joining polypeptides such as antibodies or TCRs with detectable moieties are known in the art and include, for example, recombinant DNA technology to form fusion proteins and conjugation (e.g., chemical conjugation). Methods for preparing fusion proteins by chemical conjugation or recombinant engineering are well-known in the art. Methods of covalently and non-covalently linking components are also known in the art. See, e.g., Williams (1995) Biochemistry 34:1787 1797; Dobeli (1998) Protein Expr. Purif 12:404-414; and Kroll (1993) DNA Cell. Biol. 12: 441-453.

It can be necessary, in some instances, to introduce an unstructured polypeptide linker region between a label or a moiety and one or more portion of the antibodies, TCRs, or antigen-binding fragments thereof. A linker can facilitate enhanced flexibility, and/or reduce steric hindrance between any two fragments. The linker can also facilitate the appropriate folding of each fragment to occur. The linker can be of natural origin, such as a sequence determined to exist in random coil between two domains of a protein. One linker sequence is the linker found between the C-terminal and N-terminal domains of the RNA polymerase a subunit. Other examples of naturally occurring linkers include linkers found in the 1CI and LexA proteins.

Within a linker, an amino acid sequence can be varied based on the characteristics of the linker as determined empirically or as revealed by modeling. Considerations in choosing a linker include flexibility of the linker, charge of the linker, and presence of some amino acids of the linker in the naturally-occurring subunits. The linker can also be designed such that residues in the linker contact deoxyribose nucleic acid (DNA), thereby influencing binding affinity or specificity, or to interact with other proteins. In some instances, such as when it is necessary to span a longer distance between subunits or when the domains must be held in a particular configuration, the linker can, optionally, contain an additional folded domain. In some instances, the design of a linker can involve an arrangement of domains which requires the linker to span a relatively short distance, e.g., less than about 10 Angstroms (Å). However, in certain instances, linkers span a distance of up to about 50 Angstroms.

Within the linker, the amino acid sequence can be varied based on the characteristics of the linker as determined empirically or as revealed by modeling. Considerations in choosing a linker include flexibility of the linker, charge of the linker, and presence of some amino acids of the linker in the naturally-occurring subunits. The linker can also be designed such that residues in the linker contact DNA, thereby influencing binding affinity or specificity, or to interact with other proteins. In some instances, when it is necessary to span a longer distance between subunits or when the domains must be held in a particular configuration, the linker can optionally contain an additional folded domain.

Methods for coupling polypeptides (free or cell-bound) to beads are known in the art. Methods for selecting coupled polypeptides or cells displaying a polypeptide are also known in the art. Briefly, paramagnetic polystyrene microparticles are commercially available (Spherotech, Inc., Libertyville, Ill.; Invitrogen, Carlsbad, Calif.) that couple peptides to microparticle surfaces that have been modified with functional groups or coated with various antibodies or ligands such as, for example, avidin, streptavidin or biotin.

The paramagnetic property of microparticles allows them to be separated from solution using a magnet. The microparticles can be easily re-suspended when removed from the magnet. Polypeptides can be coupled to paramagnetic polystyrene microparticles coated with a polyurethane layer in a tube. The hydroxy groups on the microparticle surface are activated by reaction with p-toluensulphonyl chloride (Nilsson K and Mosbach K. "p-Toluenesulfonyl chloride as an activating agent of agarose for the preparation of immobilized affinity ligands and proteins." Eur. J. Biochem. 1980: 112: 397-402). Alternatively, paramagnetic polystyrene microparticles containing surface carboxylic acid can be activated with a carbodiimide followed by coupling to a polypeptide, resulting in a stable amide bond between a primary amino group of the polypeptide and the carboxylic acid groups on the surface of the microparticles (Nakajima N and Ikade Y, Mechanism of amide formation by carbodiimide for bioconjugation in aqueous media, Bioconjugate Chem. 1995, 6(1), 123-130; Gilles M A, Hudson A Q and Borders C L Jr, Stability of water-soluble carbodiimides in aqueous solution, Anal Biochem. 1990 Feb. 1; 184(2):244-248; Sehgal D and Vijay I K, a method for the high efficiency of water-soluble carbodiimide-mediated amidation, Anal Biochem. 1994 April; 218(1):87-91; Szajani B et al, Effects of carbodiimide structure on the immobilization of enzymes, Appl Biochem Biotechnol. 1991 August; 30(2):225-231). Another option is to couple biotinylated polypeptides to paramagnetic polystyrene microparticles whose surfaces have been covalently linked with a monolayer of streptavidin. (Argarana C E, Kuntz I D, Birken S, Axel R, Cantor C R. Molecular cloning and nucleotide sequence of the streptavidin gene. Nucleic Acids Res. 1986; 14(4):1871-82; Pahler A, Hendrickson W A, Gawinowicz Kolks M A, Aragana C E, Cantor C R. Characterization and crystallization of core streptavidin. J Biol Chem 1987:262(29):13933-7).

Polypeptides can be conjugated to a wide variety of fluorescent dyes, quenchers and haptens such as fluorescein, R-phycoerythrin, and biotin. Conjugation can occur either during polypeptide synthesis or after the polypeptide has been synthesized and purified. Biotin is a small (244 kDa) vitamin that binds with high affinity to avidin and streptavidin proteins and can be conjugated to most peptides without altering their biological activities. Biotin-labeled polypeptides are easily purified from unlabeled polypeptides using immobilized streptavidin and avidin affinity gels, and streptavidin or avidin-conjugated probes can be used to detect biotinylated polypeptides in, for example, ELISA, dot blot or Western blot applications. N-hydroxysuccinimide esters of biotin are the most commonly used type of biotinylation agent. N-hydroxysuccinimide-activated biotins react efficiently with primary amino groups in physiological buffers to form stable amide bonds. Polypeptides have primary amines at the N-terminus and can also have several primary amines in the side chain of lysine residues that are available as targets for labeling with N-hydroxysuccinimide-activated biotin reagents. Several different N-hydroxysuccinimide esters of biotin are available, with varying properties and spacer arm length (Pierce, Rockford, Ill.). The sulfo-N-hydroxysuccinimide ester reagents are water soluble, enabling reactions to be performed in the absence of organic solvents.

The mole-to-mole ratio of biotin to polypeptide can be estimated using a 2-(4'-Hydroxyazobenzene-2-carboxylic acid) assay using art-recognized techniques (Green, N M, (1975) "Avidin. In Advances in Protein Chemistry." Academic Press, New York. 29, 85-133; Green, N M, (1971) "The use of bifunctional biotinyl compounds to determine the arrangement of subunits in avidin." Biochem J. 125, 781-791; Green, N M., (1965) "A spectrophotometric assay for avidin and biotin based on binding of dyes by avidin." Biochem. J. 94: 23c-24c). Several biotin molecules can be conjugated to a polypeptide and each biotin molecule can bind one molecule of avidin. The biotin-avidin bond formation is very rapid and stable in organic solvents, extreme pH and denaturing reagents. To quantitate biotinylation, a solution containing the biotinylated polypeptide is added to a mixture of 2-(4'-Hydroxyazobenzene-2-carboxylic acid) and avidin. Because biotin has a higher affinity for avidin, it displaces the 2-(4'-Hydroxyazobenzene-2-carboxylic acid) and the absorbance at 500 nm decreases proportionately. The amount of biotin in a solution can be quantitated in a single cuvette by measuring the absorbance of the 2-(4'-Hydroxyazobenzene-2-carboxylic acid)-avidin solution before and after addition of the biotin-containing peptide. The change in absorbance relates to the amount of biotin in the sample by the extinction coefficient of the 2-(4'-Hydroxyazobenzene-2-carboxylic acid)-avidin complex.

Alternatively, an Ig or TCR polypeptide encoded by a polynucleotide of a selected lymphocyte can be conjugated with a fluorescent moiety. Conjugating Ig or TCR polypeptides with fluorescent moieties (e.g., R-Phycoerythrin, fluorescein isothiocyanate (FITC), etc.) can be accomplished using art-recognized techniques described in, for example, Glazer, A N and Stryer L. (1984). Trends Biochem. Sci. 9:423-7; Kronick, M N and Grossman, P D (1983) Clin. Chem. 29:1582-6; Lanier, L L and Loken, M R (1984) J. Immunol., 132:151-156; Parks, D R et al. (1984) Cytometry 5:159-68; Hardy, R R et al. (1983) Nature 306:270-2; Hardy R R et al. (1984) J. Exp. Med. 159:1169-88; Kronick, M N (1986) J. Immuno. Meth. 92:1-13; Der-Balian G, Kameda, N and Rowley, G. (1988) Anal. Biochem. 173:59-63.

In one non-limiting instance, an Ig or TCR polypeptide encoded by a polynucleotide of a selected lymphocyte can be associated with (conjugated to) a detectable label, such as a radionuclide, iron-related compound, a dye, an imaging agent or a fluorescent agent for immunodetection of target protein which can be used to visualize binding of the Ig or TCR polypeptides to target protein in vitro and/or in vivo.

Non-limiting examples of radiolabels include, for example $^{32}$P, $^{33}$P, $^{43}$K, $^{52}$Fe, $^{57}$Co, $^{64}$Cu, $^{67}$Ga, $^{67}$Cu, $^{68}$Ga, $^{71}$Ge, $^{75}$Br, $^{76}$Br, $^{77}$Br, $^{77}$As, $^{77}$Br, $^{81}$Rb/$^{81}$MKr, $^{87}$MSr, $^{90}$Y, $^{97}$Ru, $^{99}$Tc, $^{100}$Pd, $^{101}$Rh, $^{103}$Pb, $^{105}$Rh, $^{109}$Pd, $^{111}$Ag, $^{111}$In, $^{113}$In, $^{119}$Sb, $^{121}$Sn, $^{123}$I, $^{125}$I, $^{127}$Cs, $^{128}$Ba, $^{129}$Cs, $^{131}$I, $^{131}$Cs, $^{143}$Pr, $^{153}$Sm, $^{161}$Tb, $^{166}$Ho, $^{169}$Eu, $^{177}$Lu, $^{186}$Re, $^{188}$Re, $^{189}$Re, $^{191}$Os, $^{193}$Pt, $^{194}$Ir, $^{197}$Hg, $^{199}$Au, $^{203}$Pb, $^{211}$At, $^{212}$Pb, $^{212}$Bi and $^{213}$Bi. Radiolabels can be attached to compounds using conventional chemistry Radiolabeled compounds are useful in in vitro diagnostics techniques and in in vivo radioimaging techniques and in radioimmunotherapy. For example, in the instance of in vivo imaging, the Ig or TCR polypeptides can be conjugated to an imaging agent rather than a radioisotope(s), including but not limited to a magnetic resonance image enhancing agent, wherein for instance an Ig or TCR polypeptide encoded by a polynucleotide of a selected lymphocyte is loaded with a large number of paramagnetic ions through chelating groups. Examples of chelating groups include EDTA, porphyrins, polyamines crown ethers and polyoximes. Examples of paramagnetic ions include gadolinium, iron, manganese, rhenium, europium, lanthanium, holmium and ferbium. Such detectable moieties also include: metals; metal chelators; lanthanides; lanthanide chelators; radiometals; radiometal chelators; positron-emitting nuclei; microbubbles (for ultrasound); liposomes; molecules microencapsulated in liposomes or nanosphere; monocrystalline iron oxide nanocompounds; magnetic resonance imaging contrast agents; light absorbing, reflecting and/or scattering agents; colloidal particles; fluorophores, such as near-infrared fluorophores. In many instances, such secondary functionality/moiety will be relatively large, e.g., at least 25 atomic mass units (amu) in size, and in many instances can be at least 50, 100 or 250 amu in size. In certain instances, the secondary functionality is a chelate moiety for chelating a metal, e.g., a chelator for a radiometal or paramagnetic ion. In instances, it is a chelator for a radionuclide useful for radiotherapy or imaging procedures.

Therapeutics

Provided herein are methods of preventing or treating one or more diseases or disorders associated with an identified target protein comprising administering a composition comprising a drug that inhibits or binds to an identified target of a polypeptide encoded by a polynucleotide of a selected lymphocyte, e.g., a selected antibody, TCR or antigen-binding fragment thereof; a peptide; a nucleic acid; or a small molecule; that binds to an identified target protein associated with the disease or disorder.

Provided herein are methods of preventing or treating one or more diseases or disorders associated with target protein comprising administering a composition comprising a drug that inhibits or binds to an identified target of a polypeptides encoded by a polynucleotide of a selected lymphocyte, e.g., a selected antibody, TCR or antigen-binding fragment thereof; a peptide; a nucleic acid; or a small molecule; that binds to protein associated with the disease or disorder, decreases complex formation between the identified target protein and a binding partner, e.g., a ligand, of the identified protein.

Compositions comprising a drug that inhibits or binds to an identified target of a polypeptides encoded by a polynucleotide of a selected lymphocyte, e.g., a selected antibody, TCR or antigen-binding fragment thereof; a peptide; a nucleic acid; or a small molecule; can be administered to a patient (e.g., a mammal such as a human or a non-human animal such as a primate, rodent, cow, horse, pig, sheep, etc.) in a therapeutically effective amount which are effective for producing some desired therapeutic effect by inhibiting a disease or disorder associated with the identified target protein, at a reasonable benefit/risk ratio applicable to any medical treatment. For the administration of the present compositions to human patients, the compositions can be formulated by methodology known by one of ordinary skill in the art. A therapeutically effective amount is an amount achieves at least partially a desired therapeutic or prophylactic effect in an organ or tissue. In one example, the amount of a drug that inhibits or binds to an identified target of a polypeptides encoded by a polynucleotide of a selected lymphocyte, e.g., a selected antibody, TCR or antigen-binding fragment thereof; a peptide; a nucleic acid; or a small molecule; necessary to bring about prevention and/or therapeutic treatment of a disease or disorder is not fixed per se. The amount of drug that inhibits or binds to an identified target of a polypeptides encoded by a polynucleotide of a selected lymphocyte, e.g., a selected antibody, TCR or antigen-binding fragment thereof; a peptide; a nucleic acid; or a small molecule; administered will vary with the type of drug, type of disease, extensiveness of the disease, and size of the mammal suffering from the disease or disorder. In some instances two or more drugs that inhibit or binds to an identified target of a polypeptides encoded by a polynucleotide of a selected lymphocyte, e.g., a selected antibody, TCR or antigen-binding fragment thereof; a peptide; a nucleic acid; or a small molecule; are administered to a patient in combination. Combinations include concomitant or subsequent administration of the drugs that inhibits or binds to an identified target of a polypeptides encoded by a polynucleotide of a selected lymphocyte, e.g., a selected antibody, TCR or antigen-binding fragment thereof; a peptide; a nucleic acid; or a small molecule.

A response is achieved when the patient experiences partial or total alleviation, or reduction of signs or symptoms of illness, and specifically includes, without limitation, prolongation of survival. The expected progression-free survival times can be measured in months to years, depending on prognostic factors including the number of relapses, stage of disease, and other factors. Prolonging survival includes without limitation times of at least 1 month, about at least 2 months, about at least 3 months, about at least 4 months, about at least months, about at least 1 year, about at least 2 years, about at least 3 years, etc. Overall survival can also be measured in months to years. The patient's symptoms can remain static or can decrease.

A physician or veterinarian having ordinary skill in the art can readily determine and prescribe the effective amount (ED50) of the composition required. For example, the physician or veterinarian could start doses of the compounds employed in the composition at levels lower than that required in order to achieve the desired therapeutic effect and gradually increase the dosage until the desired effect is achieved.

Compositions can be administered to a patient by any convenient route such as described above. Regardless of the route of administration selected, the compositions are formulated into acceptable dosage forms such as described below or by other conventional methods known to those of skill in the art.

Actual dosage levels of the active ingredients in the compositions can be varied so as to obtain an amount of the active ingredient that is effective to achieve the desired therapeutic response for a particular patient, composition, and mode of administration, without being toxic to the patient. The selected dosage level will depend upon a variety of factors including the activity of the particular compound employed, the route of administration, the time of administration, the rate of excretion of the particular compound being employed, the duration of the treatment, other drugs, compounds and/or materials used in combination with the particular composition employed, the age, sex, weight, condition, general health and prior medical history of the patient being treated, and like factors well known in the medical arts.

Ig or TCR polypeptides or other drugs can be combined with a therapeutic moiety or to a detectable (imaging) moiety using methods known in the art such as, for example, chemical conjugation, covalent or non-covalent bonds or recombinant techniques to create conjugates or fusion proteins such as described in more detail below. Alternatively, Ig or TCR polypeptides and/or other agents can be combined in separate compositions for simultaneous or sequential administration.

Pharmaceutical Compositions

Each of the compounds described herein can be used as a composition when combined with an acceptable carrier or excipient. Such compositions are useful for in vitro or in vivo analysis or for administration to a subject in vivo or ex vivo for treating a subject with the disclosed compounds.

Thus pharmaceutical compositions can include, in addition to active ingredient, a pharmaceutically acceptable excipient, carrier, buffer, stabilizer or other materials well known to those skilled in the art. Such materials should be non-toxic and should not interfere with the efficacy of the active ingredient. The precise nature of the carrier or other material will depend on the route of administration.

Pharmaceutical formulations comprising a protein of interest, e.g., Ig or TCR polypeptide encoded by a selected polynucleotide of a lymphocyte, identified by the methods described herein can be prepared for storage by mixing the Ig or TCR polypeptide having the desired degree of purity with optional physiologically acceptable carriers, excipients or stabilizers (Remington's Pharmaceutical Sciences 16th edition, Oslo, A. Ed. (1980)), in the form of lyophilized formulations or aqueous solutions. Acceptable carriers, excipients, or stabilizers are those that are non-toxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN®, PLURONICS® or polyethylene glycol (PEG).

Acceptable carriers are physiologically acceptable to the administered patient and retain the therapeutic properties of the compounds with/in which it is administered. Acceptable carriers and their formulations are and generally described in, for example, Remington' pharmaceutical Sciences (18th Edition, ed. A. Gennaro, Mack Publishing Co., Easton, Pa. 1990). One exemplary carrier is physiological saline. The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject compounds from the administration site of one organ, or portion of the body, to another organ, or portion of the body, or in an in vitro assay system. Each carrier is acceptable in the sense of being compatible with the other ingredients of the formulation and not injurious to a subject to whom it is administered. Nor should an acceptable carrier alter the specific activity of the subject compounds.

In one aspect, provided herein are pharmaceutically acceptable or physiologically acceptable compositions including solvents (aqueous or non-aqueous), solutions, emulsions, dispersion media, coatings, isotonic and absorption promoting or delaying agents, compatible with pharmaceutical administration. Pharmaceutical compositions or pharmaceutical formulations therefore refer to a composition suitable for pharmaceutical use in a subject. The pharmaceutical compositions and formulations include an amount of a compound described herein and a pharmaceutically or physiologically acceptable carrier.

Compositions can be formulated to be compatible with a particular route of administration (i.e., systemic or local). Thus, compositions include carriers, diluents, or excipients suitable for administration by various routes.

In another instance, the compositions can further comprise, if needed, an acceptable additive in order to improve the stability of the compounds in composition and/or to control the release rate of the composition. Acceptable additives do not alter the specific activity of the subject compounds. Exemplary acceptable additives include, but are not limited to, a sugar such as mannitol, sorbitol, glucose, xylitol, trehalose, sorbose, sucrose, galactose, dextran, dextrose, fructose, lactose and mixtures thereof. Acceptable additives can be combined with acceptable carriers and/or excipients such as dextrose. Alternatively, exemplary acceptable additives include, but are not limited to, a surfactant such as polysorbate 20 or polysorbate 80 to increase stability of the peptide and decrease gelling of the solution. The surfactant can be added to the composition in an amount of 0.01% to 5% of the solution. Addition of such acceptable additives increases the stability and half-life of the composition in storage.

The pharmaceutical composition can be administered, for example, by injection. Compositions for injection include aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). The carrier can be a solvent or dispersion medium containing, for example, water, ethanol, polyol (for example, glycerol, propylene glycol, and liquid polyethylene glycol, and the like), and suitable mixtures thereof. Fluidity can be maintained, for example, by the use of a coating such as lecithin, by the maintenance of the required particle size in the case of dispersion and by the use of surfactants. Antibacterial and antifungal agents include, for example, parabens, chlorobutanol, phenol, ascorbic acid and thimerosal. Isotonic agents, for example, sugars, polyalcohols such as manitol, sorbitol, and sodium chloride can be included in the composition. The resulting solutions can be packaged for use as is, or lyophilized; the lyophilized preparation can later be combined with a sterile solution prior to administration. For intravenous, injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives can be included, as needed. Sterile injectable solutions can be prepared by incorporating an active ingredient in the required amount in an appropriate solvent with one or a combination of ingredients enumerated above, as required, followed by filtered sterilization. Generally, dispersions are prepared by incorporating the active ingredient into a sterile vehicle which contains a basic dispersion medium and the required other ingredients from those enumerated above. In the case of sterile powders for the preparation of sterile injectable solutions, the preferred methods of preparation are vacuum drying and freeze drying which yields a powder of the active ingredient plus any additional desired ingredient from a previously sterile-filtered solution thereof.

Compositions can be conventionally administered intravenously, such as by injection of a unit dose, for example. For injection, an active ingredient can be in the form of a parenterally acceptable aqueous solution which is substantially pyrogen-free and has suitable pH, isotonicity and stability. One can prepare suitable solutions using, for example, isotonic vehicles such as Sodium Chloride Injection, Ringer's Injection, Lactated Ringer's Injection. Preservatives, stabilizers, buffers, antioxidants and/or other additives can be included, as required. Additionally, compositions can be administered via aerosolization. (Lahn et al., Aerosolized Anti-T-cell-Receptor Antibodies Are Effective against Airway Inflammation and Hyperreactivity, Int. Arch. Allegery Immuno., 134: 49-55 (2004)).

In one instance, the composition is lyophilized, for example, to increase shelf-life in storage. When the compositions are considered for use in medicaments or any of the methods provided herein, it is contemplated that the composition can be substantially free of pyrogens such that the composition will not cause an inflammatory reaction or an unsafe allergic reaction when administered to a human patient. Testing compositions for pyrogens and preparing compositions substantially free of pyrogens are well understood to one or ordinary skill of the art and can be accomplished using commercially available kits.

Acceptable carriers can contain a compound that stabilizes, increases or delays absorption or clearance. Such compounds include, for example, carbohydrates, such as glucose, sucrose, or dextrans; low molecular weight proteins; compositions that reduce the clearance or hydrolysis of peptides; or excipients or other stabilizers and/or buffers. Agents that delay absorption include, for example, aluminum monostearate and gelatin. Detergents can also be used to stabilize or to increase or decrease the absorption of the pharmaceutical composition, including liposomal carriers. To protect from digestion the compound can be complexed with a composition to render it resistant to acidic and enzymatic hydrolysis, or the compound can be complexed in an appropriately resistant carrier such as a liposome. Means of protecting compounds from digestion are known in the art (see, e.g., Fix (1996) Pharm Res. 13:1760 1764; Samanen (1996) J. Pharm. Pharmacol. 48:119 135; and U.S. Pat. No. 5,391,377, describing lipid compositions for oral delivery of therapeutic agents).

The compositions can be administered in a manner compatible with the dosage formulation, and in a therapeutically effective amount. The quantity to be administered depends on the subject to be treated, capacity of the subject's immune system to utilize the active ingredient, and degree of binding capacity desired. Precise amounts of active ingredient required to be administered depend on the judgment of the practitioner and are peculiar to each individual. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations in the blood are contemplated.

One instance contemplates the use of the compositions described herein to make a medicament for treating a condition, disease or disorder. For example, after identification of the of a polypeptide encoded by a polynucleotide from a selected lymphocyte, a drug, e.g., an antibody, peptide, nucleic acid, or small molecule, that inhibits the identified to make a medicament for treating a condition, disease or disorder. Medicaments can be formulated based on the physical characteristics of the patient/subject needing treatment, and can be formulated in single or multiple formulations based on the stage of the condition, disease or disorder. Medicaments can be packaged in a suitable package with appropriate labels for the distribution to hospitals and clinics wherein the label is for the indication of treating a subject having a disease described herein. Medicaments can be packaged as a single or multiple units. Instructions for the dosage and administration of the compositions can be included with the packages as described below. The invention is further directed to medicaments of a humanized anti-target protein antibody, TCR, or antigen binding fragment thereof described hereinabove and a pharmaceutically acceptable carrier.

Articles of Manufacture

In one aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers can be formed from a variety of materials such as glass or plastic. The container holds a composition which is by itself or combined with another composition effective for treating, preventing and/or diagnosing the condition and can have a sterile access port (for example the container can be an intravenous solution bag or a vial having a stopper pierceable by a hypodermic injection needle). At least one active agent in the composition is an Ig or TCR polypeptide encoded by the selected polynucleotide. The label or package insert indicates that the composition is used for treating the condition of choice. Moreover, the article of manufacture can comprise (a) a first container with a composition contained therein, wherein the composition comprises an Ig or TCR polypeptide encoded by the selected polynucleotide of the invention; and (b) a second container with a composition contained therein, wherein the composition comprises a further cytotoxic or otherwise therapeutic agent. The article of manufacture in this instance of the invention can further comprise a package insert indicating that the compositions can be used to treat a particular condition. Alternatively, or additionally, the article of manufacture can further comprise a second (or third) container comprising a pharmaceutically-acceptable buffer, such as bacteriostatic water for injection (BWFI), phosphate-buffered saline, Ringer's solution and dextrose solution. It can further include other materials desirable from a commercial and user standpoint, including other buffers, diluents, filters, needles, and syringes.

Packages and Kits

In still further instances, the present application concerns kits for use with the compounds described above. Selected antibodies, TCRs, or antigen-binding fragments thereof that bind target protein can be provided in a kit. The kits will thus comprise, in suitable container means, a composition comprising an Ig or TCR polypeptide that binds target protein. The kit can comprise an Ig or TCR polypeptide that binds target protein in suitable container means.

The container means of the kits will generally include at least one vial, test tube, flask, bottle, syringe and/or other container means, into which the at least one polypeptide can be placed, and/or preferably, suitably aliquoted. The kits can include a means for containing at least one fusion protein, detectable moiety, reporter molecule, and/or any other reagent containers in close confinement for commercial sale. Such containers can include injection and/or blow-molded plastic containers into which the desired vials are retained. Kits can also include printed material for use of the materials in the kit.

Packages and kits can additionally include a buffering agent, a preservative and/or a stabilizing agent in a pharmaceutical formulation. Each component of the kit can be enclosed within an individual container and all of the various containers can be within a single package. Invention kits can be designed for cold storage or room temperature storage.

Additionally, the preparations can contain stabilizers to increase the shelf-life of the kits and include, for example, bovine serum albumin (BSA). Where the compositions are lyophilized, the kit can contain further preparations of solutions to reconstitute the lyophilized preparations. Acceptable reconstitution solutions are well known in the art and include, for example, pharmaceutically acceptable phosphate buffered saline (PBS).

Additionally, the packages or kits provided herein can further include any of the other moieties provided herein such as, for example, one or more reporter molecules and/or one or more detectable moieties/agents.

Packages and kits can further include one or more components for an assay, such as, for example, an ELISA assay. Samples to be tested in this application include, for example, biopsies, and tissue sections. Packages and kits can further include one or more components for collection of a sample (e.g., a syringe, a cup, a swab, etc.).

Packages and kits can further include a label specifying, for example, a product description, mode of administration and/or indication of treatment. Packages provided herein can include any of the compositions as described herein. The package can further include a label for treating a disease.

Instructions can include instructions for practicing any of the methods described herein including treatment methods. Instructions can additionally include indications of a satisfactory clinical endpoint or any adverse symptoms that can occur, or additional information required by regulatory agencies such as the Food and Drug Administration for use on a human subject.

The instructions can be on "printed matter," e.g., on paper or cardboard within or affixed to the kit, or on a label affixed to the kit or packaging material, or attached to a vial or tube containing a component of the kit. Instructions can additionally be included on a computer readable medium, such as a disk (floppy diskette or hard disk), optical CD such as CD- or DVD-ROM/RAM, magnetic tape, electrical storage media such as RAM and ROM, IC tip and hybrids of these such as magnetic/optical storage media.

Additional Embodiments

Disclosed herein are molecules, materials, compositions, and components that can be used for, can be used in conjunction with, can be used in preparation for, or are products of methods and compositions disclosed herein. It is understood that when combinations, subsets, interactions, groups, etc. of these materials are disclosed and while specific reference of each various individual and collective combinations and permutation of these molecules and compounds cannot be explicitly disclosed, each is specifically contemplated and described herein. For example, if a nucleotide or nucleic acid is disclosed and discussed and a number of modifications that can be made to a number of molecules including the nucleotide or nucleic acid are discussed, each and every combination and permutation of nucleotide or nucleic acid and the modifications that are possible are specifically contemplated unless specifically indicated to the contrary. This concept applies to all aspects of this application including, but not limited to, steps in methods of making and using the disclosed methods and compositions. Thus, if there are a variety of additional steps that can be performed it is understood that each of these additional steps can be performed with any specific instance or combination of instances of the disclosed methods, and that each such combination is specifically contemplated and should be considered disclosed.

While some instances described herein have been shown and described herein, such instances are provided by way of example only. Numerous variations, changes, and substitutions will now occur to those skilled in the art without departing from the disclosure provided herein. It should be understood that various alternatives to the instances described herein can be employed in practicing the methods described herein.

Unless otherwise explained, all technical and scientific terms used herein have the same meaning as commonly understood by one of ordinary skill in the art to which this disclosure belongs. The following references contain instances of the methods and compositions that can be used herein: The Merck Manual of Diagnosis and Therapy, 18$^{th}$ Edition, published by Merck Research Laboratories, 2006; Benjamin Lewin, Genes IX, published by Jones & Bartlett Publishing, 2007; Kendrew et al. (eds.), The Encyclopedia of Mol. Biology, published by Blackwell Science Ltd., 1994; and Robert A. Meyers (ed.), Mol. Biology and Biotechnology: a Comprehensive Desk Reference, published by VCH Publishers, Inc., (1995).

Standard procedures of the present disclosure are described, e.g., in Maniatis et al., Molecular Cloning: A Laboratory Manual, Cold Spring Harbor Laboratory Press, Cold Spring Harbor, N.Y., USA (1982); Sambrook et al., Molecular Cloning: A Laboratory Manual (2 ed.), Cold Spring Harbor Laboratory Press, Cold Spring Harbor, N.Y., USA (1989); Davis et al., Basic Methods in Molecular Biology, Elsevier Science Publishing, Inc., New York, USA (1986); or Methods in Enzymology: Guide to Molecular Cloning Techniques Vol. 152, S. L. Berger and A. R. Kimmerl (eds.), Academic Press Inc., San Diego, USA (1987)). Current Protocols in Molecular Biology (CPMB) (Fred M. Ausubel, et al. ed., John Wiley and Sons, Inc.), Current Protocols in Protein Science (CPPS) (John E. Coligan, et. al., ed., John Wiley and Sons, Inc.), Current Protocols in Immunology (CPI) (John E. Coligan, et. al., ed. John Wiley and Sons, Inc.), Current Protocols in Cell Biology (CPCB) (Juan S. Bonifacino et. al. ed., John Wiley and Sons, Inc.), Culture of Animal Cells: A Manual of Basic Technique by R. Ian Freshney, Publisher: Wiley-Liss; 5th edition (2005), and Animal Cell Culture Methods (Methods in Cell Biology, Vol. 57, Jennie P. Mather and David Barnes editors, Academic Press, 1st edition, 1998).

EXAMPLES

Example 1—Protocol for Preparing Cells for Performing Emulsion-Based, Massively High Throughput Single-Cell Polynucleotide Sequencing A cell population from a diseased tissue sample comprising infiltrating tumor lymphocytes (TILs) is obtained. A corresponding normal tissue sample or NAT sample is also obtained. The cells have an intact plasma membrane so that they do not leak excessive amounts of mRNA into the surrounding media. The cells need not be viable. The samples comprise both lymphocytes as well as normal cells and/or diseased cells (e.g., cancerous cells).

T-cells or B-cells are washed by centrifugation 200 g for 10 min for twice in Cell Buffer: 1× Dulbecco's Phosphate-Buffered Saline (PBS). The cells are then diluted in Cell Buffer to a cell concentration of $3.5 \times 10^6$ cells/mL. The suspension is then pipetted through a 20 µm cell strainer.

Example 2—Protocol for Preparing the Emulsion Reaction Mixture for Performing Emulsion-Based, Massively High Throughput Single-Cell Polynucleotide Sequencing An emulsion reaction mixture containing the reagents and oligonucleotides in the tables below is mixed at room temperature in a PCR-clean hood.

| Reagent | Stock conc. (mM) | Final conc. in droplet (mM) | Final conc. in rxn phase (mM) | µL per 200 µL |
|---|---|---|---|---|
| Tris-Cl, pH 8.0 | 500.00 | 50.00 | 100.00 | 40.00 |
| MgSO$_4$ | 100.00 | 3.00 | 6.00 | 12.00 |
| DTT | 1,000.00 | 10.00 | 20.00 | 4.00 |
| dNTPs each | 10.00 | 0.50 | 1.00 | 20.00 |
| 5'biotin oligo-dT | $1.40 \times 10^{-2}$ | $2.50 \times 10^{-4}$ | $5.00 \times 10^{-4}$ | 7.14 |
| Template switch oligo | 0.1 | $1.00 \times 10^{-3}$ | $2.00 \times 10^{-3}$ | 4.00 |
| DB template molecules/µL | $1.00 \times 10^6$ | $1.75 \times 10^4$ | $3.50 \times 10^4$ | 7.00 |
| DB primer fwd | 0.2 | $5.00 \times 10^{-4}$ | $1.00 \times 10^{-3}$ | 1.00 |
| DB primer rev | 0.2 | $7.50 \times 10^{-4}$ | $1.50 \times 10^{-3}$ | 1.50 |
| HALT Protease inhibitor (X) | 200 | 1.00 | 2.00 | 2.00 |
| Enzymatic RNase Inhibitor (U/µL) | 40 | 0.40 | 0.80 | 4.00 |
| MMLV RNaseH-reverse transcriptase | | | | 10.00 |
| Phusion HF DNA polymerase | | | | 10.00 |
| Triton X-100 (% v/v) | 2.5 | 0.25 | 0.50 | 40.00 |
| Water | | | | To 200 |

Oligonucleotide Sequences:

| | |
|---|---|
| 5'biotin oligo-dT anchored reverse transcription primer | /5BiosG//iSp18/TTT TTT TTT TTT TTT TTT TTT TTT T V N |
| Droplet barcode template: | ATCCATCCACGACTGACGGACGTA TTAAANNNNWNNNNWNNNNAGATC GGAAGAGCACACGTCTGAACTCCA GTCACC |
| template switch oligo | AATACGTCCGTCAGTCGTGGATGN NTNNANNTrGrGG |

| | |
|---|---|
| Vessel Barcode forward | CATCCACGACTGACGGACGTATT |
| Vessel Barcode reverse | GTGACTGGAGTTCAGACGTGTGCT |

/5Biosg/ = 5'biotin modification;
/iSp18/ = 18-carbon spacer;
V = A, C, or G;
N = any base;
rG = riboguanosine;
W = A or T.

Example 3—Protocol for Generating Emulsions for Performing Emulsion-Based, Massively High Throughput Single-Cell Polynucleotide Sequencing Once cells and reaction mixture are prepared, the emulsion is formed. A 100-μL Hamilton Microliter syringe is used to overload a 100-μL PEEK sample loop in two injections of ~100 μL each of the reaction mixture. A 100-μL Hamilton Gastight syringe is used to load ~110 μL of the cell suspension into a ~100 μL, 0.2 mm internal diameter FEP tubing loop. The loop is attached to a mechanical rotator that is constantly inverting the cell loop approximately once every 1-2 sec to prevent cell settling and bunching. The emulsion is formed by focused flow jetting through a Dolomite 2-reagent chip with internal fluorophilic coating. The outer oil channels contained 0.5-5.0% (w/v) polyethylene glycol-based surfactant in HFE7500 (Novec 7500) fluorocarbon oil. The emulsion jet is run at a constant flow rate (equal in cell phase and reaction phase channels). The emulsion chip output is collected through a 12 cm, 0.5 mm internal diameter PEEK tube, by dropping into polypropylene PCR tubes that are kept at approximately 0° C. in a chilled block. Four fractions are collected, each containing 50 μL of aqueous material in emulsion (5 min of run time per fraction). Most of the settled oil is removed from the bottom of each tube with a capillary micropipette. Each emulsion fraction is gently overlayed with 40 μL of Overlay Solution: 50 mM Na-EDTA, pH 8.0, 0.002% (w/v) cresol red. The emulsions are incubated in a thermal cycler with the following program (min:sec):

1. 42.0° C. for 30:00 (reverse transcription)
2. 95.0° C. for 05:00 (denature reverse transcriptase and DNA templates)
3. 95.0° C. for 00:10
4. 65.0° C. for 00:30
5. 72.0° C. for 00:30
6. Go to 3, total 55 cycles (amplify Vessel Barcode and fuse to cDNA)
7. 4.0° C. for no time limit The emulsion is held at 4.0° C. overnight.

Example 4—Protocol for Breaking Emulsions for Performing Emulsion-Based, Massively High Throughput Single-Cell Polynucleotide Sequencing Using a capillary micropipette tip, as much Overlay Solution is removed as possible without removing emulsion material. To each tube, 12.5 μL Qiagen Protease solution and 2.5 μL of 0.5 M Na-EDTA, pH 8.0 is added. The emulsion is broke by adding 40 μL of 1:1 FC-40:perfluorooctanol and gently inverting about 10 times.

The contents of tube are gently centrifuged and incubated in a thermal cycler with the following program (min:sec):

1. 50° C. for 15:00 (protease digestion)
2. 70° C. for 10:00 (protease inactivation)
3. 95° C. for 03:00 (protease inactivation and DNA denaturation)
4. 4.0° C. forever The tube is centrifuges and the upper aqueous phase and interface is moved to a fresh microcentrifuge tube and centrifuged at 15,000 g for 1 minute. The upper aqueous phase is transferred to a new tube, without disturbing the interface

Example 5—Protocol for Cleaning Polynucleotides from Emulsions for Performing Emulsion-Based, Massively High Throughput Single-Cell Polynucleotide Sequencing 0.25V of NEB streptavidin beads are added in 2×BW (10 mM Tris-Cl, pH 8.0, 1 mM EDTA, 2 M NaCl, 0.2% tween-20) and incubated at RT for 15 min. The beads are then washed with 1×BW, washed three times with 0.001% tween-20, and eluted by adding 0.25V of 0.001% tween-20 and heating to 95° C. for 3 min. 5 volumes of Qiagen Buffer PB is added and applied to a silica column. The beads are then washed with 0.7 mL of wash buffer and eluted in 180 μL of: 5 mM Tris-Cl, pH 8.8, 0.1 mM EDTA, 0.001% tween-20.

Example 6—Protocol for First PCR Reaction (PCR1) of Polynucleotides for Next Generation Sequencing for Performing Emulsion-Based, Massively High Throughput Single-Cell Polynucleotide Sequencing 163.2 μL of purified cDNA is used for the PCR1.

| | Library PCR1 | | | | |
|---|---|---|---|---|---|
| Reagent | Stock (mM) | Final Concentration | μL per 20-μL rxn | 60-μL rxn | 4 60-μL rxns |
| Q5 buffer 5X | 5.00 | 1.00 | 4.00 | 12.00 | 48.00 |
| Each dNTPs | 10.00 | 0.20 | 0.40 | 1.20 | 4.80 |
| Q5 Hot Start | 125.00 | 1.00 | 0.16 | 0.48 | 1.92 |
| 633 (10 μm) | | | 0.16 | 0.48 | 1.92 |
| Ig-C primer mix (10 μm each) | | | 0.16 | 0.48 | 1.92 |
| cDNA | | | 13.60 | 40.80 | 163.20 |
| H2O | | | 1.52 | 4.56 | 18.24 |

Primer Sequences
"Ig-C" Mix:

| | |
|---|---|
| IgM | GGGTTGGGGCGGATGCAC |
| IgD | CATCCGGAGCCTTGGTGG |
| IgA | CCTTGGGGCTGGTCGGGG |
| IgE | CGGATGGGCTCTGTGTGG |
| IgG | CCGATGGGCCCTTGGTGG |
| IGKJ1 | TTTGATCTCCACCTTGGTCCCTCCGC |
| IGKJ2 | TTTGATCTCCAGCTTGGTCCCCTGG |
| IGKJ3 | TTTGATATCCACTTTGGTCCCAGGGC |
| IGKJ4 | TTTGATTTCCACCTTGGTCCCTTGGC |

| | |
|---|---|
| IGKJ5 | TTTAATCTCCAGTCGTGTCCCTTGGC |
| IGLJ1 | GAGGACGGTCACCTTGGTGCCA |
| IGLJ2 | TAGGACGGTCAGCTTGGTCCCTCC |
| IGLJ3 | GAGGACGGTCAGCTGGGTGCC |
| IGLJ4 | TAAAATGATCAGCTGGGTTCCTCCAC |
| IGLJ5 | TAGGACGGTGACCTTGGTCCCAGT |
| 633 | GTGACTGGAGTTCAGACGTGTGCTCTTCCGATCT |

4×60 µL reactions are aliquoted in PCR tubes and the following program is run in a thermocycler:
1. 98° C. for 01:00
2. 98° C. for 00:10
3. 64° C. for 00:20
4. 72° C. for 00:20
5. Go to 2 for a total of 6 cycles
6. 4° C. no time limit The PCR product is purified with 1.2 volumes of AMPure XP, washed with 80% ethanol and eluted in 60 µL Dilution Buffer (10 mM Tris-Cl, pH 8.0, 0.1 mM EDTA)

Example 7—Protocol for Second PCR Reaction (PCR2) of Polynucleotides for Next Generation Sequencing for Performing Emulsion-Based, Massively High Throughput Single-Cell Polynucleotide Sequencing 20 µL of purified PCR1 product is used for each sub-library (e.g. IgL chain or IgH chain or TCRα chain or TCRβ chain)

Library PCR2

| Reagent | Stock (mM) | Final Concentration | µL per 20-µL reaction | for 50-µL rxn |
|---|---|---|---|---|
| Q5 buffer 5X | 5.00 | 1.00 | 4.00 | 10.00 |
| Each dNTPs | 10.00 | 0.20 | 0.40 | 1.00 |
| Q5 Hot Start | 125.00 | 1.00 | 0.16 | 0.40 |
| C7-index-P7 (2 µm) | | | 1.60 | 4.00 |
| P5-IgH or P5-IgL mix (1 µm each) | | | 1.60 | 4.00 |
| cDNA | | | 8.00 | 20.00 |
| H2O | | | 4.24 | 10.60 |

Primer Sequences
P5-IgH (Heavy) Mix

| | |
|---|---|
| IgM | ACACTCTTTCCCTACACGACGCTCTTCCGATCTGGGTTGGGGCGGATGCAC |
| IgD | ACACTCTTTCCCTACACGACGCTCTTCCGATCTCATCCGGAGCCTTGGTGG |
| IgA | ACACTCTTTCCCTACACGACGCTCTTCCGATCTCCTTGGGGCTGGTCGGGG |
| IgE | ACACTCTTTCCCTACACGACGCTCTTCCGATCTCGGATGGGCTCTGTGTGG |
| IgG | ACACTCTTTCCCTACACGACGCTCTTCCGATCTCCGATGGGCCCTTGTGG |

P5-IgL (Light) Mix

| | |
|---|---|
| IGKJ1 | ACACTCTTTCCCTACACGACGCTCTTCCGATCTTTTGATCTCCACCTTGGTCCCTCCGC |
| IGKJ2 | ACACTCTTTCCCTACACGACGCTCTTCCGATCTTTTGATCTCCAGCTTGGTCCCCTGG |
| IGKJ3 | ACACTCTTTCCCTACACGACGCTCTTCCGATCTTTTGATATCCACTTTGGTCCCAGGGC |
| IGKJ4 | ACACTCTTTCCCTACACGACGCTCTTCCGATCTTTTGATTTCCACCTTGGTCCCTTGGC |
| IGKJ5 | ACACTCTTTCCCTACACGACGCTCTTCCGATCTTTTAATCTCCAGTCGTGTCCCTTGGC |
| IGLJ1 | ACACTCTTTCCCTACACGACGCTCTTCCGATCTGAGGACGGTCACCTTGGTGCCA |
| IGLJ2 | ACACTCTTTCCCTACACGACGCTCTTCCGATCTTAGGACGGTCAGCTTGGTCCCTCC |
| IGLJ3 | ACACTCTTTCCCTACACGACGCTCTTCCGATCTGAGGACGGTCAGCTGGGTGCC |
| IGLJ4 | ACACTCTTTCCCTACACGACGCTCTTCCGATCTTAAAATGATCAGCTGGGTTCCTCCAC |
| IGLJ5 | ACACTCTTTCCCTACACGACGCTCTTCCGATCTTAGGACGGTGACCTTGGTCCCAGT |
| IGLJ6 | ACACTCTTTCCCTACACGACGCTCTTCCGATCTTAGGACGGTCAGCTCGGTCCCC |

A "P7-index-C7" primer is used comprising the concatenation of Illumina C7, 6-base barcode, and P7 sequences:

n5'
CAAGCAGAAGACGGCATACGAGAT[NNNNNN]GTGACTGGAGTTCAGACGTGTGCTCTTCCGATCT

The following program is run in a thermocycler:
1. 98° C. for 01:00
2. 98° C. for 00:10
3. 64° C. for 00:20
4. 72° C. for 00:20
5. Go to 2 for a total of 6 cycles
6. 4° C. no time limit The PCR product is purified with 1.2 volumes of AMPure and eluted in 40 µL Dilution Buffer Example 8—Protocol for Third PCR Reaction (PCR3) of Polynucleotides for Next Generation Sequencing for Performing Emulsion-Based, Massively High Throughput Single-Cell Polynucleotide Sequencing 0.8 µL of purified PCR2 product is used for a pilot qPCR to determine final number of amplification cycles.

Library qPCR3a

| Reagent | Stock (mM) | Final Concentration | µL per 20-µL reaction |
|---|---|---|---|
| Q5 buffer 5X | 5.00 | 1.00 | 4.00 |
| Each dNTPs | 10.00 | 0.20 | 0.40 |
| SYBR Green 11:500 | 83.00 | 1.00 | 0.24 |
| Q5 Hot Start | 125.00 | 1.00 | 0.16 |
| C5-P5 (µM) | 10.00 | 0.40 | 0.80 |

-continued

Library qPCR3a

| Reagent | Stock (mM) | Final Concentration | μL per 20-μL reaction |
|---|---|---|---|
| C7 (μM) | 10.00 | 0.40 | 0.80 |
| cDNA | | | 8.00 |
| H2O | | | 5.60 |

Primer Sequences

P5:
AATGATACGGCGACCACCGAGATCTACACTCTTTCCCTACACGACGCTCT

TCCGATCT

C7:
CAAGCAGAAGACGGCATACGAGAT

The following program is run in a qPCR machine:
1. 98° C. for 01:00
2. 98° C. for 00:10
3. 64° C. for 00:20
4. 72° C. for 00:20
5. Read plate
6. Go to 2 for a total of 25 cycles The qPCR intensity plot is inspected to determine the amplification cycle at which fluorescence intensity is maximal but at which exponential amplification of DNA had not yet ended. This is the final cycle number for the PCR3 endpoint.

24.0 μL of purified PCR2 product is used for the endpoint PCR3.

Library qPCR3b

| Reagent | Stock (mM) | Final Concentration | μL per 60-μL rxn |
|---|---|---|---|
| Q5 buffer 5X | 5.00 | 1.00 | 12.00 |
| Each dNTPs | 10.00 | 0.20 | 1.20 |
| H2O | 83.00 | 1.00 | 0.72 |
| Q5 Hot Start | 125.00 | 1.00 | 0.48 |
| C5-P5 (μM) | 10.00 | 0.40 | 2.40 |
| C7 (μM) | 10.00 | 0.40 | 2.40 |
| cDNA | | | 24.00 |
| H2O | | | 16.80 |

The following program is run in a thermocycler:
1. 98° C. for 01:00
2. 98° C. for 00:10
3. 64° C. for 00:20
4. 72° C. for 00:20
5. Go to 2 for the determined number of cycles
6. 4° C. forever The PCR product is purified with 1.2 volumes of AMPure and eluted in 20 μL of Dilution Buffer. The libraries are ready for sequencing. They are be pooled as desired, with or without agarose gel purification to remove contaminating truncated amplicons and then sequenced using a next generation sequencing technology platform.

Example 9—Expression of a Humanized Selected Antibody Vector Constructs

Two dsDNA sequences containing codons for the humanized selected antibody $V_H$ (H1) and $V_L$ (κ1) regions are synthesized. These synthesized sequences also contain nucleotides necessary to add or conserve restriction endonuclease sites at the 5' and 3' ends. All codons are optimized for expression in Chinese Hamster Ovary (CHO) cells. Signal peptide and constant region sequences used to complete the heavy chains and light chains are derived from cDNAs. Coding region sequences of all constructs are confirmed by DNA sequencing. The protein products are selected antibody #1 (for $IgG_4$) and selected antibody #2 (for $IgG_1$).

Expression Vector Constructs

The heavy and light chain coding regions from vector constructs described above are subcloned into a bicistronic expression vector. Primers are designed to generate coding regions with terminal restriction sites to facilitate insertion into the multiple cloning sites (MCS) of the bicistronic expression vector. In addition 8-base pair restriction sites are added to facilitate generation of future constructs. The Kappa chain is ligated into restriction sites in MCS1. The IgG1 heavy chain is ligated into the suitable restriction sites of the MCS.

It has been well established that $IgG_4$ can be expressed as a one heavy chain and one light chain. To stabilize $IgG_4$, its hinge region is replaced with that of $IgG_1$. Thus in a 3-way ligation a fragment of $IgG_1$ containing the $V_H$, $C_H1$ and hinge region is ligated to a fragment of $IgG_4$ containing the $IgG_4$ Fc region. Suitable primers are used for PCR and transfer of immunoglobulin sequences from vector constructs to the bicistronic expression vector.

Example 10—Measuring Affinity of Selected Antibody for a Target Protein

Affinity of antibodies and antigen-binding fragments thereof described herein for to target protein can be assessed using conventional techniques such as, for example, surface plasmon resonance (SPR; Biacore).

Affinity constants for the binding of the various selected antibodies and antigen-binding fragments to target protein are determined by SPR using, for example, a BIAcore™ 3000 analytical system equipped with a CM5 sensor chip (BIAcore AB). The selected antibodies or antigen-binding fragments are covalently coupled to the CM5 sensor chip up to 1500 resonance units (using a concentration of 10 μg/mL in 10 mM acetate buffer and pH appropriate for the specific selected antibody or antigen-binding fragment tested). Target protein is injected (40 μL) at concentrations between 5 and 250 nM at a flow rate of 30 μL/min. Ten microliters of a 10 mM HCl solution is used to regenerate the chip after each cycle. Association and dissociation rate constants are calculated with the software of the BIAcore™ 3000 (Langmuir binding model).

Example 11—Selected Antibody Affinity for Different Species of Target Protein

Binding of selected antibody #3 to rat, mouse, rabbit and human target protein is determined by P-ELISA. The relative affinity of selected antibody is human=rabbit>mouse>rat. Preliminary assessment by ELISA yields an approximate 2 to 4-fold greater affinity for human target protein relative to the parental mouse antibody. The affinity for human and rabbit target protein can appear to be 4 to 5 times greater relative to a parental mouse antibody.

The humanized antibody binds to mouse target protein. The relative affinity of selected antibody for mouse target protein is approximately the same as that of the mouse parent antibody binding to rabbit target protein. Since the parent antibody demonstrates efficacy in a rabbit disease model, selected antibody can be expected to demonstrate efficacy in a mouse disease model. The changes made proximal to CDRs during the process of humanization, result in a higher affinity for human target protein and significant reactivity to mouse and rat target protein. Selected antibody #2 affinity for mouse target protein appears to be over 10-fold greater relative to the parent mouse anti-target protein.

Example 12—Measurement of Binding Constants of Selected Antibody to Target Protein This experiment is conducted to measure the binding constants for a humanized selected antibody) and the corresponding parental mouse antibody.

Humanized selected antibody is captured onto an anti-human IgG surface at 5 different surface densities. Humanized selected antibody #1 and parental mouse antibody #1 are diluted to a starting concentration of 100 nM and tested in a 3-fold dilution series using PBS with 0.005% Tween-20 and 0.1 mg/ml BSA. Binding data are collected at 25° C. The association phase is monitored for 5 min and the dissociation phase is monitored for 2.5 hrs. The response data for each antigen over the 5 different density antibody surfaces are globally fit to a simple 1:1 interaction model. A fit to the data is determined and binding constants are determined at 25° C. A summary of exemplary binding constants is provided in the following table.

|  | $K_a$ (M$^{-1}$s$^{-1}$) | $K_D$ (s$^{-1}$) | $K_D$ |
|---|---|---|---|
| Humanized selected antibody #1 | $8 \times 10^5$ | $8 \times 10^{-6}$ | 15 pM |
| Parental mouse antibody #1 | $4 \times 10^5$ | $4 \times 10^{-6}$ | 10 nM |

Example 13—Measurement of Binding Constants of Selected Antibody to Target Protein Several bioanalytical assays are utilized to support selection of the final drug candidate and initial pharmacokinetic assessment. These include a target protein ELISA (P-ELISA) consisting of n-terminal biotin-labeled target protein immobilized to streptavidin coated microtiter wells. Selected antibody binding is detected with HRP conjugated anti-human antibody. The sensitivity of the assay is determined to be 10-20 ng/ml.

ELISA Protocol Using Neutravidin™ Coated Plates

All reagents are brought to RT and dilutions are made in a wash buffer (1×TBS, 0.1% BSA, 0.05% Tween). Briefly, protocol steps are as follows: Add 100 µL of Neutravidin™ Pierce #31000 (0.5 µg/ml in TBS) to 96-well Immulon-4 plates. Incubate 1 hour at RT. Wash wells 3 times with 200 µl wash buffer. Add 50 µL of biotinylated target protein (0.06 nM) Incubate 1 hr at RT. Wash plate 3 times in wash buffer. Add 100 µL of selected antibody. Incubate 30 min at RT. Wash plate 3 times in wash buffer. Add 50 µL of secondary Ab-HRP (1:10,000). Incubate 30 min RT Wash plate 4 times in wash buffer. Add 100 µl TMB Reagent (substrate). Incubate at room temperature. Add 100 µL of 2 M Sulfuric Acid to stop development of the substrate. Plates are read using a 450 nm filter with a 615-620 nm filter as the reference.

Example 14—Immunohistochemical Staining

Cryostat sections (10 µm) cut onto Vectabond-coated slides are fixed in methanol (−20° C., 5 min) and stained using a three-step peroxidase method as previously described in the art. Briefly, these are labeled with the primary selected antibody overnight at 4° C. or for 1 hr at RT with antibodies against target protein #1, phosphorylated target protein #2, non-phosphorylated target protein #2 or CD45. This is followed by incubation with an appropriate horseradish peroxidase (HRP) conjugate. Sections stained for CD45 are counterstained with Mayer's hematoxylin. Omissions of primary antibody, secondary antibody or avidin biotin complex are routinely used as controls.

Example 15—Protein Extraction and Western Blotting

Snap-frozen diseased samples of animals are weighed, finely cut arid resuspended at 1:10 g wet weight/ml in Tris-HCl buffer pH 7.4 (100 mM Tris, 5 mM EDTA. 150 mM NaCl, with 1% Triton X-100). Samples are homogenized using a high-intensity ultrasonic processor and incubated on ice for 30 min. The tissue suspensions are spun at 15,000 g in an Eppendorf centrifuge for 60 min at 4° C. and the supernatants collected and stored in aliquots at −70° C. The total protein concentration of spinal cord homogenates is determined by the Folin phenol method (Lowry et al., J. Biol. Chem, 193: 265-75 (1951)).

For Western blot analysis, 40 µg of supernatant protein is resolved on a Tris-HCl sodium dodecyl sulphatepolyacrylamide gel and transferred to an Immobilon-P polyvinylidene difluoride membrane. Non-specific binding sites on the membrane are blocked with 5% Marvel® dried fat free milk dissolved in Tris-buffered saline (TBST) (10 mM Tris, pH 7.4, 150 mM NaCl and 0.1% Tween 20) for 1 hr at RT and then incubated with the primary antibody diluted 1:1000 in 5% Marvel® in TBST for 2 hr at RT. Primary antibody sources and running conditions are summarized in Table 1. After washing in TBST, the membrane is incubated with the secondary antibody, which is coupled to HRP: anti-mouse IgG HRP, anti-rabbit IgG HRP, or anti-goat IgG HRP for 1 hr at RT. After three final washes, the blots are developed by enhanced chemiluminescence. To gain a semiquantitative measure of specific proteins, resulting blots are analyzed using an analysis software package and the band density is measured in arbitrary units. To ensure equal loading of protein, membranes are stripped and probed with a control antibody for normalization to expression levels for such suitable assays.

Example 16—Enzyme-Linked Immunosorbent Assays (ELISAs) to Assess Binding Affinity of Target Protein Mutants Costar 96-well plates are coated with mouse antibodies against target protein #1, target protein #1 mutant-1 or target protein #1 mutant 2 at 4 µg/ml for 48 hr at 4° C. The wells are blocked with 1% BSA in 1×PBS overnight at 4° C. and plates are then washed with 1×PBS Tween 80 (0.004%). Protein extract samples and standards are diluted in 1×PBS containing 0.004% Tween 80, 0.1% BSA and 5 mM EDTA, and are added 180 µl per well and incubated overnight at 4° C. Standard curves are generated. After washing, a biotinylated secondary antibody is added for 1 hr at 37° C. After addition of the ABC complex (Vector) for 1 hr at RT, plates are developed using o-phenylenediamine, and the reaction is stopped using 4 M sulphuric acid. Absorbance is read at 490 nm with a reference reading at 650 nm. Assessment of target antigen substrate activity is performed by ELISA and is carried out according to the manufacturer's instructions.

Example 17—Immunohistochemical Staining

Cryostat sections of a diseased sample (5 µm thick) are fixed in paraformaldehyde 1% in 0.07 M phosphate-buffered saline (PBS; pH 7.0) for 5 min or in acetone for 10 min at RT and then incubated with the primary antibody. Selected antibodies are incubated for 1 hour at room temperature. The sections are washed in PBS (three times, 10 min each) and appropriate secondary antibody conjugated to horseradish peroxidase (HRP), or tetramethylrhodamine isothiocyanate (TRITC) are added and applied for 30 min. For immunostaining, a drop of 3-amino-9-ethylcarbazole AEC+; Dako) is added, and sections are counterstained for 1 min in hematoxylin. For immunofluorescence staining, after three washes in PBS for 10 min each and a final rinse in 10 mM Tris-HCl buffer (pH 8.8), labeling is analyzed under an inverted microscope equipped with epifluorescence optics. Specificity of staining is assessed by analyzing normal samples or normal adjacent tissue, simultaneously with the diseased sample. Data are analyzed on computer (Prism 3.0; GraphPad, San Diego Calif.). The Mann-Whitney test is used to determine whether there are significant ($P<0.05$) differences between different experimental conditions.

Example 18—Immunofluorescence Screening

Immunofluorescence screening assays were conducted using a plurality of selected antibodies. The diseased samples from seven different pancreatic cancer patients showed 88 out of 106 (83%) of the antibodies demonstrate strong staining across all seven of the patients. Many of these selected antibodies in the plurality of antibodies also demonstrated high specificity for pancreatic tumor tissue compared to normal adjacent tissue. Immunoprecipitation experiments coupled with mass spectrometry analysis are run to elucidate unknown target protein identifies. Antibody A1-108 of the plurality of selected antibodies also demonstrated strong specific staining of pancreatic ductal adenocarcinoma tissue over normal adjacent tissue when used for immunohistofluorescence staining of formaldehyde fixed paraffin-embedded (FFPE) cancer tissue samples. Furthermore, A1-108 stained both adenosquamous and neuroendocrine carcinomas of the pancreas. A1-108 staining of 14 additional normal tissues remained very weak or completely absent.

Example 19—Selected Antibody Neutralization of Target Protein

The ability of a selected antibody to neutralize target protein inhibition of substrate protease activity is determined. The data indicates that the neutralizing activity of humanized selected antibody #1 is equivalent to the parental mouse antibody #1. A human antibody control does not neutralize target protein activity. The neutralizing activity of selected antibody and variants is compared in a minimum of three assays.

Example 20—Target Protein Neutralization Assay

The functional properties of the antibodies and antigen-binding fragments thereof can be determined by assessing their ability to inhibit active target protein utilizing a target protein neutralization assay.

Target protein activity is determined using an enzyme coupled chromogenic method. Briefly, 25 µL target protein (50 ng/mL active target protein) is incubated in the wells of a 96-well microtiter plate with an equal volume of either TBS buffer (0.05 M Tris-HCl, 0.01 M NaCl pH 7.4 containing 0.01% Tween 80) or with serial 2-fold dilutions of selected antibody or antigen-binding fragment thereof, resulting in a molar excess (antibody:target protein) between 1 and 128. The mixture is allowed to react for 2 hr at room temperature. Subsequently, 50 µL of target antigen substrate (20 IU/mL or 40 ng/mL) is added and the plate is incubated for 15 min at 37° C. Then, 100 µL of a solution containing enzyme (1 µM), CNBr-digested enzyme substrate (1 µM) and chromophores (0.6 mM) is added. The absorbance change at 405 nm is recorded to measure the residual target protein activity. 100% target protein activity is the target protein activity observed in the absence of antibody. The percentage inhibition (i.e. neutralization of target protein activity) by the antibody is calculated from the residual target protein activity measured in the presence of the antibody.

Example 21—Antibody Neutralization Assay

An activity assay for a target of the selected antibody is tested which measures the selected antibody's inhibition of that target's activity. This assay can be used to determine efficiency of neutralization of the target by the antibody.

All reagents are brought to RT and the plate reader is pre-warmed to 37° C. All dilutions are conducted in Assay Buffer (0.15 M NaCl, 0.05 M Tris (pH 7.5), 0.01% Tween, 100 µg/ml BSA). The final conditions are as follows: 100 µl—duplicate wells, 1.5 U enzyme substrate of target protein/well, 8 nM active human wild-type target protein, 25 µl chromogenic substrate, 0-80 µg/ml selected antibody. Assay steps are as follows: 50 µl of dilutions of selected antibody are placed into 96 wells; add 25 µl of target protein substrate enzyme (1.5 U), 3 sec shaking on plate reader; incubate 5 min at 37° C.; add 25 µl chromogenic substrate to develop the plates. Plates are shaken for 3 sec and read every 5 min up to 30 min on a plate reader with a 405 nm filter at 37° C. Percentage (%) activity is calculated from mean V.

Example 22—Measurement of Target Protein Inactivation

The effects of selected antibodies or antigen-binding fragments thereof described herein on the rate of target protein inactivation can be determined using conventional techniques. For example, the half-life of target protein in the presence of selected antibody or antigen-binding fragment thereof can be calculated.

Target protein (40 µg/mL in PBS) is incubated with a 3-fold molar excess of selected antibody or antigen-binding fragment thereof at 37° C. At various time intervals, an aliquot is removed and incubated with a 2-fold molar excess of substrate for the target antigen (25 min at 37° C.). The reaction products are analyzed by SDS-PAGE followed by silver staining. Quantification of the reaction products is performed by subsequent densitometric scanning. Based on the amount of active target protein at each time point, the half-life of target protein in the presence of selected antibody or antigen-binding fragment thereof can be calculated.

Example 23—Measuring Inhibition of Reaction Products Generated by Target Antigen Activity Toward Substrate Effects of the selected antibodies or antigen-binding fragments thereof described herein on the reaction products generated during interaction of target protein with a substrate can be assessed using conventional techniques.

Briefly, target protein (40 µg/mL in PBS) is incubated for 10 min at 37° C. either in the absence (control) or in the presence of an 8-fold molar excess of selected antibody or antigen-binding fragment. Samples are then incubated with a 2-fold molar excess of substrate (25 min at 37° C.). The reaction is terminated by adding SDS (final concentration of 1%) and heating for 30 sec at 100° C. The reaction products are analyzed by SDS-PAGE followed by staining with Coomassie brilliant blue. Quantification of the reaction products is performed by subsequent densitometric scanning.

Example 24—In Vivo Assessment of Selected Antibodies as Therapeutics for a Disease Animals are separated into different treatment groups with multiple animals placed in each treatment group. Disease is induced. Animal test groups are then administered dosages of the anti-target protein antibody or antigen binding fragment at time points as pre-determined in multiple dosing regimens established for a trial period. Efficacy of treatment is assessed by determination of a levels or changes in levels of an analyte associated with disease progression or regression via ELISA or HPLC throughout the treatment period. Animals are sacrificed throughout the treatment period to examine various biological samples from the animals, such as organs for evidence of morphological changes associated with the disease. Additionally, immunohistochemical staining is performed throughout the treatment period for evidence of molecular changes associated with the disease. Efficacy of the anti-protein antibodies and antigen-binding fragments described herein for the treatment of diseases can be tested via an animal model of the disease.

Example 25—Detection of Protein Antibodies in Plasma

A P-ELISA can be used to monitor plasma levels of selected antibody in PK and efficacy studies. The P-ELISA is able to detect a protein antibody in spiked plasma samples compared to control IgG, antibody in the absence of plasma, or antibody+EDTA. The effect of variables that effect detection of selected antibody in plasma samples by the P-ELISA can be determined. This includes sample processing and storage conditions.

Example 26—Immune Sequencing V2

A unique identifier (UID) barcode was used to tag every single RNA molecule. The UID was then amplified in many copies so that post-sequencing the multiple sequencing read collapsed into a single sequence with higher base accuracy, and revealed true antibody sequences and mutations as opposed to PCR or sequencing errors. The UID was also used to track contamination across multiple samples.
Starting Material
RNA or DNA from immune cells composed of the V, D, J gene segments that encode for an antibody, and contains the constant region was used as starting material. In some experiments, RNA was from T-cell. In some experiments, RNA was heavy chain (V, D, J segments), or light chain (V, J segments only).
Reverse Transcription
The RNA was reverse transcribed into cDNA using one or a pool of polynucleotide composed of the following parts: a portion complementary to a region of the RNA (usually in the constant region or to the poly-A tail of the mRNA). The UID, which was a stretch of ~20 degenerate nucleotide with or without know intercalating base position (such as NNNNWNNNNWNNNNWNNNNW, where W means A or T). As the length of the UID increased, it became less likely that it will be detected twice when barcoding each RNA molecule. An overhang tail (P5) served as a read-1 sequencing priming site downstream. Multiple polynucleotides were used to anneal to the various constant regions. Each polynucleotide harbored a completely unique UID, so that each RNA molecule was actually uniquely barcoded by the UID.

Reverse transcription was performed with 500 ng of total RNA in a 20 µl reaction containing; 5 pmols of IGHC-UID-P5 primer mix, 500 µM each dNTP, 5 mM DTT, 1 µl RNAse Inhibitor (Enzymatics, Beverly, Mass.), 1 µl of SuperScript II reverse transcriptase in 1× First Strand buffer (Life Technologies, Carlsbad, Calif.). Reactions were incubated for 45 mins at 55° C., followed by an additional 5 mins at 85° C. to inactivate the enzyme. One µl of Exonuclease I (Enzymatics) was then added and the reaction was incubated for 15 mins at 37° C. Following 15 min incubation at 85° C., 1 µl of RNAse H (Enzymatics) was added and the reaction was incubated for an additional 15 mins at 37° C.
PCR1

The cDNA was PCR amplified using the following primers: (1) a forward primer pool complementary to the RNA, upstream of the V segments with an overhang tail (P7) that served as read-2 sequencing and read-3 sequencing priming sites, and (2) a reverse primer composed of the P5 sequence with an overhang (C5), to cluster on the Illumina sequencing platform. In some experiments, the forward primer was a pool of many polynucleotides for annealing to all possible V regions expressed by an immune cell. In other experiments, the forward primer had a P7, SBC, and C7 overhang. The reverse primer was located after the UID so that each unique UID was amplified.

20 µl of the reverse transcription reaction prepared above was amplified in a 50 µl PCR reaction containing; 1 µM of P5/C5 primer, 1 µM IGHV-P7 primer mix, 200 µM each dNTP, 1 unit of Phusion Hotstart II polymerase in 1× Phusion HF buffer (Thermo Fischer Scientific, Waltham, Mass.). The reaction was incubated for 1 cycle at 98° C. followed by 12 cycles of: 98° C. for 10 sec, 62° C. for 20 sec, 72° C. for 20 sec, followed by one 3 min cycle at 72° C.
qPCR One µl of Exonuclease I (Enzymatics) was then added, and the reaction was incubated for 20 mins at 37° C., followed by a 15 min incubation at 80° C. PCR2

The PCR1 product was amplified using a 2nd PCR phase with the following primers: the same P5C5 reverse primer used in PCR1, and a forward primer composed of the P7 sequence and of a sample barcode (SBC), and with a second overhang (C7), to cluster on the Illumina sequencing platform. The sample barcode was different for each sample processed in an experiment so that multiple sample could be pooled together in one sequencing run. PCR1 can introduce bias because of the multiplex pool of primers used in the PCR1 reaction. By limiting the number of PCR1 cycles and universally amplifying at the PCR2, the bias introduced was limited. The PCR2 also loaded the sample barcodes and clustering tags for sequencing.

A 25 µl Sybr green qPCR was assembled containing 1 µM of P5-C5 primer, 1 µM of P7-C7 primer, 200 µM each dNTP, 1× Sybr Green, and 0.5 units of Phusion Hotstart II polymerase in 1×Phusion HF buffer (Thermo Fischer Scientific, Waltham, Mass.). The reaction was incubated for 1 cycle at 98° C. followed by 35 cycles of: 98° C. for 10 sec, 62° C. for 20 sec, 72° C. for 20 sec, followed by one 3 min cycle at 72° C.

25 µl of the PCR-1 reaction was amplified in a 50 µl PCR reaction containing 1 µM of P5-C5 primer, 1 µM of P7-SBC-C7, 200 µM each dNTP, 1 unit of Phusion Hotstart II polymerase in 1× Phusion HF buffer (Thermo Fischer Scientific, Waltham, Mass.). The reaction was incubated for 1 cycle at 98° C. followed by a number of PCR cycles determined by qPCR analysis. Cycling; N cycles of: 98° C. 10 sec, 62° C. 20 sec, 72° C. 20 sec, followed by one 3 min cycle at 72° C. Sample are subjected to high-throughput sequencing on an Illumina Miseq or HIseq system according to manufacturer protocol.

Final Library

The resulting library was composed of the full antibody sequence with the appropriate tags and clustering segments that were sequenced. There were many copies of identical UID generated for each starting unique RNA molecule. Upon sequencing, identical UIDs were matched and the sequencing reads were collapsed into consensus sequences, thereby eliminating sequencing and PCR errors. Sequencing was done from the P5 sites for read-1 (C, J, D, V), followed by sequencing from the P7 site for read-2 (UID and VDJ), and finally from a reverse P7 site for the indexing read-3 of the SBC.

Example 26—Immune Sequencing V3

This describes the use of template switching during reverse transcription to eliminate the use of pool of multiplex V primers, therefore removing issues of PCR bias. This process was used for antibody next-generation sequencing, as well as the incorporation of Unique identifier polynucleotide (UID).

Starting Material

Starting material was RNA or DNA from immune cells or T-cells composed of the V, D, J gene segments that encodes for an antibody, and contains the constant region. In some experiments, the RNA comprised heavy chain segments (V, D, J segments), or light chain segments (V, J segments).

Reverse Transcription

To generate libraries of immunoglobulin rearranged heavy and light chain cDNAs without requiring gene-specific variable segment primers, first a reverse transcription of an RNA sample is performed in the presence of a template-switch (TS) polynucleotide. The TS polynucleotide contains three terminal riboguanosine residues, which allow the polynucleotide to act as a template for terminal cytosine residues added to the end of reverse transcription extension products by the reverse transcriptase. This creates universal sequence ends at the 3' end of all cDNA fragments. Crucially, since the TS polynucleotide carries a ~15-base degenerate barcode sequence (the Universal Identifier or UID), all cDNA molecules will carry distinct barcodes allowing identification of PCR duplicates in sequencing results, which gives a number of advantages as discussed earlier. The RNA is reverse transcribed into cDNA using one or a pool of polynucleotide composed of the following parts: a portion complementary to a region of the RNA. In this case, the portion complementary to a region of the RNA was complimentary to the constant region or to the poly-A tail of the mRNA. Multiple polynucleotides were used to anneal to the various constant regions. The reverse transcriptase used here comprised a non-template terminal transferase activity. When the reverse transcriptase reached the end of the template, it naturally added 3 non-templated cytosine residues. Superscript II (Invitrogen) was used for this purpose.

Template Switching

The previous reverse transcription reaction was conducted in the presence of a 5' tagging polynucleotide composed of the following parts: a P7 segment which was used for annealing a sequencing primer, a UID, 3 ribo-guanine residues on the 3' end (rGrGrG) (RNA bases) that were complementary to and annealed to the strand produced by the reverse transcription enzyme. In some experiments, 3 guanine residues were used instead of ribo-guanine (DNA nucleotide instead of RNA nucleotide). Upon annealing of the tagging polynucleotide to the CCC of the cDNA strand, the reverse transcriptase continued extending the cDNA into the tagging polynucleotide, thereby creating a universal tag to all cDNAs in the reaction. In other experiments, template switching was done in a separate reaction instead of being done at the same time the reverse transcription reaction was conducted. In these experiments, the 5' tagging polynucleotide was added after the reverse transcription reaction, and enzymes such as a reverse transcriptase or polymerase was used to extend into the tagging polynucleotide in a similar fashion. Because the tagging polynucleotide harbored a unique degenerate UID on every single molecule, each cDNA was uniquely tagged with a UID.

200 ng of total RNA from peripheral blood mononuclear cells (PBMCs) was subjected to reverse transcription with template switching in a 20 µl reaction containing 50 mM Tris-HCl, 75 mM KCl, 3 mM $MgCl_2$, 3 mM $MnCl_2$, 10 mM dithiothreitol, 250 µM each of dATP, dGTP, dCTP, dTTP, 2 units/µl RNAse inhibitor (Enzymatics), 10 units/µl MuMLV reverse transcriptase RNAseH-(NEB), 500 nM polynucleotide dT(18) primer and 500 nM TS polynucleotide. The reaction was set up and incubated at 42° C. for 45 minutes. Products were purified on AMPure XP beads (Beckman Coulter) and eluted in 20 µl H2O.

PCR1

PCR was conducted using primers composed of the following parts: a forward primer (P7) complementary to a tagging polynucleotide end upstream of the UID, a reverse primer composed of segments complementary to the RNA (C) and an overhang (P5) used for sequencing. The C segments were nested to the reverse transcription polynucleotide and led to increased specificity of the reaction for the correct RNA target. In other experiments, the C7 overhang and sample barcode were present on the forward P7 primer already.

Purified reverse transcription products were subjected to a first round of PCR using primers complementary to the constant segment of the immunoglobulin heavy or light chain and primers complementary to the template-switched region at the 3' end of the cDNA fragments.

The total 20 µl of purified reverse transcription product was included in a 50 ul PCR reaction containing 1×Q5 buffer (EB), 200 uM each of dATP, dGTP, dCTP, dTTP, 65 nM each heavy/light chain constant primer (IGHC, IGKC, IGLC), 40 nM long template switch primer, 800 nM short template switch primer and 0.02 units/µl Q5 Hot Start polymerase (NEB). Reactions were subjected to 1 minute at 98° C. followed by 12 cycles of: 98° C., 10 sec; 64° C., 30 sec; 72° C., 15 sec. Products were purified by AMPure XP and eluted in 25 µl H2O.

Quantitation of PCR1 Product

An aliquot of purified PCR1 product was next quantified by SYBR green quantitative PCR (qPCR). 5 µl of purified PCR1 product was included in a 25 µl PCR reaction containing 1×Q5 buffer (EB), 200 µM each of dATP, dGTP, dCTP, dTTP, 0.25×SYBR green I (Invitrogen), 400 nM Illumina compatible forward primer (P5-C5), 400 nM Illumina compatible paired-end primer (P7-SBC-C7) and 0.02 units/µl Q5 Hot Start polymerase (NEB). Reactions were subjected to 1 minute at 98° C. followed by 20 cycles of: 98° C., 10 sec; 72° C., 45 sec.

Indexing PCR2

The PCR1 product was amplified using a second PCR phase with the following primers: the same P5C5 reverse primer used in PCR1, and a forward primer composed of the P7 sequence and of a sample barcode (SBC), and with a second overhang (C7), to cluster on the Illumina sequencing platform. The sample barcode was different for each sample processed in an experiment so that multiple sample could be pooled together in one sequencing run. PCR1 can introduce bias because of the multiplex pool of primers used in the PCR1 reaction. By limiting the number of PCR1 cycles and universally amplifying at the PCR2, the bias introduced was limited. The PCR2 also loaded the sample barcodes and clustering tags for sequencing.

The remaining PCR1 product was then amplified in a PCR to add full Illumina adaptor sequences to the libraries, including sample-specific indexes for pooled sequencing. Based on the qPCR results an ideal PCR cycle number was chosen to prevent PCR running into the plateau phase, at which point undesirable PCR artifacts are likely to be created.

For the indexing PCR, 10 µl of the purified PCR1 product was included in a 50 µl PCR reaction containing 1× Q5 buffer (EB), 200 µM each of dATP, dGTP, dCTP, dTTP, 0.25×SYBR green I (Invitrogen), 400 nM Illumina compatible forward primer (P5-C5), 400 nM Illumina compatible paired-end primer (P7-SBC-C7) and 0.02 units/µL Q5 Hot Start polymerase (NEB). Reactions were subjected to 1 minute at 98° C. followed by cycles of: 98° C., 10 sec; 72° C., 45 sec, with the cycle number decided based on the results of the preceding qPCR. Products were purified with AMPure XP beads, eluted in 25 µl TE buffer and visualized by gel electrophoresis before high-throughput Illumina sequencing and analysis.

Final Library

The resulting library was composed of the full antibody sequence with the appropriate tags and clustering segments that were sequenced. There were many copies of identical UID generated for each starting unique RNA molecule. The UID was at a different location compared to the location described in Example 1. Upon sequencing, identical UIDs were matched and the sequencing reads were collapsed into consensus sequences, thereby eliminating sequencing and PCR errors. Sequencing was done from the P5 sites for read-1 (C, J, D, V), followed by sequencing from the P7 site for read-2 (UID and VDJ), and finally from a reverse P7 site for the indexing read-3 of the sample barcode (SBC).

Example 27—Sequencing TILs Directly from Tumor Samples

An ovarian tumor sample comprising 400,000 ovarian tumor dissociated cells, without isolation of TILs (i.e. the sample comprises normal epithelial cells, cancer cells, and TILs), were prepared for performing emulsion-based, massively high throughput single-cell polynucleotide sequencing as described above. Ig and TCR-encoding polynucleotides from B and T cells in the sample were sequenced without prior isolation based on cell type. The cells were washed by centrifugation 200 g for 10 min for twice in Cell Buffer: 1× Dulbecco's Phosphate-Buffered Saline (PBS). The cells were then diluted in Cell Buffer to a cell concentration of $3.5 \times 10^6$ cells/mL. The suspension was then pipetted through a 20 µm cell strainer.

The emulsion reaction mixture for performing emulsion-based, massively high throughput single-cell polynucleotide sequencing was then prepared as described above. Once the cells and reaction mixture were prepared, the emulsion was formed. A 100-µL Hamilton Microliter syringe was used to overload a 100-µL PEEK sample loop in two injections of ~100 µL each of the reaction mixture. A 100-µL Hamilton Gastight syringe was used to load ~110 µL of the cell suspension into a ~100 µL, 0.2 mm internal diameter FEP tubing loop. The loop was attached to a mechanical rotator that was constantly inverting the cell loop approximately once every 1-2 sec to prevent cell settling and bunching. The emulsion was formed by focused flow jetting through a Dolomite 2-reagent chip with internal fluorophilic coating. The outer oil channels contained 0.5-5.0% (w/v) polyethylene glycol-based surfactant in HFE7500 (Novec 7500) fluorocarbon oil. The emulsion jet was run at a constant flow rate (equal in cell phase and reaction phase channels). The emulsion chip output was collected through a 12 cm, 0.5 mm internal diameter PEEK tube, by dropping into polypropylene PCR tubes that were kept at approximately 0° C. in a chilled block. Four fractions were collected, each containing 50 µL of aqueous material in emulsion (5 min of run time per fraction). Most of the settled oil was removed from the bottom of each tube with a capillary micropipette. Each emulsion fraction was gently overlayed with 40 µL of Overlay Solution: 50 mM Na-EDTA, pH 8.0, 0.002% (w/v) cresol red. The emulsions were incubated in a thermal cycler with the following program (min:sec):

1. 42.0° C. for 30:00 (reverse transcription)
2. 95.0° C. for 05:00 (denature reverse transcriptase and DNA templates)
3. 95.0° C. for 00:10
4. 65.0° C. for 00:30
5. 72.0° C. for 00:30
6. Go to 3, total 55 cycles (amplify Vessel Barcode and fuse to cDNA)
7. 4.0° C. for no time limit The emulsion was held at 4.0° C. overnight. The emulsions were then broken open. Using a capillary micropipette tip, as much Overlay Solution was removed as possible without removing emulsion material. To each tube, 12.5 µL Qiagen Protease solution and 2.5 µL of 0.5 M Na-EDTA, pH 8.0 was added. The emulsion was broken by adding 40 µL of 1:1 FC-40:perfluorooctanol and gently inverting about 10 times. The contents of tube were gently centrifuged and incubated in a thermal cycler with the following program (min:sec):

1. 50° C. for 15:00 (protease digestion)
2. 70° C. for 10:00 (protease inactivation)
3. 95° C. for 03:00 (protease inactivation and DNA denaturation)
4. 4.0° C. forever The tube was centrifuged and the upper aqueous phase and interface was moved to a fresh microcentrifuge tube and centrifuged at 15,000 g for 1 minute. The upper aqueous phase was transferred to a new tube, without disturbing the interface. 0.25V of NEB streptavidin beads were then added in 2×BW (10 mM Tris-Cl, pH 8.0, 1 mM EDTA, 2 M NaCl, 0.2% tween-20) and incubated at RT for 15 min. The beads were then washed with 1×BW, washed three times with 0.001% tween-20, and eluted by adding 0.25V of 0.001% tween-20 and heating to 95° C. for 3 min. 5 volumes of Qiagen Buffer PB were added and applied to a silica column.

The beads were then washed with 0.7 mL of wash buffer and eluted in 180 μL of: 5 mM Tris-Cl, pH 8.8, 0.1 mM EDTA, 0.001% Tween-20. Polynucleotides were then amplified by three PCR rounds. The final PCR product was purified with 1.2 volumes of AMPure and eluted in 20 μL of Dilution Buffer. The libraries were then sequenced using a next generation sequencing technology platform.

Figure 18A:
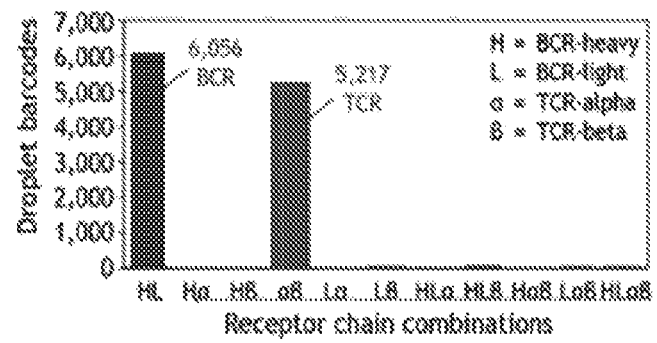
FIG. 18A exemplifies a graph of the number of droplet barcodes vs. the indicated receptor chain combinations from sequencing data obtained from an ovarian cancer sample containing about 400,000 tumor dissociated cells, without isolation of TILs (processed sample contains normal epithelial cells, cancer cells, and TILs) in which B and T-cells were sequenced simultaneously. The graph demonstrates accurate B and T-cell receptor pairing without crosstalk or contamination.
Figure 18B:
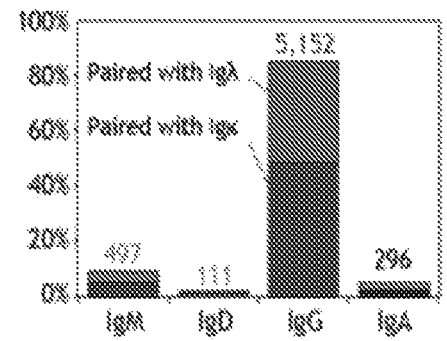
FIG. 18B exemplifies a graph of the percentage of total B cells vs. the depicted Ig isotype from the sample described in FIG. 18A. The tumor shows significant enrichment of activated Ig infiltrates from which the TILs are derived.
Figure 18C:
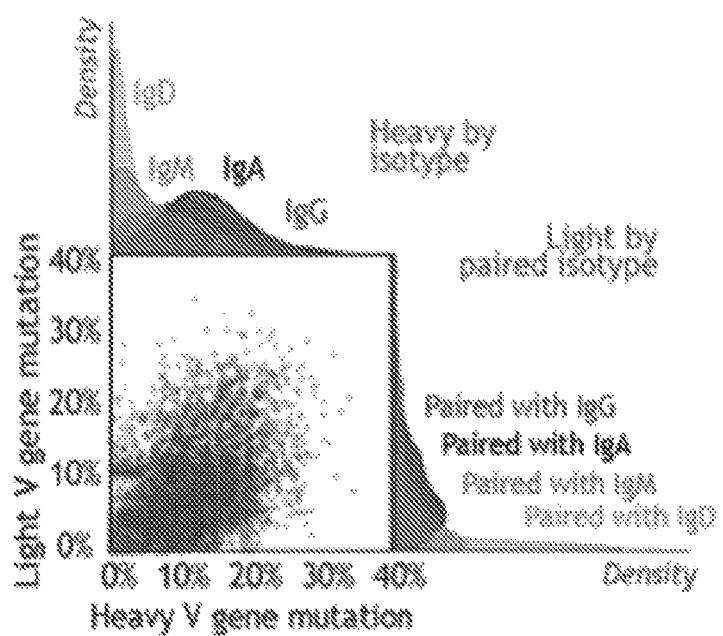
FIG. 18C exemplifies a graph of the percentage of light chain variable gene mutation percentage vs. heavy chain variable gene mutation percentage as well as the density of the heavy chain of the indicated isotypes vs the density of the light chain of the indicated paired isotypes from the sample described in FIG. 18A. The tumor shows significant enrichment of heavily mutated Ig infiltrates from which the TILs are derived.
Figure 19A:
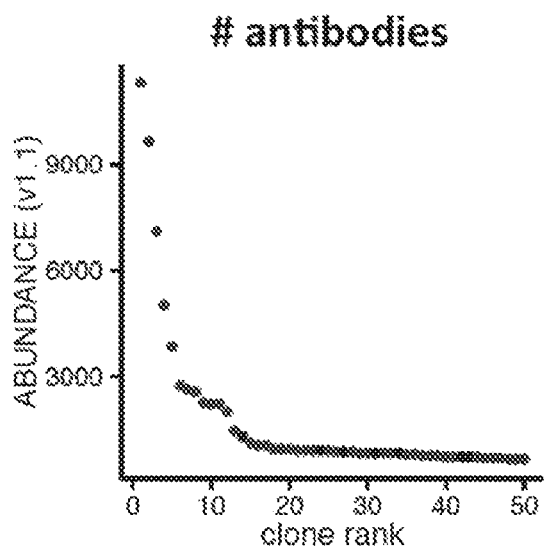
FIG. 19A exemplifies a graph of the mRNA abundance vs. clone rank from a TIL immune repertoire sequencing analysis used as a criterion for selecting and ranking TILs.
Figure 19B:
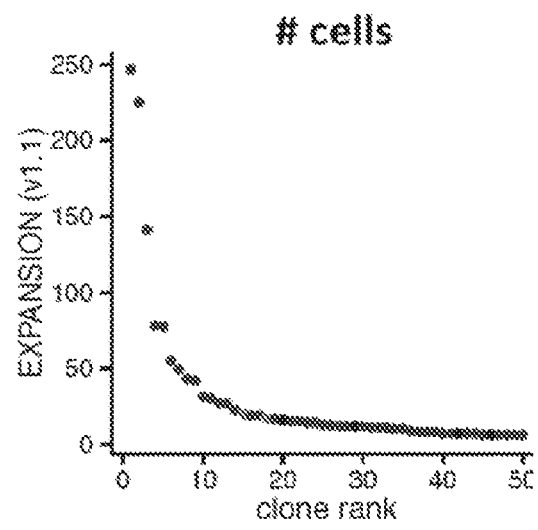
FIG. 19B exemplifies a graph of the amount of expansion (# of cells) vs. clone rank from a TIL immune repertoire sequencing analysis used as a criterion for selecting and ranking TILs.
Figure 19C:
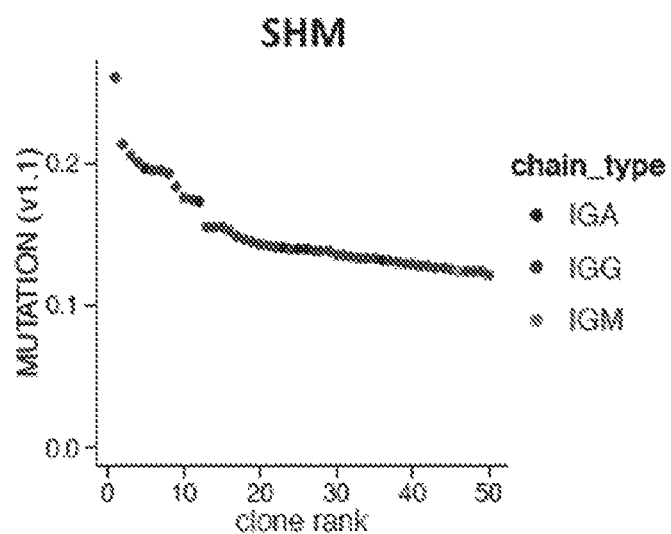
FIG. 19C exemplifies a graph of the somatic hypermutation rate vs. clone rank from a TIL immune repertoire sequencing analysis used as a criterion for selecting and ranking TILs FIG. 20 exemplifies graphs of the somatic hypermutation rates vs the amount of expansion (# of cells) of the indicated Ig isotypes from a TIL immune repertoire sequencing analysis used as a criterion for selecting and ranking TILs.
Figure 20:
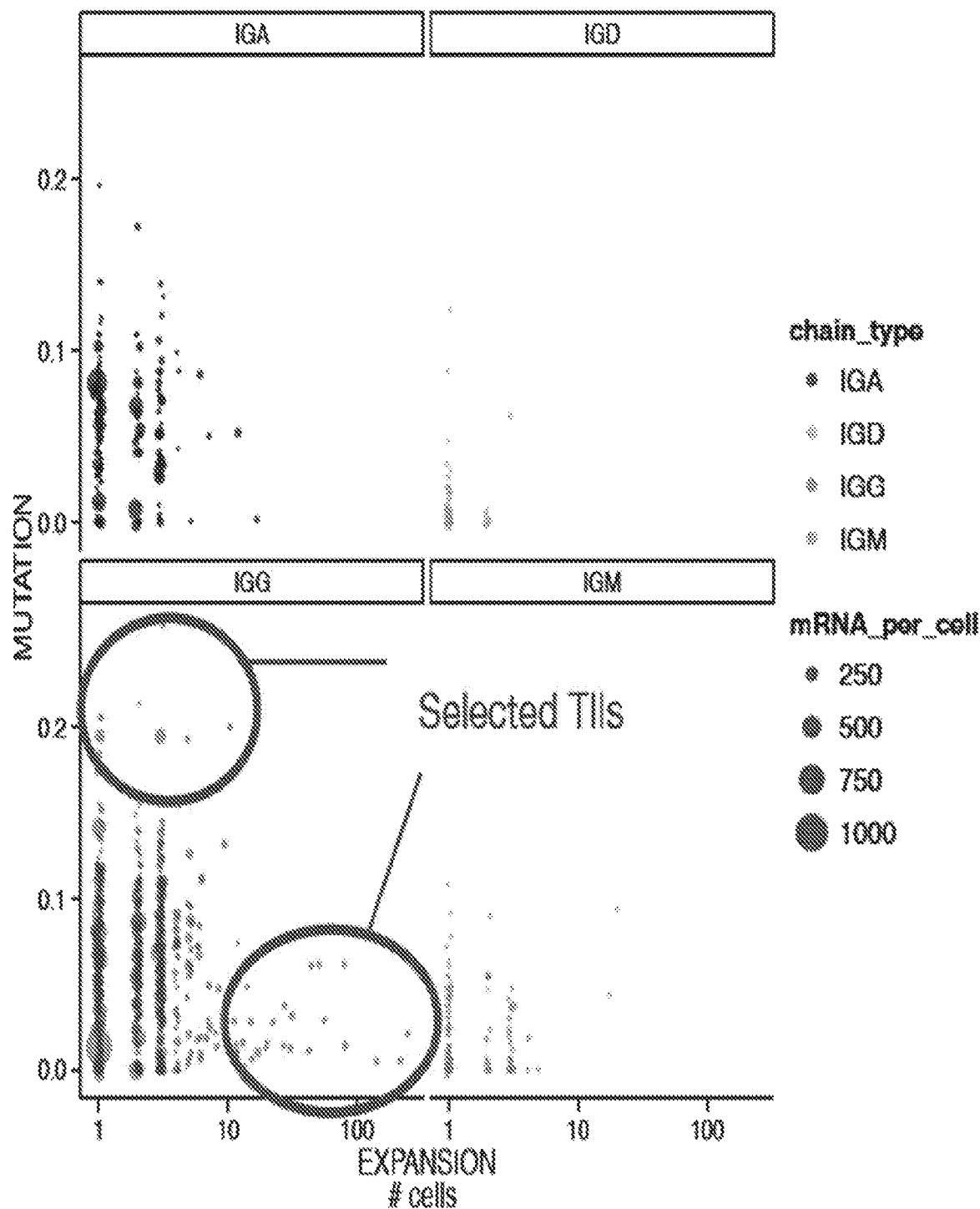
Figure 21A:
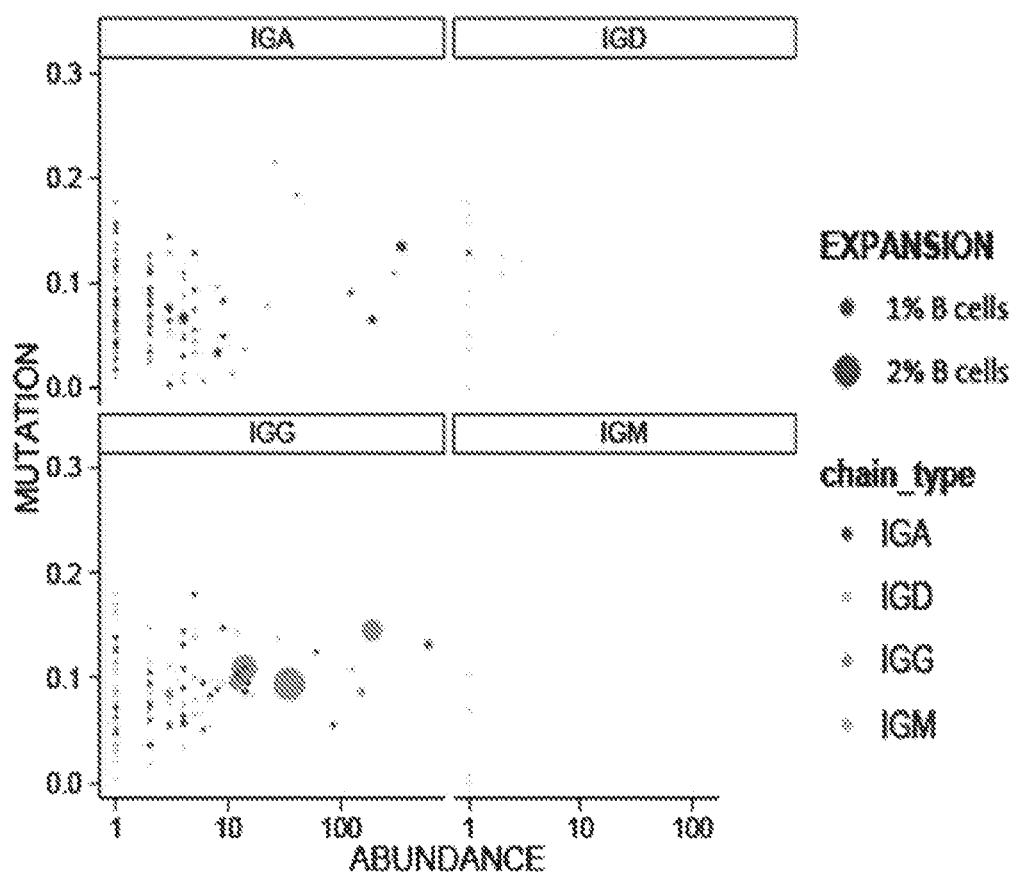
FIG. 21A exemplifies graphs of the somatic hypermutation rates vs the mRNA abundance of $CD21^{lo}$ clones of the indicated Ig isotypes from a TIL immune repertoire sequencing analysis. The data demonstrates that CD21lo clones were expanded in the analyzed lung tumor sample analyzed. The data demonstrates that secondary cell markers can be identified from the sequencing data and used to select TILs.
Figure 21B:
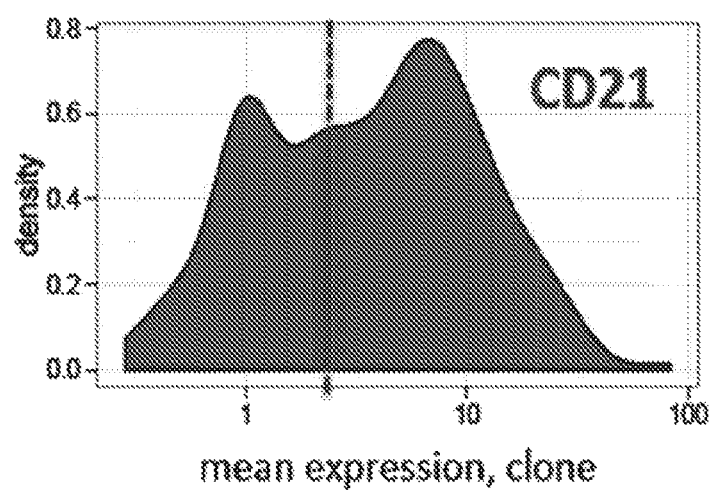
FIG. 21B exemplifies a graph of density vs mean CD21 expression of the clones depicted in FIG. 21A.
Figure 22:
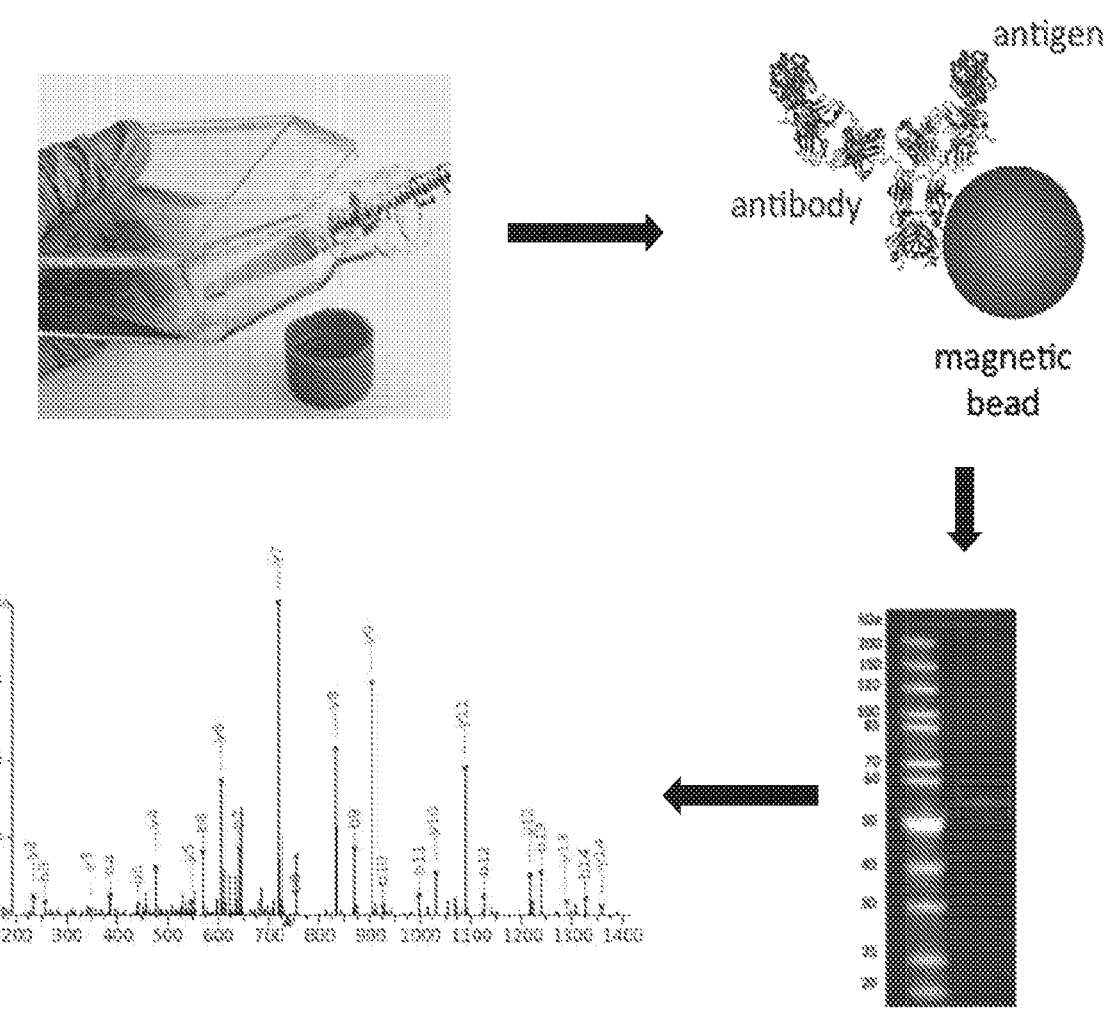
FIG. 22 exemplifies a flow chart of the steps of an exemplary method disclosed herein for identifying a target antigen of a selected TIL. Recombinant antibodies from selected TILs are produced and used in an immunoprecipitation assay coupled with mass spectrometry analysis.
Figure 23:
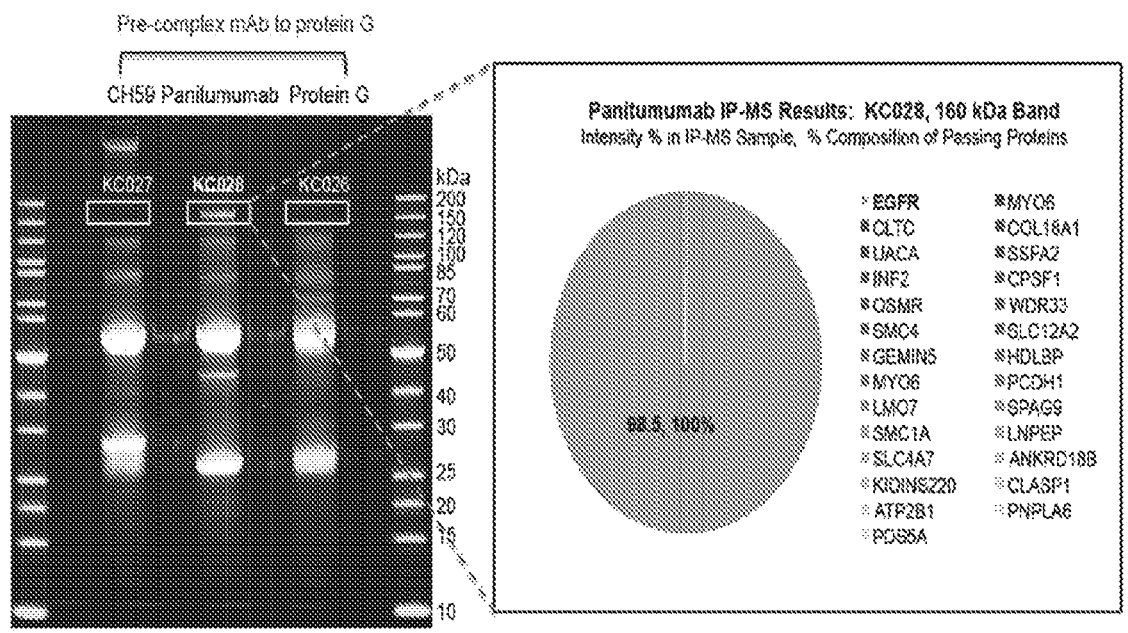
FIG. 23 exemplifies a gel stained for proteins from Mia PaCa-2 cell lysate samples immunoprecipitated with control antibody (CH59), Panitumumab, or Protein-G alone. The intensity percent of the 160 kDa band (EGFR) in the sample immunoprecipitated with Panitumumab was 98.5% of the entire composition immunoprecipitated when analyzed by mass spectrometry. This data demonstrates that the target antigen of a selected TIL can be identified with high accuracy.

As shown in FIGS. 18A-C, when B and T cells were sequenced simultaneously, 6,056 IgH-IgL receptor chain combinations, and 5,217 TCRα-TCRβ receptor chain combinations were sequenced with accurate B and T cell receptor pairing without crosstalk or contamination (FIG. 18A). Of the 6,056 IgH-IgL receptor chain combinations, 5,152 were of the IgG isotype demonstrating that the tumor showed significant enrichment of activated IgG infiltrates (FIG. 18B). The tumor showed significant enrichment of heavily mutated infiltrates (FIG. 18C) from which the TILs were derived.

What is claimed is:

1. A composition comprising a plurality of vessels, at least one vessel comprising:
   a single cell comprising RNA,
   a molecular barcoded polynucleotide,
   a vessel barcoded polynucleotide, and
   a forward primer and a reverse primer for amplifying the vessel barcoded polynucleotide,
   wherein the molecular barcoded polynucleotide comprises a 5' region complementary to a region of the vessel barcoded polynucleotide, and a 3' region complementary to three or more non-template nucleotides added to the 3' end of a cDNA generated by reverse transcription of an RNA from the single cell.

2. The composition of claim 1, wherein the single cell has not been sorted or selected based on an extracellular cell marker.

3. The composition of claim 1, wherein the single cell comprises a single tumor infiltrating lymphocyte (TIL) cell or a single non-TIL cell, and wherein the single cell has been isolated from a biological sample from a subject.

4. The composition of claim 3, wherein the TIL cell comprises a T cell or a B cell, or wherein the non-TIL cell comprises an epithelial cell, a lymphocyte, or a cancer cell.

5. The composition of claim 3, wherein the biological sample is a solid tissue sample.

6. A method comprising:
   (a) forming a plurality of vessels, at least one vessel comprising:
      a single tumor infiltrating lymphocyte (TIL) cell or a single non-TIL cell, wherein the single cell is isolated from a first biological sample from a first subject,
      a molecular barcoded polynucleotide,
      a vessel barcoded polynucleotide,
      a forward primer and a reverse primer for amplifying the vessel barcoded polynucleotide, and
      a reverse transcriptase
      wherein the molecular barcoded polynucleotide comprises a 5' region complementary to a region of the vessel barcoded polynucleotide;
   (b) generating a cDNA polynucleotide by reverse transcription of an RNA from the single cell, wherein the reverse transcriptase adds three or more non-template nucleotides to the 3' end of the cDNA polynucleotide;
   (c) annealing the molecular barcoded polynucleotide to the three or more non-template nucleotides of the cDNA polynucleotide, and extending the cDNA polynucleotide to generate a single-barcoded cDNA polynucleotide; and
   (d) amplifying the vessel barcoded polynucleotide using the forward primer and the reverse primer, thereby generating an amplified product, annealing the amplified product to the single-barcoded cDNA polynucleotide, and extending the single-barcoded cDNA polynucleotide to generate a dual-barcoded cDNA polynucleotide.

7. The method of claim 6, wherein the RNA from the single cell encodes a variable region of an immunoglobulin (Ig) or a T-cell receptor (TCR) polypeptide.

8. The method of claim 6, further comprising sequencing the dual-barcoded cDNA polynucleotide thereby obtaining sequence information.

9. The method of claim 8, wherein the single cell is not sorted or selected based on an extracellular cell marker prior to the sequencing.

10. The method of claim 8, further comprising selecting an Ig or a TCR polynucleotide sequence from a TIL based on the sequence information.

11. The method of claim 10, wherein the selected polynucleotide sequence comprises 1-500 unique Ig or TCR polynucleotide sequences.

12. The method of claim 10, wherein the selecting is based on comparing the sequence information to sequence information obtained from a second biological sample, wherein the second biological sample comprises:
   (i) a normal tissue sample from the first subject,
   (ii) a normal biological sample from a healthy subject, and/or
   (iii) a biological sample from a second subject, wherein the first and second subject have a same disease.

13. The method of claim 10, wherein the selecting is based on:
   (i) determining that the Ig or TCR polynucleotide sequence is present in the sequence information but absent in sequence information obtained from a second biological sample,
   (ii) determining that the Ig or TCR polynucleotide sequence is enriched in the sequence information compared to sequence information obtained from a second biological sample,
   (iii) a pre-determined isotype profile of the Ig or TCR polynucleotide sequence in the sequence information,
   (iv) a size or a frequency of a phylogenetic cluster of the Ig or TCR polynucleotide sequence in the sequence information, or
   (v) a similarity between the Ig or TCR polynucleotide sequence in the sequence information and the sequence information obtained from a second biological sample.

14. The method of claim 10, wherein the selected polynucleotide sequence comprises an Ig polynucleotide encoding at least one of an Ig heavy chain (IgH), an Ig light chain (IgL), an Ig constant domain region, an Ig heavy chain variable region (VH), or an Ig light chain variable region (VL); or wherein the selected polynucleotide comprises a TCR polynucleotide encoding at least one of a TCRα chain, a TCRβ chain, a TCRγ chain, a TCRδ chain, a TCRα chain variable region (Vα), a TCRβ chain variable region (vβ), a TCRγ chain variable region (Vγ), a TCRδ chain variable region (Vδ), a TCRα constant domain, a TCRβ constant domain, a TCRγ constant domain, or a TCRδ constant domain.

15. The method of claim 14, wherein the method further comprises at least one of pairing an IgH with an IgL from a same B-cell, pairing a TCRα chain with a TCRβ chain from a same T-cell, or pairing a TCRγ chain with a TCRδ chain from a same T-cell.

16. The method of claim 10, wherein the selected polynucleotide sequence encodes an Ig or TCR polypeptide comprising a framework region sequence comprising one or more mutated framework residues.

17. The method of claim 10, wherein an Ig or TCR polypeptide encoded by the selected polynucleotide sequence does not substantially interact with or bind to a cell of normal adjacent tissue or a cell from a corresponding tissue in a healthy subject.

18. The method of claim 10, further comprising producing a polypeptide comprising a variable domain of an Ig or TCR polypeptide encoded by the selected polynucleotide sequence.

19. The method of claim 18, wherein the produced polypeptide encoded by the selected polynucleotide sequence has a $K_D$ of about $1\times10^{-7}$ M or less for a disease-associated protein or a disease-specific protein.

20. The method of claim 18, further comprising identifying a target antigen of the produced polypeptide.

21. The method of claim 20, wherein the identifying is performed after the selected polynucleotide sequence is selected.

22. The method of claim 20, wherein the identifying comprises performing a whole genome siRNA screen, a protein display screen with the Ig or TCR polypeptide encoded by the selected polynucleotide sequence, a yeast-two-hybrid screen, a 2D gel electrophoresis, a protein array, a proteome screen, an immunoprecipitation, a mass spectrometry, a cell-mediated cytotoxicity assay, or a binding assay.

23. The method of claim 20, wherein the target antigen is a disease-associated or disease-specific target antigen.

24. The method of claim 23, wherein the disease is an autoimmune disease, a cancer, or a precancerous disease.

25. The method of claim 23, further comprising identifying an Ig or TCR polypeptide that kills a diseased cell.

26. The method of claim 6, wherein the first biological sample comprises at least one TIL cell and at least one non-TIL cell, wherein the at least one TIL cell and the at least one non-TIL cell are present in the first biological sample at a ratio of 1:10,000 or less.

27. The method of claim 6, wherein the first biological sample is a solid tissue sample.

28. The method of claim 6, wherein the TIL cell comprises a T cell or a B cell, or wherein the non-TIL cell comprises an epithelial cell, a lymphocyte, or a cancer cell.

29. A method comprising
(a) forming a plurality of vessels, at least one vessel comprising:
a single tumor infiltrating lymphocyte (TIL) cell or a single non-TIL cell, wherein the single cell is isolated from a first biological sample from a first subject,
a plurality of molecular barcoded polynucleotides,
a vessel barcoded polynucleotide,
a forward primer and a reverse primer for amplifying the vessel barcoded polynucleotide, and
a reverse transcriptase
wherein each molecular barcoded polynucleotide of the plurality comprises a 5' region complementary to a region of the vessel barcoded polynucleotide;
(b) generating a first cDNA polynucleotide by reverse transcription of a first polynucleotide from the single cell encoding an Ig or a TCR, or fragment thereof, wherein the reverse transcriptase adds three or more non-template nucleotides to the 3' end of the first cDNA polynucleotide;
(c) generating a second cDNA polynucleotide by reverse transcription of a second polynucleotide from the single cell encoding an Ig or a TCR, or fragment thereof, wherein the reverse transcriptase adds three or more non-template nucleotides to the 3' end of the second cDNA polynucleotide;
(d) annealing a first molecular barcoded polynucleotide of the plurality to the three or more non-template nucleotides of the first cDNA polynucleotide, and extending the first cDNA polynucleotide to generate a first single-barcoded cDNA polynucleotide;
(e) annealing a second molecular barcoded polynucleotide of the plurality to the three or more non-template nucleotides of the second cDNA polynucleotide, and extending the second cDNA polynucleotide to generate a second single-barcoded cDNA polynucleotide;
(f) amplifying the vessel barcoded polynucleotide using the forward primer and the reverse primer, thereby generating an amplified product, annealing the amplified product to the first and second single-barcoded cDNA polynucleotides, and extending the first and second single-barcoded cDNA polynucleotides to generate a library of first and second dual-barcoded cDNA polynucleotides;
(g) sequencing the library thereby obtaining sequence information; and
(h) selecting an Ig or TCR polynucleotide sequence from a TIL based on comparing the sequence information obtained to sequence information obtained from a second biological sample, wherein the second biological sample comprises:
(i) a normal tissue sample from the first subject,
(ii) a normal biological sample from a healthy subject, and/or
(iii) a biological sample from a second subject, wherein the first and second subject have a same disease.

30. The method of claim 29, wherein the first polynucleotide from the single cell encodes a variable region of a VH or TCRα polypeptide, and the second polynucleotide from the single cell encodes a variable region of a VL or TCRβ polypeptide.

31. The method of claim 29, wherein the library represents an immune state of the first biological sample.

32. The method of claim 29, wherein the first and second dual-barcoded cDNA polynucleotides comprise different molecular barcodes and a same vessel barcode.

33. The method of claim 29, wherein the single cell is not sorted or selected based on an extracellular cell marker prior to the sequencing.

34. The method of claim 29, wherein the selected polynucleotide sequence comprises 1-500 unique Ig or TCR polynucleotide sequences.

35. The method of claim 29, further comprising producing an Ig or a TCR polypeptide encoded by the selected polynucleotide sequence.

36. The method of claim 35, further comprising identifying a target antigen of the produced polypeptide.

37. The method of claim 29, wherein the first biological sample comprises at least one TIL cell and at least one non-TIL cell, wherein the at least one TIL cell and the at least one non-TIL cell are present in the first biological sample at a ratio of 1:10,000 or less.

* * * * *

UNITED STATES PATENT AND TRADEMARK OFFICE
CERTIFICATE OF CORRECTION

| | | |
|---|---|---|
| PATENT NO. | : 10,982,258 B2 | Page 1 of 1 |
| APPLICATION NO. | : 15/570075 | |
| DATED | : April 20, 2021 | |
| INVENTOR(S) | : Francois Vigneault et al. | |

It is certified that error appears in the above-identified patent and that said Letters Patent is hereby corrected as shown below:

On the Title Page

Item (73), Line 1 "AbVitro LLC, Boston, MA" should read --AbVitro LLC, Seattle, WA (US)--.

Signed and Sealed this
Eighth Day of March, 2022

Drew Hirshfeld
*Performing the Functions and Duties of the*
*Under Secretary of Commerce for Intellectual Property and*
*Director of the United States Patent and Trademark Office*